Figure 2A:
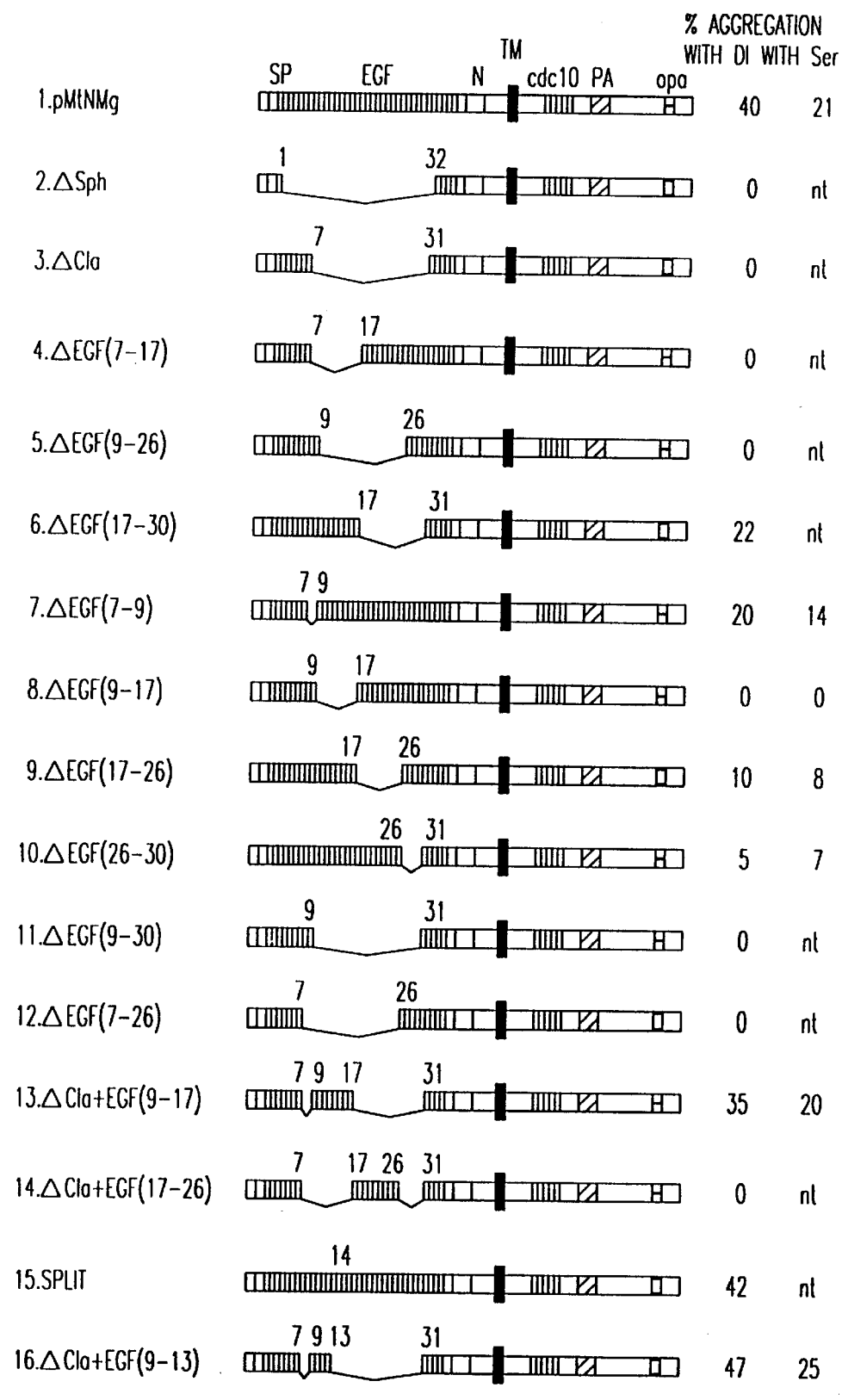

United States Patent [19]
Artavanis-Tsakonas

[11] Patent Number: 6,083,904
[45] Date of Patent: Jul. 4, 2000

[54] THERAPEUTIC AND DIAGNOSTIC METHODS AND COMPOSITIONS BASED ON NOTCH PROTEINS AND NUCLEIC ACIDS

[75] Inventor: Spyridon Artavanis-Tsakonas, Hamden, Conn.

[73] Assignee: Yale University, New Haven, Conn.

[21] Appl. No.: 08/532,384

[22] Filed: Sep. 22, 1995

Related U.S. Application Data

[63] Continuation of application No. 08/083,590, Jun. 25, 1993, Pat. No. 5,786,158, which is a continuation-in-part of application No. 07/955,012, Sep. 30, 1992, abandoned, and a continuation-in-part of application No. 07/879,038, Apr. 30, 1992, abandoned.

[51] Int. Cl.$^7$ .......................... A01N 37/18; A61K 38/00; A61K 39/395; G01N 33/574
[52] U.S. Cl. ............................ 514/2; 514/12; 424/130.1; 424/143.1; 435/7.23
[58] Field of Search .............................. 424/143.1, 130.1; 514/2, 12; 435/7.23; 530/300, 324, 350, 858

[56] References Cited

U.S. PATENT DOCUMENTS

| | | | |
|---|---|---|---|
| 5,115,096 | 5/1992 | Snoyab et al. | 530/322 |
| 5,132,212 | 7/1992 | Kirsch et al. | 435/69.4 |
| 5,264,557 | 11/1993 | Saloman et al. | 530/399 |
| 5,648,464 | 7/1997 | Artavanis-Tsakonas et al. | 530/350 |
| 5,780,300 | 7/1998 | Artavanis-Tsakonas et al. | 435/377 |
| 5,849,869 | 12/1998 | Artavanis-Tsakonas et al. | 530/350 |

FOREIGN PATENT DOCUMENTS

| | | |
|---|---|---|
| WO 92/19734 | 11/1992 | WIPO . |
| WO 93/12141 | 6/1993 | WIPO . |
| WO 94/07474 | 4/1994 | WIPO . |
| WO 97/19172 | 5/1997 | WIPO . |
| WO 97/45143 | 12/1997 | WIPO . |

OTHER PUBLICATIONS

Sun et al. "Secreted forms of Delta and Serrate define antagonists of Notch signaling in Drosophila" Development. Vol. 124, p. 3439–3448, 1997.

The Dictionary of Cell Biology. Ed. Lackie and Dow. p. 61, 1989.

Qi et al., 1999, Science 283:91–94.

Apelqvist et al., 1999, Nature 400:877–881.

Stifani, S. et al., 1992, "Human homologs of a Drosophila Enhancer of Split gene product define a novel family of nuclear proteins", Nature Genetics 2(2):119–127.

Weinmaster, G. et al., 1992, "Notch2: a second mammalian Notch gene", Development 116(4):931–941.

Adams, M.D. et al., 1991, "Complementary DNA Sequencing: Expressed Sequence Tags and Human Genome Project", Science 252:5013 1651–1656.

Artvanis–Tsakonas, S. et al., 1991, "The Notch Locus and the Cell Biology of Neuroblast Segregation", Ann. Rev. Cell Biol. 7:427–452.

Fleming, R.J. et al., 1990, "The gene Serrate encodes a putative EGF–like transmembrane protein essential for proper ectodermal development in *Drosophila melanogaster*", Gene & Development 4(12):2188–2201.

Rebay et al., 1993, Cell 74:319–329.

Doolittle, 1987, Of URFS and ORFS, A Primer on How to Analyze Derived Amino Acid Sequences, University Science Books, Mill Valley, California, pp. 10–17.

Artavanis–Tsakonas et al., 1995, Science 268:225–232.

Bray, 1998, Cell 93:499–503.

Zagouras et al., 1995, Proc. Natl. Acad. Sci. USA 92:6414–6418.

Chenn et al., 1995, Cell 82:631–641.

Ahmad et al., 1995, Mech. Develop. 53:73–85.

Kopan et al., 1994, Development 120:2385–2396.

Nye et al., 1994, Development 120:2421–2430.

Lindsell et al., 1995, Cell 80:909–917.

Fortini et al., 1993, Nature 365:555–557.

Milner et al., 1994, Blood 83(8):2057–2062.

Welshons, 1965, Analysis of a gene is Drosophila with variations, the genes of microorganisms and those of Drosophila are much the same, Science 150:1122–1129.

Portin, 1975, Allelic negative complementation at the abruptex locus of *Drosophila melanogaster*, Genetics 81:121–133.

Morita et al., 1984, Derivatives of blood coagulation factor IX contain a high affinity $Ca^{2+}$–binding site that lacks y–carboxyglutamic acid, J. Biol. Chem. 259:5698–5704.

(List continued on next page.)

*Primary Examiner*—Yvonne Eyler
*Attorney, Agent, or Firm*—Pennie & Edmonds LLP

[57] ABSTRACT

The present invention relates to therapeutic and diagnostic methods and compositions based on Notch proteins and nucleic acids. The invention provides for treatment of disorders of cell fate or differentiation by administration of a therapeutic compound of the invention. Such therapeutic compounds (termed herein "Therapeutics") include Notch proteins and analogs and derivatives (including fragments) thereof, antibodies thereto, nucleic acids encoding the Notch proteins, analogs, or derivatives, Notch antisense nucleic acids, as well as toporythmic proteins and derivatives which bind to or otherwise interact with Notch proteins and their encoding nucleic acids and antibodies. In a preferred embodiment, a Therapeutic of the invention is administered to treat a cancerous condition, or to prevent progression from a pre-neoplastic or non-malignant state into a neoplastic or a malignant state. In other embodiments, a Therapeutic is administered to treat a nervous system disorder or to promote tissue regeneration and repair. In one embodiment, Therapeutics which antagonize, or inhibit, Notch function (hereinafter "Antagonist Therapeutics") are administered for therapeutic effect. In another embodiment, Therapeutics which promote Notch function (hereinafter "Agonist Therapeutics") are administered for therapeutic effect. Diagnostic methods and methods of inhibiting Notch expression are also provided.

11 Claims, 68 Drawing Sheets

OTHER PUBLICATIONS

Sugo et al., 1984, Calcium–binding properties of bovine factor X lacking the y–carboxylglutamic acid–containing region, J. Biol. Chem. 259:5705–5710.

Lindsley and Zinn, 1985, Drosophila Information Service 62:86.

Südhof et al. 1985, The LDL receptor gene: a mosaic of exons shared with different proteins, Science 228:815–822.

Doe and Goodman, 1985, Early events in insect neurogenesis. II. The role of cell interactions and cell lineage in the determination of neuronal precursor cells, Dev. Biol. 111:206–219.

Vässin et al., 1985, Genetic interactions in early neurogenesis of *Drosophila melanogaster*, J. Neurogenet. 2:291–308.

Wharton et al., 1985, Nucleotide sequence from the neurogenic locus Notch implies a gene product that shares homology with proteins containing EGF–like repeats, Cell 43:567–581.

Kidd et al., 1986, Sequence of the Notch locus of *Drosophila melanogaster*: relationship of the encoded protein to mammalian clotting and growth factors, Mol. Cell. Biol. 6;3094–3108.

Breeden and Nasmyth, 1987, Similarity between cell–cycle genes of budding yeast and fission yeast and the Notch gene of Drosophila, Nature 329:651–654.

Appella et al., 1987, The receptor–binding sequence of urokinase. A biological function for the growth–factor module of proteases, J. Biol. Chem. 262:4437–4440.

Knust et al., 1987, EGF homologous sequences encoded in the genome of *Drosophila melanogaster*, and their relation to neurogenic genes, EMBO J. 6(3):761–766.

Suzuki et al., 1987, Structure and expression of human thrombomodulin, a thrombin receptor on endothelium acting as a cofactor for protein C activation, EMBO J. 6(7):1891–1897.

Hartley et al., 1987, The embryonic expression of the Notch locus of *Drosophila melanogaster* and the implications of point mutations in the extracellular EGF–like domain of the predicted protein, EMBO J. 6(11):3407–3417.

Reynolds et al., 1987, Analysis of DNA surrounding the breakpoints of chromosomal translocations involving the β T cell receptor gene in human lymphoblastic neoplasms, Cell 50:107–117.

Vässin et al., 1987, The neurogenic gene Delta of *Drosophila melanogaster* is expressed in neurogenic territories and encodes a putative transmembrane protein with EGF–like repeats, EMBO J. 6:3431–3440.

Kelley et al., 1987, Mutations altering the structure of epidermal growth factor–like coding sequences at the *Drosophila Notch* locus, Cell 51:539–548.

Kopczynski et al., 1988, Delta, a Drosophila neurogenic gene, is transcriptionally complex and encodes a protein related to blood coagulation factors and epidermal growth factor of vertebrates, Genes & Dev. 2:1723–1735.

Kopczynski and Muskavitch, 1989, Complex spatio–temporal accumulation of alternative transcripts from the neurogenic gene Delta during *Drosophila* embryogenesis, Development 107:623–636.

Rees et al., 1988, The role of β–hydroxyaspartate and adjacent carboxylate residues in the first EGF domain of human factor IX, EMBO J. 7(7):2053–2061.

Furie and Furie, 1988, The molecular basis of blood coagulation, Cell 53:505–518.

Artavanis–Tsakonas, 1988, DNA, differentiation & development, Trends in Genetics 4:95–100.

Kurosawa et al., 1988, A 10–kDa cyanogen bromide fragment from the epidermal growth factor homology domain of rabbit thrombomodulin contains the primary thrombin binding site, J. Biol. Chem. 263(13):5993–5996.

Yochem et al., 1988, The *Caenorhabditis elegans lin*–12 gene encodes a transmembrane protein with overall similarity to *Drosophila Notch*, Nature 335:547–550.

Rothberg et al., 1988, slit: An EGF–homologous locus of D. melanogaster involved in the development of the embryonic central nervous system, Cell 55:1047–1059.

Kidd et al., 1989, Structure and distribution of the Notch protein in developing Drosophila, Genes & Dev. 3:1113–1129.

Johansen et al., 1989, The Notch gene product is a glycoprotein expressed on the cell surface of both epidermal and neuronal precursor cells during Drosophila development, J. Cell Biol. 109:2427–2440.

Shepard et al., 1989, A tripartite interaction among alleles of Notch, Delta,and Enhancer of split during imaginal development of *Drosophila melanogaster*, Genetics 122:429–438.

Alton et al., 1989, Molecular genetics of Delta, a locus required for ectodermal differentiation in Drosophila, Dev. Genet. 10:261–272.

Handford et al., 1990, The first EGF–like domain from human factor IX contains a high–affinity calcium binding site, EMBO J. 9:475–480.

Fehon et al., 1990, Molecular interactions between the protein products of the neurogenic loci Notch and Delta, two EGF–homologous genes in Drosophila, Cell 61:523–534.

Coffman et al., 1990, Xotch, the Xenopus homolog of Drosophila Notch, Science 249:1438–1441.

Palka et al., 1990, Neurogenic and antineurogenic effects from modifications at the Notch locus, Develop. 109:167–175.

Xu et al., 1990, The Notch locus and the Egenetic circuitry involved in early Drosophila neurogenesis, Genes & Dev. 4:464–475.

Ellisen et al., 1991, TAN–1, the human homolog of the Drosophila Notch gene, is broken by chromosomal translocations in T lymphoblastic neoplasms, Cell 66:649–661.

Weinmaster et al., 1991, A homolog of Drosophila Notch expressed during mammalian development, Develop. 113:199–205.

Fehon et al., 1991, Complex spatial and temporal regulation of Notch expression during embryonic and imaginal development of Drosophila, implications for Notch function, J. Cell Biol. 113:657–669.

Coffman et al., 1993, "Expression of an extracellular deletion of xotch diverts cell fate in xenopus embryos," Cell 73:659–671.

Jhappan et al., 1992, "Expression of an activated Notch–related int–3 transgene interferes with cell differentiation and induces neoplastic transformation in mammary and salivary glands", Genes and Dev. 6: 345–355.

Robbins et al., 1992, "Mouse mammary tumor gene int–3: a member of the notch gene family transforms mammary epithelial cells," J. Virol. 66: 2594–2599.

Campos–Ortega and Knust, 1990, "Molecular analysis of a cellular decision during embryonic development of *Drosophila melanogaster*: epidermogenesis or neurogenesis," Eur. J. Biochem. 190: 1–10.

De Celis et al., 1993, "Genetic and Molecular Characterization of a Notch mutation in its Delta–and Serrate–binding domain in Drosophila", Proc. Natl. Acad. Sci. USA 90: 4037–4041.

Greenspan, 1990, "The Notch gene, adhesion, and developmental fate in the Drosophia embryo", New Biologist 2(7):595–600.

Rebay et al., 1991, "Specific EGF repeats of Notch mediate interactions with Delta and Serrate: implications for notch as a multifunctional receptor", Cell 67:687–699.

Robbins et al., 1992, "Mouse mammary tumor gene int–3: a member of the notch gene family transforms mammary epithelial cells," Biol. Abstr. 93(11):AB–465 (Abstr. 122736).

```
GAATTCGGAG GAATTATTCA AAACATAAAC ACAATAAACA ATTTGAGTAG TTGCCGCACA    60

CACACACACA CACAGCCCGT GGATTATTAC ACTAAAAGCG ACACTCAATC CAAAAAATCA   120

GCAACAAAAA CATCAATAAA C ATG CAT TGG ATT AAA TGT TTA TTA ACA GCA    171
                        Met His Trp Ile Lys Cys Leu Leu Thr Ala
                         1               5                    10

TTC ATT TGC TTC ACA GTC ATC GTG CAG GTT CAC AGT TCC GGC AGC TTT    219
Phe Ile Cys Phe Thr Val Ile Val Gln Val His Ser Ser Gly Ser Phe
             15                  20                  25

GAG TTG CGC CTG AAG TAC TTC AGC AAC GAT CAC GGG CGG GAC AAC GAG    267
Glu Leu Arg Leu Lys Tyr Phe Ser Asn Asp His Gly Arg Asp Asn Glu
         30                  35                  40

GGT CGC TGC TGC AGC GGG GAG TCG GAC GGA GCG ACG GGC AAG TGC CTG    315
Gly Arg Cys Cys Ser Gly Glu Ser Asp Gly Ala Thr Gly Lys Cys Leu
         45                  50                  55

GGC AGC TGC AAG ACG CGG TTT CGC GTC TGC CTA AAG CAC TAC CAG GCC    363
Gly Ser Cys Lys Thr Arg Phe Arg Val Cys Leu Lys His Tyr Gln Ala
         60                  65                  70

ACC ATC GAC ACC ACC TCC CAG TGC ACC TAC GGG GAC GTG ATC ACG CCC    411
Thr Ile Asp Thr Thr Ser Gln Cys Thr Tyr Gly Asp Val Ile Thr Pro
 75                  80                  85                  90

ATT CTC GGC GAG AAC TCG GTC AAT CTG ACC GAC GCC CAG CGC TTC CAG    459
Ile Leu Gly Glu Asn Ser Val Asn Leu Thr Asp Ala Gln Arg Phe Gln
                 95                 100                 105

AAC AAG GGC TTC ACG AAT CCC ATC CAG TTC CCC TTC TCG TTC TCA TGG    507
Asn Lys Gly Phe Thr Asn Pro Ile Gln Phe Pro Phe Ser Phe Ser Trp
         110                 115                 120
```

FIG.1A

```
CCG GGT ACC TTC TCG CTG ATC GTC GAG GCC TGG CAT GAT ACG AAC AAT    555
Pro Gly Thr Phe Ser Leu Ile Val Glu Ala Trp His Asp Thr Asn Asn
        125             130             135

AGC GGC AAT GCG CGA ACC AAC AAG CTC CTC ATC CAG CGA CTC TTG GTG    603
Ser Gly Asn Ala Arg Thr Asn Lys Leu Leu Ile Gln Arg Leu Leu Val
        140             145             150

CAG CAG GTA CTG GAG GTG TCC TCC GAA TGG AAG ACG AAC AAG TCG GAA    651
Gln Gln Val Leu Glu Val Ser Ser Glu Trp Lys Thr Asn Lys Ser Glu
155             160             165             170

TCG CAG TAC ACG TCG CTG GAG TAC GAT TTC CGT GTC ACC TGC GAT CTC    699
Ser Gln Tyr Thr Ser Leu Glu Tyr Asp Phe Arg Val Thr Cys Asp Leu
                175             180             185

AAC TAC TAC GGA TCC GGC TGT GCC AAG TTC TGC CGG CCC CGC GAC GAT    747
Asn Tyr Tyr Gly Ser Gly Cys Ala Lys Phe Cys Arg Pro Arg Asp Asp
            190             195             200

TCA TTT GGA CAC TCG ACT TGC TCG GAG ACG GGC GAA ATT ATC TGT TTG    795
Ser Phe Gly His Ser Thr Cys Ser Glu Thr Gly Glu Ile Ile Cys Leu
            205             210             215

ACC GGA TGG CAG GGC GAT TAC TGT CAC ATA CCC AAA TGC GCC AAA GGC    843
Thr Gly Trp Gln Gly Asp Tyr Cys His Ile Pro Lys Cys Ala Lys Gly
        220             225             230

TGT GAA CAT GGA CAT TGC GAC AAA CCC AAT CAA TGC GTT TGC CAA CTG    891
Cys Glu His Gly His Cys Asp Lys Pro Asn Gln Cys Val Cys Gln Leu
235             240             245             250

GGC TGG AAG GGA GCC TTG TGC AAC GAG TGC GTT CTG GAA CCG AAC TGC    939
Gly Trp Lys Gly Ala Leu Cys Asn Glu Cys Val Leu Glu Pro Asn Cys
            255             260             265
```

FIG.1B

```
ATC CAT GGC ACC TGC AAC AAA CCC TGG ACT TGC ATC TGC AAC GAG GGT      987
Ile His Gly Thr Cys Asn Lys Pro Trp Thr Cys Ile Cys Asn Glu Gly
        270             275             280

TGG GGA GGC TTG TAC TGC AAC CAG GAT CTG AAC TAC TGC ACC AAC CAC     1035
Trp Gly Gly Leu Tyr Cys Asn Gln Asp Leu Asn Tyr Cys Thr Asn His
        285             290             295

AGA CCC TGC AAG AAT GGC GGA ACC TGC TTC AAC ACC GGC GAG GGA TTG     1083
Arg Pro Cys Lys Asn Gly Gly Thr Cys Phe Asn Thr Gly Glu Gly Leu
        300             305             310

TAC ACA TGC AAA TGC GCT CCA GGA TAC AGT GGT GAT GAT TGC GAA AAT     1131
Tyr Thr Cys Lys Cys Ala Pro Gly Tyr Ser Gly Asp Asp Cys Glu Asn
315             320             325             330

GAG ATC TAC TCC TGC GAT GCC GAT GTC AAT CCC TGC CAG AAT GGT GGT     1179
Glu Ile Tyr Ser Cys Asp Ala Asp Val Asn Pro Cys Gln Asn Gly Gly
            335             340             345

ACC TGC ATC GAT GAG CCG CAC ACA AAA ACC GGC TAC AAG TGT CAT TGC     1227
Thr Cys Ile Asp Glu Pro His Thr Lys Thr Gly Tyr Lys Cys His Cys
            350             355             360

GCC AAC GGC TGG AGC GGA AAG ATG TGC GAG GAG AAA GTG CTC ACG TGT     1275
Ala Asn Gly Trp Ser Gly Lys Met Cys Glu Glu Lys Val Leu Thr Cys
        365             370             375

TCG GAC AAA CCC TGT CAT CAG GGA ATC TGC CGC AAC GTT CGT CCT GGC     1323
Ser Asp Lys Pro Cys His Gln Gly Ile Cys Arg Asn Val Arg Pro Gly
    380             385             390

TTG GGA AGC AAG GGT CAG GGC TAC CAG TGC GAA TGT CCC ATT GGC TAC     1371
Leu Gly Ser Lys Gly Gln Gly Tyr Gln Cys Glu Cys Pro Ile Gly Tyr
395             400             405             410
```

FIG.1C

```
AGC GGA CCC AAC TGC GAT CTC CAG CTG GAC AAC TGC AGT CCG AAT CCA    1419
Ser Gly Pro Asn Cys Asp Leu Gln Leu Asp Asn Cys Ser Pro Asn Pro
            415                 420                 425

TGC ATA AAC GGT GGA AGC TGT CAG CCG AGC GGA AAG TGT ATT TGC CCA    1467
Cys Ile Asn Gly Gly Ser Cys Gln Pro Ser Gly Lys Cys Ile Cys Pro
            430                 435                 440

GCG GGA TTT TCG GGA ACG AGA TGC GAG ACC AAC ATT GAC GAT TGT CTT    1515
Ala Gly Phe Ser Gly Thr Arg Cys Glu Thr Asn Ile Asp Asp Cys Leu
            445                 450                 455

GGC CAC CAG TGC GAG AAC GGA GGC ACC TGC ATA GAT ATG GTC AAC CAA    1563
Gly His Gln Cys Glu Asn Gly Gly Thr Cys Ile Asp Met Val Asn Gln
            460                 465                 470

TAT CGC TGC CAA TGC GTT CCC GGT TTC CAT GGC ACC CAC TGT AGT AGC    1611
Tyr Arg Cys Gln Cys Val Pro Gly Phe His Gly Thr His Cys Ser Ser
475                     480                 485                 490

AAA GTT GAC TTG TGC CTC ATC AGA CCG TGT GCC AAT GGA GGA ACC TGC    1659
Lys Val Asp Leu Cys Leu Ile Arg Pro Cys Ala Asn Gly Gly Thr Cys
            495                 500                 505

TTG AAT CTC AAC AAC GAT TAC CAG TGC ACC TGT CGT GCG GGA TTT ACT    1707
Leu Asn Leu Asn Asn Asp Tyr Gln Cys Thr Cys Arg Ala Gly Phe Thr
            510                 515                 520

GGC AAG GAT TGC TCT GTG GAC ATC GAT GAG TGC AGC AGT GGA CCC TGT    1755
Gly Lys Asp Cys Ser Val Asp Ile Asp Glu Cys Ser Ser Gly Pro Cys
            525                 530                 535

CAT AAC GGC GGC ACT TGC ATG AAC CGC GTC AAT TCG TTC GAA TGC GTG    1803
His Asn Gly Gly Thr Cys Met Asn Arg Val Asn Ser Phe Glu Cys Val
            540                 545                 550
```

FIG.1D

```
TGT GCC AAT GGT TTC AGG GGC AAG CAG TGC GAT GAG GAG TCC TAC GAT    1851
Cys Ala Asn Gly Phe Arg Gly Lys Gln Cys Asp Glu Glu Ser Tyr Asp
555                 560                 565                 570

TCG GTG ACC TTC GAT GCC CAC CAA TAT GGA GCG ACC ACA CAA GCG AGA    1899
Ser Val Thr Phe Asp Ala His Gln Tyr Gly Ala Thr Thr Gln Ala Arg
                575                 580                 585

GCC GAT GGT TTG ACC AAT GCC CAG GTA GTC CTA ATT GCT GTT TTC TCC    1947
Ala Asp Gly Leu Thr Asn Ala Gln Val Val Leu Ile Ala Val Phe Ser
                590                 595                 600

GTT GCG ATG CCT TTG GTG GCG GTT ATT GCG GCG TGC GTG GTC TTC TGC    1995
Val Ala Met Pro Leu Val Ala Val Ile Ala Ala Cys Val Val Phe Cys
                605                 610                 615

ATG AAG CGC AAG CGT AAG CGT GCT CAG GAA AAG GAC GAC GCG GAG GCC    2043
Met Lys Arg Lys Arg Lys Arg Ala Gln Glu Lys Asp Asp Ala Glu Ala
                620                 625                 630

AGG AAG CAG AAC GAA CAG AAT GCG GTG GCC ACA ATG CAT CAC AAT GGC    2091
Arg Lys Gln Asn Glu Gln Asn Ala Val Ala Thr Met His His Asn Gly
635                 640                 645                 650

AGT GGG GTG GGT GTA GCT TTG GCT TCA GCC TCT CTG GGC GGC AAA ACT    2139
Ser Gly Val Gly Val Ala Leu Ala Ser Ala Ser Leu Gly Gly Lys Thr
                655                 660                 665

GGC AGC AAC AGC GGT CTC ACC TTC GAT GGC GGC AAC CCG AAT ATC ATC    2187
Gly Ser Asn Ser Gly Leu Thr Phe Asp Gly Gly Asn Pro Asn Ile Ile
                670                 675                 680

AAA AAC ACC TGG GAC AAG TCG GTC AAC AAC ATT TGT GCC TCA GCA GCA    2235
Lys Asn Thr Trp Asp Lys Ser Val Asn Asn Ile Cys Ala Ser Ala Ala
                685                 690                 695
```

FIG.1E

```
GCA GCG GCG GCG GCG GCA GCA GCG GCG GAC GAG TGT CTC ATG TAC GGC    2283
Ala Ala Ala Ala Ala Ala Ala Ala Ala Asp Glu Cys Leu Met Tyr Gly
700             705                 710

GGA TAT GTG GCC TCG GTG GCG GAT AAC AAC AAT GCC AAC TCA GAC TTT    2331
Gly Tyr Val Ala Ser Val Ala Asp Asn Asn Asn Ala Asn Ser Asp Phe
715             720                 725                 730

TGT GTG GCT CCG CTA CAA AGA GCC AAG TCG CAA AAG CAA CTC AAC ACC    2379
Cys Val Ala Pro Leu Gln Arg Ala Lys Ser Gln Lys Gln Leu Asn Thr
                735                 740                 745

GAT CCC ACG CTC ATG CAC CGC GGT TCG CCG GCA GGC AGC TCA GCC AAG    2427
Asp Pro Thr Leu Met His Arg Gly Ser Pro Ala Gly Ser Ser Ala Lys
            750                 755                 760

GGA GCG TCT GGC GGA GGA CCG GGA GCG GCG GAG GGC AAG AGG ATC TCT    2475
Gly Ala Ser Gly Gly Gly Pro Gly Ala Ala Glu Gly Lys Arg Ile Ser
            765                 770                 775

GTT TTA GGC GAG GGT TCC TAC TGT AGC CAG CGT TGG CCC TCG TTG GCG    2523
Val Leu Gly Glu Gly Ser Tyr Cys Ser Gln Arg Trp Pro Ser Leu Ala
780             785                 790

GCG GCG GGA GTG GCC GGA GCC TGT TCA TCC CAG CTA ATG GCT GCA GCT    2571
Ala Ala Gly Val Ala Gly Ala Cys Ser Ser Gln Leu Met Ala Ala Ala
795             800                 805                 810

TCG GCA GCG GGC AGC GGA GCG GGG ACG GCG CAA CAG CAG CGA TCC GTG    2619
Ser Ala Ala Gly Ser Gly Ala Gly Thr Ala Gln Gln Gln Arg Ser Val
            815                 820                 825

GTC TGC GGC ACT CCG CAT ATG TAACTCCAAA AATCCGGAAG GGCTCCTGGT       2670
Val Cys Gly Thr Pro His Met
                830
AAATCCGGAG AAATCCGCAT GGAGGAGCTG ACAGCACATA CACAAAGAAA AGACTGGGTT  2730
GGGTTCAAAA TGTGAGAGAG ACGCCAAAAT GTTGTTGTTG ATTGAAGCAG TTTAGTCGTC  2790
ACGAAAAATG AAAAATCTGT AACAGGCATA ACTCGTAAAC TCCCTAAAAA ATTTGTATAG  2850
TAATTAGCAA AGCTGTGACC CAGCCGTTTC GATCCCGAAT TC                    2892
```

FIG.1F

FIG. 5A

```
   1  CCGAGTCGAGCCCGTGCTTCGAGGGTGATGAGCCCCTTTTCTGTCAACGCTAAAGATC
 121  AAGCACATACTAAGGTCCATATAAATAATAAATAATTGTGTGTGATAACAACATTAT
 241  GGCCGTTATTCAGCTATCCAGAGCAAGTGTAGTGTGGCAAAATAGAAACAAAAGGCA
 361  CAATCCAGAGTGAATCCGAAACAAACTCCATCTAGATCGCCAACCAGCATCACGCTCGCA

481  TCGTCGTTGGAGTCAACAATAGAATCAGCAGACAGCCTGGGAATGTCCAAGAAGACGGCG
      SerSerLeuGluSerThrIleGluSerAlaAspSerLeuGlyMetSerLysLysThrAla

601  CGCGATTGTCGATCATTAAAGTCTGCAACTTAATTGCCTGCAACTTAATTGCTTTAATTTAATACTGTTA
      ArgAspCysArgSerLeuLysSerAlaAlaCysAsnLeuIleAlaLeuIleLeuLeuLeu

721  AACAGGCCATCTACTCAACGGCTATTGCTGCGGCATGCCAGCGGAACTTAGGCCACCAAG
      AsnSerHisLeuLeuAsnGlyTyrCysCysGlyMetProAlaGluLeuArgAlaThrLys
                                                              #2
 841  ACCGAGCAGGGTGCCAGCACATATCCACGGGCTGTCGTTTGGCAAGGCCACCACCAAGATA
      ThrGluGlnGlyAlaSerIleSerThrGlyCysSerPheGlyAsnAlaThrThrLysIle

961  ACGTTTCGTTGGACGAAGTCGTTTACGTGATACTGCAGGCGTTGGATACTGCAACACA
      ThrPheArgTrpThrLysSerPheThrLeuIleLeuGlnAlaLeuAspMetTyrAsnThr
                                              #3
1081  TCGCCCGGAGTGGAAGACCTGGACCACCATCGGGACGGAACGCGGGATCACCTACCGTGTC
      SerProGluTrpLysThrLeuAspHisIleGlyArgAsnAlaArgIleThrTyrArgVal

1201  GACGATCAGTTCGGTCACTACGCCTGCGGCTCCGAGGGTCAGAAGCTCTGCCTGAATGGC
      AspAspGlnPheGlyHisTyrAlaCysGlySerGluGlyGlnLysLeuCysLeuAsnGly
```

FIG.5B

```
TACAAAACATCAGCGGCCTATCAAGTGGAAGTGTCAAGTGTGAACAAAAACAAAAGAGAG        13
CCAAACAAAACCAAACAAACAAAAACGAAGGCAAAGTGGAGAAATGATACAGCATCCAGAGTAC
CCAAAATCTGCATACATGGGCTAATTAAGGCTGCCCAGCGAATTTACATTTGTTGTGGTGC
AACGCCCCAGAATGTACAAAATGTTTAGGAAACATTTTCGGCGAAAACCAGCTACGTCG
                 MetPheArgLysHisPheArgArgLysProAlaThrSer

ACAAAAGGCAGGTCCGAGGCATCGGGTACCCAAAATCGCGACCCTGCCATGACGATC         53
ThrLysArgGlnArgProArgHisArgValProLysIleAlaThrLeuProSerThrIle

GTCCATAGAATATCCGCAGTGTAACTTCGAGCTGGAAATATTAGAAATCTCAAATACC        93
ValHisLysIleSerAlaAlaGlyAsnPheGluLeuGluIleLeuGluIleSerAsnThr
                                                    #1

ACGATAGGCTGCTCGCCATGCACGACGGCATTCCGGCTGTGCCTGAAGGAGTACCAGACC      133
ThrIleGlyCysSerProCysThrThrAlaPheArgLeuCysLeuLysGluTyrGlnThr

CTGGGTGGCTCCAGGTTTGTGCTCAGGATCCGGGTGTGGGAGCCATTGTGCTGCCCTTT      173
LeuGlyGlySerPheValLeuSerAspProGlyValGlyAlaIleValLeuProPhe

TCCTATCCAGATGCGGAGAGGTTAATTGAGGAAACATCATACTCGGGCGTGATACTGCCG     213
SerTyrProAspAlaGluArgLeuIleGluGluThrSerTyrSerGlyValIleLeuPro

CGGGTGCAATGCGAAGCCGTTACCTACTACAACACGACCTGCACGACCTTCTGCCGTCCGG     253
ArgValGlnCysGluAlaValThrTyrTyrAsnThrThrCysThrThrPheCysArgProArg
                                                      #4

TGGCAGGGGTCAACTGCGAGGAGGCCATATGCAAGGCGGGCTGCGACCCGTCCACGGC       293
TrpGlnGlyValAsnCysGluAlaIleCysLysAlaGlyCysAspProValHisGly
```

```
  1  GAATTCCGCT GGGAGAATGG TCTGAGCTAC CTGCCCGTCC TGCTGGGGCA TCAATGGCAA
 61  GTGGGGAAAG CCACACTGGG CAAACGGGCC AGGCCATTTC TGGAATGTGG TACATGGTGG
121  GCAGGGGGCC CGCAACAGCT GGAGGGCAGG TGGACTGAGG CTGGGGATCC CCCGCTGGTT
181  GGGCAATACT GCCTTTACCC ATGAGCTGGA AAGTCACAAT GGGGGGCAAG GGCTCCCGAG
241  GGTGGTTATG TGCTTCCTTC AGGTGGC
```

FIG.8A

```
  1  GAATTCCTTC CATTATACGT GACTTTTCTG AAACTGTAGC CACCCTAGTG TCTCTAACTC
 61  CCTCTGGAGT TTGTCAGCTT TGGTCTTTTC AAAGAGCAGG CTCTCTTCAA GCTCCTTAAT
121  GCGGGCATGC TCCAGTTTGG TCTGCGTCTC AAGATCACCT TTGGTAATTG ATTCTTCTTC
181  AACCCGGAAC TGAAGGCTGG CTCTCACCCT CTAGGCAGAG CAGGAATTCC GAGGTGGATG
241  TGTTAGATGT GAATGTCCGT GGCCCAGATG GCTGCACCCC ATTGATGTTG GCTTCTCTCC
301  GAGGAGGCAG CTCAGATTTG AGTGATGAAG ATGAAGATGC AGAGGACTGT TCTGCTAACA
361  TCATCACAGA CTTGGTCTAC CAGGGTGCCA GCCTCCAGAC CAGACAGACC GGACTGGTGA
421  GATGGCCCTG CACCTTGCAG CCCGCTACTC ACGGGCTGAT GCTGCCAAGC GTCTCCTGGA
481  TGCAGGTGCA GATGCCAATG CCCAGGACAA CATGGGCCGC TGTCCACTCC ATGCTGCAGT
541  GGCACGTGAT GCCAAGGTGT ATTCAGATCT GTTA
```

FIG.8B

```
  1  TCCAGATTCT GATTCGCAAC CGAGTAACTG ATCTAGATGC CAGGATGAAT GATGGTACTA
 61  CACCCCTGAT CCTGGCTGCC CGCCTGGCTG TGGAGGGAAT GGTGGCAGAA CTGATCAACT
121  GCCAAGCGGA TGTGAATGCA GTGGATGACC ATGGAAAATC TGCTCTTCAC TGGGCAGCTG
181  CTGTCAATAA TGTGGAGGCA ACTCTTTTGT TGTTGAAAAA TGGGGCCAAC CGAGACATGC
241  AGGACAACAA GGAAGAGACA CCTCTGTTTC TTGCTGCCCG GGAGGAGCTA TAAGC
```

FIG.8C

1   GAATTCCATT CAGGAGGAAA GGGTGGGGAG AGAAGCAGGC ACCCACTTTC CCGTGGCTGG
61  ACTCGTTCCC AGGTGGCTCC ACCGGCAGCT GTGACCGCCG CAGGTGGGGG CGGAGTGCCA
121 TTCAGAAAAT TCCAGAAAAG CCCTACCCCA ACTCGGACGG CAACGTCACA CCCGTGGGTA
181 GCAACTGGCA CACAAACAGC CAGCGTGTCT GGGGCACGGG GGGATGGCAC CCCCTGCAGG
241 CAGAGCTG

FIG.9A

1   CTAAAGGGAA CAAAAGCNGG AGCTCCACCG CGGGCGGCNC NGCTCTAGAA CTAGTGGANN
61  NCCCGGGCTG CAGGAATTCC GGCGGACTGG GCTCGGGCTC AGAGCGGCGC TGTGGAAGAG
121 ATTCTAGACC GGGAGAACAA GCGAATGGCT GACAGCTGGC CTCCAAAGTC ACCAGGCTCA
181 AATCGCTCGC CCTGGACATC GAGGGATGCA GAGGATCAGA ACCGGTACCT GGATGGCATG
241 ACTCGGATTT ACAAGCATGA CCAGCCTGCT TACAGGGAGC GTGANNTTTT CACATGCAGT
301 CGACAGACAC GAGCTCTATG CAT

FIG.9B

FIG. 10A

```
             10        20        30        40
  *   *   *   *   *   *   *   *   *   *   *   *   *   *   *
 TGC CAG GAG GAC GCG GGC AAC AAG GTC TGC AGC CTG CAG AAC AAC
  C   Q   E   D   A   G   N   K   V   C   S   L   Q   N   N 50        60        70        80        90
  *   *   *   *   *   *   *   *   *   *   *   *   *   *   *
 CAC GCG TGC GGC TGG GAC GGC TGG GAC TGC TCC CTC AAC TTC AAT GAC
  H   A   C   G   W   D   G   W   D   C   S   L   N   F   N   D 100       110       120       130       140
  *   *   *   *   *   *   *   *   *   *   *   *   *   *   *
 CCC TGG AAG AAC TGC ACG CAG TCT CTG CAG TGG AAG TAC TTC AGT
  P   W   K   N   C   T   Q   S   L   Q   W   K   Y   F   S 150       160       170       180       190
  *   *   *   *   *   *   *   *   *   *   *   *   *   *   *
 GAC GGC CAC TGT GAC AGC CAG AAC TCA GCC TGC TGG GGC CTC TTC GAC
  D   G   H   C   D   S   Q   N   S   A   C   W   G   L   F   D
```

```
        200                 210                 220                 230                 240
         *                   *                   *                   *                   *
GGC TTT GAC TGC CAG CGT GCG GAA GGC CAG TGC AAC CCC CTG TAC GAC
 G   F   D   C   Q   R   A   E   G   Q   C   N   P   L   Y   D  >-|

250                 260                 270                 280
         *                   *                   *                   *
CAG TAC TGC AAG GAC CAC TTC AGC GAC GGG CAC TGC GAC CAG GGC TGC
 Q   Y   C   K   D   H   F   S   D   G   H   C   D   Q   G   C  >

290                 300                 310                 320                 330
         *                   *                   *                   *                   *
AAC AGC GCG GAG TGC GTG GAG TGG GAC GGG CTG GAC TGT GCG GAG CAT GTA
 N   S   A   E   C   V   E   W   D   G   L   D   C   A   E   H   V >

340                 350                 360                 370                 380
         *                   *                   *                   *                   *
CCC GAG AGG CTG GCG GCC ACG CTG GTG GTG GTG CTG ATG CCG
 P   E   R   L   A   A   T   L   V   V   V   L   M   P  >
```

FIG.10B

```
     390                400                410                420                430
      *                  *                  *                  *                  *
CCG GAG CAG CTG CGC AAC AGC TCC TTC CAC TTC CTG CGG GAG CTC AGC
 P   E   Q   L   R   N   S   S   F   H   F   L   R   E   L   S 440                450                460                470                480
      *                  *                  *                  *                  *
CGC GTG CTG CAC ACC AAC GTG GTC TTC AAG CGT GAC GCA CAC GGC CAG
 R   V   L   H   T   N   V   V   F   K   R   D   A   H   G   Q 490                500                510                520
      *                  *                  *                  *
CAG ATG ATC TTC CCC TAC TAC GGC CGC GAG GAG GAG CTG CGC AAG CAC
 Q   M   I   F   P   Y   Y   G   R   E   E   E   L   R   K   H 530                540                550                560                570
      *                  *                  *                  *                  *
CCC ATC AAG CGT GCC GCA GAG GGC TGG GCC GCA CCT GAC GCC CTG CTG
 P   I   K   R   A   A   E   G   W   A   A   P   D   A   L   L
```

FIG. 10C

```
        580         590         600         610         620
         *           *           *           *           *
GGC CAG GTG AAG GCC TCG CTG CTC CCT GGT GGC AGC GAG GGT GGG CGG
 G   Q   V   K   A   S   L   L   P   G   G   S   E   G   G   R>

630         640         650         660         670
         *           *           *           *           *
CGG AGG GAG CTG GAC CCC ATG GAC GTC CGC GGC TCC ATC GTC TAC
 R   R   E   L   D   P   M   D   V   R   G   S   I   V   Y>

680         690         700         710         720
         *           *           *           *           *
CTG GAG ATT GAC AAC CGG CAG TGT GTG CAG GCC TCC TCG CAG TGC TTC
 L   E   I   D   N   R   Q   C   V   Q   A   S   S   Q   C   F>

730         740         750         760
         *           *           *           *
CAG AGT GCC ACC GAC GTG GCC GCA TTC CTG GGA GCG CTC GCC TCG CTG
 Q   S   A   T   D   V   A   A   F   L   G   A   L   A   S   L>
```

FIG. 10D

```
        770       780       790       800       810
         *         *         *         *         *
GGC AGC CTC AAC ATC CCC TAC AAG ATC GAG GCC GTG CAG AGT GAG ACC
 G   S   L   N   I   P   Y   K   I   E   A   V   Q   S   E   T>

820       830       840       850       860
         *         *         *         *         *
GTG GAG CCG CCC CCG CCG GCG CAG CTG CAC TTC ATG TAC GTG GCG GCG
 V   E   P   P   P   P   A   Q   L   H   F   M   Y   V   A   A>

870       880       890       900       910
         *         *         *         *         *
GCC GCC TTT GTG CTT CTG TTC TTC GTG GGC TGC GGG GTG CTG CTG TCC
 A   A   F   V   L   L   F   F   V   G   C   G   V   L   L   S>

920       930       940       950       960
         *         *         *         *         *
CGC AAG CGC CGG CGG CAG CAT GGC CAG CTC TGG TTC CCT GAG GGC TTC
 R   K   R   R   R   Q   H   G   Q   L   W   F   P   E   G   F>
```

FIG.10E

```
                  970          980          990         1000
      *       *        *        *        *        *        *
AAA GTG TCT GAG GCC AGC AAG AAG AAG CGG CGG GAG CCC CTC GGC GAG
 K   V   S   E   A   S   K   K   K   R   R   E   P   L   G   E>

1010         1020         1030         1040         1050
 *        *        *        *        *        *        *        *
GAC TCC GTG GGC CTC AAG CCC CTG AAG AAC GCT TCA GAC GGT GCC CTC
 D   S   V   G   L   K   P   L   K   N   A   S   D   G   A   L>

1060         1070         1080         1090        1100
 *        *        *        *        *        *        *        *
ATG GAC AAC CAG AAT GAG TGG GGG GAC GAG GAC CTG GAG ACC AAG
 M   D   N   Q   N   E   W   G   D   E   D   L   E   T   K>

1110         1120         1130         1140        1150
 *        *        *        *        *        *        *        *
AAG TTC CGG TTC GAG GAG CCC GTG CTG CCT GAC CTG CCT GAC GAC CAG
 K   F   R   F   E   E   P   V   L   P   D   L   P   D   D   Q>
```

FIG.10F

```
                1160                      1170                      1180                      1190                      1200
                 *                         *                         *                         *                         *
        ACA GAC CAC CGG CAG TGG ACT CAG CAG CAC CTG GAT GCC GCT GAC CTG
         T   D   H   R   Q   W   T   Q   Q   H   L   D   A   A   D   L>

1210                      1220                      1230                      1240
                 *                         *                         *                         *
        CGC ATG TCT GCC ATG GCC CCC ACA CCG CCC CAG GGT GAG GTT GAC GCC
         R   M   S   A   M   A   P   T   P   P   Q   G   E   V   D   A>

1250                      1260                      1270                      1280                      1290
        *                         *                         *                         *                         *
        GAC TGC ATG GAC GTC AAT GTC CGC GGG CCT GAT GGC TTC ACC CCG CTC
         D   C   M   D   V   N   V   R   G   P   D   G   F   T   P   L>

1300                      1310                      1320                      1330                      1340
        *                         *                         *                         *                         *
        ATG ATC GCC TCC TGC AGC GGG GGC GGC CTG GAG ACG GGC AAC AGC GAG
         M   I   A   S   C   S   G   G   G   L   E   T   G   N   S   E>
```

FIG.10G

```
      1350          1360          1370          1380          1390
       *             *             *             *             *
GAA GAG GAG GAC GCG CCG GCC GTC ATC TCC GAC TTC ATC TAC CAG GGC
 E   E   E   D   A   P   A   V   I   S   D   F   I   Y   Q   G 1400          1410          1420          1430          1440
       *             *             *             *             *
GCC AGC CTG CAC AAC CAG ACA GAC CGC ACG GGC GAG ACC GCC TTG CAC
 A   S   L   H   N   Q   T   D   R   T   G   E   T   A   L   H 1450          1460          1470          1480          1530
       *             *             *             *             *
CTG GCC GCC CGC TAC TCA CGC TCT GAT GCC GCC AAG CGC CTG CTG GAG
 L   A   A   R   Y   S   R   S   D   A   A   K   R   L   L   E 1490          1500          1510          1520          1530
       *             *             *             *             *
GCC AGC GCA GAT GCC AAC ATC CAG GAC AAC ATG GGC AAC CGC ACC CCG CTG
 A   S   A   D   A   N   I   Q   D   N   M   G   N   R   T   P   L
```

FIG. 10H

```
     1540                1550                1560                1570                1580
       *                   *                   *                   *                   *
CAT GCG GCT GTG TCT GCC GAC GCA CAA GGT GTC TTC CAG ATC CTG ATC
 H   A   A   V   S   A   D   A   Q   G   V   F   Q   I   L   I>

1590                1600                1610                1620                1630
       *                   *                   *                   *                   *
CGG AAC CGA GCC ACA GAC CTG GAT GCC CGC ATG CAT GAT GGC ACG ACG
 R   N   R   A   T   D   L   D   A   R   M   H   D   G   T   T>

1640                1650                1660                1670                1680
       *                   *                   *                   *                   *
CCA CTG ATC CTG GCT GCC CGC CTG GCC GTG GAG GGC ATG CTG GAG GAC
 P   L   I   L   A   A   R   L   A   V   E   G   M   L   E   D>

1690                1700                1710                1720
       *                   *                   *                   *
CTC ATC AAC TCA CAC GCC GAC GTC AAC GCC GTA GAT GAC CTG GGC AAG
 L   I   N   S   H   A   D   V   N   A   V   D   D   L   G   K>

1730                1740                1750                1760                1770
       *                   *                   *                   *                   *
TCC GCC CTG CAC TGG GCC GCC GCC GTG AAC AAT GTG GAT GCC GCA GTT
 S   A   L   H   W   A   A   A   V   N   N   V   D   A   A   V>
```

FIG. 10 I

```
                    1780                1790                1800                1810                1820
                     *                   *                   *                   *                   *
            GTG CTC CTG AAG AAC GGG GCT AAC AAA GAT ATG CAG AAC AAC AGG GAG
             V   L   L   K   N   G   A   N   K   D   M   Q   N   N   R   E>

1830                1840                1850                1860                1870
                     *                   *                   *                   *                   *
            GAG ACA CCC CTG CTG TTT CTG GCC GCC CGG GAG GGC AGC TAC GAG ACC GCC
             E   T   P   L   L   F   L   A   A   R   E   G   S   Y   E   T   A>

1880                1890                1900                1910                1920
                     *                   *                   *                   *                   *
            AAG GTG CTG CTG GAC CAC TTT GCC AAC CGG GAC ATC ACG GAT CAT ATG
             K   V   L   L   D   H   F   A   N   R   D   I   T   D   H   M>

1930                1940                1950                1960
                     *                   *                   *                   *
            GAC CGC CTG CCG CGC GAC ATC GCA CAG GAG CGC ATG CAT CAC GAC ATC
             D   R   L   P   R   D   I   A   Q   E   R   M   H   H   D   I>
```

FIG. 10J

```
1970        1980        1990        2000        2010
  *           *           *           *           *
GTG AGG CTG CTG GAC GAG TAC AAC CTG GTG CGC AGC CCG CAG CTG CAC
 V   R   L   L   D   E   Y   N   L   V   R   S   P   Q   L   H 2020        2030        2040        2050        2060
          *           *           *           *           *
GGA GCC CCG CTG GGG GGC ACG CCC ACC CTG TCG CCC CTC TGC TCG
 G   A   P   L   G   G   T   P   T   L   S   P   L   C   S 2070        2080        2090        2100        2110
          *           *           *           *           *
CCC AAC GGC TAC CTG GGC AGC CTC AAG CCC GGC GTG CAG GGC AAG AAG
 P   N   G   Y   L   G   S   L   K   P   G   V   Q   G   K   K 2120        2130        2140        2150        2160
          *           *           *           *           *
GTC CGC AAG CCC AGC AGC AAA GGC CTG GCC TGT GGA AGC AAG GAG GCC
 V   R   K   P   S   S   K   G   L   A   C   G   S   K   E   A
```

FIG. 10K

```
2170        2180        2190        2200
 *           *           *           *
AAG GAC CTC AAG GCA CGG AGG AAG AAG TCC CAG GAT GGC AAG GGC TGC
 K   D   L   K   A   R   R   K   K   S   Q   D   G   K   G   C 2210        2220        2230        2240        2250
 *           *           *           *           *
CTG CTG GAC AGC TCC GGC ATG CTC TCG CCC GTG GAC TCC CTG GAG TCA
 L   L   D   S   S   G   M   L   S   P   V   D   S   L   E   S 2260        2270        2280        2290        2300
 *           *           *           *           *
CCC CAT GGC TAC CTG TCA GAC GTG GCC TCG CCA CTG CTG CCC TCC
 P   H   G   Y   L   S   D   V   A   S   P   P   L   L   P   S 2310        2320        2330        2340        2350
 *           *           *           *           *
CCG TTC CAG CAG TCT CCG TCC GTG CCC CTC AAC CAC CTG CCT GGG ATG
 P   F   Q   Q   S   P   S   V   P   L   N   H   L   P   G   M
```

FIG.10L

```
         2360                2370              2380              2390              2400
          *        *          *        *        *        *        *        *        *
         CCC GAC ACC CAC CTG GGC ATC GGG CAC CTG AAC GTG GCG GCC AAG CCC
          P   D   T   H   L   G   I   G   H   L   N   V   A   A   K   P>
                  2410              2420              2430              2440
                   *        *        *        *        *        *        *
         GAG ATG GCG GCG CTG GGT GGG GGC CGG CTG GCC TTT GAG ACT GGC
          E   M   A   A   L   G   G   G   R   L   A   F   E   T   G>
 2450              2460              2470              2480              2490
  *        *        *        *        *        *        *        *        *
 CCA CCT CGT CTC TCC CAC CTG CCT GTG GCC TCT GGC ACC AGC ACC GTC
  P   P   R   L   S   H   L   P   V   A   S   G   T   S   T   V>
         2500              2510              2520              2530              2540
          *        *        *        *        *        *        *        *        *
         CTG GGC TCC AGC AGC GGA GGG GCC CTG AAT TTC ACT GTG GGC GGG TCC
          L   G   S   S   S   G   G   A   L   N   F   T   V   G   G   S>
```

FIG.10M

```
        2550      2560      2570      2580      2590
         *         *         *         *         *
ACC AGT TTG AAT GGT CAA TGC GAG TGG CTG TCC CGG CTG CAG AGC GGC
 T   S   L   N   G   Q   C   E   W   L   S   R   L   Q   S   G>

2600      2610      2620      2630      2640
         *         *         *         *         *
ATG GTG CCG AAC CAA TAC AAC CCT CTG CGG GGG AGT GTG GCA CCA GGC
 M   V   P   N   Q   Y   N   P   L   R   G   S   V   A   P   G>

2650      2660      2670      2680
         *         *         *         *
CCC CTG AGC ACA CAG GCC CCC TCC CTG CAG CAT GGC ATG GTA GGC CCG
 P   L   S   T   Q   A   P   S   L   Q   H   G   M   V   G   P>

2690      2700      2710      2720      2730
 *         *         *         *         *
CTG CAC AGT AGC CTT GCT GCC AGC GCC CTG TCC CAG ATG ATG AGC TAC
 L   H   S   S   L   A   A   S   A   L   S   Q   M   M   S   Y>
```

FIG. 10N

```
              2740           2750           2760           2770           2780
               *              *              *              *              *
        CAG GGC CTG CCC AGC ACC CGG CTG GCC ACC CAG CCT CAC CTG GTG CAG
        Q   G   L   P   S   T   R   L   A   T   Q   P   H   L   V   Q >

2790           2800           2810           2820           2830
               *              *              *              *              *
        ACC CAG CAG GTG CAG CCA CAA AAC TTA CAG ATG CAG CAG AAC CTG
        T   Q   Q   V   Q   P   Q   N   L   Q   M   Q   Q   N   L >

2840           2850           2860           2870           2880
               *              *              *              *              *
        CAG CCA AAC ATC CAG CCA CAG CAA CAG AGC CTG CAG CCG CCA CCA
        Q   P   N   I   Q   P   Q   Q   Q   S   L   Q   P   P   P >

2890           2900           2910           2920           2970
               *              *              *              *              *
        CCA CCA CAG CCG CAC CTT GGC GTG AGC TCA GCA GCC AGC GGC CAC CTG
        P   P   Q   P   H   L   G   V   S   S   A   A   S   G   H   L >

2930           2940           2950           2960           2970
               *              *              *              *              *
        GGC CGG AGC TTC CTG AGT GGA GAG CCG AGC CAG GCA GAC GTG CAG CCA
        G   R   S   F   L   S   G   E   P   S   Q   A   D   V   Q   P >
```

FIG. 10 O

```
            2980      2990      3000      3010      3020
              *         *         *         *         *
            CTG GGC CCC AGC AGC CTG GCG GTG CAC ACT ATT CTG CCC CAG GAG AGC
            L   G   P   S   S   L   A   V   H   T   I   L   P   Q   E   S >

3030      3040      3050      3060      3070
              *         *         *         *         *
            CCC GCC CTG CCC ACG TCG CTG CCA TCC TCG CTG GTC CCA CCC GTG ACC
            P   A   L   P   T   S   L   P   S   S   L   V   P   P   V   T >

3080      3090      3100      3110      3120
              *         *         *         *         *
            GCA GCC CAG TTC CTG ACG CCC TCG CAG CAC AGC TAC TCC TCG CCT
            A   A   Q   F   L   T   P   S   Q   H   S   Y   S   S   P >
```

FIG. 10P

```
        3130         3140         3150         3160
         *            *            *            *
GTG GAC AAC ACC CCC AGC CAC CAG CTA CAG GTG CCT GTT CCT GTA ATG
 V   D   N   T   P   S   H   Q   L   Q   V   P   V   P   V   M>

3170         3180         3190         3200         3210
         *            *            *            *            *
GTA ATG ATC CGA TCT TCG GAT CCT TCT AAA GGC TCA TCA ATT TTG ATC
 V   M   I   R   S   S   D   P   S   K   G   S   S   I   L   I>

3220         3230
         *            *
GAA GCT CCC GAC TCA TGG
 E   A   P   D   S   W>
```

FIG. 10Q

```
G GAG GTG GAT GTG TTA GAT GTG AAT GTC CGT GGC CCA GAT GGC TGC      46
  Glu Val Asp Val Leu Asp Val Asn Val Arg Gly Pro Asp Gly Cys
   1           5                  10                  15

ACC CCA TTG ATG TTG GCT TCT CTC CGA GGA GGC AGC TCA GAT TTG AGT   94
  Thr Pro Leu Met Leu Ala Ser Leu Arg Gly Gly Ser Ser Asp Leu Ser
                  20                  25                  30

GAT GAA GAT GAA GAT GCA GAG GAC TCT TCT GCT AAC ATC ATC ACA GAC   142
  Asp Glu Asp Glu Asp Ala Glu Asp Ser Ser Ala Asn Ile Ile Thr Asp
                  35                  40                  45

TTG GTC TAC CAG GGT GCC AGC CTC CAG GCC CAG ACA GAC CGG ACT GGT   190
  Leu Val Tyr Gln Gly Ala Ser Leu Gln Ala Gln Thr Asp Arg Thr Gly
              50                  55                  60

GAG ATG GCC CTG CAC CTT GCA GCC CGC TAC TCA CGG GCT GAT GCT GCC   238
  Glu Met Ala Leu His Leu Ala Ala Arg Tyr Ser Arg Ala Asp Ala Ala
              65                  70                  75

AAG CGT CTC CTG GAT GCA GGT GCA GAT GCC AAT GCC CAG GAC AAC ATG   286
  Lys Arg Leu Leu Asp Ala Gly Ala Asp Ala Asn Ala Gln Asp Asn Met
              80                  85                  90                  95

GGC CGC TGT CCA CTC CAT GCT GCA GTG GCA GCT GAT GCC CAA GGT GTC   334
  Gly Arg Cys Pro Leu His Ala Ala Val Ala Ala Asp Ala Gln Gly Val
                  100                 105                 110

TTC CAG ATT CTG ATT CGC AAC CGA GTA ACT GAT CTA GAT GCC AGG ATG   382
  Phe Gln Ile Leu Ile Arg Asn Arg Val Thr Asp Leu Asp Ala Arg Met
                  115                 120                 125

AAT GAT GGT ACT ACA CCC CTG ATC CTG GCT GCC CGC CTG GCT GTG GAG   430
  Asn Asp Gly Thr Thr Pro Leu Ile Leu Ala Ala Arg Leu Ala Val Glu
          130                 135                 140
```

FIG.11A

```
GGA ATG GTG GCA GAA CTG ATC AAC TGC CAA GCG GAT GTG AAT GCA GTG        478
Gly Met Val Ala Glu Leu Ile Asn Cys Gln Ala Asp Val Asn Ala Val
    145                 150                 155

GAT GAC CAT GGA AAA TCT GCT CTT CAC TGG GCA GCT GCT GTC AAT AAT        526
Asp Asp His Gly Lys Ser Ala Leu His Trp Ala Ala Ala Val Asn Asn
160                 165                 170                 175

GTG GAG GCA ACT CTT TTG TTG TTG AAA AAT GGG GCC AAC CGA GAC ATG        574
Val Glu Ala Thr Leu Leu Leu Leu Lys Asn Gly Ala Asn Arg Asp Met
                180                 185                 190

CAG GAC AAC AAG GAA GAG ACA CCT CTG TTT CTT GCT GCC CGG GAG GGG        622
Gln Asp Asn Lys Glu Glu Thr Pro Leu Phe Leu Ala Ala Arg Glu Gly
            195                 200                 205

AGC TAT GAA GCA GCC AAG ATC CTG TTA GAC CAT TTT GCC AAT CGA GAC        670
Ser Tyr Glu Ala Ala Lys Ile Leu Leu Asp His Phe Ala Asn Arg Asp
        210                 215                 220

ATC ACA GAC CAT ATG GAT CGT CTT CCC CGG GAT GTG GCT CGG GAT CGC        718
Ile Thr Asp His Met Asp Arg Leu Pro Arg Asp Val Ala Arg Asp Arg
    225                 230                 235

ATG CAC CAT GAC ATT GTG CGC CTT CTG GAT GAA TAC AAT GTG ACC CCA        766
Met His His Asp Ile Val Arg Leu Leu Asp Glu Tyr Asn Val Thr Pro
240                 245                 250                 255

AGC CCT CCA GGC ACC GTG TTG ACT TCT GCT CTC TCA CCT GTC ATC TGT        814
Ser Pro Pro Gly Thr Val Leu Thr Ser Ala Leu Ser Pro Val Ile Cys
                260                 265                 270

GGG CCC AAC AGA TCT TTC CTC AGC CTG AAG CAC ACC CCA ATG GGC AAG        862
Gly Pro Asn Arg Ser Phe Leu Ser Leu Lyn His Thr Pro Met Gly Lys
            275                 280                 285
```

FIG.11B

```
AAG TCT AGA CGG CCC AGT GCC AAG AGT ACC ATG CCT ACT AGC CTC CCT    910
Lys Ser Arg Arg Pro Ser Ala Lys Ser Thr Met Pro Thr Ser Leu Pro
        290             295             300

AAC CTT GCC AAG GAG GCA AAG GAT GCC AAG GGT AGT AGG AGG AAG AAG    958
Asn Leu Ala Lys Glu Ala Lys Asp Ala Lys Gly Ser Arg Arg Lys Lys
        305             310             315

TCT CTG AGT GAG AAG GTC CAA CTG TCT GAG AGT TCA GTA ACT TTA TCC   1006
Ser Leu Ser Glu Lys Val Gln Leu Ser Glu Ser Ser Val Thr Leu Ser
320             325             330             335

CCT GTT GAT TCC CTA GAA TCT CCT CAC ACG TAT GTT TCC GAC ACC ACA   1054
Pro Val Asp Ser Leu Glu Ser Pro His Thr Tyr Val Ser Asp Thr Thr
                340             345             350

TCC TCT CCA ATG ATT ACA TCC CCT GGG ATC TTA CAG GCC TCA CCC AAC   1102
Ser Ser Pro Met Ile Thr Ser Pro Gly Ile Leu Gln Ala Ser Pro Asn
            355             360             365

CCT ATG TTG GCC ACT GCC GCC CCT CCT GCC CCA GTC CAT GCC CAG CAT   1150
Pro Met Leu Ala Thr Ala Ala Pro Pro Ala Pro Val His Ala Gln His
        370             375             380

GCA CTA TCT TTT TCT AAC CTT CAT GAA ATG CAG CCT TTG GCA CAT GGG   1198
Ala Leu Ser Phe Ser Asn Leu His Glu Met Gln Pro Leu Ala His Gly
        385             390             395

GCC AGC ACT GTG CTT CCC TCA GTG AGC CAG TTG CTA TCC CAC CAC CAC   1246
Ala Ser Thr Val Leu Pro Ser Val Ser Gln Leu Leu Ser His His His
400             405             410             415

ATT GTG TCT CCA GGC AGT GGC AGT GCT GGA AGC TTG AGT AGG CTC CAT   1294
Ile Val Ser Pro Gly Ser Gly Ser Ala Gly Ser Leu Ser Arg Leu His
            420             425             430

CCA GTC CCA GTC CCA GCA GAT TGG ATG AAC CGC ATG GAG GTG AAT GAG   1342
Pro Val Pro Val Pro Ala Asp Trp Met Asn Arg Met Glu Val Asn Glu
        435             440             445
```

FIG.11C

```
ACC CAG TAC AAT GAG ATG TTT GGT ATG GTC CTG GCT CCA GCT GAG GGC   1390
Thr Gln Tyr Asn Glu Met Phe Gly Met Val Leu Ala Pro Ala Glu Gly
        450                 455                 460

ACC CAT CCT GGC ATA GCT CCC CAG AGC AGG CCA CCT GAA GGG AAG CAC   1438
Thr His Pro Gly Ile Ala Pro Gln Ser Arg Pro Pro Glu Gly Lys His
        465                 470                 475

ATA ACC ACC CCT CGG GAG CCC TTG CCC CCC ATT GTG ACT TTC CAG CTC   1486
Ile Thr Thr Pro Arg Glu Pro Leu Pro Pro Ile Val Thr Phe Gln Leu
480                 485                 490                 495

ATC CCT AAA GGC AGT ATT GCC CAA CCA GCG GGG GCT CCC CAG CCT CAG   1534
Ile Pro Lys Gly Ser Ile Ala Gln Pro Ala Gly Ala Pro Gln Pro Gln
                500                 505                 510

TCC ACC TGC CCT CCA GCT GTT GCG GGC CCC CTG CCC ACC ATG TAC CAG   1582
Ser Thr Cys Pro Pro Ala Val Ala Gly Pro Leu Pro Thr Met Tyr Gln
        515                 520                 525

ATT CCA GAA ATG GCC CGT TTG CCC AGT GTG GCT TTC CCC ACT GCC ATG   1630
Ile Pro Glu Met Ala Arg Leu Pro Ser Val Ala Phe Pro Thr Ala Met
        530                 535                 540

ATG CCC CAG CAG GAC GGG CAG GTA GCT CAG ACC ATT CTC CCA GCC TAT   1678
Met Pro Gln Gln Asp Gly Gln Val Ala Gln Thr Ile Leu Pro Ala Tyr
        545                 550                 555

CAT CCT TTC CCA GCC TCT GTG GGC AAG TAC CCC ACA CCC CCT TCA CAG   1726
His Pro Phe Pro Ala Ser Val Gly Lys Tyr Pro Thr Pro Pro Ser Gln
560                 565                 570                 575

CAC AGT TAT GCT TCC TCA AAT GCT GCT GAG CGA ACA CCC AGT CAC AGT   1774
His Ser Tyr Ala Ser Ser Asn Ala Ala Glu Arg Thr Pro Ser His Ser
                580                 585                 590

GGT CAC CTC CAG GGT GAG CAT CCC TAC CTG ACA CCA TCC CCA GAG TCT   1822
Gly His Leu Gln Gly Glu His Pro Tyr Leu Thr Pro Ser Pro Glu Ser
        595                 600                 605
```

FIG.11D

```
CCT GAC CAG TGG TCA AGT TCA TCA CCC CAC TCT GCT TCT GAC TGG TCA      1870
Pro Asp Gln Trp Ser Ser Ser Ser Pro His Ser Ala Ser Asp Trp Ser
        610             615                 620

GAT GTG ACC ACC AGC CCT ACC CCT GGG GGT GCT GGA GGA GGT CAG CGG      1918
Asp Val Thr Thr Ser Pro Thr Pro Gly Gly Ala Gly Gly Gly Gln Arg
        625             630                 635

GGA CCT GGG ACA CAC ATG TCT GAG CCA CCA CAC AAC AAC ATG CAG GTT      1966
Gly Pro Gly Thr His Met Ser Glu Pro Pro His Asn Asn Met Gln Val
640             645                 650                 655

TAT GCG TGAGAGAGTC CACCTCCAGT GTAGAGACAT AACTGACTTT TGTAAATGCT       2022
Tyr Ala

GCTGAGGAAC AAATGAAGGT CATCCGGGAG AGAAATGAAG AAATCTCTGG AGCCAGCTTC    2082

TAGAGGTAGG AAAGAGAAGA TGTTCTTATT CAGATAATGC AAGAGAAGCA ATTCGTCAGT    2142

TTCACTGGGT ATCTGCAAGG CTTATTGATT ATTCTAATCT AATAAGACAA GTTTGTGGAA    2202

ATGCAAGATG AATACAAGCC TTGGGTCCAT GTTACTCTC TTCTATTTGG AGAATAAGAT     2262

GGATGCTTAT TGAAGCCCAG ACATTCTTGC AGCTTGGACT GCATTTTAAG CCCTGCAGGC    2322

TTCTGCCATA TCCATGAGAA GATTCTACAC TAGCGTCCTG TTGGGAATTA TGCCCTGGAA    2382

TTCTGCCTGA ATTGACCTAC GCATCTCCTC CTCCTTGGAC ATTCTTTTGT CTTCATTTGG    2442

TGCTTTTGGT TTTGCACCTC TCCGTGATTG TAGCCCTACC AGCATGTTAT AGGGCAAGAC    2502

CTTTGTGCTT TTGATCATTC TGGCCCATGA AAGCAACTTT GGTCTCCTTT CCCCTCCTGT    2562

CTTCCCGGTA TCCCTTGGAG TCTCACAAGG TTTACTTTGG TATGGTTCTC AGCACAAACC    2622

TTTCAAGTAT GTTGTTTCTT TGGAAAATGG ACATACTGTA TTGTGTTCTC CTGCATATAT    2682

CATTCCTGGA GAGAGAAGGG GAGAAGAATA CTTTTCTTCA ACAAATTTTG GGGCAGGAG     2742

ATCCCTTCAA GAGGCTGCAC CTTAATTTTT CTTGTCTGTG TGCAGGTCTT CATATAAACT    2802
```

FIG. 11E

```
TTACCAGGAA GAAGGGTGTG AGTTTGTTGT TTTTCTGTGT ATGGGCCTGG TCAGTGTAAA    2862

GTTTTATCCT TGATAGTCTA GTTACTATGA CCCTCCCCAC TTTTTTAAAA CCAGAAAAAG    2922

GTTTGGAATG TTGGAATGAC CAAGAGACAA GTTAACTCGT GCAAGAGCCA GTTACCCACC    2982

CACAGGTCCC CCTACTTCCT GCCAAGCATT CCATTGACTG CCTGTATGGA ACACATTTGT    3042

CCCAGATCTG AGCATTCTAG GCCTGTTTCA CTCACTCACC CAGCATATGA AACTAGTCTT    3102

AACTGTTGAG CCTTTCCTTT CATATCCACA GAAGACACTG TCTCAAATGT TGTACCCTTG    3162

CCATTTAGGA CTGAACTTTC CTTAGCCCAA GGGACCCAGT GACAGTTGTC TTCCGTTTGT    3222

CAGATGATCA GTCTCTACTG ATTATCTTGC TGCTTAAAGG CCTGCTCACC AATCTTTCTT    3282

TCACACCGTG TGGTCCGTGT TACTGGTATA CCCAGTATGT TCTCACTGAA GACATGGACT    3342

TTATATGTTC AAGTGCAGGA ATTGGAAAGT TGGACTTGTT TTCTATGATC CAAAACAGCC    3402

CTATAAGAAG GTTGGAAAAG GAGGAACTAT ATAGCAGCCT TTGCTATTTT CTGCTACCAT    3462

TTCTTTTCCT CTGAAGCGGC CATGACATTC CCTTTGGCAA CTAACGTAGA AACTCAACAG    3522
```

FIG.11F

```
AACATTTTCC TTTCCTAGAG TCACCTTTTA GATGATAATG GACAACTATA GACTTGCTCA    3582

TTGTTCAGAC TGATTGCCCC TCACCTGAAT CCACTCTCTG TATTCATGCT CTTGGCAATT    3642

TCTTTGACTT TCTTTTAAGG GCAGAAGCAT TTTAGTTAAT TGTAGATAAA GAATAGTTTT    3702

CTTCCTCTTC TCCTTGGGCC AGTTAATAAT TGGTCCATGG CTACACTGCA ACTTCCGTCC    3762

AGTGCTGTGA TGCCCATGAC ACCTGCAAAA TAAGTTCTGC CTGGGCATTT TGTAGATATT    3822

AACAGGTGAA TTCCCGACTC TTTTGGTTTG AATGACAGTT CTCATTCCTT CTATGGCTGC    3882

AAGTATGCAT CAGTGCTTCC CACTTACCTG ATTTGTCTGT CGGTGGCCCC ATATGGAAAC    3942

CCTGCGTGTC TGTTGGCATA ATAGTTTACA AATGGTTTTT TCAGTCCTAT CCAAATTTAT    4002

TGAACCAACA AAAATAATTA CTTCTGCCCT GAGATAAGCA GATTAAGTTT GTTCATTCTC    4062

TGCTTTATTC TCTCCATGTG GCAACATTCT GTCAGCCTCT TTCATAGTGT GCAAACATTT    4122

TATCATTCTA AATGGTGACT CTCTGCCCTT GGACCCATTT ATTATTCACA GATGGGGAGA    4182

ACCTATCTGC ATGGACCCTC ACCATCCTCT GTGCAGCACA CACAGTGCAG GGAGCCAGTG    4242

GCGATGGCGA TGACTTTCTT CCCCTG                                         4268
```

FIG. 11G

FIG.12C

PEST-CONTAINING REGION

```
                                              Potential signal cleavage site
                                                                    ↓
hum N    MP————— —————— ———ALRPAL LWALLALWLC CA———APA HA———————L
TAN-1    MP————— —————— ——————PL LAPLLCLALL PA———LAA RG———————P
Xen N    MD————— —————— —————— RIGLAVLLCS LP———VLT QG———————L
Dros N   MQSQRSRRRS RAPNTWICFW INKMHAVASL PASLPLLLLT LAFANLPNIV RGTDTALVAA hum N    MLGKATCRCA SGFTGEDCQY STSHPCFVSR PCLNGGTCHM LSRDT-YECT CQVGFTGKEC
Tan-1    GVADYACSCA LGFSGPLCLT PLDNAC-LTN PCRNGGTCDL LT-LTEYKCR CPPGWSGKSC
Xen N    NAIDFICHCP VGFTDKVCLT PVDNAC-VNN PCRNGGTCEL LNSVTEYKCR CPPGWTGDSC
Dros N   GRPGISCKCP LGFDESLCEI AVPNAC-DHV TCLNGGTCQL KT-LEEYTCA CANGYTGERC hum N    NLPGSYQCQC PQGFTGQYCD SLYVPCAPSP CVNGGTCRQT GDFTFECNCL PGFEGSTCER
TAN-1    NEVGSYRCVC RATHTGPNCE RPYVPCSPSP CQNGGTCRPT GDVTHECACL PGFTGQNCEE
Xen N    NEFGSYRCTC QNRFTGRNCD EPYVPCNPSP CLNGGTCRQT DDTSYDCTCL PGFSGQNCEE
Dros N   NTHGSYQCMC PTGYTGKDCD TKYNPCSPSP CQNAGICRSN G-LSYECKCP KGFEGKNCEQ
```

EGF-like Repeats

```
QCRDGYEPCV NEGMCVTYHN GTGYCKCPEG FLGEYCQHRD PCE-KNRCQN GGTC——VAQA    83
RCSQPGETCL NGGKCEA-AN GTEACVCGGA FVGPRCQDPN PCL-STPCKN AGTCHVVDRR    80
RCTQTAEMCL NGGRCEMTPG GTGVCLCGNL YFGERCQFPN PCTIKNQCMN FGTCEPVLQG    90
SCTSVG——CQ NGGTCVTQLN GKTYCACDSH YVGDYCEHRN PCN-SMRCQN GGTCQVTFRN   117

QWTDACLSHP CANGSTCTTV —ANQFSCKC LTGFTGQKCE TDVNEC-DIP GHCQHGGTCL   199
QQADPCASNP CANGGQCLPF —EASYICHC PPSFHGPTCR QDVNECGQKP RLCRHGGTCH   196
QQADPCASNP CANGGKCLPF —EIQYICKC PPGFHGATCK QDINEC-S-Q NPCKNGGQCI   195
ETKNLCASSP CRNGATCTAL AGSSSFTCSC PPGFTGDTCS YDIEEC-Q-S NPCKYGGICV   233

NIDDCPNHRC QNGGVCVDGV NTYNCRCPPQ WTGQFCTEDV DECLLQPNA- CQNGGTCANR   318
NIDDCPGNNC KNGGACVDGV NTYNCPCPPE WTGQYCTEDV DECQLMPNA- CQNGGTCHNT   315
NIDDCPSNNC RNGGTCVDGV NTYNCQCPPD WTGQYCTEDV DECQLMPNA- CQNGGTCHNT   314
NYDDCLGHLC QNGGTCIDGI SDYTCRCPPN FTGRFCQDDV DECAQRDHPV CQNGATCTNT   352
```

FIG.13A

| hum N  | NGGYGCVCVN | GWSGDDCSEN | IDDCAFASCT | PGSTCIDRVA | SFSCMCPEGK | AGLLCHLDDA |
|--------|------------|------------|------------|------------|------------|------------|
| TAN-1  | HGGYNCVCVN | GWTGEDCSEN | IDDCASAACF | HGATCHDRVA | SFYCECPHGR | TGLLCHLNDA |
| Xen N  | YGGYNCVCVN | GWTGEDCSEN | IDDCANAACH | SGATCHDRVA | SFYCECPHGR | TGLLCHLDNA |
| Dros N | HGSYSCICVN | GWAGLDCSNN | TDDCKQAACF | YGATCIDGVG | SFYCQCTKGK | TGLLCHLDDA |

| hum N  | AFHCECLKGY | AGPRCEMDIN | ECHSDPCQND | ATCLDKIGGF | TCLCMPGFKG | VHCELEINEC |
|--------|------------|------------|------------|------------|------------|------------|
| TAN-1  | SFECQCLQGY | TGPRCEIDVN | ECVSNPCQND | ATCLDQIGEF | QCMCMPGYEG | VHCEVNTDEC |
| Xen N  | SFQCNCPQGY | AGPRCEIDVN | ECLSNPCQND | STCLDQIGEF | QCICMPGYEG | LYCETNIDEC |
| Dros N | SYRCNCSQGF | TGPRCETNIN | ECESHPCQNE | GSCLDDPGTF | RCVCMPGFTG | TQCEIDIDEC |

| hum N  | ATGFTGVLCE | ENIDNCDPDP | CHHGQCQDGI | DSYTCICNPG | YMGAICSDQI | DECYSSPCLN |
|--------|------------|------------|------------|------------|------------|------------|
| TAN-1  | TEGYTGTHCE | VDIDECDPDP | CHYGSCKDGV | ATFTCLCRPG | YTGHHCETNI | NECSSQPCRL |
| Xen N  | TEGFTGRHCE | QDINECIPDP | CHYGTCKDGI | ATFTCLCRPG | YTGRLCDNDI | NECLSKPCLN |
| Dros N | PPGYTGTSCE | ININDCDSNP | CHRGKCIDDV | NSFKCLCDPG | YTGYICQKQI | NECESNPCQF |

| CISNPCHKGA | LCDTNPLNGQ | YICTCPQGYK | GADCTEDVDE | CAMANSNPCE | HAGKCVNTDG | 438 |
|------------|------------|------------|------------|------------|------------|-----|
| CISNPCNEGS | NCDTNPVNGK | AICTCPSGYT | GPACSQDVDE | CSLG-ANPCE | HAGKCINTLG | 434 |
| CISNPCNEGS | NCDTNPVNGK | AICTCPPGYT | GPACNNDVDE | CSLG-ANPCE | HGGRCTNTLG | 433 |
| CTSNPCHADA | ICDTSPINGS | YACSCATGYK | GVDCSEDIDE | CDQG--SPCE | HNGICVNTPG | 470 |

| QSNPCVNNGQ | CVDKVNRFQC | LCPPGFTGPV | CQIDIDDCSS | TPCLNGAKCI | DHPNGYECQC | 558 |
|------------|------------|------------|------------|------------|------------|-----|
| ASSPCLHNGR | CLDKINEFQC | ECPTGFTGHL | CQYDVDECAS | TPCKNGAKCL | DGPNTYTCVC | 554 |
| ASNPCLHNGK | CIDKINEFRC | DCPTGFSGNL | CQHDFDECTS | TPCKNGAKCL | DGPNSYTCQC | 553 |
| QSNPCLNDGT | CHDKINGFKC | SCALGFTGAR | CQINIDDCQS | QPCRNRGICH | DSIAGYSCEC | 590 |

| DGRCIDLVNG | YQCNCQPGTS | GVNCEINFDD | CASNPCIHG- | ICMDGINRYS | CVCSPGFTGQ | 677 |
|------------|------------|------------|------------|------------|------------|-----|
| RGTCQDPDNA | YLCFCLKGTT | GPNCEINLDD | CASSPCDSG- | TCLDKIDGYE | CACEPGYTGS | 673 |
| GGQCTDRENG | YICTCPKGTT | GVNCETKIDD | CASNLCDNG- | KCIDKIDGYE | CTCEPGYTGK | 672 |
| DGHCQDRVGS | YYCQCQAGTS | GKNCEVNVNE | CHSNPCNNGA | TCIDGINSYK | CQCVPGFTGQ | 710 |

FIG.13B

```
hum N    RCNIDIDECA SNPCRKGATC INGVNGFRCI CPEGPHHPSC YSQVNECLSN PCI-HGNCTG
TAN-1    MCNSNIDECA GNPCHNGGTC EDGINGFTCR CPEGYHDPTC LSEVNECNSN PCV-HGACRD
Xen N    LCNININECD SNPCRNGGTC KDQINGFTCV CPDGYHDHMC LSEVNECNSN PCI-HGACHD
Dros N   HCEKNVDECI SSPCANNGVC IDQVNGYKCE CPRGFYDAHC LSDVDECASN PCVNEGRCED hum N    DECASNPCLN QGTCFDDISG YTCHCVLPYT GKNCQTVLAP CSPNPCENAA VCKESPNFES
TAN-1    NECASNPCLN KGTCIDDVAG YKCNCLLPYT GATCEVVLAP CAPSPCRNGG ECRQSEDYES
Xen N    NECSSNPCLN HGTCIDDVAG YKCNCMLPYT GAICEAVLAP CAGSPCKNGG RCKESEDFET
Dros N   DDCVTNPCGN GGTCIDKVNG YKCVCKVPFT GRDCESKMDP CASNRCKNEA KCTPSSNFLD hum N    CLANPCQNGG SCMDGVNTFS CLCLPGFTGD KCQTDNMECL SEPCKNGGTC SDYVNSYTCK
TAN-1    CRPNPCHNGG SCTDGINTAF CDCLPGFRGT FCEEDINECA SDPCRNGANC TDCVDSYTCT
Xen N    CQPNPCHNGG SCSDGINMFF CNCPAGFRGP KCEEDINECA SNPCKNGANC TDCVNSYTCT
Dros N   CASFPCQNGG TCLDGIGDYS CLCVDGFDGK HCETDINECL SQPCQNGATC SQYVNSYTCT
```

```
GLSGYKCLCD AGWVGINCEV DKNECLSNPC QNGGTCDNLV NGYRCTCKKG FKGYNCQVNI   796
SLNGYKCDCD PGWSGTNCDI NNNECESNPC VNGGTCKDMT SGIVCTCREG FSGPNCQTNI   792
GVNGYKCDCE AGWSGSNCDI NNNECESNPC MNGGTCKDMT GAYICTCKAG FSGPNCQTNI   791
GINEFICHCP PGYTGKRCEL DIDECSSNPC QHGGTCYDKL NAFSCQCMPG YTGQKCETNI   830

YTCLCA-PGW QGQRCTIDID EC-ISKPCMN HGLCHNTQGS YMCECPPGFS GMDCEEDIDD   914
FSCVCPTAGA KGQTCEVDIN EC-VLSPCRH GASCQNTHGG YRCHCQAGYS GRNCETDIDD   911
FSCECP-PGW QGQTCEIDMN EC-VNRPCRN GATCQNTNGS YKCNCKPGYT GRNCEMDIDD   909
FSCTCK-LGY TGRYCDEDID ECSLSSPCRN GASCLNVPGS YRCLCTKGYE GRDCAINTDD   949

CQAGFDGVHC ENNINECTES SCFNGGTCVD GINSFSCLCP VGFTGSFCLH EINECSSHPC  1034
CPAGFSGIHC ENNTPDCTES SCFNGGTCVD GINSFTCLCP PGFTGSYCQH VVNECDSRPC  1031
CQPGFSGIHC ESNTPDCTES SCFNGGTCID GINTFTCQCP PGFTGSYCQH DINECDSKPC  1029
CPLGFSGINC QTNDEDCTES SCLNGGSCID GINGYNCSCL AGYSGANCQY KLNKCDSNPC  1069
```

FIG.13C

| | | | | | | |
|---|---|---|---|---|---|---|
| hum N | LNEGTCVDGL | GTYRCSCPLG | YTGKNCQTLV | NLCSRSPCKN | KGTCVQKKAE | SQCLCPSGWA |
| TAN-1 | LLGGTCQDGR | GLHRCTCPQG | YTGPNCQNLV | HWCDSSPCKN | GGKCWQTHTQ | YRCECPSGWT |
| Xen N | LNGGTCQDSY | GTYKCTCPQG | YTGLNCQNLV | RWCDSSPCKN | GGKCWQTNNF | YRCECKSGWT |
| Dros N | LNGATCHEQN | NEYTCHCPSG | FTGKQCSEYV | DWCGQSPCEN | GATCSQMKHQ | FSCKCSAGWT |

| | | | | | | |
|---|---|---|---|---|---|---|
| hum N | SNPCQHGATC | SDFIGGYRCE | CVPGYQGVNC | EYEVDECQNQ | PCQNGGTCID | LVNHFKCSCP |
| TAN-1 | PSPCQNGATC | TDYLGGYSCK | CVAGYHGVNC | SEEIDECLSH | PCQNGGTCLD | LPNTYKCSCP |
| Xen N | PNPCQNGATC | TDYLGGYSCE | CVAGYHGVNC | SEEINECLSH | PCQNGGTCID | LINTYKCSCP |
| Dros N | SQPCQNGGTC | RDLIGAYECQ | CRQGFQGQNC | ELNIDDCAPN | PCQNGGTCHD | RVMNFSCSCP |

| | | | | | | |
|---|---|---|---|---|---|---|
| hum N | CLSNPCSSEG | SLDCIQLTND | YLCVCRSAFT | GRHCETFVDV | CPQMPCLNGG | TCAVASNMPD |
| TAN-1 | CLSNPCDARG | TQNCVQRVND | FHCECRAGHT | GRRCESVING | CKGKPCKNGG | TCAVASNTAR |
| Xen N | CLSNPCDSRG | TQNCIQLVND | YRCECRQGFT | GRRCESVVDG | CKGMPCRNGG | TCAVASNTER |
| Dros N | CLSNPCSNAG | TLDCVQLVNN | YHCNCRPGHM | GRHCEHKVDF | CAQSPCQNGG | NCNI—RQS |

| | | | | | | |
|---|---|---|---|---|---|---|
| GAYCDVPNVS | CDIAASRRGV | LVEHLCQHSG | VCINAGNTHY | CQCPLGYTGS | YCEEQLDECA | 1154 |
| GLYCDVPSVS | CEVAAQRQGV | DVARLCQHGG | LCVDAGNTHH | CRCQAGYTGS | YCEDLVDECS | 1151 |
| GVYCDVPSVS | CEVAAKQQGV | DIVHLCRNSG | MCVDTGNTHF | CRCQAGYTGS | YCEEQVDECS | 1149 |
| GKLCDVQTIS | CQDAADRKGL | SLRQLC-NNG | TCKDYGNSHV | CYCSQGYAGS | YCQKEIDECQ | 1188 |

| | | | | | | |
|---|---|---|---|---|---|---|
| PGTRGLLCEE | NIDDCAR—— | ——GPHCLN | GGQCMDRIGG | YSCRCLPGFA | GERCEGDINE | 1267 |
| RGTQGVHCEI | NVDDCNPPVD | PVSRSPKCFN | NGTCVDQVGG | YSCTCPPGFV | GERCEGDVNE | 1271 |
| RGTQGVHCEI | NVDDCTPFYD | SFTLEPKCFN | NGKCIDRVGG | YNCICPPGFV | GERCEGDVNE | 1269 |
| PGTMGIICEI | NKDDCKP—— | ——GACHN | NGSCIDRVGG | FECVCQPGFV | GARCEGDINE | 1300 |

| | | | | | | |
|---|---|---|---|---|---|---|
| GFICRCPPGF | SGARCQS—— | SCGQVKCRKG | EQCVHTAS— | GPRCFCPSP- | —RDCES—— | 1376 |
| GFICKCPAGF | EGATCENDAR | TCGSLRCLNG | GTCISGPR— | SPTCLCLGPF | TGPECQFPAS | 1389 |
| GFICKCPPGF | DGATCEYDSR | TCSNLRCQNG | GTCISVLT— | SSKCVCSEGY | TGATCQYPVI | 1387 |
| GHHCICNNGF | YGKNCELSGQ | DCDSNPCRVG | -NCVVADEGF | GYRCECPRGT | LGEHCEIDTL | 1415 |

FIG.13D

```
hum N    -GC-ASSPCQ  HGGSCHPQRQ  PPYYSCQCAP  PFSGSRCEL  -YTAPP----  -S------TPP
TAN-1    SPCLGGNPCY  NQGTCEPTSE  SPFYRCLCPA  KFNGLLCHIL DYSFGG----  -GAGRDIPPP
Xen N    SPC-ASHPCY  NGGTCQFFAE  EPFFQCFCPK  NFNGLFCHIL DYEFPG----  -GLGKNITPP
Dros N   DEC-SPNPCA  QGAACEDLLG  D—YECLCPS   KWKGKRCDIY DANYPGWNGG  SGSGNDRYAA hum N    NN-QCDELCN  TVECLFDNFE  CQGNSKTCK-  -YDKYCADHF KDNHCNQGCN  SEECGWDGLD
TAN-1    SDGHCDSQCN  SAGCLFDGFD  CQRAEGQCNP  LYDQYCKDHF SDGHCDQGCN  SAECEWDGLD
Xen N    NDGKCDSQCN  NTGCLYDGFD  CQKVEVQCNP  LYDQYCKDHF QDGHCDQGCN  NAECEWDGLD
Dros N   KNGKCNEECN  NAACHYDGHD  CERKLKSCDS  LFDAYCQKHY GDGFCDYGCN  NAECSWDGLD hum N    YYGEKSAAMK  KQ—R------  ----------  ----MTRRSL PGEQ------E QEVAGSKVFL
TAN-1    YYGREEELRK  HPIKRAAEGW  AAPDALLGQV  KASLLPGGSE GGRRRRELDP  MDVRGSIVYL
Xen N    YYGNEEELKK  HHIKRSTDYW  SDAPSAI---  -FSTMKESIL LGRHRRELDE  MEVRGSIVYL
Dros N   WKDNVRVPEI  EDTDFARKNK  ILYTQQVHQ-  ---------- ----------  ---TGIQIYL
```

LNR (Notch/Lin-12 Repeats)

```
—A—TCL SQYCADKARD GVCDEACNSH ACQWDGGDCS LTMENPWANC SSPLPCWDYI  1476
LIEE—ACE LPECQEDAGN KVCSLQCNNH ACGWDGGDCS LNFNDPWKNC TQSLQCWKYF  1501
DNDD—ICE NEQCSELADN KVCNANCNNH ACGWDGGDCS LNFNDPWKNC TQSLQCWKYF  1498
DLEQQRAMCD KRGCTEKQGN GICDSDCNTY ACNFDGNDCS LGI-NPWANC TAN-EXWNKF 1531

CAADQPEN-L AEGTLVIVVL MPPEQLLQDA R-SFLRALGT LLHTNLRIKR DSQGELMVYP  1591
CAEHVPER-L AAGTL-VVVV LMPPEQLRNS SFHFLRELSR VLHTNVVFKR DAHGQQMIFP  1619
C-ANMPEN-L AEGTLVLVVL MPPERLKNNS V-NFLRELSR VLHTNVVFKK DSKGEYKIYP  1615
CENKTQSPVL AEGAMSVVML MNVEAFREIQ A-QFLRNMSH MLRTTVRLKK DALGHDIIIN  1650

TM
EIDNRQCVQD SDHCFKNTDA AAALLASHAI QG--TLSYP LVSVVSESLT PERT-Q-LLY  1680
EIDNRQCVQA SSQCFQSATD VAAFLGALAS LGSL-NIPYK IEAVQSETVE PPPPAQ-LHF  1737
EIDNRQCYKS SSQCFNSATD VAAFLGALAS LGSLDTLSYK IEAVKSENME TPKPST-LYP  1730
EIDNRKCTEC FTHAVEAAEF LAATAAKHQL RNDFQ-IHSV RGIKNPGDED NGEPPANVKY  1745
```

FIG.13E

```
hum N   LLAVAVVIIL FIILLGVIMA KRKRK—HGS LWLPEGFTLR RDASNHKRRE PVGQDAVGLK
TAN-1   MYVAAAAFVL LFFVGCGVLL SRKRRRQHGQ LWFPEGFKV- SEASKKKRRE ELGEDSVGLK
Xen N   MLSMLVIPLL IIFVFMMVIV NKKRRREHDS FGSPTALFQK NPA-KRNGET PW-EDSVGLK
Dros N  VITGIILVII ALAFFGMVL- STQRKRAHGV TWFPEGFRAP AAVMSRRRRD PHGQEMRNLN
```

CDC-10/Ankyrin Repeats

```
hum N   PIDRRPWTQQ HLEAADIRRT PSLALTPPQA EQEVDVLDVN VRGPDGCTPL MLASLRGGSS
TAN-1   QTDHRQWTQQ HLDAADL-RM SAMAPTPPQG EVDADCMDVN VRGPDGFTPL MIASCSGGGL
Xen N   KTDPRQWTRQ HLDAADL-RI SSMAPTPPQG EIEADCMDVN VRGPDGFTPL MIASCSGGGL
Dros N  EADQRVWSQA HLDVVDV-R- AIM—TPP-A HQDGGKHDVD ARGPCGLTPL MIAAVRGGGL hum N   ANAQDNMGRC PLHAAVAADA QGVFQILIRN RVTDLDARMN DGTTPLILAA RLAVEGMVAE
TAN-1   ANIQDNMGRT PLHAAVSADA QGVFQILIRN RATDLDARMH DGTTPLILAA RLAVEGMLED
Xen N   ANVQDNMGRT PLHAAVAADA QGVFQILIRN RATDLDARMF DGTTPLILAA RLAVEGMVEE
Dros N  ANCQDNTGRT PLHAAVAADA MGVFQILLRN RATNLNARMH DGTTPLILAA RLAIEGMVED NLSVQVSEAN LIGTGTSEHW VDDE————         ————G PQPKKVKAED EALLSE-EDD 1782
        PLK-NASDGA LMDDNQNE-W GDED————          ———— LETKKFRFEE PVVLPD-LDD 1837
        PIK-NMTDGS FMDDNQNE-W GDEET———          ———— LENKRFRFEE QVILPELVDD 1831
        KQVAMQSQGV GQPGAH——W SDDESDMPLP KRQRSDPVSG VGLGNNGGYA SDHTMVSEYE 1861

DLSDEDEDAE DSSANIITDL VYQGASLQAQ TDRTGEMALH LAARYSRADA AKRLLDAGAD 1902
        ETGNSEEE-E DAPA-VISDF IYQGASLHNQ TDRTGETALH LAARYSRSDA AKRLLEASAD 1954
        ETGNSEEE-E DASANMISDF IGQGAQLHNQ TDRTGETALH LAARYARADA AKRLLESSAD 1949
        DTGEDIENNE DSTAQVISDL LAQGAELNAT MDKTGETSLH LAARFARADA AKRLLDAGAD 1976

LINCQADVNA VDDHGKSALH WAAAVNNVEA TLLLLKNGAN RDMQDNKEET PLFLAAREGS 2022
        LINSHADVNA VDDLGKSALH WAAAVNNVDA AVVLLKNGAN KDMQNNREET PLFLAAREGS 2074
        LINAHADVNA VDEFGKSALH WAAAVNNVDA AAVLLKNSAN KDMQNNKEET SLFLAAREGS 2069
        LITADADINA ADNSGKTALH WAAAVNNTEA VNILLMHHAN RDAQDDKDET PLFLAAREGS 2096
```

FIG.13F

```
           NLS
hum  N    YEAAKILLDH FANRDITDHM DRLPRDVARD RMHHDIVRLL DEYNVTPSPP —GTVL—TS
TAN-1     YETAKVLLDH FANRDITDHM DRLPRDIAQE RMHHDIVRLL DEYNLVRSPQ LHGAPLGGTP
Xen  N    YETAKVLLDH YANRDITDHM DRLPRDIAQE RMHHDIVHLL DEYNLVKSPT LHNGPLGAT-
Dros N    YEACKALLDN FANREITDHM DRLPRDVASE RLHHDIVRLL DE-HVPRSPQ MLSMTPQAMI NLS                      CK II         cdc2         cdc2
hum  N    GSRRKKSLSE KVQLSE—SS  VTLSPVDSLE SPHTYVSDTT SSPM
TAN-1     A-RRKKSQDG KGCLLD—SS  GMLSPVDSLE SPHGYLSDVA SPPL
Xen  N    A-RRKKSQDG KTTLLDSGSS GVLSPVDSLE STHGYLSDVS SPPL
Dros N    GS-PDNGLDA TGSLRRKASS KKTSAASKKA ANLNGLNPGQ LTGGVSGVPG VPPTNSAAQA
          BNTS hum  N    —————————— —————————— —————————— ITSPGILQAS PNPML—ATA APPAPVHAQH
TAN-1     —————————— —————————— —————————— LPSPF—QQS  PSVPLNHLPG MPDTHLGIGH
Xen  N    —————————— —————————— —————————— MTSPF—QQS  PSMPLNHLTS MPESQLGMNH
Dros N    YEDCIKNAQS MQSLQGNGLD MIKLDNYAYS MGSPF—QQE  LLNGQGLGMN GNGQRNGVGP
          CK II                                 cdc2

ALSPV—————— ——————ICGP NRSFLSLKHT PMGKKSRRPS AKSTMPTSLP NLAKEAKDAK   2127
TLSPP—————— ——————LCSP NGYLGSLKPG VQGKKVRKPS SKGLACGS— ——KEAKDLK    2178
TLSPP—————— ——————ICSP NGYMGNMKPS VQSKKARKPS IKGNGC——— ——KEAKELK    2170
GSPPPGQQQP  QLITQPTVIS AGNGGNNGNG NASGKQSNQT AKQKAA——— ——KKAKLIE    2208

—————————— —————————— —————————— —————————— —————————— ——————————   2169
—————————— —————————— —————————— —————————— —————————— ——————————   2219
—————————— —————————— —————————— —————————— —————————— ——————————   2213
AAAAAAAVAA MSHELEGSPV GVGMGGNLPS PYDTSSMYSN AMAAPLANGN PNTGAKQPPS    2327

ALSFSNLHEM Q————————— —————————— -PLAHGASTV LPSVSQLLSH HHIVSPGS—    2235
LNVAA-KPEM AALGGGGRLA FETGPPRLSH LPVASGTSTV LGSSSGGALN FTVGGSTSLN    2306
INMAT-KQEM AA—GSNRMA  FDAMVPRLTH L-NASSPNTI MS——NGSMH  FTVGGAPTMN    2294
GVLPGGLCGM GGLSGAGNGN SHEQGLSPPY SNQSPPHSVQ SSLALSPHAY LGSPSPAKSR    2445
```

FIG. 13G

```
hum N    GSAGSLSRLH PVPVPADW— MNRMEVNETQ YNEMFGMVLA PAEG-THPGI APQSRPPEGK
TAN-1    GQCEWLSRLQ SGMVPNQYNP LRGSVAPGPL STQAPSLQHG -MVGPLHSSL AASALSQMMS
Xen N    SQCDWLARLQ NGMVQNQYDP IRNGIQQGN- AQQAQALQHG LMTS-LHNGL PATTLSQMMT
Dros N   PSLPTSPTHI QAMRHATQQK QFGGSNLNSL LGGANGGGVV GGGGGGGGGV GQGPQNSPVS hum N    APQPQSTCPP AVAGPLPTMY QIP————EM ARL-PSVAFP TAMMPQQDGQ VAQTILPAYH
TAN-1    PPQPHLGVSS AASGHLGRSF LSGEPSQADV QPLGPSSLAV HTILPQ-ESP ALPTSLPSSL
Xen N    MQQQHHN-SS TTSTHINSPF CSSDISQTDL QQM—SSNNI HSVMPQ-DTQ IFAASLPSNL
Dros N   QQQLGGLEFG SAGLDLNG-F CGSPDSFHSG QMNPPS——I QSSMSG-SSP STNMLSPSSQ hum N    SDWSDVTTSP TPGGAGGGQR GPGTHMSEPPHNN MQVYA
TAN-1    SDWSEGVSSP PT————SMQ SQIARIPEAFK
Xen N    SDWSEGISSP PT————SMQ PQRTHIPEAFK
Dros N   SDWSEGVQSP AANNLYISGG HQANKGSEAIYI
```

```
                    ————HITTPRE PLPP-IV-TF QLIPKGSIAQ PAG——— ————       2320
                    -YQGLPSTRL ATQPHLVQTQ QVQPQNLQMQ QQNLQPANIQ QQQSLQPPPP 2414
                    -YQAMPNTRL ANQPHLMQAQ QMQQQQN—— ————LQLHQS              2384
LGIISPTGSD MGIMLAPPQS SKNSAIMQTI SPQQQQQQQQ QQQQHQQQQ QQQQQQQQQQ         2565

PEST -containing Region
PFPASVGKYP TPPSQHSYAS SNAAERTPSH SGHLQGEHPY LTPSPESPDQ WSSSSPHSA-       2433
VPPVTAAQFL TPPSQHSY-S S-PVENTPSH QLQVP-EGPF LTPSPESPDQ WSSSSPHSNV       2530
TQSMTTAQFL TPPSQHSY-S S-PMDNTPSH QLQVP-DHPF LTPSPESPDQ WSSSSPHSNM       2497
HNQQAFYQYL TPSSQHS—— ——GGHTPQH LVQTL-D-SY PTPSPESPGH WSSSSPRSN-          2671

2471
                                                                       2556
                                                                       2523
                                                                       2703
```

FIG.13H

```
         10         20         30         40         50         60         70         80         90
         *          *          *          *          *          *          *          *          *
 GGAATTCCGC CCGCCCTGCG CCCCCCTCTG CTGTGGGCGC TGCTGGCGCT CTGGCTGTGC TGCCGGGCCC CCGCCCATGC ATTGCAGTGT
          P  A  L  R  P  A  L  L  W  A  L  L  A  L  W  L  C  C  A  A  P  A  H  A  L  Q  C>

100        110        120        130        140        150        160        170        180
         *          *          *          *          *          *          *          *          *
 CCAGATGGCT ATGAACCCTG TGTAAATGAA GGAATGTGTG TTACCTACCA CAATGGCACA GGATACTGCA AATGTCCAGA AGGCTTCTTG
     R  D  G  Y  E  P  C  V  N  E  G  M  C  V  T  Y  H  N  G  T  G  Y  C  K  C  P  E  G  F  L>

190        200        210        220        230        240        250        260        270
         *          *          *          *          *          *          *          *          *
 GGGGAATATT GTCAACATCG AGACCCCTGT GAGAAGAACC GCTGCCAGAA TGGTGGGACT TGTGTGGCCC AGGCCATGCT GGGGAAAGCC
      G  E  Y  C  Q  H  R  D  P  C  E  K  N  R  C  Q  N  G  G  T  C  V  A  Q  A  M  L  G  K  A>

280        290        300        310        320        330        340        350        360
         *          *          *          *          *          *          *          *          *
 ACGTGCCGAT GTGCCTCAGG GTTTACAGGA GAGGACTGCC AGTACTCAAC ATCTCATCCA TGCTTTGTGT CTCGACCCTG CCTGAATGGC
      T  C  R  C  A  S  G  F  T  G  E  D  C  Q  Y  S  T  S  H  P  C  F  V  S  R  P  C  L  N  G>

370        380        390        400        410        420        430        440        450
         *          *          *          *          *          *          *          *          *
 GGCACATGCC ATATGCTCAG CCGGGATACC TATGAGTGCA CCTGTCAAGT CGGGTTTACA GGTAAGGAGT GCCAATGGAC GGATGCCTGC
      G  T  C  H  M  L  S  R  D  T  Y  E  C  T  C  Q  V  G  F  T  G  K  E  C  Q  W  T  D  A  C>

460        470        480        490        500        510        520        530        540
         *          *          *          *          *          *          *          *          *
 CTGTCTCATC CCTGTGCAAA TGGAAGTACC TGTACCACTG TGGCCAACCA GTTCTCCTGC AAATGCCTCA CAGGCTTCAC AGGGCAGAAA
      L  S  H  P  C  A  N  G  S  T  C  T  T  V  A  N  Q  F  S  C  K  C  L  T  G  F  T  G  Q  K>

550        560        570        580        590        600        610        620        630
         *          *          *          *          *          *          *          *          *
 TGTGAGACTG ATGTCAATGA GTGTGACATT CCAGGACACT GCCAGCATGG TGGCACCTGC CTCAACCTGC CTGGTTCCTA CCAGTGCCAG
      C  E  T  D  V  N  E  C  D  I  P  G  H  C  Q  H  G  G  T  C  L  N  L  P  G  S  Y  Q  C  Q>

640        650        660        670        680        690        700        710        720
         *          *          *          *          *          *          *          *          *
 TGCCCTCAGG GCTTCACAGG CCAGTACTGT GACAGCCTGT ATGTGCCCTG TGCACCCTCA CCTTGTGTCA ATGGAGGCAC CTGTCGGCAG
      C  P  Q  G  F  T  G  Q  Y  C  D  S  L  Y  V  P  C  A  P  S  P  C  V  N  G  G  T  C  R  Q>

730        740        750        760        770        780        790        800        810
         *          *          *          *          *          *          *          *          *
 ACTGGTGACT TCACTTTTGA GTGCAACTGC CTTCCAGGTT TTGAAGGGAG CACCTGTGAG AGGAATATTG ATGACTGCCC TAACCACAGG
      T  G  D  F  T  F  E  C  N  C  L  P  G  F  E  G  S  T  C  E  R  N  I  D  D  C  P  N  H  R>
```

FIG.17A

```
        820        830        840        850        860        870        880        890        900
         *          *          *          *          *          *          *          *          *
TGTCAGAATG GAGGGGTTTG TGTGGATGGG GTCAACACTT ACAACTGCCG CTGTCCCCCA CAATGGACAG GACAGTTCTG CACAGAGGAT
 C Q N   G G V   V D G   V N T   Y N C R   P P Q W   T G Q F C   T E D>

910        920        930        940        950        960        970        980        990
         *          *          *          *          *          *          *          *          *
GTGGATGAAT GCCTGCTGCA GCCCAATGCC TGTCAAAATG GGGGCACCTG TGCCAACCGC AATGGAGGCT ATGGCTGTGT ATGTGTCAAC
 V D E   C L L Q   P N A   C Q N   G G T C   A N R   N G G   Y G C V   C V N>

1000       1010       1020       1030       1040       1050       1060       1070       1080
         *          *          *          *          *          *          *          *          *
GGCTGGAGTG GAGATGACTG CAGTGAGAAC ATTGATGATT GTGCCTTCGC CTCCTGTACT CCAGGCTCCA CCTGCATCGA CCGTGTGGCC
 G W S   G D D C   S E N   I D D   C A F A   S C T   P G S   T C I D   R V A>

1090       1100       1110       1120       1130       1140       1150       1160       1170
         *          *          *          *          *          *          *          *          *
TCCTTCTCTT GCATGTGCCC AGAGGGGAAG GCAGGTCTCC TGTGTCATCT GGATGATGCA TGCATCAGCA ATCCTTGCCA CAAGGGGGCA
 S F S   C M C P   E G K   A G L   L C H L   D D A   C I S   N P C H   K G A>

1180       1190       1200       1210       1220       1230       1240       1250       1260
         *          *          *          *          *          *          *          *          *
CTGTGTGACA CCAACCCCCT AAATGGGCAA TATATTTGCA CCTGCCCACA AGGCTACAAA GGGGCTGACT GCACAGAAGA TGTGGATGAA
 L C D   T N P L   N G Q   Y I C   T C P Q   G Y K   G A D   C T E D   V D E>

1270       1280       1290       1300       1310       1320       1330       1340       1350
         *          *          *          *          *          *          *          *          *
TGTGCCATGG CCAATAGCAA TCCTTGTGAG CATGCAGGAA AATGTGTGAA CACGGATGGC GCCTTCCACT GTGAGTGTCT GAAGGGTTAT
 C A M   A N S N   P C E   H A G   K C V N   T D G   A F H   C E C L   K G Y>

1360       1370       1380       1390       1400       1410       1420       1430       1440
         *          *          *          *          *          *          *          *          *
GCAGGACCTC GTTGTGAGAT GGACATCAAT GAGTGCCATT CAGACCCCTG CCAGAATGAT GCTACCTGTC TGGATAAGAT TGGAGGCTTC
 A G P   R C E M   D I N   E C H   S D P C   Q N D   A T C   L D K I   G G F>

1450       1460       1470       1480       1490       1500       1510       1520       1530
         *          *          *          *          *          *          *          *          *
ACATGTCTGT GCATGCCAGG TTTCAAAGGT GTGCATTGTG AATTAGAAAT AAATGAATGT CAGAGCAACC TTGTGTGAA CAATGGGCAG
 T C L   C M P G   F K G   V H C   E L E I   N E C   Q S N   P C V N   N G Q>

1540       1550       1560       1570       1580       1590       1600       1610       1620
         *          *          *          *          *          *          *          *          *
TGTGTGGATA AAGTCAATCG TTTCCAGTGC CTGTGTCCTC CTGGTTTCAC TGGGCCAGTT TGCCAGATTG ATATTGATGA CTGTTCCAGT
 C V D   K V N R   F Q C   L C P   P G F T   G P V   C Q I   D I D D   C S S>
```

FIG.17B

```
        1630       1640       1650       1660       1670       1680       1690       1700       1710
          *          *          *          *          *          *          *          *          *
    ACTCCGTGTC TGAATGGGGC AAAGTGTATC GATCACCCGA ATGGCTATGA ATGCCAGTGT GCCACAGGTT TCACTGGTGT GTTGTGTGAG
     T  P  C   L  N  G  A  K  C  I   D  H  P   N  G  Y  E   C  Q  C    A  T  G   F  T  G  V  L  C  E>

1720       1730       1740       1750       1760       1770       1780       1790       1800
          *          *          *          *          *          *          *          *          *
    GAGAACATTG ACAACTGTGA CCCCGATCCT TGCCACCATG GTCAGTGTCA GGATGGTATT GATTCCTACA CCTGCATCTG CAATCCCGGG
     E  N  I   D  N  C  D  P  D  P   C  H  H    G  Q  C  Q   D  G  I   D  S  Y   T  C  I   C  N  P  G>

1810       1820       1830       1840       1850       1860       1870       1880       1890
          *          *          *          *          *          *          *          *          *
    TACATGGGCG CCATCTGCAG TGACCAGATT GATGAATGTT ACAGCAGCCC TTGCCTGAAC GATGGTCGCT GCATTGACCT GGTCAATGGC
     Y  M  G   A  I  C  S  D  Q  I   D  E  C   Y  S  S  P   C  L  N   D  G  R   C  I  D  L  V  N  G>

1900       1910       1920       1930       1940       1950       1960       1970       1980
          *          *          *          *          *          *          *          *          *
    TACCAGTGCA ACTGCCAGCC AGGCACGTCA GGGGTTAATT GTGAAATTAA TTTTGATGAC TGTGCAAGTA ACCCTTGTAT CCATGGAATC
     Y  Q  C   N  C  Q  P  G  T  S   G  V  N   C  E  I  N   F  D  D   C  A  S   N  P  C  I  H  G  I>

1990       2000       2010       2020       2030       2040       2050       2060       2070
          *          *          *          *          *          *          *          *          *
    TGTATGGATG GCATTAATCG CTACAGTTGT GTCTGCTCAC CAGGATTCAC AGGGCAGAGA TGTAACATTG ACATTGATGA GTGTGCCTCC
     C  M  D   G  I  N  R  Y  S  C   V  C  S   P  G  F  T   G  Q  R   C  N  I   D  I  D  E  C  A  S>

2080       2090       2100       2110       2120       2130       2140       2150       2160
          *          *          *          *          *          *          *          *          *
    AATCCCTGTC GCAAGGGTGC AACATGTATC AACGGTGTGA ATGGTTTCCG CTGTATATGC CCCGAGGGAC CCCATCACCC CAGCTGCTAC
     N  P  C   R  K  G  A  T  C  I   N  G  V   N  G  F  R   C  I  C   P  E  G   P  H  H  P  S  C  Y>

2170       2180       2190       2200       2210       2220       2230       2240       2250
          *          *          *          *          *          *          *          *          *
    TCACAGGTGA ACGAATGCCT GAGCAATCCC TGCATCCATG GAAACTGTAC TGGAGGTCTC AGTGGATATA AGTGTCTCTG TGATGCAGGC
     S  Q  V   N  E  C  L  S  N  P   C  I  H   G  N  C  T   G  G  L   S  G  Y   K  C  L  C  D  A  G>

2260       2270       2280       2290       2300       2310       2320       2330       2340
          *          *          *          *          *          *          *          *          *
    TGGGTTGGCA TCAACTGTGA AGTGGACAAA AATGAATGCC TTTCGAATCC ATGCCAGAAT GGAGGAACTT GTGACAATCT GGTGAATGGA
     W  V  G   I  N  C  E  V  D  K   N  E  C   L  S  N  P   C  Q  N   G  G  T   C  D  N  L  V  N  G>

2350       2360       2370       2380       2390       2400       2410       2420       2430
          *          *          *          *          *          *          *          *          *
    TACAGGTGTA CTTGCAAGAA GGGCTTTAAA GGCTATAACT GCCAGGTGAA TATTGATGAA TGTGCCTCAA ATCCATGCCT GAACCAAGGA
     Y  R  C   T  C  K  F  G  F  K   G  Y  N   C  Q  V  N   I  D  E   C  A  S   N  P  C  L  N  Q  G>
```

FIG.17C

```
          2440       2450       2460       2470       2480       2490       2500       2510       2520
            *          *          *          *          *          *          *          *          *
     ACCTGCTTTG ATGACATAAG TGGCTACACT TGCCACTGTG TGCTGCCATA CACAGGCAAG AATTGTCAGA CAGTATTGGC TCCCTGTTCC
      T  C  F   D  D  I  S   G  Y  T   C  H  C   V  L  P  Y   T  G  K   N  C  Q   T  V  L  A   P  C  S>

2530       2540       2550       2560       2570       2580       2590       2600       2610
            *          *          *          *          *          *          *          *          *
     CCAAACCCTT GTGAGAATGC TGCTGTTTGC AAAGAGTCAC CAAATTTTGA GAGTTATACT TGCTTGTGTG CTCCTGCCTG GCAAGGTCAG
      P  N  P   C  E  N  A   A  V  C   K  E  S   P  N  F  E   S  Y  T   C  L  C   A  P  G  W   Q  G  Q>

2620       2630       2640       2650       2660       2670       2680       2690       2700
            *          *          *          *          *          *          *          *          *
     CGGTGTACCA TTGACATTGA CGAGTGTATC TCCAAGCCCT GCATGAACCA TGGTCTCTGC CATAACACCC AGGGCAGCTA CATGTGTGAA
      R  C  T   I  D  I  D   E  C  I   S  K  P   C  M  N  H   G  L  C   H  N  T   Q  G  S  Y   M  C  E>

2710       2720       2730       2740       2750       2760       2770       2780       2790
            *          *          *          *          *          *          *          *          *
     TGTCCACCAG GCTTCAGTGG TATGGACTGT GAGGAGGACA TTGATGACTG CCTTGCCAAT CCTTGCCAGA ATGGAGGTTC CTGTATGGAT
      C  P  P   G  F  S  G   M  D  C   E  E  D   I  D  D  C   L  A  N   P  C  Q   N  G  G  S   C  M  D>

2800       2810       2820       2830       2840       2850       2860       2870       2880
            *          *          *          *          *          *          *          *          *
     GGAGTGAATA CTTTCTCCTG CCTCTGCCTT CCGGGTTTCA CTGGGGATAA GTGCCAGACA GACATGAATG AGTGTCTGAG TGAACCCTGT
      G  V  N   T  F  S  C   L  C  L   P  G  F   T  G  D  K   C  Q  T   D  M  N   E  C  L  S   E  P  C>

2890       2900       2910       2920       2930       2940       2950       2960       2970
            *          *          *          *          *          *          *          *          *
     AAGAATGGAG GGACCTGCTC TGACTACGTC AACAGTTACA CTTGCAAGTG CCAGGCAGGA TTTGATGGAG TCCATTGTGA GAACAACATC
      K  N  G   G  T  C  S   D  Y  V   N  S  Y   T  C  K  C   Q  A  G   F  D  G   V  H  C  E   N  N  I>

2980       2990       3000       3010       3020       3030       3040       3050       3060
            *          *          *          *          *          *          *          *          *
     AATGAGTGCA CTGAGAGCTC CTGTTTCAAT GGTGGCACAT GTGTTGATGG GATTAACTCC TTCTCTTGCT TGTGCCCTGT GGGTTTCACT
      N  E  C   T  E  S  S   C  F  N   G  G  T   C  V  D  G   I  N  S   F  S  C   L  C  P  V   G  F  T>

3070       3080       3090       3100       3110       3120       3130       3140       3150
            *          *          *          *          *          *          *          *          *
     GGATCCTTCT GCCTCCATGA GATCAATGAA TGCAGCTCTC ATCCATGCCT GAATGAGGGA ACGTGTGTTG ATGGCCTGGG TACCTACCGC
      G  S  F   C  L  H  E   I  N  E   C  S  S   H  P  C  L   N  E  G   T  C  V   D  G  L  G   T  Y  R>

3160       3170       3180       3190       3200       3210       3220       3230       3240
            *          *          *          *          *          *          *          *          *
     TGCAGCTGCC CCCTGGGCTA CACTGGGAAA AACTGTCAGA CCCTGGTGAA TCTCTGCAGT CGGTCTCCAT GTAAAAACAA AGGTACTTGT
      C  S  C   P  L  G  Y   T  G  K   N  C  Q   T  L  V  N   L  C  S   R  S  P   C  K  N  K   G  T  C>
```

FIG.17D

```
        3250      3260       3270       3280       3290       3300       3310       3320       3330
          •         •          •          •          •          •          •          •          •
   GTTCAGAAAA AAGCAGAGTC CCACTGCCTA TGTCCATCTG GATGGGCTGG TGCCTATTGT GACGTGCCCA ATGTCTCTTG TGACATAGCA
    V Q K   K A E S   Q C L   C P S   G W A   G A Y C   D V P   N V S C   D I A>

3340      3350       3360       3370       3380       3390       3400       3410       3420
          •         •          •          •          •          •          •          •          •
   GCCTCCAGGA GAGGTGTGCT TGTTGAACAC TTGTGCCACC ACTCAGGTGT CTCCATCAAT GCTGGCAACA CGCATTACTG TCAGTGCCCC
    A S R   R G V L   V E H   L C Q   H S G V   C I N   A G N   T H Y C   Q C P>

3430      3440       3450       3460       3470       3480       3490       3500       3510
          •         •          •          •          •          •          •          •          •
   CTGGGCTATA CTGGGAGCTA CTGTGAGGAG CAACTCGATG AGTGTGCGTC CAACCCCTGC CAGCACGGGG CAACATGCAG TGACTTCATT
    L G Y   T G S Y   C E E   Q L D   E C A S   N P C   Q H G   A T C S   D F I>

3520      3530       3540       3550       3560       3570       3580       3590       3600
          •         •          •          •          •          •          •          •          •
   GGTGGATACA GATGCGAGTG TGTCCCAGGC TATCAGGGTG TCAACTGTGA GTATGAAGTG GATGAGTGCC AGAATCAGCC CTGCCAGAAT
    G G Y   R C E C   V P G   Y Q G   V N C   E Y E V   D E C   Q N Q P   C Q N>

3610      3620       3630       3640       3650       3660       3670       3680       3690
          •         •          •          •          •          •          •          •          •
   GGAGGCACCT GTATTGACCT TGTGAACCAT TTCAAGTGCT CTTGCCCACC AGGCACTCGG GGCCTACTCT GTGAAGAGAA CATTGATGAC
    G G T   C I D L   V N H   F K C   S C P P   G T R   G L L   C E E N   I D D>

3700      3710       3720       3730       3740       3750       3760       3770       3780
          •         •          •          •          •          •          •          •          •
   TGTGCCCGGG GTCCCCATTG CCTTAATGGT GGTCAGTGCA TGGATAGGAT TGGAGGCTAC AGTTGTCGCT GCTTGCCTGG CTTTGCTGGG
    C A R   G P H C   L N G   G Q C   M D R I   G G Y   S C R   C L P G   F A G>

3790      3800       3810       3820       3830       3840       3850       3860       3870
          •         •          •          •          •          •          •          •          •
   GAGCGTTGTG AGGGAGACAT CAACGAGTGC CTCTCCAACC CCTGCAGCTC TGAGGGCAGC CTGGACTGTA TACAGCTCAC CAATGACTAC
    E R C   E G D I   N E C   L S N   P C S S   E G S   L D C   I Q L T   N D Y>

3880      3890       3900       3910       3920       3930       3940       3950       3960
          •         •          •          •          •          •          •          •          •
   CTGTGTGTTT GCCGTAGTGC CTTTACTGGC CGGCACTGTG AAACCTTCGT CGATGTGTGT CCCCAGATGC CCTGCCTGAA TGGAGGGACT
    L C V   C R S A   F T G   R H C   E T F V   D V C   P Q M   P C L N   G G T>

3970      3980       3990       4000       4010       4020       4030       4040       4050
          •         •          •          •          •          •          •          •          •
   TGTGCTGTGG CCAGTAACAT GCCTGATGGT TTCATTTGCC GTTGTCCCCC GGGATTTTCC GGGGCAAGGT GCCAGAGCAG CTGTGGACAA
    C A V   A S N M   P D G   F I C   R C P P   G F S   G A R   C Q S S   C G Q>
```

FIG.17E

```
       4060       4070       4080       4090       4100       4110       4120       4130       4140
         *          *          *          *          *          *          *          *          *
GTGAAATGTA GGAAGGGGGA GCAGTGTGTG CACACCGCCT CTGGACCCCG CTGCTTCTGC CCCAGTCCCC GGGACTGCCA GTCAGGCTGT
 V K C      R K G E    Q C V      H T A      S G P R    C F C      P S P      R D C E    S G C>

4150       4160       4170       4180       4190       4200       4210       4220       4230
         *          *          *          *          *          *          *          *          *
GCCAGTAGCC CCTGCCAGCA CGGGGGCAGC TGCCACCCTC AGCGCCAGCC TCCTTATTAC TCCTGCCAGT GTGCCCCACC ATTCTCGGGT
 A S S      P C Q H    G G S      C H P      Q R Q P    P Y Y      S C Q      C A P P    F S G>

4240       4250       4260       4270       4280       4290       4300       4310       4320
         *          *          *          *          *          *          *          *          *
AGCCGCTGTG AACTCTACAC GGCACCCCCC AGCACCCCTC CTGCCACCTG TCTGAGCCAG TATTGTGCCG ACAAAGCTCG GGATGGCGTC
 S R C      E L Y T    A P P      S T P      P A T C    L S Q      Y C A      D K A R    D G V>

4330       4340       4350       4360       4370       4380       4390       4400       4410
         *          *          *          *          *          *          *          *          *
TGTGATGAGG CCTGCAACAG CCATGCCTGC CAGTGGGATG GGGTGACTG TTCTCTCACC ATGGAGAACC CCTGGGCCAA CTGCTCCTCC
 C D E      A C N S    H A C      Q W D      G G D C    S L T      M E N      P W A N    C S S>

4420       4430       4440       4450       4460       4470       4480       4490       4500
         *          *          *          *          *          *          *          *          *
CCACTTCCCT GCTGGGATTA TATCAACAAC CAGTGTGATG AGCTGTGCAA CACGGTCGAG TGCCTGTTTG ACAACTTTGA ATGCCAGGGG
 P L P      C W D Y    I N N      Q C D      E L C N    T V E      C L F      D N F E    C Q G>

4510       4520       4530       4540       4550       4560       4570       4580       4590
         *          *          *          *          *          *          *          *          *
AACAGCAAGA CATGCAAGTA TGACAAATAC TGTGCAGACC ACTTCAAAGA CAACCACTGT AACCAGGGGT GCAACAGTGA GGAGTGTGGT
 N S K      T C K Y    D K Y      C A D      H F K D    N H C      N Q G      C N S E    E C G>

4600       4610       4620       4630       4640       4650       4660       4670       4680
         *          *          *          *          *          *          *          *          *
TGGGATGGGC TGGACTGTGC TGCTGACCAA CCTGAGAACC TGGCAGAAGG TACCCTGGTT ATTGTGGTAT TGATGCCACC TGAACAACTG
 W D G      L D C A    A D Q      P E N      L A E G    T L V      I V V      L M P P    E Q L>

4690       4700       4710       4720       4730       4740       4750       4760       4770
         *          *          *          *          *          *          *          *          *
CTCCAGGATG CTGGCAGCTT CTTGCGGGCA CTGGGTACCC TGCTCCACAC CAACCTGCGC ATTAAGCGGG ACTCCCAGGG GGAACTCATG
 L Q D      A R S F    L R A      L G T      L L H T    N L R      I K R      D S Q G    E L M>

4780       4790       4800       4810       4820       4830       4840       4850       4860
         *          *          *          *          *          *          *          *          *
GTGTACCCCT ATTATGGTGA GAAGTCAGCT GCTATGAAGA AACAGAGGAT GACACGCAGA TCCCTTCCTG GTAACAAGA ACAGGAGGTG
 V Y P      Y Y G E    K S A      A M K      K Q R M    T R R      S L P      G E Q E    Q E V>
```

FIG.17F

```
     4870       4880       4890       4900       4910       4920       4930       4940       4950
       *          *          *          *          *          *          *          *          *
GCTGGCTCTA AAGTCTTTCT GGAAATTGAC AACCGCCAGT GTGTTCAAGA CTCAGACCAC TGCTTCAAGA ACACGGATGC AGCAGCAGCT
 A  G  S  K  V  F  L  E  I  D  N  R  Q  C  V  Q  D  S  D  H  C  F  K  N  T  D  A  A  A  A>

4960       4970       4980       4990       5000       5010       5020       5030       5040
       *          *          *          *          *          *          *          *          *
CTCCTGGCCT CTCACGCCAT ACAGGGGACC CTGTCATACC CTCTTGTGTC TGTCGTCAGT GAATCCCTGA CTCCAGAACG CACTCAGCTC
 L  L  A  S  H  A  I  Q  G  T  L  S  Y  P  L  V  S  V  V  S  E  S  L  T  P  E  R  T  Q  L>

5050       5060       5070       5080       5090       5100       5110       5120       5130
       *          *          *          *          *          *          *          *          *
CTCTATCTCC TTGCTGTTGC TGTTGTCATC ATTCTGTTTA TTATTCTGCT GGGGGTAATC ATGGCAAAAC GAAAGCGTAA GCATGGCTCT
 L  Y  L  L  A  V  A  V  V  I  I  L  F  I  I  L  L  G  V  I  M  A  K  R  K  R  K  H  G  S>

5140       5150       5160       5170       5180       5190       5200       5210       5220
       *          *          *          *          *          *          *          *          *
CTCTGGCTGC CTGAAGGTTT CACTCTTCGC CGAGATGCAA GCAATCACAA GCGTCGTGAG CCAGTGGGAC AGGATGCTGT GGGGCTGAAA
 L  W  L  P  E  G  F  T  L  R  R  D  A  S  N  H  K  R  R  E  P  V  G  Q  D  A  V  G  L  K>

5230       5240       5250       5260       5270       5280       5290       5300       5310
       *          *          *          *          *          *          *          *          *
AATCTCTCAG TGCAAGTCTC AGAAGCTAAC CTAATTGGTA CTGGAACAAG TGAACACTGG GTCGATGATG AAGGGCCCCA GCCAAAGAAA
 N  L  S  V  Q  V  S  E  A  N  L  I  G  T  G  T  S  E  H  W  V  D  D  E  G  P  Q  P  K  K>

5320       5330       5340       5350       5360       5370       5380       5390       5400
       *          *          *          *          *          *          *          *          *
GTAAAGGCTG AAGATGAGGC CTTACTCTCA GAAGAAGATG ACCCCATTGA TCGACGGCCA TGGACACAGC AGCACCTTGA AGCTGCAGAC
 V  K  A  E  D  E  A  L  L  S  E  E  D  D  P  I  D  R  R  P  W  T  Q  Q  H  L  E  A  A  D>

5410       5420       5430       5440       5450       5460       5470       5480       5490
       *          *          *          *          *          *          *          *          *
ATCCGTAGGA CACCATCGCT GGCTCTCACC CCTCCTCAGG CAGAGCAGGA GGTGGATGTG TTAGATGTGA ATGTCCGTGG CCCAGATGGC
 I  R  R  T  P  S  L  A  L  T  P  P  Q  A  E  Q  E  V  D  V  L  D  V  N  V  R  G  P  D  G>

5500       5510       5520       5530       5540       5550       5560       5570       5580
       *          *          *          *          *          *          *          *          *
TGCACCCCAT TGATGTTGGC TTCTCTCCGA GGAGGCAGCT CAGATTTGAG TGATGAAGAT GAAGATGCAG AGGACTCTTC TGCTAACATC
 C  T  P  L  M  L  A  S  L  R  G  G  S  S  D  L  S  D  E  D  E  D  A  E  D  S  S  A  N  I>

5590       5600       5610       5620       5630       5640       5650       5660       5670
       *          *          *          *          *          *          *          *          *
ATCACAGACT TGGTCTACCA GGGTGCCAGC CTCCAGGCCC AGACAGACCG GACTGGTGAG ATGGCCCTGC ACCTTGCAGC CCGCTACTCA
 I  T  D  L  V  Y  Q  G  A  S  L  Q  A  Q  T  D  R  T  G  E  M  A  L  H  L  A  A  R  Y  S>
```

FIG.17G

```
      5680       5690       5700       5710       5720       5730       5740       5750       5760
        •          •          •          •          •          •          •          •          •
CGGGCTGATC CTGCCAAGCG TCTCCTGGAT GCAGGTGCAG ATGCCAATGC CCAGGACAAC ATGGGCCGCT GTCCACTCCA TGCTGCAGTG
  R  A  D   A  A  K  R   L  L  D   A  G  A   D  A  N  A   Q  D  N   M  G  R   C  P  L  H  A  A  V>

5770       5780       5790       5800       5810       5820       5830       5840       5850
        •          •          •          •          •          •          •          •          •
GCAGCTGATG CCCAAGGTGT CTTCCAGATT CTGATTCGCA ACCGAGTAAC TGATCTAGAT GCCAGGATGA ATGATGGTAC TACACCCCTG
  A  A  D   A  Q  G  V   F  Q  I   L  I  R   N  R  V  T   D  L  D   A  R  M   N  D  G  T   T  P  L>

5860       5870       5880       5890       5900       5910       5920       5930       5940
        •          •          •          •          •          •          •          •          •
ATCCTGGCTG CCCGCCTGGC TGTGGAGGGA ATGGTGGCAG AACTGATCAA CTGCCAAGCG GATGTGAATG CAGTGGATGA CCATGGAAAA
  I  L  A   A  R  L  A   V  E  G   M  V  A   E  L  I  N   C  Q  A   D  V  N   A  V  D  D   H  G  K>

5950       5960       5970       5980       5990       6000       6010       6020       6030
        •          •          •          •          •          •          •          •          •
TCTGCTCTTC ACTGGGCAGC TGCTGTCAAT AATGTGGAGG CAACTCTTTT GTTGTTGAAA AATGGGGCCA ACCGAGACAT GCAGGACAAC
  S  A  L   H  W  A  A   A  V  N   N  V  E   A  T  L  L   L  L  K   N  G  A   N  R  D  M   Q  D  N>

6040       6050       6060       6070       6080       6090       6100       6110       6120
        •          •          •          •          •          •          •          •          •
AAGGAAGACA CACCTCTGTT TCTTGCTGCC CGGGAGGGGA GCTATGAAGC AGCCAAGATC CTGTTAGACC ATTTTGCCAA TCGAGACATC
  K  E  E   T  P  L  F   L  A  A   R  E  G   S  Y  E  A   A  K  I   L  L  D   H  F  A  N   R  D  I>

6130       6140       6150       6160       6170       6180       6190       6200       6210
        •          •          •          •          •          •          •          •          •
ACAGACCATA TGGATCGTCT TCCCCGGGAT GTGGCTCGGG ATCGCATGCA CCATGACATT GTGCGCCTTC TGGATGAATA CAATGTGACC
  T  D  H   M  D  R  L   P  R  D   V  A  R   D  R  M  H   H  D  I   V  R  L   L  D  E  Y   N  V  T>

6220       6230       6240       6250       6260       6270       6280       6290       6300
        •          •          •          •          •          •          •          •          •
CCAAGCCCTC CAGGCACCGT GTTGACTTCT GCTCTCTCAC CTGTCATCTG TGGGCCCAAC AGATCTTTCC TCAGCCTGAA GCACACCCCA
  P  S  P   P  G  T  V   L  T  S   A  L  S   P  V  I  C   G  P  N   R  S  F   L  S  L  K   H  T  P>

6310       6320       6340       6350       6360       6370       6380       6390       6400
        •          •          •          •          •          •          •          •          •
ATGGGCAAGA AGTCTAGACG GCCCAGTGCC AAGAGTACCA TGCCTACTAG CCTCCCTAAC CTTGCCAAGG AGGCAAAGGA TGCCAAGGGT
  M  G  K   K  S  R  R   P  S  A   K  S  T   M  P  T  S   L  P  N   L  A  K   E  A  K  D   A  K  G>

6400       6410       6420       6430       6440       6450       6460       6470       6480
        •          •          •          •          •          •          •          •          •
AGTAGGAGGA AGAAGTCTCT GAGTGAGAAG GTCCAACTGT CTGAGAGTTC AGTAACTTTA TCCCCTGTTG ATTCCCTAGA ATCTCCTCAC
  S  R  R   K  K  S  L   S  E  K   V  Q  L   S  E  S  S   V  T  L   S  P  V   D  S  L  E   S  P  H>
```

FIG.17H

```
      6490       6500       6510       6520       6530       6540       6550       6560       6570
        *          *          *          *          *          *          *          *          *
ACGTATGTTT CCGACACCAC ATCCTCTCCA ATGATTACAT CCCCTGGGAT CTTACAGGCC TCACCCAACC CTATGTTGGC CACTGCCGCC
 T Y V  S D T T  S S P  M I T  S P G I  L Q A  S P N  P M L A  T A A>

6580       6590       6600       6610       6620       6630       6640       6650       6660
        *          *          *          *          *          *          *          *          *
CCTCCTGCCC CAGTCCATGC CCAGCATGCA CTATCTTTTT CTAACCTTCA TGAAATGCAG CCTTTGGCAC ATGGGCCAG CACTGTGCTT
 P P A  P V H A  Q H A  L S F  S N L H  E M Q  P L A  H G A S  T V L>

6670       6680       6690       6700       6710       6720       6730       6740       6750
        *          *          *          *          *          *          *          *          *
CCCTCAGTGA GCCAGTTGCT ATCCCACCAC CACATTGTGT CTCCAGGCAG TGGCAGTGCT GGAAGCTTGA GTAGGCTCCA TCCAGTCCCA
 P S V  S Q L L  S H H  H I V  S P G S  G S A  G S L  S R L H  P V P>

6760       6770       6780       6790       6800       6810       6820       6830       6840
        *          *          *          *          *          *          *          *          *
GTCCCAGCAG ATTGGATGAA CCGCATGGAG GTGAATGAGA CCCAGTACAA TGAGATGTTT GGTATGGTCC TGGCTCCAGC TGAGGGCACC
 V P A  D W M N  R M E  V N E  T Q Y N  E M F  G M V  L A P A  E G T>

6850       6860       6870       6880       6890       6900       6910       6920       6930
        *          *          *          *          *          *          *          *          *
CATCCTGGCA TAGCTCCCCA GAGCAGGCCA CCTGAAGGGA AGCACATAAC CACCCCTCGG GAGCCCTTGC CCCCCATTGT GACTTTCCAG
 H P G  I A P Q  S R P  P E G  K H I T  T P R  E P L  P P I V  T F Q>

6940       6950       6960       6970       6980       6990       7000       7010       7020
        *          *          *          *          *          *          *          *          *
CTCATCCCTA AAGGCAGTAT TGCCCAACCA GCGGGGGCTC CCCAGCCTCA GTCCACCTGC CCTCCAGCTG TTGCGGGCCC CCTGCCCACC
 L I P  K G S I  A Q P  A G A  P Q P Q  S T C  P P A  V A G P  L P T>

7030       7040       7050       7060       7070       7080       7090       7100       7110
        *          *          *          *          *          *          *          *          *
ATGTACCAGA TTCCAGAAAT GGCCCGTTTG CCCAGTGTGG CTTTCCCCAC TGCCATGATG CCCCAGCAGG ACGGGCAGGT AGCTCAGACC
 M Y Q  I P E M  A R L  P S V  A F P T  A M M  P Q Q  D G Q V  A Q T>

7120       7130       7140       7150       7160       7170       7180       7190       7200
        *          *          *          *          *          *          *          *          *
ATTCTCCCAG CCTATCATCC TTTCCCAGCC TCTGTGGGCA AGTACCCCAC ACCCCCTTCA CAGCACAGTT ATGCTTCCTC AAATGCTGCT
 I L P  A Y H P  F P A  S V G  K Y P T  P P S  Q H S  Y A S S  N A A>

7210       7220       7230       7240       7250       7260       7270       7280       7290
        *          *          *          *          *          *          *          *          *
GAGCGAACAC CCAGTCACAG TGGTCACCTC CAGGGTGAGC ATCCCTACCT GACACCATCC CCAGAGTCTC CTGACCAGTG GTCAAGTTCA
 E R T  P S H S  G H L  Q G E  H P Y L  T P S  P E S  P D Q W  S S S>
```

FIG.171

```
     7300       7310       7320       7330       7340       7350       7360       7370       7380
       *          *          *          *          *          *          *          *          *
TCACCCCACT CTGCTTCTGA CTGGTCAGAT GTGACCACCA GCCCTACCCC TGGGGGTGCT GGAGGAGGTC AGCGGGGACC TGGGACACAC
 S  P  H    S  A  S  D    W  S  D    V  T  T    S  P  T  P    G  G  A    G  G  G    Q  R  G  P    G  T  H>

7390       7400       7410       7420       7430       7440       7450       7460       7470
       *          *          *          *          *          *          *          *          *
ATGTCTGAGC CACCACACAA CAACATGCAG GTTTATGCGT GAGAGAGTCC ACCTCCAGTG TAGAGACATA ACTGACTTTT GTAAATGCTG
 M  S  E    P  P  H  N    N  M  Q    V  Y  A>

7480       7490       7500       7510       7520       7530       7540       7550       7560
       *          *          *          *          *          *          *          *          *
CTGAGGAACA AATGAAGGTC ATCCGGGAGA GAAATGAAGA AATCTCTGGA GCCAGCTTCT AGAGGTAGGA AAGAGAAGAT GTTCTTATTC 7570       7580       7590       7600       7610       7620       7630       7640       7650
       *          *          *          *          *          *          *          *          *
AGATAATGCA AGAGAAGCAA TTCGTCAGTT TCACTGGGTA TCTGCAAGGC TTATTGATTA TTCTAATCTA ATAAGACAAG TTTGTGGAAA 7660       7670       7680       7690       7700       7710       7720       7730       7740
       *          *          *          *          *          *          *          *          *
TGCAAGATGA ATACAAGCCT TGGGTCCATG TTTACTCTCT TCTATTTGGA GAATAAGATG GATGCTTATT GAAGCCCAGA CATTCTTGCA 7750       7760       7770       7780       7790       7800       7810       7820       7830
       *          *          *          *          *          *          *          *          *
GCTTGGACTG CATTTTAAGC CCTGCAGGCT TCTGCCATAT CCATGAGAAG ATTCTACACT AGCGTCCTGT TGGGAATTAT GCCCTGGAAT 7840       7850       7860       7870       7880       7890       7900       7910       7920
       *          *          *          *          *          *          *          *          *
TCTGCCTGAA TTGACCTACG CATCTCCTCC TCCTTGGACA TTCTTTTGTC TTCATTTGGT GCTTTTGGTT TTGCACCTCT CCGTGATTGT 7930       7940       7950       7960       7970       7980       7990       8000       8010
       *          *          *          *          *          *          *          *          *
AGCCCTACCA GCATGTTATA GGGCAAGACC TTTGTGCTTT TGATCATTCT GGCCCATGAA AGCAACTTTG GTCTCCTTTC CCCTCCTGTC 8020       8030       8040       8050       8060       8070       8080       8090       8100
       *          *          *          *          *          *          *          *          *
TTCCCGGTAT CCCTTGGAGT CTCACAAGGT TTACTTTGGT ATGGTTCTCA GCACAAACCT TCAAGTATG TTGTTTCTTT GGAAAATGGA 8110       8120       8130       8140       8150       8160       8170       8180       8190
       *          *          *          *          *          *          *          *          *
CATACTGTAT TGTGTTCTCC TGCATATATC ATTCCTGGAC AGAGAAGGGG AGAAGAATAC TTTTCTTCAA CAAATTTTGG GGGCAGGAGA 8200       8210       8220       8230       8240       8250       8260       8270       8280
       *          *          *          *          *          *          *          *          *
TCCCTTCAAG AGGCTGCACC TTAATTTTTC TTGTCTGTGT GCAGGTCTTC ATATAAACTT TACCAGGAAG AAGGGTGTGA GTTTGTTGTT
```

FIG.17J

```
      8290       8300       8310       8320       8330       8340       8350       8360       8370
        *          *          *          *          *          *          *          *          *
  TTTCTGTGTA TGGGCCTGGT CAGTGTAAAG TTTTATCCTT GATAGTCTAG TTACTATGAC CCTCCCCACT TTTTTAAAAC CAGAAAAAGG 8380       8390       8400       8410       8420       8430       8440       8450       8460
        *          *          *          *          *          *          *          *          *
  TTTGGAATGT TGGAATGACC AAGAGACAAG TTAACTCGTG CAAGAGCCAG TTACCCACCC ACAGGTCCCC CTACTTCCTG CCAAGCATTC 8470       8480       8490       8500       8510       8520       8530       8540       8550
        *          *          *          *          *          *          *          *          *
  CATTGACTGC CTGTATGGAA CACATTTGTC CCAGATCTGA GCATTCTAGG CCTGTTTCAC TCACTCACCC AGCATATGAA ACTAGTCTTA 8560       8570       8580       8590       8600       8610       8620       8630       8640
        *          *          *          *          *          *          *          *          *
  ACTGTTGAGC CTTTCCTTTC ATATCCACAG AAGACACTGT CTCAAATGTT GTACCCTTGC CATTTAGGAC TGAACTTTCC TTAGCCCAAG 8650       8660       8670       8680       8690       8700       8710       8720       8730
        *          *          *          *          *          *          *          *          *
  GGACCCAGTG ACAGTTGTCT TCCGTTTGTC AGATGATCAG TCTCTACTGA TTATCTTCCT GCTTAAAGGC CTGCTCACCA ATCTTTCTTT 8740       8750       8760       8770       8780       8790       8800       8810       8820
        *          *          *          *          *          *          *          *          *
  CACACCGTGT GGTCCGTGTT ACTGGTATAC CCAGTATGTT CTCACTGAAG ACATGGACTT TATATGTTCA AGTGCAGGAA TTGGAAAGTT 8830       8840       8850       8860       8870       8880       8890       8900       8910
        *          *          *          *          *          *          *          *          *
  GGACTTGTTT TCTATGATCC AAAACAGCCC TATAAGAAGG TTGGAAAAGG AGGAACTATA TAGCAGCCTT TGCTATTTTC TGCTACCATT 8920       8930       8940       8950       8960       8970       8980       8990       9000
        *          *          *          *          *          *          *          *          *
  TCTTTTCCTC TGAAGCGGCC ATGACATTCC CTTTGGCAAC TAACGTAGAA ACTCAACAGA ACATTTTCCT TTCCTAGAGT CACCTTTTAG 9010       9020       9030       9040       9050       9060       9070       9080       9090
        *          *          *          *          *          *          *          *          *
  ATGATAATCG ACAACTATAG ACTTGCTCAT TGTTCAGACT GATTGCCCCT CACCTGAATC CACTCTCTGT ATTCATGCTC TTGGCAATTT 9100       9110       9120       9130       9140       9150       9160       9170       9180
        *          *          *          *          *          *          *          *          *
  CTTTGACTTT CTTTTAAGGG CAGAAGCATT TTAGTTAATT GTAGATAAAG AATAGTTTTC TTCCTCTTCT CCTTGGGCCA GTTAATAATT 9190       9200       9210       9220       9230       9240       9250       9260       9270
        *          *          *          *          *          *          *          *          *
  GGTCCATGCC TACACTGCAA CTTCCGTCCA GTGCTGTGAT GCCCATGACA CCTGCAAAAT AAGTTCTGCC TGGGCATTTT GTAGATATTA
```

FIG.17K

```
      9280       9290       9300       9310       9320       9330       9340       9350       9360
        *          *          *          *          *          *          *          *          *
ACAGGTGAAT TCCCGACTCT TTTGGTTTGA ATGACAGTTC TCATTCCTTC TATGGCTGCA AGTATGCATC AGTGCTTCCC ACTTACCTGA 9370       9380       9390       9400       9410       9420       9430       9440       9450
        *          *          *          *          *          *          *          *          *
TTTGTCTGTC GGTGGCCCCA TATGGAAACC CTGCGTGTCT GTTGGCATAA TAGTTTACAA ATGGTTTTTT CAGTCCTATC CAAATTTATT 9460       9470       9480       9490       9500       9510       9520       9530       9540
        *          *          *          *          *          *          *          *          *
GAACCAACAA AAATAATTAC TTCTGCCCTG AGATAAGCAG ATTAAGTTTC TTCATTCTCT GCTTTATTCT CTCCATGTGG CAACATTCTG 9550       9560       9570       9580       9590       9600       9610       9620       9630
        *          *          *          *          *          *          *          *          *
TCAGCCTCTT TCATAGTGTG CAAACATTTT ATCATTCTAA ATGGTGACTC TCTGCCCTTG GACCCATTTA TTATTCACAG ATGGGGAGAA 9640       9650       9660       9670       9680       9690       9700       9710       9720
        *          *          *          *          *          *          *          *          *
CCTATCTGCA TGGACCCTCA CCATCCTCTG TGCAGCACAC ACAGTGCAGG GAGCCAGTGG CGATGGCGAT GACTTTCTTC CCCTGGGAAT
TCC
```

FIG.17L

THERAPEUTIC AND DIAGNOSTIC METHODS AND COMPOSITIONS BASED ON NOTCH PROTEINS AND NUCLEIC ACIDS

This application is a continuation of application Ser. No. 08/083,590 filed Jun. 25, 1993, now U.S. Pat. No. 5,786,158, which is a continuation-in-part of both application Ser. No. 07/955,012 filed Sep. 30, 1992, now abandoned, and application Ser. No. 07/879,038 filed Apr. 30, 1992, now abandoned, each of which is incorporated by reference herein in its entirety.

This invention was made in part with government support under grant numbers GM 29093 and NS 26084 awarded by the National Institutes of Health. The government has certain rights in the invention.

1. INTRODUCTION

The present invention relates to therapeutic compositions comprising Notch proteins, analogs and derivatives thereof, antibodies thereto, nucleic acids encoding the Notch proteins, derivatives or analogs, Notch antisense nucleic acids, and toporythmic proteins which bind to Notch and their nucleic acids and antibodies. Therapeutic and diagnostic methods are also provided.

2. BACKGROUND OF THE INVENTION

2.1. The Notch Gene and Protein

Null mutations in any one of the zygotic neurogenic loci—Notch (N), Delta (Dl), mastermind (mam), Enhancer of Split (E(spl), neuralized (neu), and big brain (bib)—result in hypertrophy of the nervous system at the expense of ventral and lateral epidermal structures. This effect is due to the misrouting of epidermal precursor cells into a neuronal pathway, and implies that neurogenic gene function is necessary to divert cells within the neurogenic region from a neuronal fate to an epithelial fate. Studies that assessed the effects of laser ablation of specific embryonic neuroblasts in grasshoppers (Doe and Goodman 1985, Dev. Biol. 111, 206–219) have shown that cellular interactions between neuroblasts and the surrounding accessory cells serve to inhibit these accessory cells from adopting a neuroblast fate. Together, these genetic and developmental observations have led to the hypothesis that the protein products of the neurogenic loci function as components of a cellular interaction mechanism necessary for proper epidermal development (Artavanis-Tsakonas, 1988, Trends Genet. 4, 95–100).

Sequence analyses (Wharton et al., 1985, Cell 43, 567–581; Kidd et al., 1986, Mol. Cell. Biol. 6, 3094–3108; Vassin et al., 1987, EMBO J. 6, 3431–3440; Kopczynski et al., 1988, Genes Dev. 2, 1723–1735) have shown that two of the neurogenic loci, Notch and Delta, appear to encode transmembrane proteins that span the membrane a single time. The Drosophila Notch gene encodes a ~300 kd protein (we use "Notch" to denote this protein) with a large N-terminal extracellular domain that includes 36 epidermal growth factor (EGF)-like tandem repeats followed by three other cysteine-rich repeats, designated Notch/lin-12 repeats (Wharton et al., 1985, Cell 43, 567–581; Kidd et al., 1986, Mol. Cell Biol. 6, 3094–3108; Yochem et al., 1988, Nature 335, 547–550). The sequences of Xenopus (Coffman et al., 1990, Science 249:1438–1441) and a human Notch homolog termed TAN-1 (Ellisen et al., 1991, Cell 66:649–661) have also been reported. Delta encodes a ~100 kd protein (we use "Delta" to denote DLZM, the protein product of the predominant zygotic and maternal transcripts; Kopczynski et al., 1988, Genes Dev. 2, 1723–1735) that has nine EGF-like repeats within its extracellular domain (Vassin et al., 1987, EMBO J. 6, 3431–3440; Kopczynski et al., 1988, Genes Dev. 2, 1723–1735). Although little is known about the functional significance of these repeats, the EGF-like motif has been found in a variety of proteins, including those involved in the blood clotting cascade (Furie and Furie, 1988, Cell 53, 505–518). In particular, this motif has been found in extracellular proteins such as the blood clotting factors IX and X (Rees et al., 1988, EMBO J. 7, 2053–2061; Furie and Furie, 1988, Cell 53, 505–518), in other Drosophila genes (Knust et al., 1987, EMBO J. 761–766; Rothberg et al., 1988, Cell 55, 1047–1059), and in some cell-surface receptor proteins, such as thrombomodulin (Suzuki et al., 1987, EMBO J. 6, 1891–1897) and LDL receptor (Sudhof et al., 1985, Science 228, 815–822). A protein binding site has been mapped to the EGF repeat domain in thrombomodulin and urokinase (Kurosawa et al., 1988, J. Biol. Chem 263, 5993–5996; Appella et al., 1987, J. Biol. Chem. 262, 4437–4440).

An intriguing array of interactions between Notch and Delta mutations has been described (Vassin, et al., 1985, J. Neurogenet. 2, 291–308; Shepard et al., 1989, Genetics 122, 429–438; Xu et al., 1990, Genes Dev., 4, 464–475). A number of genetic studies (summarized in Alton et al., 1989, Dev. Genet. 10, 261–272) has indicated that the gene dosages of Notch and Delta in relation to one another are crucial for normal development. A 50% reduction in the dose of Delta in a wild-type Notch background causes a broadening of the wing veins creating a "delta" at the base (Lindsley and Grell, 1968, Publication Number 627, Washington, D.C., Carnegie Institute of Washington). A similar phenotype is caused by a 50% increase in the dose of Notch in a wild-type Delta background (a "Confluens" phenotype; Welshons, 1965, Science 150, 1122–1129). This Delta phenotype is partially suppressed by a reduction in the Notch dosage. Work has shown that lethal interactions between alleles that correlate with alterations in the EGF-like repeats in Notch can be rescued by reducing the dose of Delta (Xu et al., 1990, Genes Dev. 4, 464–475). Xu et al. (1990, Genes Dev. 4, 464–475) found that null mutations at either Delta or mam suppress lethal interactions between heterozygous combinations of certain Notch alleles, known as the Abruptex (Ax) mutations. Ax alleles are associated with missense mutations within the EGF-like repeats of the Notch extracellular domain (Kelley et al., 1987, Cell 51, 539–548; Hartley et al., 1987, EMBO J. 6, 3407–3417).

Recent studies have shown that Notch and Delta, and Notch and Serrate, directly interact on the molecular level (Fehon et al., 1990, Cell 61:523–534; Rebay et al., 1991, Cell 67:687–699).

Notch is expressed on axonal processes during the outgrowth of embryonic neurons (Johansen et al., 1989, J. Cell Biol. 109:2427–2440; Kidd et al., 1989, Genes Dev. 3:1113–1129; Fehon et al., 1991, J. Cell Biol. 113:657–669).

A study has shown that certain Ax alleles of Notch can severely alter axon pathfinding during sensory neural outgrowth in the imaginal discs, although it is not yet known whether aberrant Notch expression in the axon itself or the epithelium along which it grows is responsible for this defect (Palka et al., 1990, Development 109, 167–175).

2.2. Cancer

A neoplasm, or tumor, is a neoplastic mass resulting from abnormal uncontrolled cell growth, which may cause swelling on the body surface, and which can be benign or malignant. Benign tumors generally remain localized. Malignant tumors are collectively termed cancers. The term "malignant" generally means that the tumor can invade and destroy neighboring body structures and spread to distant sites to cause death (for review, see Robbins and Angell, 1976, *Basic Pathology*, 2d Ed., W.B. Saunders Co., Philadelphia, pp. 68–122).

Effective treatment and prevention of cancer remains a long-felt need, and a major goal of biomedical research.

3. SUMMARY OF THE INVENTION

The present invention relates to therapeutic and diagnostic methods and compositions based on Notch proteins and nucleic acids. The invention provides for treatment of disorders of cell fate or differentiation by administration of a therapeutic compound of the invention. Such therapeutic compounds (termed herein "Therapeutics") include: Notch proteins and analogs and derivatives (including fragments) thereof; antibodies thereto; nucleic acids encoding the Notch proteins, analogs, or derivatives; Notch antisense nucleic acids; as well as toporythmic proteins and derivatives which bind to or otherwise interact with Notch proteins, and their encoding nucleic acids and antibodies. In a preferred embodiment, a Therapeutic of the invention is administered to treat a cancerous condition, or to prevent progression from a pre-neoplastic or non-malignant state into a neoplastic or a malignant state. In other specific embodiments, a Therapeutic of the invention is administered to treat a nervous system disorder or to promote tissue regeneration and repair.

In one embodiment, Therapeutics which antagonize, or inhibit, Notch function (hereinafter "Antagonist Therapeutics") are administered for therapeutic effect; disorders which can be thus treated can be identified by in vitro assays such as described in Section 5.1, infra. Such Antagonist Therapeutics include but are not limited to Notch antisense nucleic acids, anti-Notch neutralizing antibodies, and competitive inhibitors of Notch protein-protein interactions (e.g., a protein comprising Notch ELR-11 and ELR-12 and derivatives thereof), all as detailed infra.

In another embodiment, Therapeutics which promote Notch function (hereinafter "Agonist Therapeutics") are administered for therapeutic effect; disorders which can thus be treated can be identified by in vitro assays such as described in Section 5.1, infra. Such Agonist Therapeutics include but are not limited to Notch proteins and derivatives thereof comprising the intracellular domain, and proteins that interact with Notch (e.g., a protein comprising a Delta sequence homologous to Drosophila Delta amino acids 1–230 (see FIG. 1 and SEQ ID NO:2), or comprising a Serrate sequence homologous to Drosophila Serrate amino acids 79–282 (see FIG. 5 and SEQ ID NO:4)).

Disorders of cell fate, in particular hyperproliferative (e.g., cancer) or hypoproliferative disorders, involving aberrant or undesirable levels of expression or activity of Notch protein can be diagnosed by detecting such levels, as described more fully infra.

In a preferred aspect, a Therapeutic of the invention is a protein consisting of at least a fragment (termed herein "adhesive fragment") of the proteins encoded by toporythmic genes which mediates binding to Notch proteins or adhesive fragments thereof. Toporythmic genes, as used herein, shall mean the genes Notch, Delta, and Serrate, as well as other members of the Delta/Serrate family which may be identified by virtue of sequence homology or genetic interaction, and in general, members of the "Notch cascade" or the "Notch group" of genes, which are identified by molecular interactions (e.g., binding in vitro) or genetic interactions (as detected phenotypically, e.g., in Drosophila).

In another aspect, the invention is directed to human Notch proteins; in particular, that encoded by the hN homolog, and proteins comprising the extracellular domain of the protein and subsequences thereof. Nucleic acids encoding the foregoing, and recombinant cells are also provided.

The nucleic acid and amino acid sequences and antibodies thereto of the invention can be used for the detection and quantitation of mRNA for human Notch and Delta and adhesive molecules, to study expression thereof, to produce human Notch and Delta and adhesive sequences, in the study and manipulation of differentiation processes.

3.1. Definitions

As used herein, the following terms shall have the meanings indicated:

AA=amino acid

EGF=epidermal growth factor

ELR=EGF-like (homologous) repeat

IC=intracellular

PCR=polymerase chain reaction

As used herein, underscoring the name of a gene shall indicate the gene, in contrast to its encoded protein product which is indicated by the name of the gene in the absence of any underscoring. For example, "Notch" shall mean the Notch gene, whereas "Notch" shall indicate the protein product of the Notch gene.

4. DESCRIPTION OF THE FIGURES

FIG. 1. Primary Nucleotide Sequence of the Delta cDNA Dl1 (SEQ ID NO:1) and Delta amino acid sequence (SEQ ID NO:2). The DNA sequence of the 5'-3' strand of the Dl1 cDNA is shown, which contains a number of corrections in comparison to that presented in Kopczynkski et al. (1988, Genes Dev. 2:1723–1735).

Figure 2B:
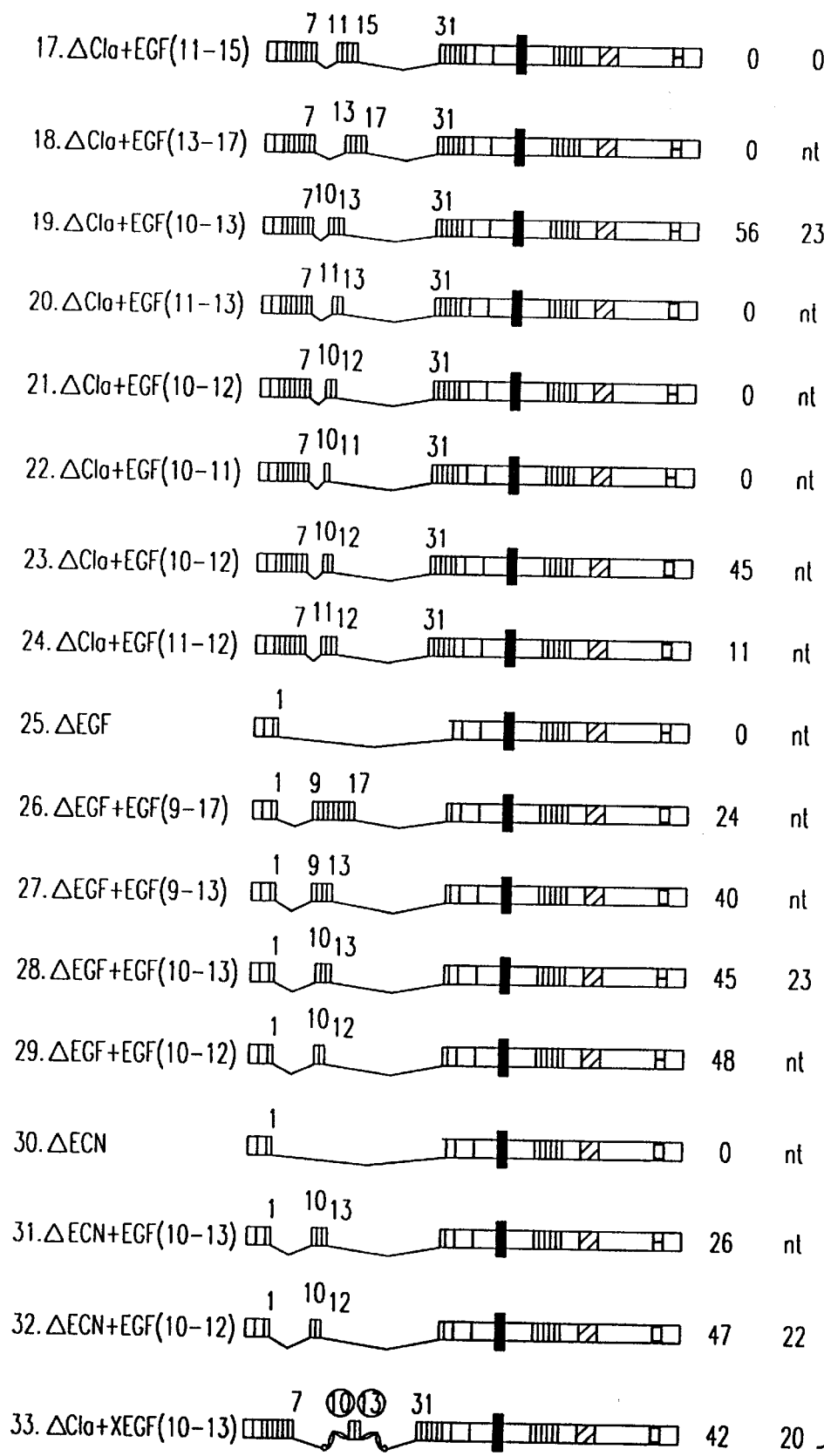

FIG. 2. Notch Expression Constructs and the Deletion Mapping of the Delta/Serrate Binding Domain. S2 cells in log phase growth were transiently transfected with the series of expression constructs shown; the drawings represent the predicted protein products of the various Notch deletion mutants created. All expression constructs were derived from construct #1 pMtNMg. Transiently transfected cells were mixed with Delta expressing cells from the stably transformed line L49-6-7 or with transiently transfected Serrate expressing cells, induced with $CuSO_4$, incubated under aggregation conditions and then scored for their ability to aggregate using specific antisera and immunofluorescence microscopy. Aggregates were defined as clusters of four or more cells containing both Notch and Delta/Serrate expressing cells. The values given for % Aggregation refer to the percentage of all Notch expressing cells found in such clusters either with Delta (Dl) (left column) or with Serrate (Ser) (right column). The various Notch deletion constructs are represented diagrammatically with splice lines indicating the ligation junctions. Each EGF repeat is denoted as a stippled rectangular box and numbers of the EGF repeats on either side of a ligation junction are noted. At the ligation junctions, partial EGF repeats produced by the various deletions are denoted by open boxes and closed brackets (for example see #23 ΔCla+EGF(10–12)). Constructs #3–13 represent the ClaI deletion series. As diagrammed, four of the ClaI sites, in repeats 7, 9, 17 and 26, break the repeat in the middle, immediately after the third cysteine (denoted by open box repeats; see FIG. 3 for further clarification), while the fifth and most 3' site breaks neatly between EGF repeats 30 and 31 (denoted by closed box repeat 31; again see FIG. 3). In construct #15 split, EGF repeat 14 which carries the slit point mutation, is drawn as a striped box. In construct #33 ΔCla+XEGF(10–13), the Xenopus Notch derived EGF repeats are distinguished from Drosophila repeats by a different pattern of shading. SP, signal peptide; EGF, epidermal growth factor repeat; N, Notch/lin-12 repeat; TM, transmembrane domain; cdc10, cdc10/ankyrin repeats; PA, putative nucleotide binding consensus sequence; opa, polyglutamine stretch termed opa; Dl, Delta; Ser, Serrate.

Figure 3:
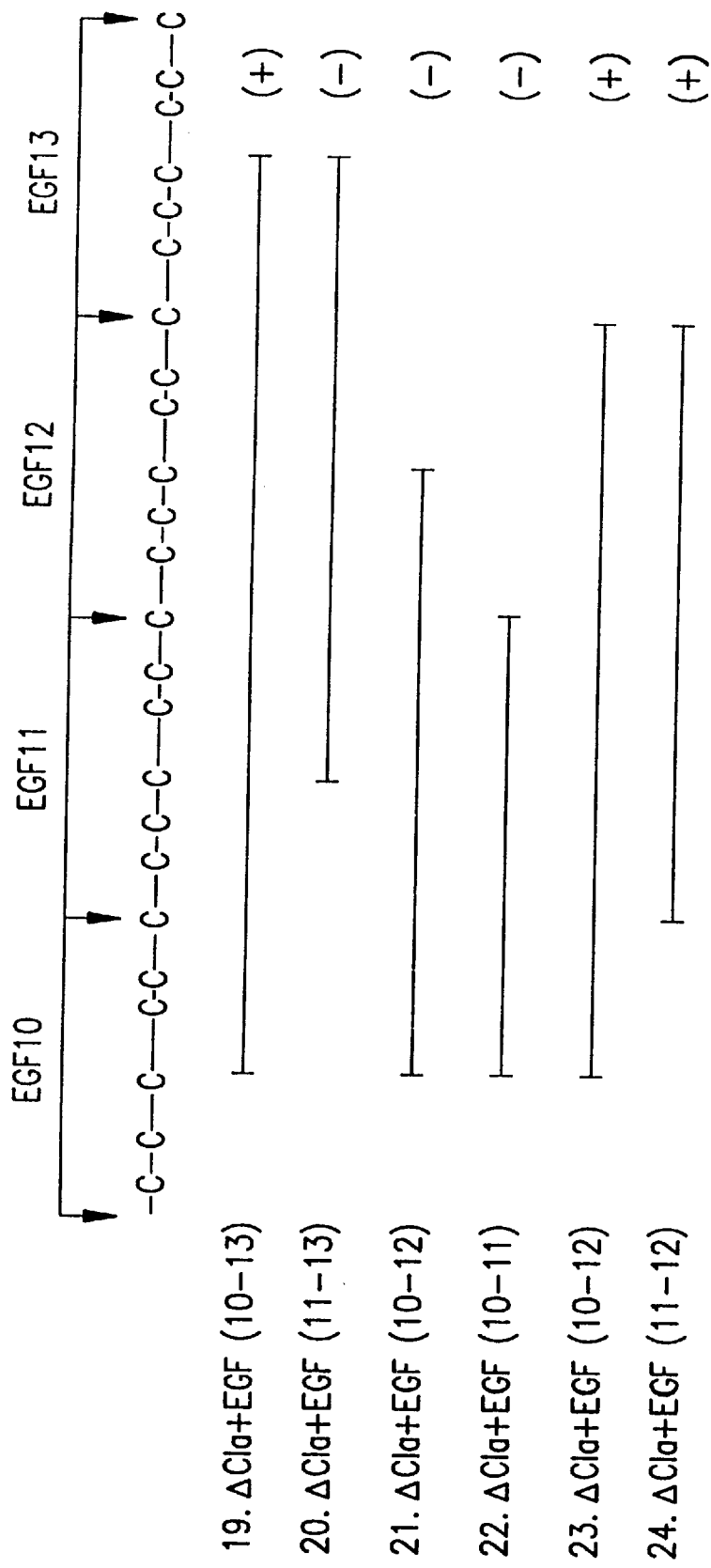

FIG. 3. Detailed Structure of Notch Deletion Constructs #19–24: Both EGF Repeats 11 and 12 are Required for Notch-Delta Aggregation. EGF repeats 10–13 are diagrammed at the top showing the regular spacing of the six cysteine residues (C). PCR products generated for these constructs (names and numbers as given in FIG. 2) are represented by the heavy black lines and the exact endpoints are noted relative to the various EGF repeats. Ability to aggregate with Delta is recorded as (+) or (−) for each construct. The PCR fragments either break the EGF repeats in the middle, just after the third cysteine in the same place as four out of the five ClaI sites, or exactly in between two repeats in the same place as the most C-terminal ClaI site.

Figure 4:
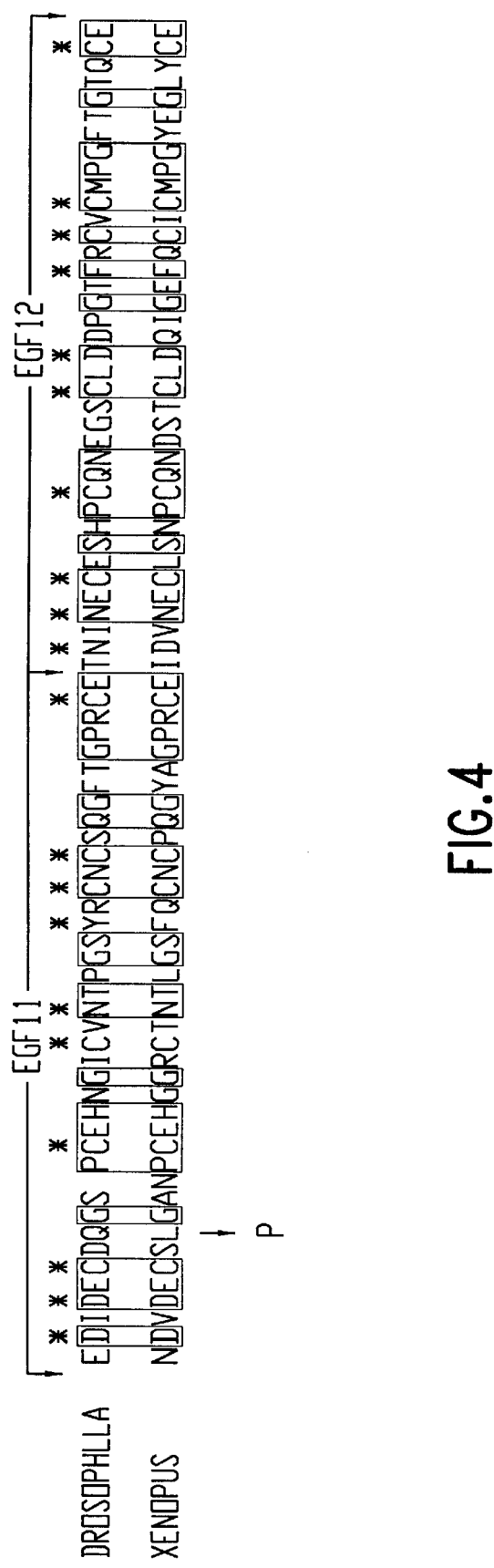

FIG. 4. Comparison of Amino Acid Sequence of EGF Repeats 11 and 12 from Drosophila and Xenopus Notch. The amino acid sequence of EGF repeats 11 and 12 of Drosophila Notch (SEQ ID NO:14) (Wharton et al., 1985, Cell 43:567–581; Kidd et al., 1986, Mol. Cell Biol. 6:3094–3108) is aligned with that of the same two EGF repeats from Xenopus Notch (SEQ ID NO:15) (Coffman et al., 1990, Science 249:1438–1441). Identical amino acids are boxed. The six conserved cysteine residues of each EGF repeat and the Ca$^{++}$ binding consensus residues (Rees et al., 1988, EMBO J. 7:2053–2061) are marked with an asterisk (*). The leucine to proline change found in the Xenopus PCR clone that failed to aggregate is noted underneath.

FIG. 5. Nucleic Acid Sequence Homologies Between Serrate and Delta. A portion of the Drosophila Serrate nucleotide sequence (SEQ ID NO:3), with the encoded Serrate protein sequence (SEQ ID NO:4) written below (Fleming et al., 1990, Genes & Dev. 4:2188–2201 at 2193–94) is shown. The four regions showing high sequence homology with the Drosophila Delta sequence are numbered above the line and indicated by brackets. The total region of homology spans nucleotide numbers 627 through 1290 of the Serrate nucleotide sequence (numbering as in FIG. 4 of Fleming et al., 1990, Genes & Dev. 4:2188–2201).

Figure 6:
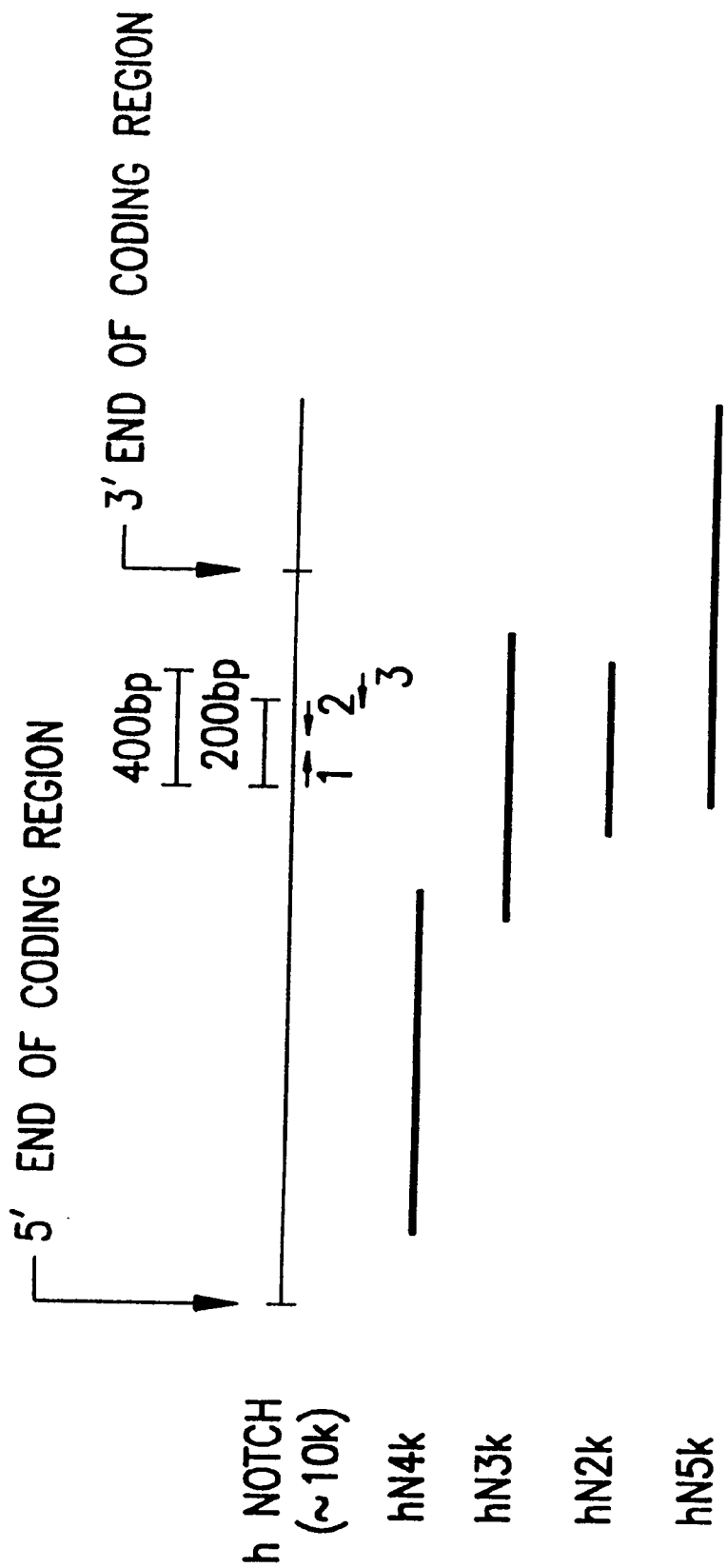

FIG. 6. Schematic Diagram of Human Notch Clones. A schematic diagram of human Notch is shown. Heavy boldface lines below the diagram show that portion of the Notch sequence contained in each of the four cDNA clones. The location of the primers used in PCR, and their orientation, are indicated by arrows.

Figure 7:
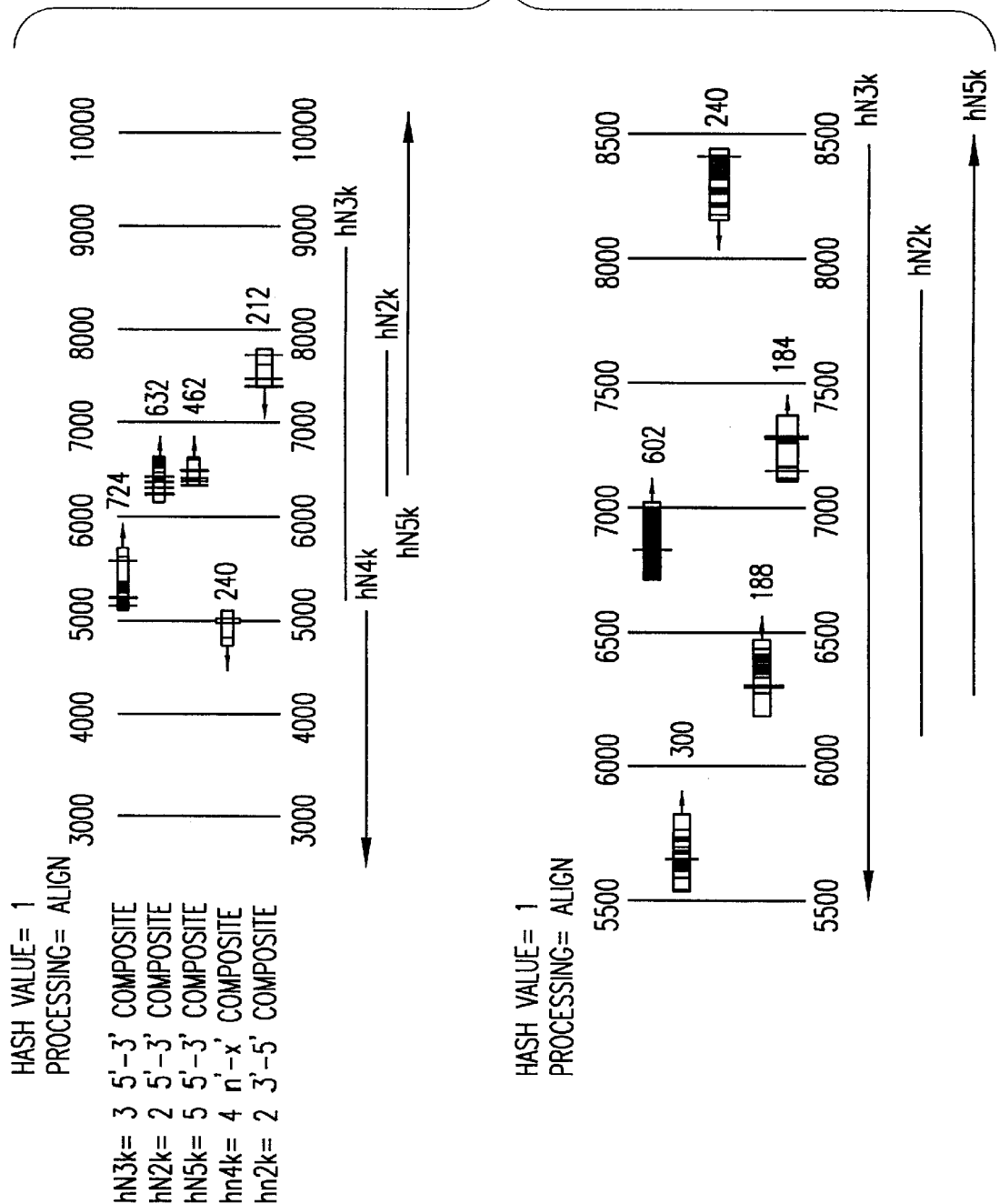

FIG. 7. Human Notch Sequences Aligned with Drosophila Notch Sequence. Numbered vertical lines correspond to Drosophila Notch coordinates. Horizontal lines below each map show where clones lie relative to stretches of sequence (thick horizontal lines).

FIG. 8. Nucleotide Sequences of Human Notch Contained in Plasmid cDNA Clone hN2k. FIG. 8A: The DNA sequence (SEQ ID NO:5) of a portion of the human Notch insert is shown, starting at the EcoRI site at the 3' end, and proceeding in the 3' to 5' direction. FIG. 8B: The DNA sequence (SEQ ID NO:6) of a portion of the human Notch insert is shown, starting at the EcoRI site at the 5' end, and proceeding in the 5' to 3' direction. FIG. 8C: The DNA sequence (SEQ ID NO:7) of a portion of the human Notch insert is shown, starting 3' of the sequence shown in FIG. 8B, and proceeding in the 5' to 3' direction. The sequences shown are tentative, subject to confirmation by determination of overlapping sequences.

FIG. 9. Nucleotide Sequences of Human Notch Contained in Plasmid cDNA clone hN4k. FIG. 9A: The DNA sequence (SEQ ID NO:8) of a portion of the human Notch insert is shown, starting at the EcoRI site at the 5' end, and proceeding in the 5' to 3' direction. FIG. 9B: The DNA sequence (SEQ ID NO:9) of a portion of the human Notch insert is shown, starting near the 3' end, and proceeding in the 3' to 5' direction. The sequences shown are tentative, subject to confirmation by determination of overlapping sequences.

FIG. 10. DNA (SEQ ID NO:10) and Amino Acid (SEQ ID NO:11) Sequences of Human Notch Contained in Plasmid cDNA Clone hN3k.

FIG. 11. DNA (SEQ ID NO:12) and Amino Acid (SEQ ID NO:13) Sequences of Human Notch Contained in Plasmid cDNA Clone hN5k.

Figure 12A:
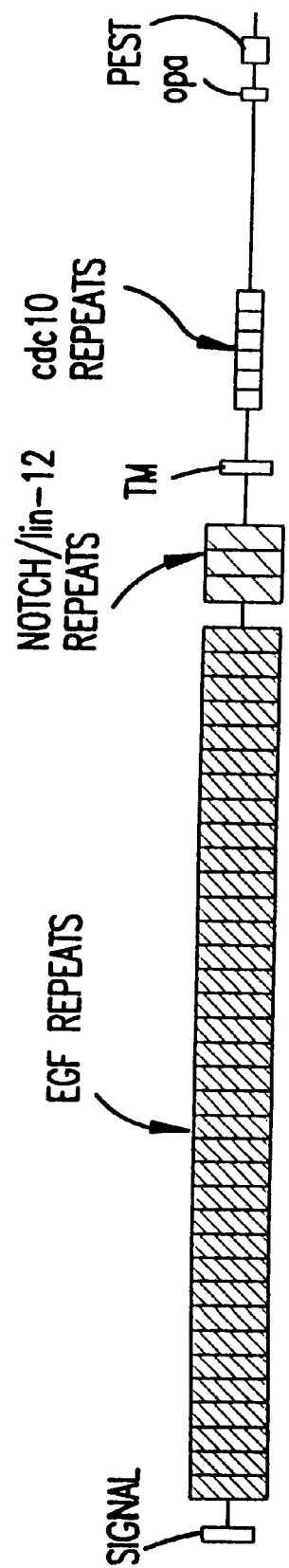
Figure 12B:
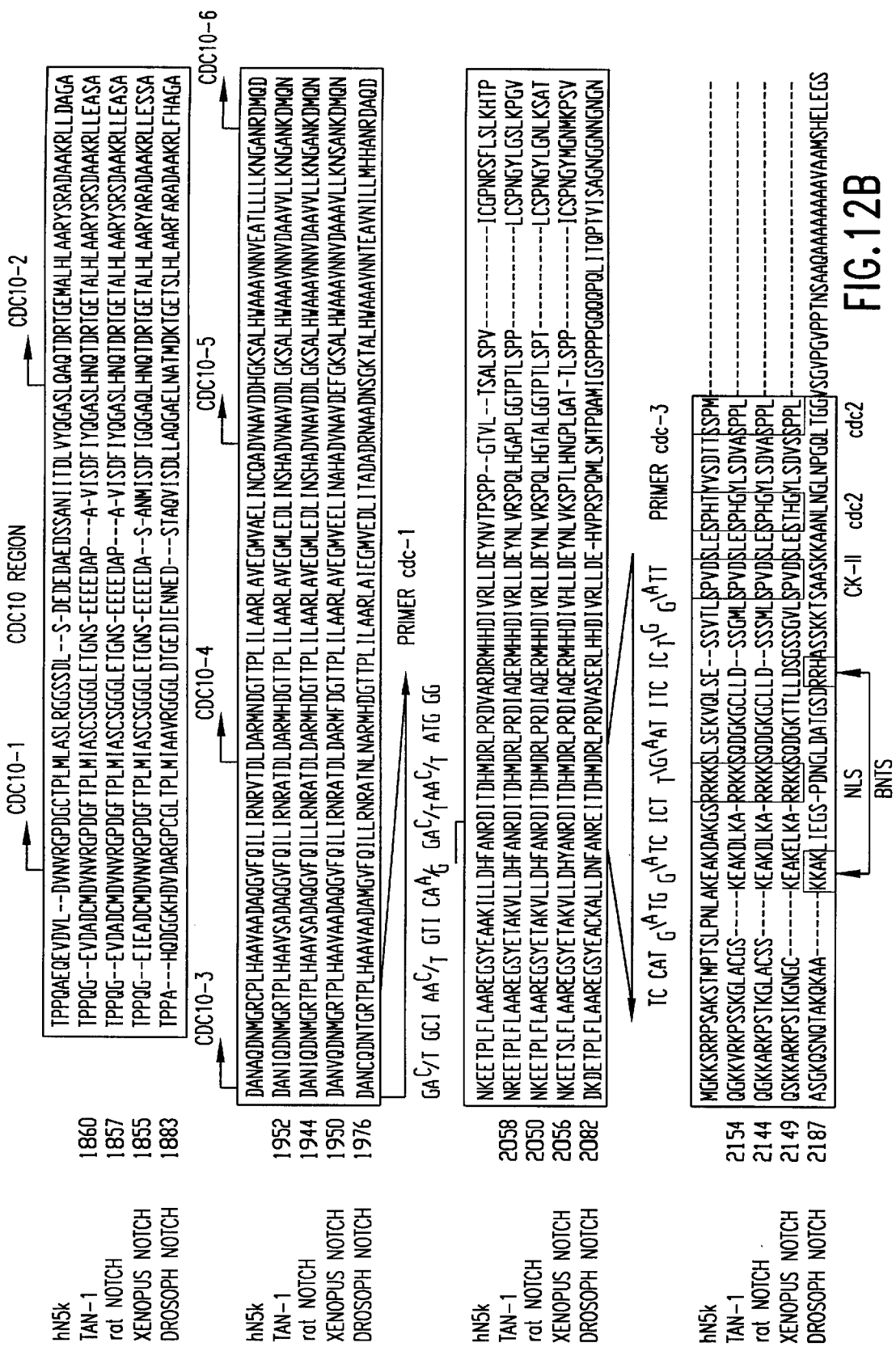
Figure 12C:
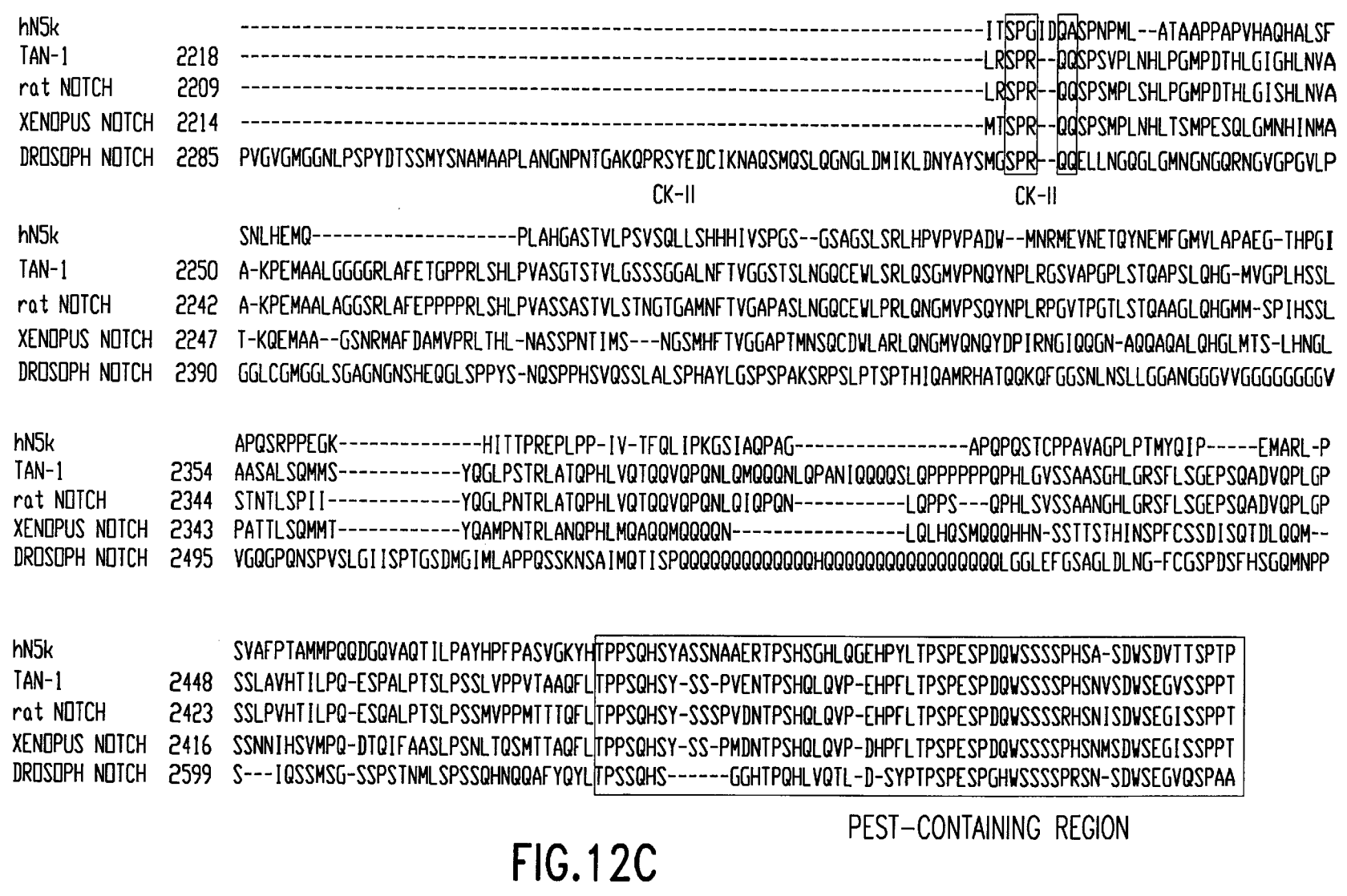

FIG. 12. Comparison of hN5k With Other Notch Homologs. FIG. 12A. Schematic representation of Drosophila Notch. Indicated are the signal sequence (signal), the 36 EGF-like repeats, the three Notch/lin-12 repeats, the transmembrane domain (TM), the six CDC10 repeats, the OPA repeat, and the PEST (proline, glutamic acid, serine, threonine)-rich region. FIG. 12B. Alignment of the deduced amino acid sequence of hN5k with sequences of other Notch homologs. Amino acids are numbered on the left side. The cdc10 and PEST-rich regions are both boxed, and individual cdc10 repeats are marked. Amino acids which are identical in three or more sequences are highlighted. The primers used to clone hN5k are indicated below the sequences from which they were designed. The nuclear localization sequence (NLS), casein kinase II (CKII), and cdc2 kinase (cdc2) sites of the putative CcN motif of the vertebrate Notch homologs are boxed. The possible bipartite nuclear targeting sequence (BNTS) and proximal phosphorylation sites of Drosophila Notch are also boxed.

FIG. 13. Aligned amino acid sequences of Notch proteins of various species. humN: the human Notch protein encoded by the hN homolog (contained in part in plasmid hN5k) (SEQ ID NO:19). TAN-1: the human Notch protein encoded by the TAN-1 homolog (SEQ ID NO:20) (the sequence shown is derived partly from our own work and partly from the TAN-1 sequence as published by Ellisen et al., 1991, Cell 66:649–661); Xen N: Xenopus Notch protein (Coffman et al., 1990, Science 249:1438–1441). Dros N: Drosophila Notch protein (Wharton et al., 1985, Cell 43:567–581). Structural domains are indicated.

Figure 14:
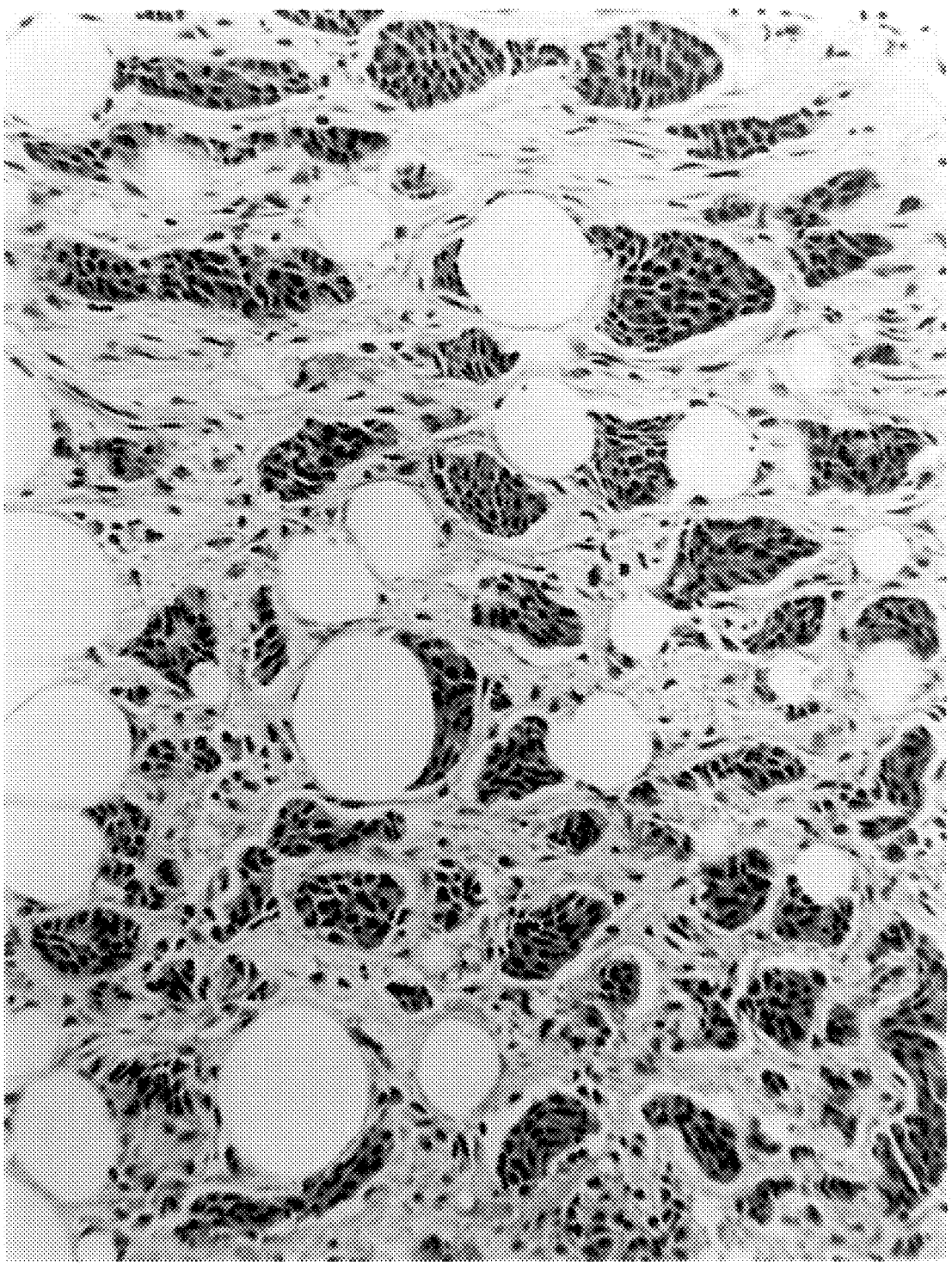

FIG. 14. Immunocytochemical staining of breast cancer tissue from a human patient. Malignant breast tissue in a sample obtained from a human patient was embedded in a paraffin section, and subjected to immunocytochemical staining with anti-human Notch monoclonal antibody P4, directed against the TAN-1 protein. Non-malignant breast tissue exhibited much less staining (not shown).

Figure 15A:
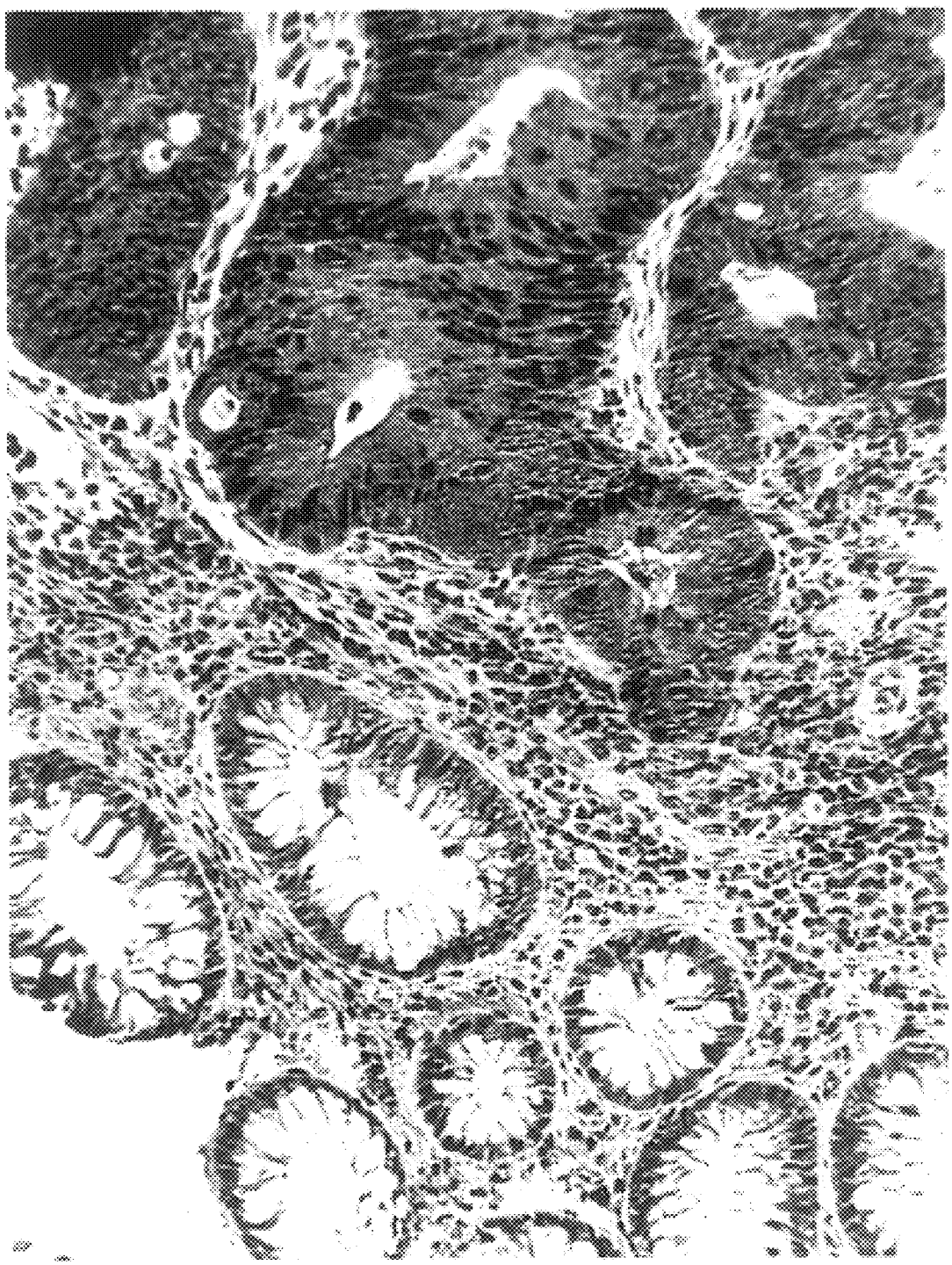

FIGS. 15A&B. Immunocytochemical staining of colon tissue from a human patient with colon cancer. A colon tissue sample obtained from a patient with colon cancer was embedded in a paraffin section, and subjected to immunocytochemical staining with anti-human Notch monoclonal antibody P1, directed against the hN-encoded protein. Areas of increased staining are those areas in which malignant cells are present, as determined by cell morphology.

Figure 16A:
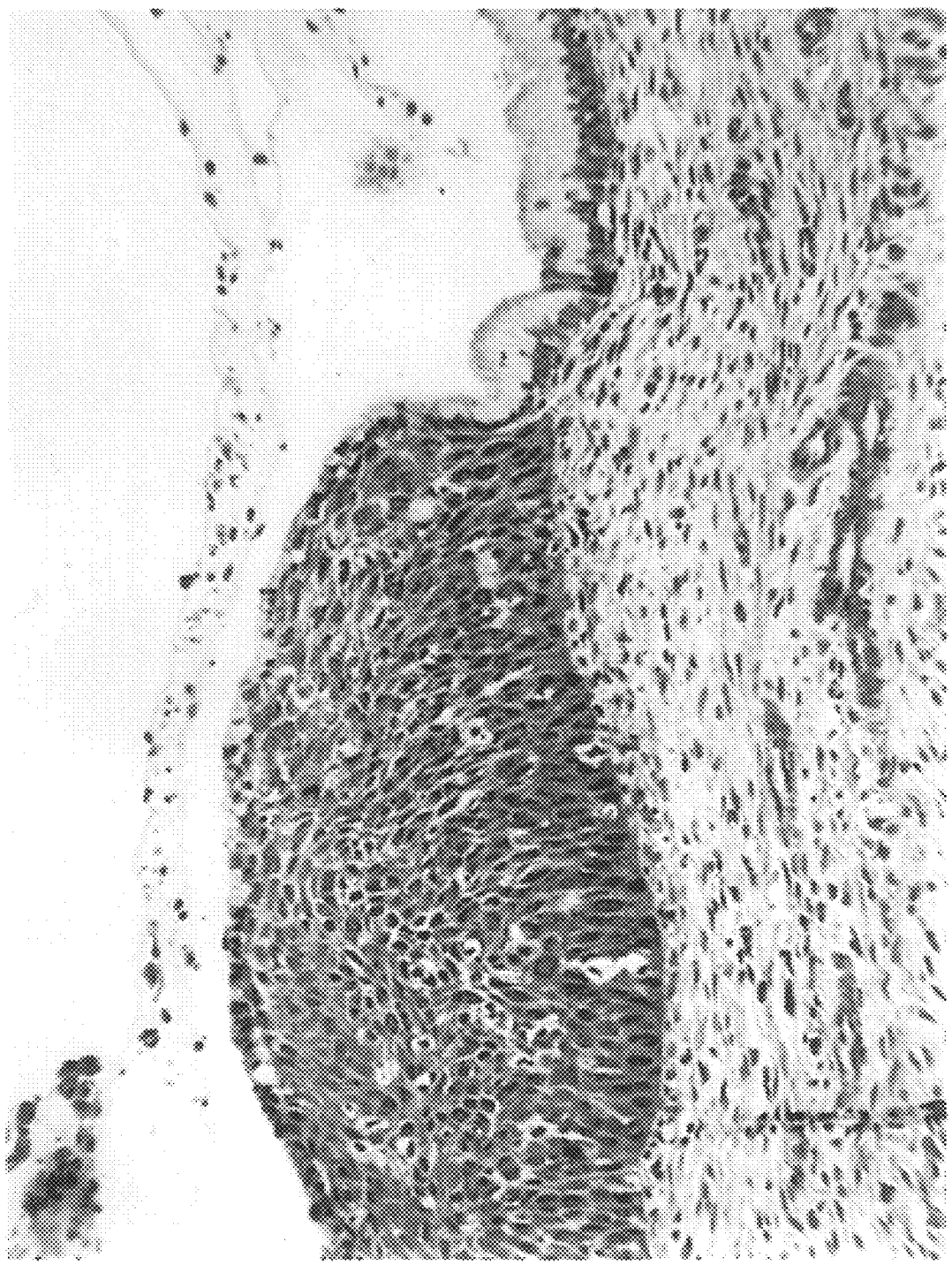
Figure 16B:

FIG. 16. Immunocytochemical staining of cervical tissue. Human tissue samples were obtained, containing cancer of the cervix (FIG. 16A) or normal cervical epithelium (FIG. 16B) from the same patient, embedded in a paraffin section, and subjected to immunocytochemical staining with anti-human Notch monoclonal antibody directed against the TAN-1 protein. Areas containing malignant cells (as determined by morphology) exhibited increasing staining relative to non-malignant cells. Among non-malignant cells, connective tissue and the basal layer of the epithelium (containing stem cells) stained with the anti-Notch antibody.

FIG. 17. DNA (SEQ ID NO:21) and encoded amino acid sequence (contained in SEQ ID NO:19) of human Notch homolog hN. The entire DNA coding sequence is presented (as well as noncoding sequence), with the exclusion of that encoding the initiator Met.

5. DETAILED DESCRIPTION OF THE INVENTION

The present invention relates to therapeutic and diagnostic methods and compositions based on Notch proteins and nucleic acids. The invention provides for treatment of disorders of cell fate or differentiation by administration of a therapeutic compound of the invention. Such therapeutic compounds (termed herein "Therapeutics") include: Notch proteins and analogs and derivatives (including fragments) thereof; antibodies thereto; nucleic acids encoding the Notch proteins, analogs, or derivatives; Notch antisense nucleic acids; as well as toporythmic proteins and derivatives and analogs thereof which bind to or otherwise interact with Notch proteins, and their encoding nucleic acids and antibodies. Also included are proteins and derivatives and analogs thereof which are capable of inhibiting the interactions of a Notch protein with another toporythmic protein (e.g. Delta, Serrate). In a preferred embodiment, a Therapeutic of the invention is administered to treat a cancerous condition, or to prevent progression from a pre-neoplastic or non-malignant state (e.g., metaplastic condition) into a neoplastic or a malignant state. In another specific embodiment, a Therapeutic of the invention is administered to treat a nervous system disorder, such as nerve injury or a degenerative disease. In yet another specific embodiment, a Therapeutic of the invention is administered to promote tissue regeneration and repair for treatment of various conditions.

In one embodiment, Therapeutics which antagonize, or inhibit, Notch function (hereinafter "Antagonist Therapeutics") are administered for therapeutic effect; disorders which can be thus treated can be identified by in vitro assays such as described in Section 5.1, infra. Such Antagonist Therapeutics include but are not limited to Notch antisense nucleic acids, anti-Notch neutralizing antibodies, competitive inhibitors of Notch protein-protein interactions (e.g., a protein comprising Notch ELR-11 and ELR-12), and molecules which interfere with notch intracellular function such as that mediated by the cdc10 repeats, as detailed infra.

In another embodiment, Therapeutics which promote Notch function (hereinafter "Agonist Therapeutics") are administered for therapeutic effect; disorders which can thus be treated can be identified by in vitro assays such as described in Section 5.1, infra. Such Agonist Therapeutics include but are not limited to Notch proteins and derivatives thereof comprising the intracellular domain, Notch nucleic acids encoding the foregoing, and proteins comprising toporythmic protein domains that interact with Notch (e.g., a protein comprising an extracellular domain of a Delta protein or a Delta sequence homologous to Drosophila Delta amino acids 1–230 (see FIG. 1 and SEQ ID NO:2), or comprising a Serrate sequence homologous to Drosophila Serrate amino acids 79–282 (see FIG. 5 and SEQ ID NO:4)).

Disorders of cell fate, in particular precancerous conditions such as metaplasia and dysplasia, and hyperproliferative (e.g., cancer) or hypoproliferative disorders, involving aberrant or undesirable levels of expression or activity of Notch protein can be diagnosed by detecting such levels, as described more fully infra.

In a preferred aspect, a Therapeutic of the invention is a protein consisting of at least a fragment (termed herein "adhesive fragment") of the proteins encoded by toporythmic genes which mediates binding to Notch proteins or adhesive fragments thereof. Toporythmic genes, as used herein, shall mean the genes Notch, Delta, and Serrate, as well as other members of the Delta/Serrate family which may be identified by virtue of sequence homology or genetic interaction, and, more generally, members of the "Notch cascade" or the "Notch group" of genes, which are identified by molecular interactions (e.g., binding in vitro) or genetic interactions (as detected phenotypically, e.g., in Drosophila).

The nucleic acid and amino acid sequences and antibodies thereto of the invention can be used for the detection and quantitation of mRNA for human Notch and Delta and adhesive molecules, to study expression thereof, to produce human Notch and Delta and adhesive sequences, in the study and manipulation of differentiation processes.

For clarity of disclosure, and not by way of limitation, the detailed description of the invention is divided into the following subsections:

(i) Therapeutic Uses;

(ii) Prophylactic Uses;

(iii) Demonstration of Therapeutic or Prophylactic Utility;

(iv) Therapeutic/Prophylactic Administration and Compositions;

(v) Antisense Regulation of Notch Expression;

(vi) Diagnostic Utility;

(vii) Notch Nucleic Acids;

(viii) Recombinant Production of Protein Therapeutics;

(ix) Derivatives and Analogs of Notch and Other Toporythmic Proteins;

(x) Assays of Notch Proteins, Derivatives and Analogs; and (xi) Antibodies to Notch Proteins, Derivatives and Analogs.

5.1. Therapeutic Uses

As stated supra, the Antagonist Therapeutics of the invention are those Therapeutics which antagonize, or inhibit, a Notch function. Such Antagonist Therapeutics are most preferably identified by use of known convenient in vitro assays, e.g., based on their ability to inhibit binding of Notch to other proteins (see Sections 6–8 herein), or inhibit any known Notch function as assayed in vitro, although genetic assays (e.g., in Drosophila) may also be employed. In a preferred embodiment, the Antagonist Therapeutic is a protein or derivative thereof comprising a functionally active fragment such as an adhesive fragment of Notch. In specific embodiments, such an Antagonist Therapeutic may be those adhesive proteins encoded by the appropriate constructs described in Sections 6 and 7 infra, or proteins comprising the Notch extracellular region, in particular ELR-11 and ELR-12, or an antibody thereto, or an analog/competitive inhibitor of a Notch intracellular signal-transducing region, a nucleic acid capable of expressing a Notch adhesive fragment, or a Notch antisense nucleic acid (see Section 5.5 herein). It should be noted that in certain instances, a Notch adhesive fragment (or possibly other presumed Antagonist Therapeutics) may alternatively act as an Agonist Therapeutic, depending on the developmental history of the tissue being exposed to the Therapeutic; preferably, suitable in vitro or in vivo assays, as described infra, should be utilized to determine the effect of a specific Therapeutic and whether its administration is indicated for treatment of the affected tissue.

In another embodiment of the invention, a nucleic acid containing a portion of a Notch gene is used, as an Antagonist Therapeutic, to promote Notch inactivation by homologous recombination (Koller and Smithies, 1989, Proc. Natl. Acad. Sci. USA 86:8932–8935; Zijlstra et al., 1989, Nature 342:435–438).

The Agonist Therapeutics of the invention, as described supra, promote Notch function. Such Agonist Therapeutics include but are not limited to proteins and derivatives comprising the portions of toporythmic proteins such as Delta or Serrate that mediate binding to Notch, and nucleic acids encoding the foregoing (which can be administered to express their encoded products in vivo). In a specific embodiment, such a portion of Delta is *D. melanogaster* Delta amino acids 1–230 (SEQ ID NO:1) or a portion of a human Delta most homologous thereto. In another specific embodiment, such a portion of Serrate is *D. melanogaster* Serrate amino acids 79–282 (SEQ ID NO:5), or a portion of a human Serrate most homologous thereto. In other specific embodiments, such a portion of Delta or Serrate is the extracellular portion of such protein.

Further descriptions and sources of Therapeutics of the inventions are found in Sections 5.4 through 5.8 herein.

The Agonist and Antagonist Therapeutics of the invention have therapeutic utility for disorders of cell fate. The Agonist Therapeutics are administered therapeutically (including prophylactically): (1) in diseases or disorders involving an absence or decreased (relative to normal, or desired) levels of Notch function, for example, in patients where Notch protein is lacking, genetically defective, biologically inactive or underactive, or underexpressed; and (2) in diseases or disorders wherein in vitro (or in vivo) assays (see infra) indicate the utility of Notch agonist administration. The absence or decreased levels in Notch function can be readily detected, e.g., by obtaining a patient tissue sample (e.g., from biopsy tissue) and assaying it in vitro for protein levels, structure and/or activity of the expressed Notch protein. Many methods standard in the art can be thus employed, including but not limited to immunoassays to detect and/or visualize Notch protein (e.g., Western blot, immunoprecipitation followed by sodium dodecyl sulfate polyacrylamide gel electrophoresis, immunocytochemistry, etc.; see also those assays listed in Section 5.6, infra), and/or hybridization assays to detect Notch expression by detecting and/or visualizing Notch mRNA (e.g., Northern assays, dot blots, in situ hybridization, etc.)

In vitro assays which can be used to determine whether administration of a specific Agonist Therapeutic or Antagonist Therapeutic is indicated, include in vitro cell culture assays in which a patient tissue sample is grown in culture, and exposed to or otherwise administered a Therapeutic, and the effect of such Therapeutic upon the tissue sample is observed. In one embodiment, where the patient has a malignancy, a sample of cells from such malignancy is plated out or grown in culture, and the cells are then exposed to a Therapeutic. A Therapeutic which inhibits survival or growth of the malignant cells (e.g., by promoting terminal differentiation) is selected for therapeutic use in vivo. Many assays standard in the art can be used to assess such survival and/or growth; for example, cell proliferation can be assayed by measuring $^3$H-thymidine incorporation, by direct cell count, by detecting changes in transcriptional activity of known genes such as proto-oncogenes (e.g.,fos, myc) or cell cycle markers; cell viability can be assessed by trypan blue staining, differentiation can be assessed visually based on changes in morphology, etc. In a specific aspect, the malignant cell cultures are separately exposed to (1) an Agonist Therapeutic, and (2) an Antagonist Therapeutic; the result of the assay can indicate which type of Therapeutic has therapeutic efficacy.

In another embodiment, a Therapeutic is indicated for use which exhibits the desired effect, inhibition or promotion of cell growth, upon a patient cell sample from tissue having or suspected of having a hyper- or hypoproliferative disorder, respectively. Such hyper- or hypoproliferative disorders include but are not limited to those described in Sections 5.1.1 through 5.1.3 infra.

In another specific embodiment, a Therapeutic is indicated for use in treating nerve injury or a nervous system degenerative disorder (see Section 5.1.2) which exhibits in vitro promotion of nerve regeneration/neurite extension from nerve cells of the affected patient type.

In addition, administration of an Antagonist Therapeutic of the invention is also indicated in diseases or disorders determined or known to involve a Notch dominant activated phenotype ("gain of function" mutations.) Administration of an Agonist Therapeutic is indicated in diseases or disorders determined or known to involve a Notch dominant negative phenotype ("loss of function" mutations). We have investigated the functions of various structural domains of the Notch protein in vivo, by ectopically expressing a series of Drosophila Notch deletion mutants under the hsp70 heat-shock promoter, as well as eye-specific promoters. Two classes of dominant phenotypes were observed, one suggestive of Notch loss-of function mutations and the other of Notch gain-of-function mutations. Dominant "activated" phenotypes resulted from overexpression of a protein lacking most extracellular sequences, while dominant "negative" phenotypes resulted from overexpression of a protein lacking most intracellular sequences. Our results indicate that Notch functions as a receptor whose extracellular domain mediates ligand-binding, resulting in the transmission of developmental signals by the cytoplasmic domain. The phenotypes observed also suggested that the cdc10/ankyrin repeat region within the intracellular domain plays an essential role in Notch mediated signal transduction events (intracellular function).

In various specific embodiments, in vitro assays can be carried out with representative cells of cell types involved in a patient's disorder, to determine if a Therapeutic has a desired effect upon such cell types.

In another embodiment, cells of a patient tissue sample suspected of being pre-neoplastic are similarly plated out or grown in vitro, and exposed to a Therapeutic. The Therapeutic which results in a cell phenotype that is more normal (i.e., less representative of a pre-neoplastic state, neoplastic state, malignant state, or transformed phenotype) is selected for therapeutic use. Many assays standard in the art can be used to assess whether a pre-neoplastic state, neoplastic state, or a transformed or malignant phenotype, is present (see Section 5.2.1). For example, characteristics associated with a transformed phenotype (a set of in vitro characteristics associated with a tumorigenic ability in vivo) include a more rounded cell morphology, looser substratum attachment, loss of contact inhibition, loss of anchorage dependence, release of proteases such as plasminogen activator, increased sugar transport, decreased serum requirement, expression of fetal antigens, disappearance of the 250,000 dalton surface protein, etc. (see Luria et al., 1978, *General Virology*, 3d Ed., John Wiley & Sons, New York pp. 436–446).

In other specific embodiments, the in vitro assays described supra can be carried out using a cell line, rather than a cell sample derived from the specific patient to be treated, in which the cell line is derived from or displays characteristic(s) associated with the malignant, neoplastic or pre-neoplastic disorder desired to be treated or prevented, or is derived from the neural or other cell type upon which an effect is desired, according to the present invention.

The Antagonist Therapeutics are administered therapeutically (including prophylactically): (1) in diseases or disorders involving increased (relative to normal, or desired) levels of Notch function, for example, where the Notch protein is overexpressed or overactive; and (2) in diseases or disorders wherein in vitro (or in vivo) assays indicate the utility of Notch antagonist administration. The increased levels of Notch function can be readily detected by methods such as those described above, by quantifying protein and/or RNA. In vitro assays with cells of patient tissue sample or the appropriate cell line or cell type, to determine therapeutic utility, can be carried out as described above.

5.1.1. Malignancies

Malignant and pre-neoplastic conditions which can be tested as described supra for efficacy of intervention with Antagonist or Agonist Therapeutics, and which can be treated upon thus observing an indication of therapeutic utility, include but are not limited to those described below in Sections 5.1.1 and 5.2.1.

Malignancies and related disorders, cells of which type can be tested in vitro (and/or in vivo), and upon observing the appropriate assay result, treated according to the present invention, include but are not limited to those listed in Table 1 (for a review of such disorders, see Fishman et al., 1985, *Medicine*, 2d Ed., J.B. Lippincott Co., Philadelphia):

TABLE 1

MALIGNANCIES AND RELATED DISORDERS

Leukemia
  acute leukemia
    acute lymphocytic leukemia
    acute myelocytic leukemia
      myeloblastic
      promyelocytic
      myelomonocytic
      monocytic
      erythroleukemia
  chronic leukemia
    chronic myelocytic (granulocytic) leukemia
    chronic lymphocytic leukemia
Polycythemia vera
Lymphoma
  Hodgkin's disease
  non-Hodgkin's disease TABLE 1-continued

MALIGNANCIES AND RELATED DISORDERS

Multiple myeloma
Waldenström's macroglobulinemia
Heavy chain disease
Solid tumors
  sarcomas and carcinomas
    fibrosarcoma
    myxosarcoma
    liposarcoma
    chondrosarcoma
    osteogenic sarcoma
    chordoma
    angiosarcoma
    endotheliosarcoma
    lymphangiosarcoma
    lymphangioendotheliosarcoma
    synovioma
    mesothelioma
    Ewing's tumor
    leiomyosarcoma
    rhabdomyosarcoma
    colon carcinoma
    pancreatic cancer
    breast cancer
    ovarian cancer
    prostate cancer
    squamous cell carcinoma
    basal cell carcinoma
    adenocarcinoma
    sweat gland carcinoma
    sebaceous gland carcinoma
    papillary carcinoma
    papillary adenocarcinomas
    cystadenocarcinoma
    medullary carcinoma
    bronchogenic carcinoma
    renal cell carcinoma
    hepatoma
    bile duct carcinoma
    choriocarcinoma
    seminoma
    embryonal carcinoma
    Wilms' tumor
    curvical cancer
    testicular tumor
    lung carcinoma
    small cell lung carcinoma
    bladder carcinoma
    epithelial carcinoma
    glioma
    astrocytoma
    medulloblastoma
    craniopharyngioma
    ependymoma
    pinealoma
    hemangioblastoma
    acoustic neuroma
    oligodendroglioma
    menangioma
    melanoma
    neuroblastoma
    retinoblastoma In specific embodiments, malignancy or dysproliferative changes (such as metaplasias and dysplasias) are treated or prevented in epithelial tissues such as those in the cervix, esophagus, and lung.

As detailed in the examples section 10.1 infra, malignancies of the breast, colon, and cervix exhibit increased expression of human Notch relative to such non-malignant tissue. Thus, in specific embodiments, malignancies of the breast, colon, or cervix are treated or prevented by administering an effective amount of an Antagonist Therapeutic of the invention. The presence of increased Notch expression in breast, colon, and cervical cancer suggests that many more cancerous conditions exhibit upregulated Notch. Thus, we envision that many more cancers, e.g., seminoma, melanoma, and lung cancer, can be treated or prevented by administration of an Antagonist Therapeutic.

5.1.2. Nervous System Disorders

Nervous system disorders, involving cell types which can be tested as described supra for efficacy of intervention with Antagonist or Agonist Therapeutics, and which can be treated upon thus observing an indication of therapeutic utility, include but are not limited to nervous system injuries, and diseases or disorders which result in either a disconnection of axons, a diminution or degeneration of neurons, or demyelination. Nervous system lesions which may be treated in a patient (including human and non-human mammalian patients) according to the invention include but are not limited to the following lesions of either the central (including spinal cord, brain) or peripheral nervous systems:

(i) traumatic lesions, including lesions caused by physical injury or associated with surgery, for example, lesions which sever a portion of the nervous system, or compression injuries;

(ii) ischemic lesions, in which a lack of oxygen in a portion of the nervous system results in neuronal injury or death, including cerebral infarction or ischemia, or spinal cord infarction or ischemia;

(iii) malignant lesions, in which a portion of the nervous system is destroyed or injured by malignant tissue which is either a nervous system associated malignancy or a malignancy derived from non-nervous system tissue;

(iv) infectious lesions, in which a portion of the nervous system is destroyed or injured as a result of infection, for example, by an abscess or associated with infection by human immunodeficiency virus, herpes zoster, or herpes simplex virus or with Lyme disease, tuberculosis, syphilis;

(v) degenerative lesions, in which a portion of the nervous system is destroyed or injured as a result of a degenerative process including but not limited to degeneration associated with Parkinson's disease, Alzheimer's disease, Huntington's chorea, or amyotrophic lateral sclerosis;

(vi) lesions associated with nutritional diseases or disorders, in which a portion of the nervous system is destroyed or injured by a nutritional disorder or disorder of metabolism including but not limited to, vitamin B12 deficiency, folic acid deficiency, Wernicke disease, tobacco-alcohol amblyopia, Marchiafava-Bignami disease (primary degeneration of the corpus callosum), and alcoholic cerebellar degeneration;

(vii) neurological lesions associated with systemic diseases including but not limited to diabetes (diabetic neuropathy, Bell's palsy), systemic lupus erythematosus, carcinoma, or sarcoidosis;

(viii) lesions caused by toxic substances including alcohol, lead, or particular neurotoxins; and (ix) demyelinated lesions in which a portion of the nervous system is destroyed or injured by a demyelinating disease including but not limited to multiple sclerosis, human immunodeficiency virus-associated myelopathy, transverse myelopathy or various etiologies, progressive multifocal leukoencephalopathy, and central pontine myelinolysis.

Therapeutics which are useful according to the invention for treatment of a nervous system disorder may be selected by testing for biological activity in promoting the survival or differentiation of neurons (see also Section 5.1). For example, and not by way of limitation, Therapeutics which elicit any of the following effects may be useful according to the invention:

(i) increased survival time of neurons in culture;

(ii) increased sprouting of neurons in culture or in vivo;

(iii) increased production of a neuron-associated molecule in culture or in vivo, e.g., choline acetyltransferase or acetylcholinesterase with respect to motor neurons; or (iv) decreased symptoms of neuron dysfunction in vivo. Such effects may be measured by any method known in the art. In preferred, non-limiting embodiments, increased survival of neurons may be measured by the method set forth in Arakawa et al. (1990, J. Neurosci. 10:3507–3515); increased sprouting of neurons may be detected by methods set forth in Pestronk et al. (1980, Exp. Neurol. 70:65–82) or Brown et al. (1981, Ann. Rev. Neurosci. 4:17–42); increased production of neuron-associated molecules may be measured by bioassay, enzymatic assay, antibody binding, Northern blot assay, etc., depending on the molecule to be measured; and motor neuron dysfunction may be measured by assessing the physical manifestation of motor neuron disorder, e.g., weakness, motor neuron conduction velocity, or functional disability.

In a specific embodiments, motor neuron disorders that may be treated according to the invention include but are not limited to disorders such as infarction, infection, exposure to toxin, trauma, surgical damage, degenerative disease or malignancy that may affect motor neurons as well as other components of the nervous system, as well as disorders that selectively affect neurons such as amyotrophic lateral sclerosis, and including but not limited to progressive spinal muscular atrophy, progressive bulbar palsy, primary lateral sclerosis, infantile and juvenile muscular atrophy, progressive bulbar paralysis of childhood (Fazio-Londe syndrome), poliomyelitis and the post polio syndrome, and Hereditary Motorsensory Neuropathy (Charcot-Marie-Tooth Disease).

5.1.3. Tissue Repair and Regeneration

In another embodiment of the invention, a Therapeutic of the invention is used for promotion of tissue regeneration and repair, including but not limited to treatment of benign dysproliferative disorders. Specific embodiments are directed to treatment of cirrhosis of the liver (a condition in which scarring has overtaken normal liver regeneration processes), treatment of keloid (hypertrophic scar) formation (disfiguring of the skin in which the scarring process interferes with normal renewal), psoriasis (a common skin condition characterized by excessive proliferation of the skin and delay in proper cell fate determination), and baldness (a condition in which terminally differentiated hair follicles (a tissue rich in Notch) fail to function properly).

5.2. Prophylactic Uses

5.2.1. Malignancies

The Therapeutics of the invention can be administered to prevent progression to a neoplastic or malignant state, including but not limited to those disorders listed in Table 1. Such administration is indicated where the Therapeutic is shown in assays, as described supra, to have utility for treatment or prevention of such disorder. Such prophylactic use is indicated in conditions known or suspected of preceding progression to neoplasia or cancer, in particular, where non-neoplastic cell growth consisting of hyperplasia, metaplasia, or most particularly, dysplasia has occurred (for review of such abnormal growth conditions, see Robbins and Angell, 1976, Basic Pathology, 2d Ed., W.B. Saunders Co., Philadelphia, pp. 68–79.) Hyperplasia is a form of controlled cell proliferation involving an increase in cell number in a tissue or organ, without significant alteration in structure or function. As but one example, endometrial hyperplasia often precedes endometrial cancer. Metaplasia is a form of controlled cell growth in which one type of adult or fully differentiated cell substitutes for another type of adult cell. Metaplasia can occur in epithelial or connective tissue cells. A typical metaplasia involves a somewhat disorderly metaplastic epithelium. Dysplasia is frequently a forerunner of cancer, and is found mainly in the epithelia; it is the most disorderly form of non-neoplastic cell growth, involving a loss in individual cell uniformity and in the architectural orientation of cells. Dysplastic cells often have abnormally large, deeply stained nuclei, and exhibit pleomorphism. Dysplasia characteristically occurs where there exists chronic irritation or inflammation, and is often found in the cervix, respiratory passages, oral cavity, and gall bladder.

Alternatively or in addition to the presence of abnormal cell growth characterized as hyperplasia, metaplasia, or dysplasia, the presence of one or more characteristics of a transformed phenotype, or of a malignant phenotype, displayed in vivo or displayed in vitro by a cell sample from a patient, can indicate the desirability of prophylactic/therapeutic administration of a Therapeutic of the invention. As mentioned supra, such characteristics of a transformed phenotype include morphology changes, looser substratum attachment, loss of contact inhibition, loss of anchorage dependence, protease release, increased sugar transport, decreased serum requirement, expression of fetal antigens, disappearance of the 250,000 dalton cell surface protein, etc. (see also id., at pp. 84–90 for characteristics associated with a transformed or malignant phenotype).

In a specific embodiment, leukoplakia, a benign-appearing hyperplastic or dysplastic lesion of the epithelium, or Bowen's disease, a carcinoma in situ, are pre-neoplastic lesions indicative of the desirability of prophylactic intervention.

In another embodiment, fibrocystic disease (cystic hyperplasia, mammary dysplasia, particularly adenosis (benign epithelial hyperplasia)) is indicative of the desirability of prophylactic intervention.

In other embodiments, a patient which exhibits one or more of the following predisposing factors for malignancy is treated by administration of an effective amount of a Therapeutic: a chromosomal translocation associated with a malignancy (e.g., the Philadelphia chromosome for chronic myelogenous leukemia, t(14;18) for follicular lymphoma, etc.), familial polyposis or Gardner's syndrome (possible forerunners of colon cancer), benign monoclonal gammopathy (a possible forerunner of multiple myeloma), and a first degree kinship with persons having a cancer or precancerous disease showing a Mendelian (genetic) inheritance pattern (e.g., familial polyposis of the colon, Gardner's syndrome, hereditary exostosis, polyendocrine adenomatosis, medullary thyroid carcinoma with amyloid production and pheochromocytoma, Peutz-Jeghers syndrome, neurofibromatosis of Von Recklinghausen, retinoblastoma, carotid body tumor, cutaneous melanocarcinoma, intraocular melanocarcinoma, xeroderma pigmentosum, ataxia telangiectasia, Chediak-Higashi syndrome, albinism, Fanconi's aplastic anemia, and Bloom's syndrome; see Robbins and Angell, 1976, Basic Pathology, 2d Ed., W.B. Saunders Co., Philadelphia, pp. 112–113) etc.)

In another specific embodiment, an Antagonist Therapeutic of the invention is administered to a human patient to prevent progression to breast, colon, or cervical cancer.

5.2.2. Other Disorders

In other embodiments, a Therapeutic of the invention can be administered to prevent a nervous system disorder described in Section 5.1.2, or other disorder (e.g., liver cirrhosis, psoriasis, keloids, baldness) described in Section 5.1.3.

5.3. Demonstration of Therapeutic or Prophylactic Utility

The Therapeutics of the invention can be tested in vivo for the desired therapeutic or prophylactic activity. For example, such compounds can be tested in suitable animal model systems prior to testing in humans, including but not limited to rats, mice, chicken, cows, monkeys, rabbits, etc. For in vivo testing, prior to administration to humans, any animal model system known in the art may be used.

5.4. Therapeutic/Prophylactic Administration and Compositions

The invention provides methods of treatment (and prophylaxis) by administration to a subject of an effective amount of a Therapeutic of the invention. In a preferred aspect, the Therapeutic is substantially purified. The subject is preferably an animal, including but not limited to animals such as cows, pigs, chickens, etc., and is preferably a mammal, and most preferably human.

Various delivery systems are known and can be used to administer a Therapeutic of the invention, e.g., encapsulation in liposomes, microparticles, microcapsules, expression by recombinant cells, receptor-mediated endocytosis (see, e.g., Wu and Wu, 1987, J. Biol. Chem. 262:4429–4432), construction of a Therapeutic nucleic acid as part of a retroviral or other vector, etc. Methods of introduction include but are not limited to intradermal, intramuscular, intraperitoneal, intravenous, subcutaneous, intranasal, and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir.

In a specific embodiment, it may be desirable to administer the pharmaceutical compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. In one embodiment, administration can be by direct injection at the site (or former site) of a malignant tumor or neoplastic or pre-neoplastic tissue.

In a specific embodiment, administration of a Therapeutic into a Notch-expressing cell is accomplished by linkage of the Therapeutic to a Delta (or other toporythmic) protein or portion thereof capable of mediating binding to Notch. Contact of a Notch-expressing cell with the linked Therapeutic results in binding of the linked Therapeutic via its Delta portion to Notch on the surface of the cell, followed by uptake of the linked Therapeutic into the Notch-expressing cell.

In a specific embodiment wherein an analog of a Notch intracellular signal-transducing domain is employed as a Therapeutic, such that it can inhibit Notch signal transduction, the analog is preferably delivered intracellularly (e.g., by expression from a nucleic acid vector, or by linkage to a Delta protein capable of binding to Notch followed by binding and internalization, or by receptor-mediated mechanisms).

In a specific embodiment where the Therapeutic is a nucleic acid encoding a protein Therapeutic, the nucleic acid can be administered in vivo to promote expression of its encoded protein, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot et al., 1991, Proc. Natl. Acad. Sci. USA 88:1864–1868), etc. Alternatively, a nucleic acid Therapeutic can be introduced intracellularly and incorporated within host cell DNA for expression, by homologous recombination.

In specific embodiments directed to treatment or prevention of particular disorders, preferably the following forms of administration are used:

| Disorder | Preferred Forms of Administration |
|---|---|
| Cervical cancer | Topical |
| Gastrointestinal cancer | Oral; intravenous |
| Lung cancer | Inhaled; intravenous |
| Leukemia | Intravenous; extracorporeal |
| Metastatic carcinomas | Intravenous; oral |
| Brain cancer | Targeted; intravenous; intrathecal |
| Liver cirrhosis | Oral; intravenous |
| Psoriasis | Topical |
| Keloids | Topical |
| Baldness | Topical |
| Spinal cord injury | Targeted; intravenous; intrathecal |
| Parkinson's disease | Targeted; intravenous; intrathecal |
| Motor neuron disease | Targeted; intravenous; intrathecal |
| Alzheimer's disease | Targeted; intravenous; intrathecal |

The present invention also provides pharmaceutical compositions. Such compositions comprise a therapeutically effective amount of a Therapeutic, and a pharmaceutically acceptable carrier or excipient. Such a carrier includes but is not limited to saline, buffered saline, dextrose, water, glycerol, ethanol, and combinations thereof. The carrier and composition can be sterile. The formulation should suit the mode of administration.

The composition, if desired, can also contain minor amounts of wetting or emulsifying agents, or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The Therapeutics of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The amount of the Therapeutic of the invention which will be effective in the treatment of a particular disorder or condition will depend on the nature of the disorder or condition, and can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. However, suitable dosage ranges for intravenous administration are generally about 20–500 micrograms of active compound per kilogram body weight. Suitable dosage ranges for intranasal administration are generally about 0.01 pg/kg body weight to 1 mg/kg body weight. Effective doses may be extrapolated from dose-response curves derived from in vitro or animal model test systems.

Suppositories generally contain active ingredient in the range of 0.5% to 10% by weight; oral formulations preferably contain 10% to 95% active ingredient.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

5.5. Antisense Regulation of Notch Expression

The present invention provides the therapeutic or prophylactic use of nucleic acids of at least six nucleotides that are antisense to a gene or cDNA encoding Notch or a portion thereof. "Antisense" as used herein refers to a nucleic acid capable of hybridizing to a portion of a Notch RNA (preferably mRNA) by virtue of some sequence complementarity. Such antisense nucleic acids have utility as Antagonist Therapeutics of the invention, and can be used in the treatment or prevention of disorders as described supra in Section 5.1 and its subsections.

The antisense nucleic acids of the invention can be oligonucleotides that are double-stranded or single-stranded, RNA or DNA or a modification or derivative thereof, which can be directly administered to a cell, or which can be produced intracellularly by transcription of exogenous, introduced sequences.

In a specific embodiment, the Notch antisense nucleic acids provided by the instant invention can be used for the treatment of tumors or other disorders, the cells of which tumor type or disorder can be demonstrated (in vitro or in vivo) to express the Notch gene. Such demonstration can be by detection of Notch RNA or of Notch protein.

The invention further provides pharmaceutical compositions comprising an effective amount of the Notch antisense nucleic acids of the invention in a pharmaceutically acceptable carrier, as described supra in Section 5.4. Methods for treatment and prevention of disorders (such as those described in Sections 5.1 and 5.2) comprising administering the pharmaceutical compositions of the invention are also provided.

In another embodiment, the invention is directed to methods for inhibiting the expression of a Notch nucleic acid sequence in a prokaryotic or eukaryotic cell comprising providing the cell with an effective amount of a composition comprising an antisense Notch nucleic acid of the invention.

In another embodiment, the identification of cells expressing functional Notch receptors can be carried out by observing the ability of Notch to "rescue" such cells from the cytotoxic effects of a Notch antisense nucleic acid.

In an alternative embodiment of the invention, nucleic acids antisense to a nucleic acid encoding a ("adhesive") toporythmic protein or fragment that binds to Notch, are envisioned as Therapeutics.

Notch antisense nucleic acids and their uses are described in detail below.

5.5.1. Notch Antisense Nucleic Acids

The Notch antisense nucleic acids are of at least six nucleotides and are preferably oligonucleotides (ranging from 6 to about 50 oligonucleotides). In specific aspects, the oligonucleotide is at least 10 nucleotides, at least 15 nucleotides, at least 100 nucleotides, or at least 200 nucleotides. The oligonucleotides can be DNA or RNA or chimeric mixtures or derivatives or modified versions thereof, single-stranded or double-stranded. The oligonucleotide can be modified at the base moiety, sugar moiety, or phosphate backbone. The oligonucleotide may include other appending groups such as peptides, or agents facilitating transport across the cell membrane (see, e.g., Letsinger et al., 1989, Proc. Natl. Acad. Sci. U.S.A. 86:6553–6556; Lemaitre et al., 1987, Proc. Natl. Acad. Sci. 84:648–652; PCT Publication No. WO 88/09810, published Dec. 15, 1988) or blood-brain barrier (see, e.g., PCT Publication No. WO 89/10134, published Apr. 25, 1988), hybridization-triggered cleavage agents (see, e.g., Krol et al., 1988, BioTechniques 6:958–976) or intercalating agents (see, e.g., Zon, 1988, Pharm. Res. 5:539–549).

In a preferred aspect of the invention, a Notch antisense oligonucleotide is provided, preferably of single-stranded DNA. In a most preferred aspect, such an oligonucleotide comprises a sequence antisense to the sequence encoding ELR 11 and ELR 12 of Notch, most preferably, of human Notch. The oligonucleotide may be modified at any position on its structure with substituents generally known in the art.

The Notch antisense oligonucleotide may comprise at least one modified base moiety which is selected from the group including but not limited to 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

In another embodiment, the oligonucleotide comprises at least one modified sugar moiety selected from the group including but not limited to arabinose, 2-fluoroarabinose, xylulose, and hexose.

In yet another embodiment, the oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the oligonucleotide is an α-anomeric oligonucleotide. An α-anomeric oligonucleotide forms specific double-stranded hybrids with complementary RNA in which, contrary to the usual β-units, the strands run parallel to each other (Gautier et al., 1987, Nucl. Acids Res. 15:6625–6641).

The oligonucleotide may be conjugated to another molecule, e.g., a peptide, hybridization triggered crosslinking agent, transport agent, hybridization-triggered cleavage agent, etc.

Oligonucleotides of the invention may be synthesized by standard methods known in the art, e.g. by use of an automated DNA synthesizer (such as are commercially available from Biosearch, Applied Biosystems, etc.). As examples, phosphorothioate oligos may be synthesized by the method of Stein et al. (1988, Nucl. Acids Res. 16:3209), methylphosphonate oligos can be prepared by use of controlled pore glass polymer supports (Sarin et al., 1988, Proc. Natl. Acad. Sci. U.S.A. 85:7448–7451), etc.

In a specific embodiment, the Notch antisense oligonucleotide comprises catalytic RNA, or a ribozyme (see, e.g., PCT International Publication WO 90/11364, published Oct. 4, 1990; Sarver et al., 1990, Science 247:1222–1225). In another embodiment, the oligonucleotide is a 2'-0-methylribonucleotide (Inoue et al., 1987, Nucl. Acids Res. 15:6131–6148), or a chimeric RNA-DNA analogue (Inoue et al., 1987, FEBS Lett. 215:327–330).

In an alternative embodiment, the Notch antisense nucleic acid of the invention is produced intracellularly by transcription from an exogenous sequence. For example, a vector can be introduced in vivo such that it is taken up by a cell, within which cell the vector or a portion thereof is transcribed, producing an antisense nucleic acid (RNA) of the invention. Such a vector would contain a sequence encoding the Notch antisense nucleic acid. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the Notch antisense RNA can be by any promoter known in the art to act in mammalian, preferably human, cells. Such promoters can be inducible or constitutive. Such promoters include but are not limited to: the SV40 early promoter region (Bernoist and Chambon, 1981, Nature 290:304–310), the promoter contained in the 3' long terminal repeat of Rous sarcoma virus (Yamamoto et al., 1980, Cell 22:787–797), the herpes thymidine kinase promoter (Wagner et al., 1981, Proc. Natl. Acad. Sci. U.S.A. 78:1441–1445), the regulatory sequences of the metallothionein gene (Brinster et al., 1982, Nature 296:39–42), etc.

The antisense nucleic acids of the invention comprise a sequence complementary to at least a portion of an RNA transcript of a Notch gene, preferably a human Notch gene. However, absolute complementarity, although preferred, is not required. A sequence "complementary to at least a portion of an RNA," as referred to herein, means a sequence having sufficient complementarity to be able to hybridize with the RNA, forming a stable duplex; in the case of double-stranded Notch antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with a Notch RNA it may contain and still form a stable duplex (or triplex, as the case may be). One skilled in the art can ascertain a tolerable degree of mismatch by use of standard procedures to determine the melting point of the hybridized complex.

5.5.2. Therapeutic Utility of Notch Antisense Nucletic Acids

The Notch antisense nucleic acids can be used to treat (or prevent) malignancies, of a cell type which has been shown to express Notch RNA. Malignant, neoplastic, and pre-neoplastic cells which can be tested for such expression include but are not limited to those described supra in Sections 5.1.1 and 5.2.1. In a preferred embodiment, a single-stranded DNA antisense Notch oligonucleotide is used.

Malignant (particularly, tumor) cell types which express Notch RNA can be identified by various methods known in the art. Such methods include but are not limited to hybridization with a Notch-specific nucleic acid (e.g. by Northern hybridization, dot blot hybridization, in situ hybridization), observing the ability of RNA from the cell type to be translated in vitro into Notch, etc. In a preferred aspect, primary tumor tissue from a patient can be assayed for Notch expression prior to treatment.

Pharmaceutical compositions of the invention (see Section 5.1.4), comprising an effective amount of a Notch antisense nucleic acid in a pharmaceutically acceptable carrier, can be administered to a patient having a malignancy which is of a type that expresses Notch RNA.

The amount of Notch antisense nucleic acid which will be effective in the treatment of a particular disorder or condition will depend on the nature of the disorder or condition, and can be determined by standard clinical techniques. Where possible, it is desirable to determine the antisense cytotoxicity of the tumor type to be treated in vitro, and then in useful animal model systems prior to testing and use in humans.

In a specific embodiment, pharmaceutical compositions comprising Notch antisense nucleic acids are administered via liposomes, microparticles, or microcapsules. In various embodiments of the invention, it may be useful to use such compositions to achieve sustained release of the Notch antisense nucleic acids. In a specific embodiment, it may be desirable to utilize liposomes targeted via antibodies to specific identifiable tumor antigens (Leonetti et al., 1990, Proc. Natl. Acad. Sci. U.S.A. 87:2448–2451; Renneisen et al., 1990, J. Biol. Chem. 265:16337–16342).

5.6. Diagnostiic Utility

Notch proteins, analogues, derivatives, and subsequences thereof, Notch nucleic acids (and sequences complementary thereto), anti-Notch antibodies, and other toporythmic proteins and derivatives and analogs thereof which interact with Notch proteins, and inhibitors of North-toporythmic protein interactions, have uses in diagnostics. Such molecules can be used in assays, such as immunoassays, to detect, prognose, diagnose, or monitor various conditions, diseases, and disorders affecting Notch expression, or monitor the treatment thereof. In particular, such an immunoassay is carried out by a method comprising contacting a sample derived from a patient with an anti-Notch antibody under conditions such that immunospecific binding can occur, and detecting or measuring the amount of any immunospecific binding by the antibody. In a specific embodiment, antibody to Notch can be used to assay in a patient tissue or serum sample for the presence of Notch where an aberrant level of Notch is an indication of a diseased condition.

The immunoassays which can be used include but are not limited to competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few.

Notch genes and related nucleic acid sequences and subsequences, including complementary sequences, and other toporythmic gene sequences, can also be used in hybridization assays. Notch nucleic acid sequences, or subsequences thereof comprising about at least 8 nucleotides, can be used as hybridization probes. Hybridization assays can be used to detect, prognose, diagnose, or monitor conditions, disorders, or disease states associated with aberrant changes in Notch expression and/or activity as described supra. In particular, such a hybridization assay is carried out by a method comprising contacting a sample containing nucleic acid with a nucleic acid probe capable of hybridizing to Notch DNA or RNA, under conditions such that hybridization can occur, and detecting or measuring any resulting hybridization.

As detailed in examples section 10.1 infra, increased Notch expression occurs in human breast, colon, and cervical cancer. Accordingly, in specific embodiments, human breast, colon, or cervical cancer or premalignant changes in such tissues is diagnosed by detecting increased Notch expression in patient samples relative to the level of Notch expression in an analogous non-malignant sample (from the patient or another person, as determined experimentally or as is known as a standard level in such samples).

In one embodiment, the Notch protein (or derivative having Notch antigenicity) that is detected or measured is on the cell surface. In another embodiment, the Notch protein (or derivative) is a cell free soluble molecule (e.g., as measured in a blood or serum sample) or is intracellular. Without intending to be bound mechanistically, Applicants believe that cell free Notch may result from secretion or shedding from the cell surface. In yet another embodiment, soluble, cell-surface, and intracellular amounts of Notch protein or derivative are detected or measured.

5.7. Notch Nucleic Acids

Therapeutics of the invention which are Notch nucleic acids or Notch antisense nucleic acids, as well as nucleic acids encoding protein Therapeutics, include those described below, which can be obtained by methods known in the art, and in particular, as described below.

In particular aspects, the invention provides amino acid sequences of Notch, preferably human Notch, and fragments and derivatives thereof which comprise an antigenic determinant (i.e., can be recognized by an antibody) or which are functionally active, as well as nucleic acid sequences encoding the foregoing. "Functionally active" material as used herein refers to that material displaying one or more known functional activities associated with the full-length (wild-type) Notch protein product, e.g., binding to Delta, binding to Serrate, binding to any other Notch ligand, antigenicity (binding to an anti-Notch antibody), etc.

In specific embodiments, the invention provides fragments of a Notch protein consisting of at least 40 amino acids, or of at least 75 amino acids. In other embodiments, the proteins comprise or consist essentially of the intracellular domain, transmembrane region, extracellular domain, cdc10 region, Notch/lin-12 repeats, or the EGF-homologous repeats, or any combination of the foregoing, of a Notch protein. Fragments, or proteins comprising fragments, lacking some or all of the EGF-homologous repeats of Notch are also provided. Nucleic acids encoding the foregoing are provided.

In other specific embodiments, the invention provides nucleotide sequences and subsequences of Notch, preferably human Notch, consisting of at least 25 nucleotides, at least 50 nucleotides, or at least 150 nucleotides. Nucleic acids encoding the proteins and protein fragments described above are provided, as well as nucleic acids complementary to and capable of hybridizing to such nucleic acids. In one embodiment, such a complementary sequence may be complementary to a Notch cDNA sequence of at least 25 nucleotides, or of at least 100 nucleotides. In a preferred aspect, the invention utilizes cDNA sequences encoding human Notch or a portion thereof. In a specific embodiment, such sequences of the human Notch gene or cDNA are as contained in plasmids hN3k, hN4k, or hN5k (see Section 9, infra) or in the gene corresponding thereto; such a human Notch protein sequence can be as shown in FIGS. 10 (SEQ ID NO:11) or 11 (SEQ ID NO:13). In other embodiments, the Notch nucleic acid and/or its encoded protein has at least a portion of the sequence shown in one of the following publications: Wharton et al., 1985, Cell 43:567–581 (Drosophila Notch); Kidd et al., 1986, Mol. Cell. Biol. 6:30943108 (Drosophila Notch); Coffman et al., 1990, Science 249:1438–1441 (Xenopus Notch); Ellisen et al., 1991, Cell 66:649–661 (a human Notch). In another aspect, the sequences of human Notch are those encoding the human Notch amino acid sequences or a portion thereof as shown in FIG. 13. In a particular aspect, the human Notch sequences are those of the hN homolog (represented in part by plasmid hN5k) or the TAN-1 homolog.

In one embodiment of the invention, the invention is directed to the full-length human Notch protein encoded by the hN homolog as depicted in FIG. 13, both containing the signal sequence (I.e., the precursor protein; amino acids 1–2169) and lacking the signal sequence (i.e., the mature protein; amino acids ~26–2169), as well as portions of the foregoing (e.g., the extracellular domain, EGF homologous repeat region, EGF-like repeats 11 and 12, cdc-10/ankyrin repeats, etc.) and proteins comprising the foregoing, as well as nucleic acids encoding the foregoing.

As is readily apparent, as used herein, a "nucleic acid encoding a fragment or portion of a Notch protein" shall be construed as referring to a nucleic acid encoding only the recited fragment or portion of the Notch protein and not other portions of the Notch protein.

In a preferred, but not limiting, aspect of the invention, a human Notch DNA sequence can be cloned and sequenced by the method described in Section 9, infra.

In another preferred aspect, PCR is used to amplify the desired sequence in the library, prior to selection. For example, oligonucleotide primers representing part of the adhesive domains encoded by a homologue of the desired gene can be used as primers in PCR.

The above-methods are not meant to limit the following general description of methods by which clones of Notch may be obtained.

Any eukaryotic cell can potentially serve as the nucleic acid source for the molecular cloning of the Notch gene. The DNA may be obtained by standard procedures known in the art from cloned DNA (e.g., a DNA "library"), by chemical synthesis, by cDNA cloning, or by the cloning of genomic DNA, or fragments thereof, purified from the desired human cell (see, for example Sambrook et al., 1989, Molecular Cloning, A Laboratory Manual, Cold Spring Harbor Laboratory, 2d. Ed., Cold Spring Harbor, N.Y.; Glover, D. M. (ed.), 1985, DNA Cloning: A Practical Approach, MRL Press, Ltd., Oxford, U.K. Vol. I, II.) Clones derived from genomic DNA may contain regulatory and intron DNA regions in addition to coding regions; clones derived from cDNA will contain only exon sequences. Whatever the source, the gene should be molecularly cloned into a suitable vector for propagation of the gene.

In the molecular cloning of the gene from genomic DNA, DNA fragments are generated, some of which will encode the desired gene. The DNA may be cleaved at specific sites using various restriction enzymes. Alternatively, one may use DNAse in the presence of manganese to fragment the DNA, or the DNA can be physically sheared, as for example, by sonication. The linear DNA fragments can then be separated according to size by standard techniques, including but not limited to, agarose and polyacrylamide gel electrophoresis and column chromatography.

Once the DNA fragments are generated, identification of the specific DNA fragment containing the desired gene may be accomplished in a number of ways. For example, if an amount of a portion of a Notch (of any species) gene or its specific RNA, or a fragment thereof e.g., the adhesive domain, is available and can be purified and labeled, the generated DNA fragments may be screened by nucleic acid hybridization to the labeled probe (Benton, W. and Davis, R., 1977, Science 196, 180; Grunstein, M. And Hogness, D., 1975, Proc. Natl. Acad. Sci. U.S.A. 72, 3961). Those DNA fragments with substantial homology to the probe will hybridize. It is also possible to identify the appropriate fragment by restriction enzyme digestion(s) and comparison of fragment sizes with those expected according to a known restriction map if such is available. Further selection can be carried out on the basis of the properties of the gene. Alternatively, the presence of the gene may be detected by assays based on the physical, chemical, or immunological properties of its expressed product. For example, cDNA clones, or DNA clones which hybrid-select the proper mRNAs, can be selected which produce a protein that, e.g., has similar or identical electrophoretic migration, isolectric focusing behavior, proteolytic digestion maps, in vitro aggregation activity ("adhesiveness") or antigenic properties as known for Notch. If an antibody to Notch is available, the Notch protein may be identified by binding of labeled antibody to the putatively Notch synthesizing clones, in an ELISA (enzyme-linked immunosorbent assay)-type procedure.

The Notch gene can also be identified by mRNA selection by nucleic acid hybridization followed by in vitro translation. In this procedure, fragments are used to isolate complementary mRNAs by hybridization. Such DNA fragments may represent available, purified Notch DNA of another species (e.g., Drosophila). Immunoprecipitation analysis or functional assays (e.g., aggregation ability in vitro; see examples infra) of the in vitro translation products of the isolated products of the isolated mRNAs identifies the mRNA and, therefore, the complementary DNA fragments that contain the desired sequences. In addition, specific mRNAs may be selected by adsorption of polysomes isolated from cells to immobilized antibodies specifically directed against Notch or Delta protein. A radiolabelled Notch cDNA can be synthesized using the selected mRNA (from the adsorbed polysomes) as a template. The radiolabelled mRNA or cDNA may then be used as a probe to identify the Notch DNA fragments from among other genomic DNA fragments.

Alternatives to isolating the Notch genomic DNA include, but are not limited to, chemically synthesizing the gene sequence itself from a known sequence or making cDNA to the mRNA which encodes the Notch gene. For example, RNA for cDNA cloning of the Notch gene can be isolated from cells which express Notch. Other methods are possible and within the scope of the invention.

The identified and isolated gene can then be inserted into an appropriate cloning vector. A large number of vector-host systems known in the art may be used. Possible vectors include, but are not limited to, plasmids or modified viruses, but the vector system must be compatible with the host cell used. Such vectors include, but are not limited to, bacteriophages such as lambda derivatives, or plasmids such as PBR322 or pUC plasmid derivatives. The insertion into a cloning vector can, for example, be accomplished by ligating the DNA fragment into a cloning vector which has complementary cohesive termini. However, if the complementary restriction sites used to fragment the DNA are not present in the cloning vector, the ends of the DNA molecules may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. In an alternative method, the cleaved vector and Notch or Delta gene may be modified by homopolymeric tailing. Recombinant molecules can be introduced into host cells via transformation, transfection, infection, electroporation, etc., so that many copies of the gene sequence are generated.

In an alternative method, the desired gene may be identified and isolated after insertion into a suitable cloning vector in a "shot gun" approach. Enrichment for the desired gene, for example, by size fractionization, can be done before insertion into the cloning vector.

In specific embodiments, transformation of host cells with recombinant DNA molecules that incorporate the isolated Notch gene, cDNA, or synthesized DNA sequence enables generation of multiple copies of the gene. Thus, the gene may be obtained in large quantities by growing transformants, isolating the recombinant DNA molecules from the transformants and, when necessary, retrieving the inserted gene from the isolated recombinant DNA.

The Notch sequences provided by the instant invention include those nucleotide sequences encoding substantially the same amino acid sequences as found in native Notch protein, and those encoded amino acid sequences with functionally equivalent amino acids, all as described in Section 5.6 infra for Notch derivatives.

Similar methods to those described supra can be used to obtain a nucleic acid encoding Delta, Serrate, or adhesive portions thereof, or other toporythmic gene of interest. In a specific embodiment, the Delta nucleic acid has at least a portion of the sequence shown in FIG. 1 (SEQ ID NO:1). In another specific embodiment, the Serrate nucleic acid has at least a portion of the sequence shown in FIG. 5 (SEQ ID NO:3). The nucleic acid sequences encoding toporythmic proteins can be isolated from porcine, bovine, feline, avian, equine, or canine, as well as primate sources and any other species in which homologs of known toporythmic genes [including but not limited to the following genes (with the publication of sequences in parentheses): Delta (Vassin et al., 1987, EMBO J. 6, 3431–3440; Kopczynski et al., 1988, Genes Dev. 2, 1723–1735; note corrections to the Kopczynski et al. sequence found in FIG. 1 hereof (SEQ ID NO:1 and SEQ ID NO:2)) and Serrate (Fleming et al., 1990, Genes & Dev. 4, 2188–2201)] can be identified. Such sequences can be altered by substitutions, additions or deletions that provide for functionally equivalent molecules, as described supra.

5.8. Recombinant Production of Protein Therapeutics

The nucleic acid coding for a protein Therapeutic of the invention can be inserted into an appropriate expression vector, i.e., a vector which contains the necessary elements for the transcription and translation of the inserted protein-coding sequence. The necessary transcriptional and translational signals can also be supplied by the native toporythmic gene and/or its flanking regions. A variety of host-vector systems may be utilized to express the protein-coding sequence. These include but are not limited to mammalian cell systems infected with virus (e.g., vaccinia virus, adenovirus, etc.); insect cell systems infected with virus (e.g., baculovirus); microorganisms such as yeast containing yeast vectors, or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used. In a specific embodiment, the adhesive portion of the Notch gene, e.g., that encoding EGF-like repeats (ELR) 11 and 12, is expressed. In other specific embodiments, the human Notch gene is expressed, or a sequence encoding a functionally active portion of human Notch.

Any of the methods previously described for the insertion of DNA fragments into a vector may be used to construct expression vectors containing a chimeric gene consisting of appropriate transcriptional/translational control signals and the protein coding sequences. These methods may include in vitro recombinant DNA and synthetic techniques and in vivo recombinants (genetic recombination). Expression of nucleic acid sequence encoding a Notch protein or peptide fragment may be regulated by a second nucleic acid sequence so that the Notch protein or peptide is expressed in a host transformed with the recombinant DNA molecule. For example, expression of a Notch protein may be controlled by any promoter/enhancer element known in the art. Promoters which may be used to control toporythmic gene expression include, but are not limited to, the SV40 early promoter region (Bernoist and Chambon, 1981, Nature 290, 304–310), the promoter contained in the 3' long terminal repeat of Rous sarcoma virus (Yamamoto, et al., 1980, Cell 22, 787–797), the herpes thymidine kinase promoter (Wagner et al., 1981, Proc. Natl. Acad. Sci. U.S.A. 78, 1441–1445), the regulatory sequences of the metallothionein gene (Brinster et al., 1982, Nature 296, 39–42); prokaryotic expression vectors such as the β-lactamase promoter (Villa-Kamaroff, et al., 1978, Proc. Natl. Acad. Sci. U.S.A. 75, 3727–3731), or the tac promoter (DeBoer, et al., 1983, Proc. Natl. Acad. Sci. U.S.A. 80, 21–25); see also "Useful proteins from recombinant bacteria" in Scientific American, 1980, 242, 74–94; plant expression vectors comprising the nopaline synthetase promoter region (Herrera-Estrella et al., Nature 303, 209–213) or the cauliflower mosaic virus 35S RNA promoter (Gardner, et al., 1981, Nucl. Acids Res. 9, 2871), and the promoter of the photosynthetic enzyme ribulose biphosphate carboxylase (Herrera-Estrella et al., 1984, Nature 310, 115–120); promoter elements from yeast or other fungi such as the Gal 4 promoter, the ADC (alcohol dehydrogenase) promoter, PGK (phosphoglycerol kinase) promoter, alkaline phosphatase promoter, and the following animal transcriptional control regions, which exhibit tissue specificity and have been utilized in transgenic animals: elastase I gene control region which is active in pancreatic acinar cells (Swift et al., 1984, Cell 38, 639–646; Ornitz et al., 1986, Cold Spring Harbor Symp. Quant. Biol. 50, 399–409; MacDonald, 1987, Hepatology 7, 425–515); insulin gene control region which is active in pancreatic beta cells (Hanahan, 1985, Nature 315, 115–122), immunoglobulin gene control region which is active in lymphoid cells (Grosschedl et al., 1984, Cell 38, 647–658; Adames et al., 1985, Nature 318, 533–538; Alexander et al., 1987, Mol. Cell. Biol. 7, 1436–1444), mouse mammary tumor virus control region which is active in testicular, breast, lymphoid and mast cells (Leder et al., 1986, Cell 45, 485–495), albumin gene control region which is active in liver (Pinkert et al., 1987, Genes and Devel. 1, 268–276), alpha-fetoprotein gene control region which is active in liver (Krumlauf et al., 1985, Mol. Cell. Biol. 5, 1639–1648; Hammer et al., 1987, Science 235, 53–58; alpha 1-antitrypsin gene control region which is active in the liver (Kelsey et al., 1987, Genes and Devel. 1, 161–171), beta-globin gene control region which is active in myeloid cells (Mogram et al., 1985, Nature 315, 338–340; Kollias et al., 1986, Cell 46, 89–94; myelin basic protein gene control region which is active in oligodendrocyte cells in the brain (Readhead et al., 1987, Cell 48, 703–712); myosin light chain-2 gene control region which is active in skeletal muscle (Sani, 1985, Nature 314, 283–286), and gonadotropic releasing hormone gene control region which is active in the hypothalamus (Mason et al., 1986, Science 234, 1372–1378).

Expression vectors containing Notch gene inserts can be identified by three general approaches: (a) nucleic acid hybridization, (b) presence or absence of "marker" gene functions, and (c) expression of inserted sequences. In the first approach, the presence of a foreign gene inserted in an expression vector can be detected by nucleic acid hybridization using probes comprising sequences that are homologous to an inserted toporythmic gene. In the second approach, the recombinant vector/host system can be identified and selected based upon the presence or absence of certain "marker" gene functions (e.g., thymidine kinase activity, resistance to antibiotics, transformation phenotype, occlusion body formation in baculovirus, etc.) caused by the insertion of foreign genes in the vector. For example, if the Notch gene is inserted within the marker gene sequence of the vector, recombinants containing the Notch insert can be identified by the absence of the marker gene function. In the third approach, recombinant expression vectors can be identified by assaying the foreign gene product expressed by the recombinant. Such assays can be based, for example, on the physical or functional properties of the Notch gene product in vitro assay systems, e.g., aggregation (adhesive) ability (see Sections 6–7, infra).

Once a particular recombinant DNA molecule is identified and isolated, several methods known in the art may be used to propagate it. Once a suitable host system and growth conditions are established, recombinant expression vectors can be propagated and prepared in quantity. As previously explained, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few.

In addition, a host cell strain may be chosen which modulates the expression of the inserted sequences, or modifies and processes the gene product in the specific fashion desired. Expression from certain promoters can be elevated in the presence of certain inducers; thus, expression of the genetically engineered Notch protein may be controlled. Furthermore, different host cells have characteristic and specific mechanisms for the translational and post-translational processing and modification (e.g., glycosylation, cleavage) of proteins. Appropriate cell lines or host systems can be chosen to ensure the desired modification and processing of the foreign protein expressed. For example, expression in a bacterial system can be used to produce an unglycosylated core protein product. Expression in yeast will produce a glycosylated product. Expression in mammalian cells can be used to ensure "native" glycosylation of a heterologous mammalian toporythmic protein. Furthermore, different vector/host expression systems may effect processing reactions such as proteolytic cleavages to different extents.

In other specific embodiments, the Notch protein, fragment, analog, or derivative may be expressed as a fusion, or chimeric protein product (comprising the protein, fragment, analog, or derivative joined via a peptide bond to a heterologous protein sequence (of a different protein)). Such a chimeric product can be made by ligating the appropriate nucleic acid sequences encoding the desired amino acid sequences to each other by methods known in the art, in the proper coding frame, and expressing the chimeric product by methods commonly known in the art. Alternatively, such a chimeric product may be made by protein synthetic techniques, e.g., by use of a peptide synthesizer.

Both cDNA and genomic sequences can be cloned and expressed.

In other embodiments, a Notch cDNA sequence may be chromosomally integrated and expressed. Homologous recombination procedures known in the art may be used.

5.8.1. Identification and Purification of the Expressed Gene Product

Once a recombinant which expresses the Notch gene sequence is identified, the gene product may be analyzed. This can be achieved by assays based on the physical or functional properties of the product, including radioactive labelling of the product followed by analysis by gel electrophoresis.

Once the Notch protein is identified, it may be isolated and purified by standard methods including chromatography (e.g., ion exchange, affinity, and sizing column chromatography), centrifugation, differential solubility, or by any other standard technique for the purification of proteins. The functional properties may be evaluated using any suitable assay, including, but not limited to, aggregation assays (see Sections 6–7).

5.9. Derivatives and Analogs of Notch and Other Toporythmic Proteins

The invention further provides, as Therapeutics, derivatives (including but not limited to fragments) and analogs of Notch proteins. Also provided as Therapeutics are other toporythmic proteins and derivatives and analogs thereof, or Notch ligands, in particular, which promote or, alternatively, inhibit the interactions of such other toporythmic proteins with Notch.

The production and use of derivatives and analogs related to Notch are within the scope of the present invention. In a specific embodiment, the derivative or analog is functionally active, i.e., capable of exhibiting one or more functional activities associated with a full-length, wild-type Notch protein. As one example, such derivatives or analogs which have the desired antigenicity can be used, for example, in diagnostic immunoassays as described in Section 5.3. Molecules which retain, or alternatively inhibit, a desired Notch property, e.g., binding to Delta or other toporythmic proteins, binding to a intracellular ligand, can be used therapeutically as inducers, or inhibitors, respectively, of such property and its physiological correlates. Derivatives or analogs of Notch can be tested for the desired activity by procedures known in the art, including but not limited to the assays described infra. In one specific embodiment, peptide libraries can be screened to select a peptide with the desired activity; such screening can be carried out by assaying, e.g., for binding to Notch or a Notch binding partner such as Delta.

In particular, Notch derivatives can be made by altering Notch sequences by substitutions, additions or deletions that provide for functionally equivalent molecules. Due to the degeneracy of nucleotide coding sequences, other DNA sequences which encode substantially the same amino acid sequence as a Notch gene may be used in the practice of the present invention. These include but are not limited to nucleotide sequences comprising all or portions of Notch genes which are altered by the substitution of different codons that encode a functionally equivalent amino acid residue within the sequence, thus producing a silent change. Likewise, the Notch derivatives of the invention include, but are not limited to, those containing, as a primary amino acid sequence, all or part of the amino acid sequence of a Notch protein including altered sequences in which functionally equivalent amino acid residues are substituted for residues within the sequence resulting in a silent change. For example, one or more amino acid residues within the sequence can be substituted by another amino acid of a similar polarity which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid.

Derivatives or analogs of Notch include but are not limited to those peptides which are substantially homologous to Notch or fragments thereof, or whose encoding nucleic acid is capable of hybridizing to a Notch nucleic acid sequence.

The Notch derivatives and analogs of the invention can be produced by various methods known in the art. The manipulations which result in their production can occur at the gene or protein level. For example, the cloned Notch gene sequence can be modified by any of numerous strategies known in the art (Maniatis, T., 1989, Molecular Cloning, A Laboratory Manual, 2d ed., Cold Spring Harbor Laboratory, Cold Spring Harbor, N.Y.). The sequence can be cleaved at appropriate sites with restriction endonuclease(s), followed by further enzymatic modification if desired, isolated, and ligated in vitro. In the production of the gene encoding a derivative or analog of Notch, care should be taken to ensure that the modified gene remains within the same translational reading frame as Notch, uninterrupted by translational stop signals, in the gene region where the desired Notch activity is encoded.

Additionally, the Notch-encoding nucleic acid sequence can be mutated in vitro or in vivo, to create and/or destroy translation, initiation, and/or termination sequences, or to create variations in coding regions and/or form new restriction endonuclease sites or destroy preexisting ones, to facilitate further in vitro modification. Any technique for mutagenesis known in the art can be used, including but not limited to, in vitro site-directed mutagenesis (Hutchinson, C., et al., 1978, J. Biol. Chem 253:6551), use of TAB® linkers (Pharmacia), etc.

Manipulations of the Notch sequence may also be made at the protein level. Included within the scope of the invention are Notch protein fragments or other derivatives or analogs which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited to specific chemical cleavage by cyanogen bromide, trypsin, chymotrypsin, papain, V8 protease, $NaBH_4$; acetylation, formylation, oxidation, reduction; metabolic synthesis in the presence of tunicamycin; etc.

In addition, analogs and derivatives of Notch can be chemically synthesized. For example, a peptide corresponding to a portion of a Notch protein which comprises the desired domain, or which mediates the desired aggregation activity in vitro, or binding to a receptor, can be synthesized by use of a peptide synthesizer. Furthermore, if desired, nonclassical amino acids or chemical amino acid analogs can be introduced as a substitution or addition into the Notch sequence. Non-classical amino acids include but are not limited to the D-isomers of the common amino acids, α-amino isobutyric acid, 4-aminobutyric acid, hydroxyproline, sarcosine, citrulline, cysteic acid, t-butylglycine, t-butylalanine, phenylglycine, cyclohexylalanine, β-alanine, designer amino acids such as β-methyl amino acids, Cα-methyl amino acids, and Nα-methyl amino acids.

In a specific embodiment, the Notch derivative is a chimeric, or fusion, protein comprising a Notch protein or fragment thereof fused via a peptide bond at its amino- and/or carboxy-terminus to a non-Notch amino acid sequence. In one embodiment, such a chimeric protein is produced by recombinant expression of a nucleic acid encoding the protein (comprising a Notch-coding sequence joined in-frame to a non-Notch coding sequence). Such a chimeric product can be made by ligating the appropriate nucleic acid sequences encoding the desired amino acid sequences to each other by methods known in the art, in the proper coding frame, and expressing the chimeric product by methods commonly known in the art. Alternatively, such a chimeric product may be made by protein synthetic techniques, e.g., by use of a peptide synthesizer. In a specific embodiment, a chimeric nucleic acid encoding a mature Notch protein with a heterologous signal sequence is expressed such that the chimeric protein is expressed and processed by the cell to the mature Notch protein. As another example, and not by way of limitation, a recombinant molecule can be constructed according to the invention, comprising coding portions of both Notch and another toporythmic gene, e.g., Delta. The encoded protein of such a recombinant molecule could exhibit properties associated with both Notch and Delta and portray a novel profile of biological activities, including agonists as well as antagonists. The primary sequence of Notch and Delta may also be used to predict tertiary structure of the molecules using computer simulation (Hopp and Woods, 1981, Proc. Natl. Acad. Sci. U.S.A. 78:3824–3828); Notch/Delta chimeric recombinant genes could be designed in light of correlations between tertiary structure and biological function. Likewise, chimeric genes comprising portions of Notch fused to any heterologous (non-Notch) protein-encoding sequences may be constructed. A specific embodiment relates to a chimeric protein comprising a fragment of Notch of at least six amino acids.

In another specific embodiment, the Notch derivative is a fragment of Notch comprising a region of homology with another toporythmic protein. As used herein, a region of a first protein shall be considered "homologous" to a second protein when the amino acid sequence of the region is at least 30% identical or at least 75% either identical or involving conservative changes, when compared to any sequence in the second protein of an equal number of amino acids as the number contained in the region.

Derivatives of Serrate, Delta, other toporythmic proteins, and the adhesive portions thereof, can be made by methods similar to those described supra.

5.9.1. Derivatives of Notch Containing One or More Domains of the Protein

In a specific embodiment, the invention provides Therapeutics that are Notch derivatives and analogs, in particular Notch fragments and derivatives of such fragments, that comprise one or more domains of the Notch protein, including but not limited to the extracellular domain, transmembrane domain, intracellular domain, membrane-associated region, one or more of the EGF-like repeats (ELR) of the Notch protein, the cdc10 repeats, and the Notch/lin-12 repeats. In specific embodiments, the Notch derivative may lack all or a portion of the ELRs, or one or more other regions of the protein.

In a specific embodiment, relating to a Notch protein of a species other than *D. melanogaster*, preferably human, the fragments comprising specific portions of Notch are those comprising portions in the respective Notch protein most homologous to specific fragments of the Drosophila Notch protein (e.g., ELR 11 and ELR 12).

5.9.2. Derivatives of Notch or Other Toporythmic Proteins that Mediate Binding to Toporythmic Protein Domains, and Inhibitors Thereof The invention also provides Notch fragments, and analogs or derivatives of such fragments, which mediate binding to toporythmic proteins (and thus are termed herein "adhesive"), and nucleic acid sequences encoding the foregoing.

Also included as Therapeutics of the invention are toporythmic (e.g., Delta, Serrate) protein fragments, and analogs or derivatives thereof, which mediate heterotypic binding to Notch (and thus are termed herein "adhesive"), and nucleic acid sequences relating to the foregoing.

Also included as Therapeutics of the invention are inhibitors (e.g., peptide inhibitors) of the foregoing toporythmic protein interactions with Notch.

The ability to bind to a toporythmic protein can be demonstrated by in vitro aggregation assays with cells expressing such a toporythmic protein as well as cells expressing Notch or a Notch derivative (See Section 6). That is, the ability of a protein fragment to bind to a Notch protein can be demonstrated by detecting the ability of the fragment, when expressed on the surface of a first cell, to bind to a Notch protein expressed on the surface of a second cell. Inhibitors of the foregoing interactions can be detected by their ability to inhibit such aggregation in vitro.

The nucleic acid sequences encoding toporythmic proteins or adhesive domains thereof, for use in such assays, can be isolated from human, porcine, bovine, feline, avian, equine, canine, or insect, as well as primate sources and any other species in which homologs of known toporythmic genes can be identified.

In a specific embodiment, the adhesive fragment of Notch is that comprising the portion of Notch most homologous to ELR 11 and 12, i.e., amino acid numbers 447 through 527 (SEQ ID NO:14) of the Drosophila Notch sequence (see FIG. 4). In yet another specific embodiment, the adhesive fragment of Delta mediating binding to Notch is that comprising the portion of Delta most homologous to about amino acid numbers 1–230 of the Drosophila Delta sequence (SEQ ID NO:2). In a specific embodiment relating to an adhesive fragment of Serrate, such fragment is that comprising the portion of Serrate most homologous to about amino acid numbers 85–283 or 79–282 of the Drosophila Serrate sequence (see FIG. 5 (SEQ ID NO:4)).

Due to the degeneracy of nucleotide coding sequences, other DNA sequences which encode substantially the same amino acid sequence as the adhesive sequences may be used in the practice of the present invention. These include but are not limited to nucleotide sequences comprising all or portions of the Notch, Delta, or Serrate genes which are altered by the substitution of different codons that encode a functionally equivalent amino acid residue within the sequence, thus producing a silent change. Likewise, the adhesive protein fragments or derivatives thereof, of the invention include, but are not limited to, those containing, as a primary amino acid sequence, all or part of the amino acid sequence of the adhesive domains including altered sequences in which functionally equivalent amino acid residues are substituted for residues within the sequence resulting in a silent change.

Adhesive fragments of toporythmic proteins and potential derivatives, analogs or peptides related to adhesive toporythmic protein sequences, can be tested for the desired binding activity e.g., by the in vitro aggregation assays described in the examples herein. Adhesive derivatives or adhesive analogs of adhesive fragments of toporythmic proteins include but are not limited to those peptides which are substantially homologous to the adhesive fragments, or whose encoding nucleic acid is capable of hybridizing to the nucleic acid sequence encoding the adhesive fragments, and which peptides and peptide analogs have positive binding activity e.g., as tested in vitro by an aggregation assay such as described in the examples sections infra. Such derivatives and analogs are envisioned as Therapeutics and are within the scope of the present invention.

The adhesive-protein related derivatives, analogs, and peptides of the invention can be produced by various methods known in the art. The manipulations which result in their production can occur at the gene or protein level (see Section 5.6).

Additionally, the adhesive-encoding nucleic acid sequence can be mutated in vitro or in vivo; and manipulations of the adhesive sequence may also be made at the protein level (see Section 5.6).

In addition, analogs and peptides related to adhesive fragments can be chemically synthesized.

5.10. Assays of Notch Proteins, Derivatives and Analogs

The in vitro activity of Notch proteins, derivatives and analogs, and other toporythmic proteins which bind to Notch, can be assayed by various methods.

For example, in one embodiment, where one is assaying for the ability to bind or compete with wild-type Notch for binding to anti-Notch antibody, various immunoassays known in the art can be used, including but not limited to competitive and non-competitive assay systems using techniques such as radioimmunoassays, ELISA (enzyme linked immunosorbent assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labelled. Many means are known in the art for detecting binding in an immunoassay and are within the scope of the present invention.

In another embodiment, where one is assaying for the ability to mediate binding to Notch, one can carry out an in vitro aggregation assay such as described infra in Section 6 or 7 (see also Fehon et al., 1990, Cell 61:523–534; Rebay et al., 1991, Cell 67:687–699).

In another embodiment, where another ligand for Notch is identified, ligand binding can be assayed, e.g., by binding assays well known in the art. In another embodiment, physiological correlates of ligand binding to cells expressing a Notch receptor (signal transduction) can be assayed.

In another embodiment, in insect or other model systems, genetic studies can be done to study the phenotypic effect of a Notch mutant that is a derivative or analog of wild-type Notch.

Other methods will be known to the skilled artisan and are within the scope of the invention.

5.11. Antibodies to Notch Proteins, Derivatives and Analogs

According to one embodiment of the invention, antibodies and fragments containing the binding domain thereof, directed against Notch are Therapeutics. Accordingly, Notch proteins, fragments or analogs or derivatives thereof, in particular, human Notch proteins or fragments thereof, may be used as immunogens to generate anti-Notch protein antibodies. Such antibodies can be polyclonal, monoclonal, chimeric, single chain, Fab fragments, or from an Fab expression library. In a specific embodiment, antibodies specific to EGF-like repeats 11 and 12 of Notch may be prepared. In other embodiments, antibodies reactive with the extracellular domain of Notch can be generated. One example of such antibodies may prevent aggregation in an in vitro assay. In another embodiment, antibodies specific to human Notch are produced.

Various procedures known in the art may be used for the production of polyclonal antibodies to a Notch protein or peptide. In a particular embodiment, rabbit polyclonal antibodies to an epitope of the human Notch protein encoded by a sequence depicted in FIG. 10 or 11, or a subsequence thereof, can be obtained. For the production of antibody, various host animals can be immunized by injection with the native Notch protein, or a synthetic version, or fragment thereof, including but not limited to rabbits, mice, rats, etc. Various adjuvants may be used to increase the immunological response, depending on the host species, and including but not limited to Freund's (complete and incomplete), mineral gels such as aluminum hydroxide, surface active substances such as lysolecithin, pluronic polyols, polyanions, peptides, oil emulsions, keyhold limpet hemocyanins, dinitrophenol, and potentially useful human adjuvants such as BCG (bacille Calmette-Guerin) and corynebacterium parvum.

For preparation of monoclonal antibodies directed toward a Notch protein sequence, any technique which provides for the production of antibody molecules by continuous cell lines in culture may be used. For example, the hybridoma technique originally developed by Kohler and Milstein (1975, Nature 256, 495–497), as well as the trioma technique, the human B-cell hybridoma technique (Kozbor et al., 1983, Immunology Today 4, 72), and the EBV-hybridoma technique to produce human monoclonal antibodies (Cole et al., 1985, in Monoclonal Antibodies and Cancer Therapy, Alan R. Liss, Inc., pp. 77–96).

Antibody fragments which contain the idiotype (binding domain) of the molecule can be generated by known techniques. For example, such fragments include but are not limited to: the F(ab')$_2$ fragment which can be produced by pepsin digestion of the antibody molecule; the Fab' fragments which can be generated by reducing the disulfide bridges of the F(ab')$_2$ fragment, and the Fab fragments which can be generated by treating the antibody molecule with papain and a reducing agent.

In the production of antibodies, screening for the desired antibody can be accomplished by techniques known in the art, e.g. ELISA (enzyme-linked immunosorbent assay). For example, to select antibodies which recognize the adhesive domain of a Notch protein, one may assay generated hybridomas for a product which binds to a protein fragment containing such domain. For selection of an antibody specific to human Notch, one can select on the basis of positive binding to human Notch and a lack of binding to Drosophila Notch.

In addition to therapeutic utility, the foregoing antibodies have utility in diagnostic immunoassays as described in Section 5.6 supra.

Similar procedures to those described supra can be used to make Therapeutics which are antibodies to domains of other proteins (particularly toporythmic proteins) that bind or otherwise interact with Notch (e.g., adhesive fragments of Delta or Serrate).

6. Domains of Notch Mediate Binding with Delta

Intermolecular association between the products of the Notch and Delta genes was detected by studying the effects of their expression on aggregation in Drosophila Schneider's 2 (S2) cells (Fehon et al., 1990, Cell 61, 523–534). Direct evidence of intermolecular interactions between Notch and Delta is described herein, as well as an assay system that can be used in dissecting the components of this interaction. Normally nonadhesive Drosophila S2 cultured cells that express Notch bind specifically in a calcium-dependent manner to cells that express Delta. Furthermore, while cells that express Notch do not bind to one another, cells that express Delta do bind to one another, suggesting that Notch and Delta can compete for binding to Delta at the cell surface. Notch and Delta form detergent-soluble complexes both in cultured cells and embryonic cells, suggesting that Notch and Delta interact directly at the molecular level in vitro and in vivo. The analyses suggest that Notch and Delta proteins interact at the cell surface via their extracellular domains.

6.1. Experimental Procedures

6.1.1. Expression Constructs

Expression constructs are described in Fehon et al., 1990, Cell 61:523–534. Briefly, Notch encoded by the MgIIa minigene a cDNA/genomic chimeric construct (Ramos et al., 1989, Genetics 123, 337–348) was expressed following insertion into pRmHa-3 (Bunch, et al., 1988, Nucl. Acids Res. 16, 1043–1061). In the resulting construct, designated pMtNMg, the metallothionein promoter in pRmHa-3 is fused to Notch sequences starting 20 nucleotides upstream of the translation start site.

The extracellular Notch construct (ECN1), was derived from a Notch cosmid (Ramos et al., 1989, Genetics 123, 337–348), and has an internal deletion of the Notch coding sequences from amino acids 1790 to 2625 inclusive (Wharton et al., 1985, Cell 43, 567–581), and a predicted frameshift that produces a novel 59 amino acid carboxyl terminus.

For the Delta expression construct, the Dl1 cDNA (Kopczynski et al., 1988, Genes Dev. 2, 1723–1735; FIG. 1; SEQ ID NO:1), which includes the complete coding capacity for Delta, was inserted into the EcoRI site of pRmHa-3. This construct was called pMTDl1.

6.1.2. Antibody Preparation

Hybridoma cell line C17.9C6 was obtained from a mouse immunized with a fusion protein based on a 2.1 kb SalI-HindIII fragment that includes coding sequences for most of the intracellular domain of Notch (amino acids 1791–2504; Wharton et al., 1985, Cell 43, 567–581). The fragment was subcloned into pUR289 (Ruther and Muller-Hill, 1983, EMBO J. 2, 1791–1794), and then transferred into the pATH 1 expression vector (Dieckmann and Tzagoloff, 1985, J. Biol. Chem. 260, 1513–1520) as a BglII-HindIII fragment. Soluble fusion protein was expressed, precipitated by 25% (NH$_4$)$_2$SO$_4$, resuspended in 6 M urea, and purified by preparative isoelectric focusing using a Rotofor (Bio-Rad) (for details, see Fehon, 1989, Rotofor Review No. 7, Bulletin 1518, Richmond, Calif.: Bio-Rad Laboratories).

Mouse polyclonal antisera were raised against the extracellular domain of Notch using four BstYl fragments of 0.8 kb (amino acids 237–501: Wharton et al., 1985, Cell 43, 567–581), 1.1 kb (amino acids 501–868), 0.99 kb (amino acids 868–1200), and 1.4 kb (amino acids 1465–1935) length, which spanned from the fifth EGF-like repeat across the transmembrane domain, singly inserted in-frame into the appropriate pGEX expression vector (Smith and Johnson, 1988, Gene 67, 31–40). Fusion proteins were purified on glutathione-agarose beads (SIGMA). Mouse and rat antisera were precipitated with 50% (NH$_4$)$_2$SO$_4$ and resuspended in PBS (150 mM NaCl, 14 mM Na$_2$HPO$_4$, 6 mM NaH$_2$PO$_4$) with 0.02% NaN$_3$.

Hybridoma cell line 201 was obtained from a mouse immunized with a fusion protein that includes coding sequences from the extracellular domain of Delta (Kopczynski et al., 1988, Genes Dev. 2, 1723–1735), including sequences extending from the fourth through the ninth EGF-like repeats in Delta (amino acids 350–529).

Rat polyclonal antisera were obtained following immunization with antigen derived from the same fusion protein construct. In this case, fusion protein was prepared by lysis of IPTG-induced cells in SDS-Laemmli buffer (Carroll and Laughon, 1987, in DNA Cloning, Volume III, D. M. Glover, ed. (Oxford: IRL Press), pp. 89–111), separation of proteins by SDS-PAGE, excision of the appropriate band from the gel, and electroelution of antigen from the gel slice for use in immunization (Harlow and Lane, 1988, Antibodies: A Laboratory Manual (Cold Spring Harbor, N.Y.: Cold Spring Harbor Laboratory)).

6.1.3. Cell Culture and Transfection

The S2 cell line (Schneider, 1972, J. Embryol. Exp. Morph. 27, 353–365) was grown in M3 medium (prepared by Hazleton Co.) supplemented with 2.5 mg/ml Bacto-Peptone (Difco), 1 mg/ml TC Yeastolate (Difco), 11% heat-inactivated fetal calf serum (FCS) (Hyclone), and 100 U/ml penicillin-100 µg/ml streptomycin-0.25 µg/ml fungizone (Hazleton). Cells growing in log phase at ~2×10$^6$ cells/ml were transfected with 20 µg of DNA-calcium phosphate coprecipitate in 1 ml per 5 ml of culture as previously described (Wigler et al., 1979, Proc. Natl. Acad. Sci. USA 78, 1373–1376), with the exception that BES buffer (SIGMA) was used in place of HEPES buffer (Chen and Okayama, 1987, Mol. Cell. Biol. 7, 2745–2752). After 16–18 hr, cells were transferred to conical centrifuge tubes, pelleted in a clinical centrifuge at full speed for 30 seconds, rinsed once with ¼ volume of fresh complete medium, resuspended in their original volume of complete medium, and returned to the original flask. Transfected cells were then allowed to recover for 24 hr before induction.

6.1.4. Aggregation Assays

Expression of the Notch and Delta metallothionein constructs was induced by the addition of $CuSO_4$ to 0.7 mM. Cells transfected with the ECN1 construct were treated similarly. Cells were then mixed, incubated under aggregation conditions, and scored for their ability to aggregate using specific antisera and immunofluorescence microscopy to visualize expressing cells.

Two types of aggregation assays were used. In the first assay, a total of 3 ml of cells ($5-10\times10^6$ cells/ml) was placed in a 25 ml Erlenmeyer flask and rotated at 40–50 rpm on a rotary shaker for 24–48 hr at room temperature. For these experiments, cells were mixed 1–4 hr after induction began and induction was continued throughout the aggregation period. In the second assay, ~0.6 ml of cells were placed in a 0.6 ml Eppendorf tube (leaving a small bubble) after an overnight induction (12–16 hr) at room temperature and rocked gently for 1–2 hr at 4° C. The antibody inhibition and $Ca^{2+}$ dependence experiments were performed using the latter assay. For $Ca^{2+}$ dependence experiments, cells were first collected and rinsed in balanced saline solution (BSS) with 11% FCS (BSS-FCS; FCS was dialyzed against 0.9% NaCl, 5 mM Tris [pH 7.5]) or in $Ca^{2+}$ free BSS-FCS containing 10 mM EGTA (Snow et al., 1989, Cell 59, 313–323) and then resuspended in the same medium at the original volume. For the antibody inhibition experiments, Notch-transfected cells were collected and rinsed in M3 medium and then treated before aggregation in M3 medium for 1 hr at 4° C. with a 1:250 dilution of immune or preimmune sera from each of the four mice immunized with fusion proteins containing segments from the extracellular domain of Notch (see Antibody Preparation above).

6.1.5. Immunofluorescence

Cells were collected by centrifugation (3000 rpm for 20 seconds in an Eppendorf microcentrifuge) and fixed in 0.6 ml Eppendorf tubes with 0.5 ml of freshly made 2% paraformaldehyde in PBS for 10 min at room temperature. After fixing, cells were collected by centrifugation, rinsed twice in PBS, and stained for 1 hr in primary antibody in PBS with 0.1% saponin (SIGMA) and 1% normal goat serum (Pocono Rabbit Farm, Canadensis, Pa.). Monoclonal antibody supernatants were diluted 1:10 and mouse or rat sera were diluted 1:1000 for this step. Cells were then rinsed once in PBS and stained for 1 hr in specific secondary antibodies (double-labeling grade goat anti-mouse and goat anti-rat, Jackson Immunoresearch) in PBS-saponin-normal goat serum. After this incubation, cells were rinsed twice in PBS and mounted on slides in 90% glycerol, 10% 1 M Tris (pH 8.0), and 0.5% n-propyl gallate. Cells were viewed under epifluorescence on a Leitz Orthoplan 2 microscope.

Confocal micrographs were taken using the Bio-Rad MRC 500 system connected to a Zeiss Axiovert compound microscope. Images were collected using the BHS and GHS filter sets, aligned using the ALIGN program, and merged using MERGE. Fluorescent bleed-through from the green into the red channel was reduced using the BLEED program (all software provided by Bio-Rad). Photographs were obtained directly from the computer monitor using Kodak Ektar 125 film.

6.1.6. Cell Lysates, Immunoprecipitations, and Western Blots

Nondenaturing detergent lysates of tissue culture and wild-type Canton-S embryos were prepared on ice in ~10 cell vol of lysis buffer (300 mM NaCl, 50 mM Tris [pH 8.0], 0.5% NP-40, 0.5% deoxycholate, 1 mM $CaCl_2$, 1 mM $MgCl_2$) with 1 mM phenylmethysulfonyl fluoride (PMSF) and diisopropyl fluorophosphate diluted 1:2500 as protease inhibitors. Lysates were sequentially triturated using 18G, 21G, and 25G needles attached to 1 cc tuberculin syringes and then centrifuged at full speed in a microfuge 10 min at 4° C. to remove insoluble material. Immunoprecipitation was performed by adding ~1 µg of antibody (1–2 µl of polyclonal antiserum) to 250–500 µl of cell lysate and incubating for 1 hr at 4° C. with agitation. To this mixture, 15 µg of goat anti-mouse antibodies (Jackson Immunoresearch; these antibodies recognize both mouse and rat IgG) were added and allowed to incubate for 1 hr at 4° C. with agitation. This was followed by the addition of 100 µl of fixed Staphylococcus aureus (Staph A) bacteria (Zysorbin, Zymed; resuspended according to manufacturer's instructions), which had been collected, washed five times in lysis buffer, and incubated for another hour. Staph A-antibody complexes were then pelleted by centrifugation and washed three times in lysis buffer followed by two 15 min washes in lysis buffer. After being transferred to a new tube, precipitated material was suspended in 50 µl of SDS-PAGE sample buffer, boiled immediately for 10 min, run on 3%–15% gradient gels, blotted to nitrocellulose, and detected using monoclonal antibodies and HRP-conjugated goat anti-mouse secondary antibodies as previously described (Johansen et al., 1989, J. Cell Biol. 109, 2427–2440). For total cellular protein samples used on Western blots, cells were collected by centrifugation, lysed in 10 cell vol of sample buffer that contained 1 mM PMSF, and boiled immediately.

6.2. Results

6.2.1. The Expression of Notch and Delta in Cultured Cells

To detect interactions between Notch and Delta, we examined the behavior of cells expressing these proteins on their surfaces using an aggregation assay. We chose the S2 cell line (Schneider, 1972, J. Embryol. Exp. Morph. 27, 353–365) for these studies. S2 cells express an aberrant Notch message and no detectable Notch due to a rearrangement of the 5' end of the Notch coding sequence. These cells also express no detectable Delta.

Results of Western blot and immunofluorescent analysis clearly showed that the Notch and Delta constructs support expression of proteins of the expected sizes and subcellular localization.

6.2.2. Cells that Express Notch and Delta Aggregate

A simple aggregation assay was used to detect interactions between Notch and Delta expressed on the surface of S2 cells.

S2 cells in log phase growth were separately transfected with either the Notch or Delta metallothionein promoter construct. After induction with $CuSO_4$, transfected cells were mixed in equal numbers and allowed to aggregate overnight at room temperature (for details, see Experimental Procedures, Section 6.1). Alternatively, in some experiments intended to reduce metabolic activity, cells were mixed gently at 4° C. for 1–2 hr. To determine whether aggregates had formed, cells were processed for immunofluorescence microscopy using antibodies specific for each gene product and differently labeled fluorescent secondary antibodies.

Expressing cells usually constituted less than 5% of the total cell population because transient rather than stable transformants were used. The remaining cells either did not express a given protein or expressed at levels too low for detection by immunofluorescence microscopy. As controls, we performed aggregations with only a single type of transfected cell.

The results (Fehon et al., 1990, Cell 61:523–534) showed that while Notch-expressing (Notch$^+$) cells alone did not form aggregates in the assay, Delta-expressing (Delta$^+$) cells did. The tendency for Delta$^+$ cells to aggregate was apparent even in nonaggregated control samples, where cell clusters of 4–8 cells that probably arose from adherence between mitotic sister cells commonly occurred. However, clusters were more common after incubation under aggregation conditions (e.g., 19% of Delta$^+$ cells in aggregates before incubation vs. 37% of Delta$^+$ cells in aggregates after incubation), indicating that Delta$^+$ cells are able to form stable contacts with one another in this assay.

In remarkable contrast to control experiments with Notch$^+$ cells alone, aggregation of mixtures of Notch$^+$ and Delta$^+$ cells resulted in the formation of clusters of up to 20 or more cells. The fraction of expressing cells found in clusters of four or more stained cells after 24 hr of aggregation ranged from 32%–54% in mixtures of Notch$^+$ and Delta$^+$ cells. This range was similar to that seen for Delta$^+$ cells alone (37%–40%) but very different from that for Notch$^+$ cells alone (only 0%–5%). Although a few clusters that consisted only of Delta$^+$ cells were found, Notch$^+$ cells were never found in clusters of greater than four to five cells unless Delta$^+$ cells were also present. Again, all cells within these clusters expressed either Notch or Delta, even though transfected cells composed only a small fraction of the total cell population. At 48 hr, the degree of aggregation appeared higher (63%–71%), suggesting that aggregation had not yet reached a maximum after 24 hr under these conditions. Also, cells cotransfected with Notch and Delta constructs (so that all transfected cells express both proteins) aggregated in a similar fashion under the same experimental conditions.

Notch involvement in the aggregation process was directly tested by examining the effect of a mixture of polyclonal antisera directed against fusion proteins that spanned almost the entire extracellular domain of Notch on aggregation (see Experimental Procedures, Section 6.1). To minimize artifacts that might arise due to a metabolic response to patching of surface antigens, antibody treatment and the aggregation assay were performed at 4° C. in these experiments. Notch$^+$ cells were incubated with either preimmune or immune mouse sera for 1 hr, Delta$^+$ cells were added, and aggregation was performed for 1–2 hr. While Notch$^+$ cells pretreated with preimmune sera aggregated with Delta$^+$ cells (in one of three experiments, 23% of the Notch$^+$ cells were in Notch$^+$-Delta$^+$ cell aggregates), those treated with immune sera did not (only 2% of Notch$^+$ cells were in aggregates). This result suggested that the extracellular domain of Notch was required for Notch$^+$-Delta$^+$ cell aggregation.

6.2.3. Notch-Delta-Mediated Aggregation is Calcium Dependent

The ability of expressing cells to aggregate in the presence or absence of $Ca^{2+}$ ions was tested to determine whether there is a $Ca^{2+}$ ion requirement for Notch-Delta aggregation. To minimize possible nonspecific effects due to metabolic responses to the removal of $Ca^{2+}$, these experiments were performed at 4° C. The results clearly demonstrated a dependence of Notch-Delta-mediated aggregation on exogenous $Ca^{2+}$.

6.2.4. Notch and Delta Interact Within a Single Cell

The question whether Notch and Delta are associated within the membrane of one cell that expresses both proteins was posed by examining the distributions of Notch and Delta in cotransfected cells. To test whether the observed colocalization was coincidental or represented a stable interaction between Notch and Delta, live cells were treated with an excess of polyclonal anti-Notch antiserum. This treatment resulted in "patching" of Notch on the surface of expressing cells into discrete patches as detected by immunofluorescence. There was a distinct correlation between the distributions of Notch and Delta on the surfaces of these cells after this treatment, indicating that these proteins are associated within the membrane.

6.2.5. Interactions with Delta do not Require the Intracellular Domain of Notch In addition to a large extracellular domain that contains EGF-like repeats, Notch has a sizeable intracellular (IC) domain of ~940 amino acids. The IC domain includes a phosphorylation site (Kidd et al., 1989, Genes Dev. 3, 1113–1129), a putative nucleotide binding domain, a polyglutamine stretch (Wharton et al., 1985, Cell 43, 567–581; Kidd, et al., 1986, Mol. Cell. Biol. 6, 3094–3108), and sequences homologous to the yeast cdc10 gene, which is involved in cell cycle control in yeast (Breeden and Nasmyth, 1987, Nature 329, 651–654). A variant Notch construct was used from which coding sequences for ~835 amino acids of the IC domain, including all of the structural features noted above, had been deleted (leaving 25 membrane-proximal amino acids and a novel 59 amino acid carboxyl terminus; see Experimental Procedures).

In aggregation assays, cells that expressed the ECN1 construct consistently formed aggregates with Delta$^+$ cells, but not with themselves, just as was observed for cells that expressed intact Notch. Sharp bands of ECN1 staining were observed within regions of contact with Delta$^+$ cells, again indicating a localization of ECN1 within regions of contact between cells. To test for interactions within the membrane, surface antigen co-patching experiments were conducted using cells cotransfected with the ECN1 and Delta constructs. As observed for intact Notch, when ECN1 was patched using polyclonal antisera against the extracellular domain of Notch, ECN1 and Delta colocalized at the cell surface. These results demonstrate that the observed interactions between Notch and Delta within the membrane do not require the deleted portion of the IC domain of Notch and are therefore probably mediated by the extracellular domain.

6.2.6. Notch and Delta Form Detergent-Soluble Intermolecular Complexes

The preceding results indicated molecular interactions between Notch and Delta present within the same membrane and between these proteins expressed on different cells. A further test for such interactions is whether these proteins would coprecipitate from nondenaturing detergent extracts of cells that express Notch and Delta. If Notch and Delta form a stable intermolecular complex either between or within cells, then it should be possible to precipitate both proteins from cell extracts using specific antisera directed against one of these proteins. This analysis was performed by immunoprecipitating Delta with polyclonal antisera from NP-40/deoxycholate lysates (see Experimental Procedures) of cells cotransfected with the Notch and Delta constructs that had been allowed to aggregate overnight or of 0–24 hr wild-type embryos.

Coprecipitation of Notch was detected in Delta immunoprecipitates from cotransfected cells and embryos. However, coprecipitating Notch appeared to be present in much smaller quantities than Delta and was therefore difficult to detect. The fact that immunoprecipitation of Delta results in the coprecipitation of Notch constitutes direct evidence that these two proteins form stable intermolecular complexes in transfected S2 cells and in embryonic cells.

6.3. Discussion

Use of an in vitro aggregation assay that employs normally nonadhesive S2 cells showed that cells that express Notch and Delta adhere specifically to one another.

7. EGF Repeats 11 and 12 of Notch are Required and Sufficient for Notch-Delta-Mediated Aggregation The same aggregation assay was used as described in Section 6, together with deletion mutants of Notch to identify regions within the extracellular domain of Notch necessary for interactions with Delta. The evidence shows that the EGF repeats of Notch are directly involved in this interaction and that only two (ELR 11 and 12) of the 36 EGF repeats appear necessary. These two EGF repeats are sufficient for binding to Delta and that the calcium dependence of Notch-Delta mediated aggregation also associates with these two repeats. Finally, the two corresponding EGF repeats from the Xenopus homolog of Notch also mediate aggregation with Delta, implying that not only has the structure of Notch been evolutionarily conserved, but also its function. These results suggest that the extracellular domain of Notch is surprisingly modular, and could potentially bind a variety of proteins in addition to Delta. (See Rebay et al., 1991, Cell 67:687–699.)

7.1. Experimental Produdures

7.1.1. Expression Constructs

The constructs described are all derivatives of the full length Notch expression construct #1 pMtNMg (see Section 6, supra), and were made as described (Rebay et al., 1991, Cell 67:687–699).

7.1.2. Cell Culture and Transfection

The Drosophila S2 cell line was grown and transfected as described in Section 6, supra. The Delta-expressing stably transformed S2 cell line L-49-6-7 (kindly established by L. Cherbas) was grown in M3 medium (prepared by Hazleton Co.) supplemented with 11% heat inactivated fetal calf serum (FCS) (Hyclone), 100 U/ml penicillin-100 μg/ml streptomycin-0.25 μg/ml fungizone (Hazleton), $2 \times 10^{-7}$ M methotrexate, 0.1 mM hypoxanthine, and 0.016 mM thymidine.

7.1.3. Aggregation Assays and Immunofluorescence

Aggregation assays and $Ca^{++}$ dependence experiments were as described supra, Section 6. Cells were stained with the anti-Notch monoclonal antibody 9C6.C17 and anti-Delta rat polyclonal antisera (details described in Section 6, supra). Surface expression of Notch constructs in unpermeabilized cells was assayed using rat polyclonal antisera raised against the 0.8 kb (amino acids 237–501; Wharton et al., 1985, Cell 43, 567–581) BstYI fragment from the extracellular domain of Notch. Cells were viewed under epifluorescence on a Leitz Orthoplan 2 microscope.

7.2. Results

7.2.1. EGF Repeats 11 and 12 of Notch are Requires for Notch-Delta Mediated Aggregation An extensive deletion analysis was undertaken of the extracellular domain of the Notch protein, which was shown (supra, Section 6; Fehon et al., 1990, Cell 61:523–534) to be involved in Notch-Delta interactions, to identify the precise domain of Notch mediating these interactions. The ability of cells transfected with the various deletion constructs to interact with Delta was tested using the aggregation assay described in Section 6. Briefly, Notch deletion constructs were transiently transfected into Drosophila S2 cells, induced with $CuSO_4$, and then aggregated overnight at room temperature with a small amount of cells from the stably transformed Delta expressing cell line L49-6-7(Cherbas), yielding a population typically composed of ~1% Notch expressing cells and ~5% Delta expressing cells, with the remaining cells expressing neither protein.

Schematic drawings of the constructs tested and results of the aggregation experiments are shown in FIG. 2. To assay the degree of aggregation, cells were stained with antisera specific to each gene product and examined with immunofluorescence microscopy. Aggregates were defined as clusters of four or more cells containing both Notch and Delta expressing cells, and the values shown in FIG. 2 represent the percentage of all Notch expressing cells found in such clusters. All numbers reflect the average result from at least two separate transfection experiments in which at least 100 Notch expressing cell units (either single cells or clusters) were scored.

The initial constructs (#2 DSph and #3 ΔCla) deleted large portions of the EGF repeats. Their inability to promote Notch-Delta aggregation suggested that the EGF repeats of Notch were involved in the interaction with Delta. A series of six in-frame ClaI restriction sites was used to further dissect the region between EGF repeats 7 and 30. Due to sequence homology between repeats, five of the ClaI sites occur in the same relative place within the EGF repeat, just after the third cysteine, while the sixth site occurs just before the first cysteine of EGF repeat 31 (FIG. 3). Thus, by performing a partial ClaI digestion and then religating, deletions were obtained that not only preserved the open reading frame of the Notch protein but in addition frequently maintained the structural integrity and conserved spacing, at least theoretically, of the three disulfide bonds in the chimeric EGF repeats produced by the religation (FIG. 2, constructs #4–14). Unfortunately, the most 3' ClaI site was resistant to digestion while the next most 3' ClaI site broke between EGF repeats 30 and 31. Therefore, when various ClaI digestion fragments were reinserted into the framework of the complete ClaI digest (construct #3 ΔCla), the overall structure of the EGF repeats was apparently interrupted at the 3' junction.

Several points about this series of constructs are worth noting. First, removal of the ClaI restriction fragment breaking in EGF repeats 9 and 17 (construct #8 ΔEGF9–17) abolished aggregation with Delta, while reinsertion of this piece into construct #3 ΔCla, which lacks EGF repeats 7–30, restored aggregation to roughly wild type levels (construct

13 ΔCla+EGF9–17), suggesting that EGF repeats 9 through 17 contain sequences important for binding to Delta. Second, all constructs in this series (#4–14) were consistent with the binding site mapping to EGF repeats 9 through 17. Expression constructs containing these repeats (#6, 7, 9, 10, 13) promoted Notch-Delta interactions while constructs lacking these repeats (#4, 5, 8, 11, 12, 14) did not. To confirm that inability to aggregate with Delta cells was not simply due to failure of the mutagenized Notch protein to reach the cell surface, but actually reflected the deletion of the necessary binding site, cell surface expression of all constructs was tested by immunofluorescently staining live transfected cells with antibodies specific to the extracellular domain of Notch. All constructs failing to mediate Notch-Delta interactions produced a protein that appeared to be expressed normally at the cell surface. Third, although the aggregation assay is not quantitative, two constructs which contained EGF repeats 9–17, #9 ΔEGF17–26 or most noticeably #10 ΔEGF26–30, aggregated at a seemingly lower level. Cells transfected with constructs #9 ΔEGF17–26 and 10 ΔEGF26–30 showed considerably less surface staining than normal, although fixed and permeabilized cells reacted with the same antibody stained normally, indicating the epitopes recognized by the antisera had not been simply deleted. By comparing the percentage of transfected cells in either permeabilized or live cell populations, it was found that roughly 50% of transfected cells for construct #9 ΔEGF17–26 and 10% for construct #10 ΔEGF26–30 produced detectable protein at the cell surface. Thus these two constructs produced proteins which often failed to reach the cell surface, perhaps because of misfolding, thereby reducing, but not abolishing, the ability of transfected cells to aggregate with Delta-expressing cells.

Having mapped the binding site to EGF repeats 9 through 17, further experiments (Rebay et al., 1991, Cell 67:687–699) revealed that EGF repeat 14 of Notch was not involved in the interactions with Delta modelled by the tissue culture assay.

To further map the Delta binding domain within EGF repeats 9–17, specific oligonucleotide primers and the PCR technique were used to generate several subfragments of this region. Three overlapping constructs, #16, 17 and 18 were produced, only one of which, #16 ΔCla+EGF9–13, when transfected into S2 cells, allowed aggregation with Delta cells. Construct #19 ΔCla+EGF(10–13), which lacks EGF repeat 9, further defined EGF repeats 10–13 as the region necessary for Notch-Delta interactions.

Constructs #20–24 represented attempts to break this domain down even further using the same PCR strategy (see FIG. 3). Constructs #20 ΔCla+EGF(11–13), in which EGF repeat 12 is the only entire repeat added, and #21 ΔCla+EGF(10–12), in which EGF repeat 11 is the only entire repeat added, failed to mediate aggregation, suggesting that the presence of either EGF repeat 11 or 12 alone was not sufficient for Notch-Delta interactions. However, since the 3' ligation juncture of these constructs interrupted the overall structure of the EGF repeats, it was possible that a short "buffer" zone was needed to allow the crucial repeat to function normally. Thus for example in construct #19 ΔCla+EGF(10–13), EGF repeat 12 might not be directly involved in binding to Delta but instead might contribute the minimum amount of buffer sequence needed to protect the structure of EGF repeat 11, thereby allowing interactions with Delta. Constructs #22–24 addressed this issue. Constructs #22 ΔCla+EGF(10–11), which did not mediate aggregation, and #23 ΔCla+EGF(10–12), which did, again suggested that both repeats 11 and 12 are required while the flanking sequence from repeat 13 clearly is not. Finally, construct #24 ΔCla+EGF(11–12), although now potentially structurally disrupted at the 5' junction, convincingly demonstrated that the sequences from EGF repeat 10 are not crucial. Thus based on entirely consistent data from 24 constructs, EGF repeats 11 and 12 of Notch together define the smallest functional unit obtainable from this analysis that contains the necessary sites for binding to Delta in transfected S2 cells.

7.2.2. EGF Repeats 11 and 12 of Notch are Sufficient for Notch-Delta Mediated Aggregation The large ClaI deletion into which PCR fragments were inserted (#3 ΔCla) retains roughly ⅓ of the original 36 EGF repeats as well as the three Notch/lin-12 repeats. While these are clearly not sufficient to promote aggregation, it is possible that they form a necessary framework within which specific EGF repeats can interact with Delta. To test whether only a few EGF repeats were in fact sufficient to promote aggregation, two constructs were designed, #25 ΔEGF which deleted all 36 EGF repeats except for the first two-thirds of repeat 1, and #30 ΔECN which deleted the entire extracellular portion of Notch except for the first third of EGF repeat 1 and ~35 amino acids just before the transmembrane domain. Fragments which had mediated Notch-Delta aggregation in the background of construct #3 ΔCla, when inserted into construct #25 ΔEGF, were again able to promote interactions with Delta (constructs #26–30). Analogous constructs (#31,32) in which the Notch/lin-12 repeats were also absent, again successfully mediated Notch-Delta aggregation. Thus EGF repeats 11 and 12 appear to function as independent modular units which are sufficient to mediate Notch-Delta interactions in S2 cells, even in the absence of most of the extracellular domain of Notch.

7.2.3. EGF Repeats 11 and 12 of Notch Maintain the Calcium Dependence of Notch-Delta Mediated Aggregation The ability of cells expressing certain deletion constructs to aggregate with Delta expressing cells was examined in the presence or absence of $Ca^{++}$ ions. The calcium dependence of the interaction was preserved in even the smallest construct, consistent with the notion that the minimal constructs containing EGF repeats 11 and 12 bind to Delta in a manner similar to that of full length Notch.

7.2.4. The Delta Binding Function of EGF Repeats 11 and 12 of Notch is Conserved in the Xenopus Homolog of Notch PCR primers based on the Xenopus Notch sequence (Coffman et al., 1990, Science 249, 1438–1441) were used to obtain an ~350 bp fragment from a Xenopus Stage 17 cDNA library that includes EGF repeats 11 and 12 flanked by half of repeats 10 and 13 on either side. This fragment was cloned into construct #3 ΔCla, and three independent clones were tested for ability to interact with Delta in the cell culture aggregation assay. Two of the clones, #33a&bΔCla+XEGF(10–13), when transfected into S2 cells were able to mediate Notch-Delta interactions at a level roughly equivalent to the analogous Drosophila Notch construct #19ΔCla+EGF(10–13), and again in a calcium dependent manner (Table III). However, the third clone #33cΔCla+XEGF(10–13) failed to mediate Notch-Delta interactions although the protein was expressed normally at the cell surface as judged by staining live unpermeabilized cells. Sequence comparison of the Xenopus PCR product in constructs #33a and 33c revealed a missense mutation resulting in a leucine to proline change (amino acid #453, Coffman, et al., 1990, Science 249, 1438–1441) in EGF repeat 11 of construct #33c. Although this residue is not conserved between Drosophila and Xenopus Notch (FIG. 8), the introduction of a proline residue might easily disrupt the structure of the EGF repeat, and thus prevent it from interacting properly with Delta.

Comparison of the amino acid sequence of EGF repeats 11 and 12 of Drosophila and Xenopus Notch reveals a high degree of amino acid identity, including the calcium binding consensus sequence (FIG. 4, SEQ ID NO:1 and NO:2). However the level of homology is not strikingly different from that shared between most of the other EGF repeats, which overall exhibit about 50% identity at the amino acid level. This one to one correspondence between the individual EGF repeats of Drosophila and Xenopus Notch, together with the functional conservation of ELR 11 and 12, suggests that the 36 EGF repeats of Notch comprise a tandem area of conserved functional units.

7.3. Discussion

An extensive deletion analysis of the extracellular domain of Notch was used to show that the regions of Notch containing EGF-homologous repeats 11 and 12 are both necessary and sufficient for Notch-Delta-mediated aggregation, and that this Delta binding capability has been conserved in the same two EGF repeats of Xenopus Notch. The finding that the aggregation mapped to EGF repeats 11 and 12 of Notch demonstrates that the EGF repeats of Notch also function as specific protein binding domains. EGF repeats 11 and 12 alone (#32ΔECN+EGF(11–12)) were sufficient to maintain the $Ca^{++}$ dependence of Notch-Delta interactions.

The various deletion constructs suggest that ELR 11 and ELR 12 function as a modular unit, independent of the immediate context into which they are placed. Thus, neither the remaining 34 EGF repeats nor the three Notch/lin-12 repeats appear necessary to establish a structural framework required for EGF repeats 11 and 12 to function. Interestingly, almost the opposite effect was observed: although the aggregation assay does not measure the strength of the interaction, as the binding site was narrowed down to smaller and smaller fragments, an increase was observed in the ability of the transfected cells to aggregate with Delta expressing cells, suggesting that the normal flanking EGF sequences actually impede association between the proteins. The remaining 34 EGF repeats may also form modular binding domains for other proteins interacting with Notch at various times during development.

The finding that EGF repeats 11 and 12 of Notch form a discrete Delta binding unit represents the first concrete evidence supporting the idea that each EGF repeat or small subset of repeats may play a unique role during development, possibly through direct interactions with other proteins. The homologies seen between the adhesive domain of Delta and Serrate (FIG. 5) suggest that the homologous portion of Serrate is "adhesive" in that it mediates binding to other toporythmic proteins (see Section 8, infra). In addition, the gene scabrous, which encodes a secreted protein with similarity to fibrinogen, may interact with Notch.

In addition to the EGF repeat, multiple copies of other structural motifs commonly occur in a variety of proteins. One relevant example is the cdc10/ankyrin motif, six copies of which are found in the intracellular domain of Notch. Ankyrin contains 22 of these repeats. Perhaps repeated arrays of structural motifs may in general represent a linear assembly of a series of modular protein binding units. Given these results together with the known structural, genetic and developmental complexity of Notch, Notch may interact with a number of different ligands in a precisely regulated temporal and spacial pattern throughout development. Such context specific interactions with extracellular proteins could be mediated by the EGF and Notch/lin-12 repeats, while interactions with cytoskeletal and cytoplasmic proteins could be mediated by the intracellular cdc10/ankyrin motifs.

8. Sequences Which Mediate Notch-Serrate Interactions

As described herein, the two EGF repeats of Notch which mediate interactions with Delta, namely EGF repeats 11 and 12, also constitute a Serrate binding domain (see Rebay et al., 1991, Cell 67:687–699).

To test whether Notch and Serrate directly interact, S2 cells were transfected with a Serrate expression construct and mixed with Notch expressing cells in an aggregation assay. For the Serrate expression construct, a synthetic primer containing an artificial BamHI site immediately 5' to the initiator AUG at position 442 (all sequence numbers are according to Fleming et al., 1990, Genes & Dev. 4:2188–2201) and homologous through position 464, was used in conjunction with a second primer from position 681–698 to generate a DNA fragment of ~260 base pairs. This fragment was cut with BamHI and KpnI (position 571) and ligated into Bluescript KS+ (Stratagene). This construct, BTSer5'PCR, was checked by sequencing, then cut with KpnI. The Serrate KpnI fragment (571–2981) was inserted and the proper orientation selected, to generate BTSer5'PCR-Kpn. The 5' SacII fragment of BTSer5'PCR-Kpn (SacII sites in Bluescript polylinker and in Serrate (1199)) was isolated and used to replace the 5' SacII fragment of cDNA C1 (Fleming et al., 1990, Genes & Dev. 4:2188–2201), thus regenerating the full length Serrate cDNA minus the 5' untranslated regions. This insert was isolated by a SalI and partial BamHI digestion and shuttled into the BamHI and SalI sites of pRmHa-3 to generate the final expression construct, Ser-mtn.

Serrate expressing cells adhered to Notch expressing cells in a calcium dependent manner (FIG. 2 and Rebay et al., 1991, supra). However, unlike Delta, under the experimental conditions tested, Serrate did not appear to interact homotypically. In addition, no interactions were detected between Serrate and Delta.

A subset of Notch deletion constructs were tested, and showed that EGF repeats 11 and 12, in addition to binding to Delta, also mediate interactions with Serrate (FIG. 2; Constructs #1, 7–10, 13, 16, 17, 19, 28, and 32). In addition, the Serrate-binding function of these repeats also appears to have been conserved in the corresponding two EGF repeats of Xenopus Notch (#33ΔCla+XEGF(10–13)). These results unambiguously show that Notch interacts with both Delta and Serrate, and that the same two EGF repeats of Notch mediate both interactions. The Serrate region which is essential for the Notch/Serrate aggregation was also defined. Deleting nucleotides 676–1287 (i.e. amino acids 79–282) (See FIG. 5; SEQ ID NO:3 and NO:4) eliminates the ability of the Serrate protein to aggregate with Notch.

Notch and Serrate appear to aggregate less efficiently than Notch and Delta, perhaps because the Notch-Serrate interaction is weaker. One trivial explanation for this reduced amount of aggregation could be that the Serrate construct simply did not express as much protein at the cell surface as the Delta construct, thereby diminishing the strength of the interaction. Alternatively, the difference in strength of interaction may indicate a fundamental functional difference between Notch-Delta and Notch-Serrate interactions that may be significant in vivo.

9. The Cloning, Sequencing, and Expression of Human Notch

9.1. Isolation and Sequencing of Human Notch

Clones for the human Notch sequence were originally obtained using the polymerase chain reaction (PCR) to amplify DNA from a 17–18 week human fetal brain cDNA library in the Lambda Zap II vector (Stratagene).

The 400 bp fragment obtained in this manner was then used as a probe with which to screen the same library for human Notch clones. The original screen yielded three unique clones, hN3k, hN2K, and hN5k, all of which were shown by subsequent sequence analysis to fall in the 3' end of human Notch (FIG. 6). A second screen using the 5' end of hN3k as probe was undertaken to search for clones encompassing the 5' end of human Notch. One unique clone, hN4k, was obtained from this screen, and preliminary sequencing data indicate that it contains most of the 5' end of the gene (FIG. 6). Together, clones hN4k, hN3k and hN5k encompass about 10 kb of the human Notch homolog(s), beginning early in the EGF-repeats and extending into the 3' untranslated region of the gene. All three clones are cDNA inserts in the EcoRI site of pBluescript SK⁻ (Stratagene). The host *E. coli* strain is XL1-Blue (see Maniatis, T., 1990, Molecular Cloning, A Laboratory Manual, 2d ed., Cold Spring Harbor Laboratory, Cold Spring Harbor, N.Y., p. A12). An alignment of the human Notch sequences with Drosophila Notch is shown in FIG. 7.

The sequence of various portions of Notch contained in the cDNA clones was determined (by use of Sequenases®, U.S. Biochemical Corp.) and is shown for hN2k and hN4k in FIGS. 8 (SEQ ID NO:5–7) and 9 (SEQ ID NO:8, 9), respectively. Further sequence analysis of hN2k revealed that it encodes a human Notch sequence overlapping that contained in hN5k.

The complete nucleotide sequences of the human Notch cDNA contained in hN3k and hN5k was determined by the dideoxy chain termination method using the Sequenase® kit (U.S. Biochemical Corp.). Those nucleotide sequences encoding human Notch, in the appropriate reading frame, were readily identified since there are no introns and translation in only one out of the three possible reading frames yields a sequence which, upon comparison with the published Drosophila Notch deduced amino acid sequence, yields a sequence with a substantial degree of homology to the Drosophila Notch sequence. The DNA and deduced protein sequences of the human Notch cDNA in hN3k and hN5k are presented in FIGS. 10 (SEQ ID NO:10, 11) and 11 (SEQ ID NO:12, 13), respectively. Clone hN3k encodes a portion of a Notch polypeptide starting at approximately the third Notch/lin-12 repeat to several amino acids short of the carboxy-terminal amino acid. Clone hN5k encodes a portion of a Notch polypeptide starting approximately before the cdc10 region through the end of the polypeptide, and also contains a 3' untranslated region.

Comparing the DNA and protein sequences presented in FIG. 10 (SEQ ID NO:10, 11) with those in FIG. 11 (SEQ ID NO:12, 13) reveals significant differences between the sequences, suggesting that hN3k and hN5k represent part of two distinct Notch-homologous genes. The data thus suggest that the human genome harbors more than one Notch-homologous gene. This is unlike Drosophila, where Notch appears to be a single-copy gene.

Comparison of the DNA and amino acid sequences of the human Notch homologs contained in hN3k and hN5k with the corresponding Drosophila Notch sequences (as published in Wharton et al., 1985, Cell 43:567–581) and with the corresponding Xenopus Notch sequences (as published in Coffman et al., 1990, Science 249:1438–1441 or available from Genbank® (accession number M33874)) also revealed differences.

The amino acid sequence shown in FIG. 10 (hN3k) was compared with the predicted sequence of the TAN-1 polypeptide shown in FIG. 2 of Ellisen et al., August 1991, Cell 66:649–661. Some differences were found between the deduced amino acid sequences; however, overall the hN3k Notch polypeptide sequence is 99% identical to the corresponding TAN-1 region (TAN-1 amino acids 1455 to 2506). Four differences were noted: in the region between the third Notch/lin-12 repeat and the first cdc10 motif, there is an arginine (hN3k) instead of an X (TAN-1 amino acid 1763); (2) there is a proline (hN3k) instead of an X (TAN-1, amino acid 1787); (3) there is a conservative change of an aspartic acid residue (hN3k) instead of a glutamic acid residue (TAN-1, amino acid 2495); and (4) the carboxyl-terminal region differs substantially between TAN-1 amino acids 2507 and 2535.

The amino acid sequence shown in FIG. 11 (hN5k) was compared with the predicted sequence of the TAN-1 polypeptide shown in FIG. 2 of Ellisen et al., August 1991, Cell 66:649–661. Differences were found between the deduced amino acid sequences. The deduced Notch polypeptide of hN5k is 79% identical to the TAN-1 polypeptide (64% identical to Drosophila Notch) in the cdc10 region that encompasses both the cc10 motif (TAN-1 amino acids 1860 to 2217) and the well-conserved flanking regions (FIG. 12). The cdc10 region covers amino acids 1860 through 2217 of the TAN-1 sequence. In addition, the hN5k encoded polypeptide is 65% identical to the TAN-1 polypeptide (44% identical to Drosophila Notch) at the carboxy-terminal end of the molecule containing a PEST (proline, glutamic acid, serine, threonine)-rich region (TAN-1 amino acids 2482 to 2551) (FIG. 12B). The stretch of 215 amino acids lying between the aforementioned regions is not well conserved among any of the Notch-homologous clones represented by hN3k, hN5k, and TAN-1. Neither the hN5k polypeptide nor Drosophila Notch shows significant levels of amino acid identity to the other proteins in this region (e.g., hN5k/TAN-1=24% identity; hN5k/Drosophila Notch=11% identity; TAN-1/Drosophila Notch=17% identity). In contrast, Xenopus Notch (Xotch) (SEQ ID NO:16), rat Notch (SEQ ID NO:17), and TAN-1 (SEQ ID NO:18) continue to share significant levels of sequence identity with one another (e.g., TAN-1/rat Notch=75% identity, TAN-1/Xenopus Notch=45% identity, rat Notch/Xenopus Notch=50% identity).

Examination of the sequence of the intracellular domains of the vertebrate Notch homologs shown in FIG. 12B revealed an unexpected finding: all of these proteins, including hN5k, contain a putative CcN motif, associated with nuclear targeting function, in the conserved region following the last of the six cdc10 repeats (FIG. 12B). Although Drosophila Notch lacks such a defined motif, closer inspection of its sequence revealed the presence of a possible bipartite nuclear localization sequence (Robbins et al., 1991, Cell 64:615–623), as well as of possible CK II and cdc2 phosphorylation sites, all in relative proximity to one another, thus possibly defining an alternative type of CcN motif (FIG. 12B).

To isolate clones covering the 5' end of hN (the human Notch homolog contained in part in hN5k), clone hN2k was used as a probe to screen 260,000 plaques of human fetal brain phage library, commercially available from Stratagene, for crosshybridizing clones. Four clones were identified and isolated using standard procedures (Maniatis et al., 1982, *Molecular Cloning: A Laboratory Manual*, Cold Spring Harbor Laboratory, Cold Spring Harbor, N.Y.). Four clones were also isolated by hybridization to the Notch-homologous sequence of Adams et al., 1992, Nature 355:632–655, which was obtained from the ATCC.

To isolate clones covering the 5' end of TAN-1, the human fetal brain library that is commercially available from Stratagene was screened for clones which would extend the sequence to the 5' end. 880,000 plaques were screened and four clones were identified which crosshybridized with the hN3k sequences. Sequencing confirmed the relative position of these sequences within the Notch protein encoded by TAN-1.

The 5' sequence of our isolated TAN-1 homolog has been determined through nucleotide number 972 (nucleotide number 1 being the A in the ATG initiation codon), and compared to the sequence as published by Ellisen et al (1991, Cell 66:649–661). At nucleotide 559, our TAN-1 homolog has a G, whereas Ellisen et al. disclose an A, which change results in a different encoded amino acid. Thus, within the first 324 amino acids, our TAN-1-encoded protein differs from that taught by Ellisen et al., since our protein has a Gly at position 187, whereas Ellisen et al. disclose an Arg at that position (as presented in FIG. 13.)

The full-length amino acid sequences of both the hN (SEQ ID NO:19) and TAN-1-encoded (SEQ ID NO:20) proteins, as well as Xenopus and Drosophila Notch proteins, are shown in FIG. 13. The full-length DNA coding sequence (except for that encoding the initiator Met) (contained in SEQ ID NO:21) and encoded amino acid sequence (except that the initiator Met is not shown) (contained in SEQ ID NO:19) of hN are shown in FIG. 17.

9.2. Expression of Human Notch

Expression constructs were made using the human Notch cDNA clones discussed in Section 9.1 above. In the cases of hN3k and hN2k, the entire clone was excised from its vector as an EcoRI restriction fragment and subcloned into the EcoRI restriction site of each of the three pGEX vectors (Glutathione S-Transferase expression vectors; Smith and Johnson, 1988, Gene 7, 31–40). This allows for the expression of the Notch protein product from the subclone in the correct reading frame. In the case of hN5k, the clone contains two internal EcoRI restriction sites, producing 2.6, 1.5 and 0.6 kb fragments. Both the 2.6 and the 1.5 kb fragments have also been subcloned into each of the pGEX vectors.

The pGEX vector system was used to obtain expression of human Notch fusion (chimeric) proteins from the constructs described below. The cloned Notch DNA in each case was inserted, in phase, into the appropriate pGEX vector. Each construct was then electroporated into bacteria *E. coli*), and was expressed as a fusion protein containing the Notch protein sequences fused to the carboxyl terminus of glutathione S-transferase protein. Expression of the fusion proteins was confirmed by analysis of bacterial protein extracts by polyacrylamide gel electrophoresis, comparing protein extracts obtained from bacteria containing the pGEX plasmids with and without the inserted Notch DNA. The fusion proteins were soluble in aqueous solution, and were purified from bacterial lysates by affinity chromatography using glutathione-coated agarose (since the carboxyl terminus of glutathione S-transferase binds to glutathionine). The expressed fusion proteins were bound by an antibody to Drosophila Notch, as assayed by Western blotting.

The constructs used to make human Notch-glutathione S-transferase fusion proteins were as follows:

hNFP#2—PCR was used to obtain a fragment starting just before the cdc10 repeats at nucleotide 192 of the hN5k insert to just before the PEST-rich region at nucleotide 1694. The DNA was then digested with BamHI and SmaI and the resulting fragment was ligated into pGEX-3. After expression, the fusion protein was purified by binding to glutathione agarose. The purified polypeptide was quantitated on a 4–15% gradient polyacrylamide gel. The resulting fusion protein had an approximate molecular weight of 83 kD.

hN3FP#1—The entire hN3k DNA insert (nucleotide 1 to 3235) was excised from the Bluescript (SK) vector by digesting with EcoRI. The DNA was ligated into pGEX-3.

hN3FP#2—A 3' segment of hN3k DNA (nucleotide 1847 to 3235) plus some of the polylinker was cut out of the Bluescript (SK) vector by digesting with XmaI. The fragment was ligated into pGEX-1.

Following purification, these fusion proteins are used to make either polyclonal and/or monoclonal antibodies to human Notch.

10. Notch Expression in Normal and Malignant Cells

Various human patient tissue samples and cell lines, representing both normal and a wide variety of malignant cells are assayed to detect and/or quantitate expression of Notch. Patient tissue samples are obtained from the pathology department at the Yale University School of Medicine.

The following assays are used to measure Notch expression in patient tissue samples: (a) Northern hybridization; (b) Western blots; (c) in situ hybridization; and (d) immunocytochemistry. Assays are carried out using standard techniques. Northern hybridization and in situ hybridization are carried out (i) using a DNA probe specific to the Notch sequence of clone hN3k; and (ii) using a DNA probe specific to the Notch sequence of clone hN5k. Western blots and immunocytochemistry are carried out using an antibody to Drosophila Notch protein (which also recognizes human Notch proteins).

Northern hybridization and Western blots, as described above, are also used to analyze numerous human cell lines, representing various normal or cancerous tissues. The cell lines tested are listed in Table 2.

TABLE 2

| HUMAN CELL LINES | |
|---|---|
| Tissue/Tumor | Cell line |
| Bone marrow | IM-9 |
|  | KG-1 |
| Brain | A-172 |
|  | HS 683 |
|  | U-87MG |
|  | TE 671 |

TABLE 2-continued

HUMAN CELL LINES

| Tissue/Tumor | Cell line |
|---|---|
| Breast | BT-20 |
| | Hs 578Bs |
| | MDA-MB-330 |
| Colon | Caco-2 |
| | SW 48 |
| | T84 |
| | WiDr |
| Embryo | FHs 173We |
| Kidney | A-498 |
| | A-704 |
| | Caki-2 |
| Leukemia | ARH-77 |
| | KG-1 |
| Liver | Hep G2 |
| | WRL 68 |
| Lung | Calu-1 |
| | HLF-a |
| | SK-Lu-1 |
| Lymphoblasts | CCRF-CEM |
| | HuT 78 |
| Lymphoma | Hs 445 |
| | MS116 |
| | U-937 |
| Melanoma | A-375 |
| | G-361 |
| | Hs 294T |
| | SK-MEL-1 |
| Myeloma | IM-9 |
| | RPMI 8226 |
| Neuroblastoma | IMR-32 |
| | SK-N-SH |
| | SK-N-MC |
| Ovary | Caov-3 |
| | Caov-4 |
| | PA-1 |
| Plasma Cells | ARH-77 |
| Sarcoma | A-204 |
| | A673 |
| | HOS |
| Skin | Amdur II |
| | BUD-8 |
| Testis | Tera-1 |
| | Tera-2 |
| Thymus | Hs67 |
| Uterus | AN3 Ca |
| | HEC-1-A |

Malignancies of malignant cell tissue types which are thus shown to specifically express Notch can be treated as described in Section 5.1 et seq.

10.1. Expression of Human Notch Protein is Increased in Various Malignancies As described below, we have found that human Notch protein expression is increased in at least three human cancers, namely cervical, breast, and colon cancer. Immunocytochemical staining of tissue samples from cervical, breast, and colon cancers of human patients showed clearly that the malignant tissue expresses high levels of Notch, at increased levels relative to non-malignant tissue sections. This broad spectrum of different neoplasias in which there is elevated Notch expression suggests that many more cancerous conditions will be seen to upregulate Notch.

Slides of human tumor samples (for breast, colon, and cervical tumors) were obtained from the tissue bank of the Pathology Department, Yale Medical School. The stainings were done using monoclonal antibodies raised against the P1 and P4 fusion proteins which were generated from sequences of hN and TAN-1, respectively.

The P1 and P4 fusion proteins were obtained by insertion of the desired human Notch sequence into the appropriate pGEX expression vector (Smith and Johnson, 1988, Gene 7:3140; AMRAD Corp., Melbourne, Australia) and were affinity-purified according to the instructions of the manufacturer (AMRAD Corp.). For production of the P1 fusion protein, pGEX-2 was cut with BamHI and ligated to a concatamer which consists of three copies of a 518 bp BamHI-BglII fragment of hN. Rats were immunized with the expressed protein and monoclonal antibodies were produced by standard procedures. For production of the P4 fusion protein, pGEX-2 was cut with BamHI and ligated to a concatamer which consists of three copies of a 473 bp BamHI-BglII fragment of TAN-1. Rats were immunized with the expressed protein, and monoclonal antibodies were produced by standard procedures.

Figure 15B:
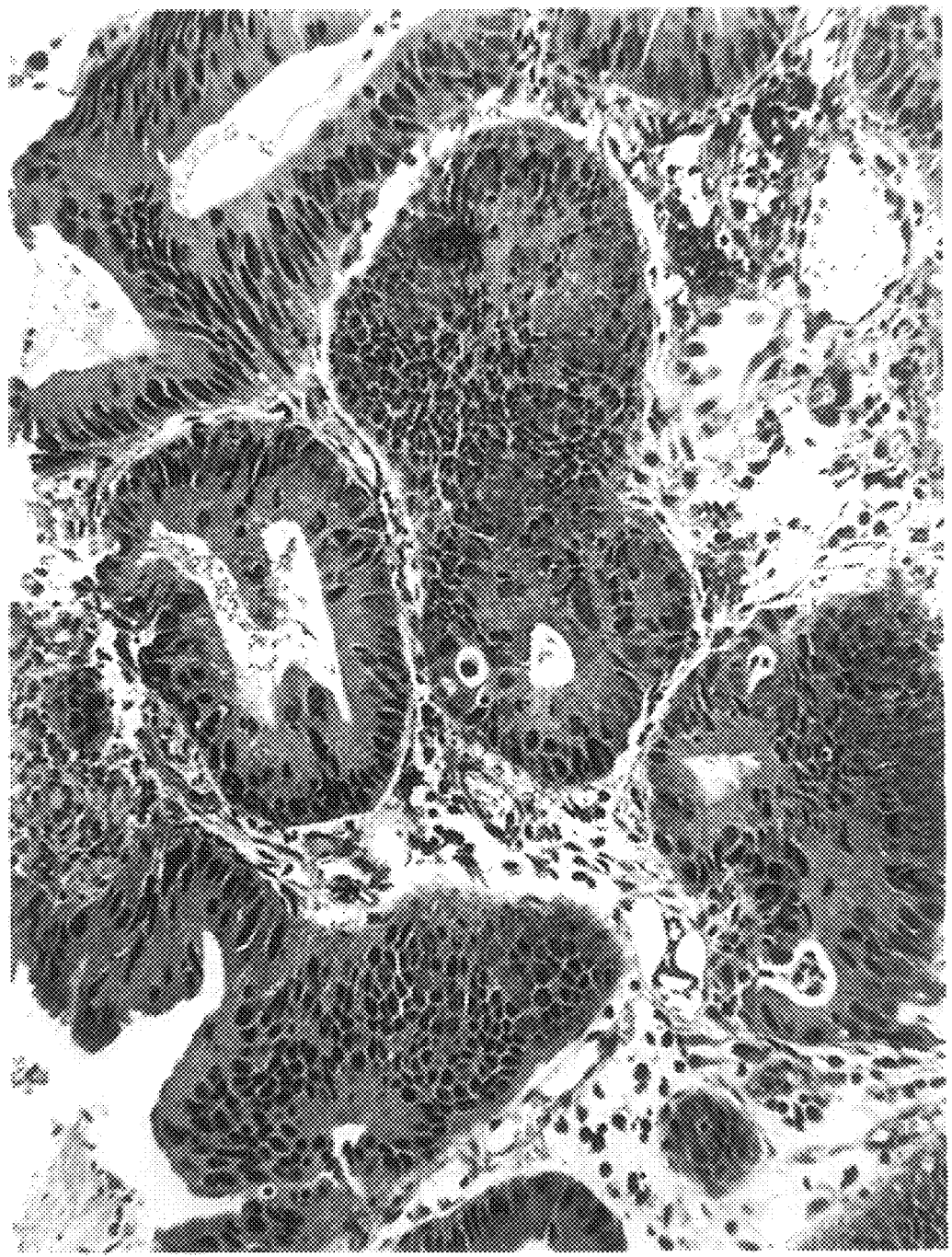

In all tumors examined, the Notch proteins encoded by both human Notch homologs TAN-1 and hN were present at increased levels in the malignant part of the tissue compared to the normal part. Representative stainings are shown in the pictures provided (FIGS. 14–16).

The staining procedure was as follows: The tissues were fixed in paraformaldehyde, embedded in paraffin, cut in 5 micrometer thick sections and placed on glass slides. Then the following steps were carried out:

1. Deparafinization through 4 changes of xylene, 4 minutes each.
2. Removal of xylene through 3 changes in absolute ethanol, 4 minutes each.
3. Gradual rehydration of the tissues by immersing the slides into 95%, 90%, 80%, 60% and 30% ethanol, 4 minutes each. At the end the slides were rinsed in distilled water for 5 minutes.
4. Quenching of endogenous, peroxidase by incubating for 30 minutes in 0.3% hydrogen peroxide in methanol.
5. Washing in PBS (10 mM sodium phosphate pH 7.5, 0.9% NaCl) for 20 minutes.
6. Incubation for 1 hour in blocking solution. (Blocking solution: PBS containing 4% normal rabbit serum and 0.1 Triton X-100.)
7. Incubation overnight at 4° C. with primary antibody diluted in blocking solution. Final concentration of primary antibody 20–50 μg/ml.
8. Washing for 20 minutes with PBS+0.1% Triton X-100 (3 changes).
9. Incubation for 30 minutes with biotinylated rabbit anti-rat antibody: 50 μl of biotinylated antibody (VECTOR) in 10 ml of blocking solution.
10. Washing for 20 minutes with PBS+0.1% Triton X-100 (3 changes).
11. Incubation with ABC reagent (VECTOR) for 30 minutes (the reagent is made in PBS+0.1% Triton X-100).
12. Washing for 20 minutes in PBS+0.1% Triton X-100. Followed by incubation for 2 minutes in PBS+0.5% Triton X-100.
13. Incubation for 2–5 minutes in peroxidase substrate solution. Peroxidase substrate solution: Equal volumes of 0.02% hydrogen peroxide in distilled water and 0.1% diaminobenzidine tetrahydrochloride (DAB) in 0.1 M Tris buffer pH 7.5 are mixed just before the incubation with the tissues. Triton X-100 is added to the final solution at a concentration of 0.5%.
14. Washing for 15 minutes in tap water.

15. Counterstaining for 10 minutes with Mayer's hematoxylin.
16. Washing for 15 minutes in tap water.
17. Dehydration through changes in 30%, 60%, 80%, 90%, 95% and absolute ethanol (4 minutes each).
18. Immersion into xylene (2 changes, 4 minutes each).
19. Mounting, light microscopy.

11. Deposit of Microorganisms

The following recombinant bacteria, each carrying a plasmid encoding a portion of human Notch, were deposited on May 2, 1991 with the American Type Culture Collection, 10801 University Boulevard, Manassas, Va. 20110–2209, under the provisions of the Budapest Treaty on the International Recognition of the Deposit of Microorganisms for the Purposes of Patent Procedures.

| Bacteria | | Plasmid | ATCC Accession No. |
|---|---|---|---|
| E. coli XL1-Blue | carrying | hN4k | 68610 |
| E. coli XL1-Blue | | hN3k | 68609 |
| E. coli XL1-Blue | | hN5k | 68611 |

The present invention is not to be limited in scope by the microorganisms deposited or the specific embodiments described herein. Indeed, various modifications of the invention in addition to those described herein will become apparent to those skilled in the art from the foregoing description and accompanying figures. Such modifications are intended to fall within the scope of the appended claims.

Various publications are cited herein, the disclosures of which are incorporated by reference in their entireties.

SEQUENCE LISTING (1) GENERAL INFORMATION:

(iii) NUMBER OF SEQUENCES: 21

(2) INFORMATION FOR SEQ ID NO:1:

(i) SEQUENCE CHARACTERISTICS:
       (A) LENGTH: 2892 base pairs
       (B) TYPE: nucleic acid
       (C) STRANDEDNESS: double
       (D) TOPOLOGY: unknown (ii) MOLECULE TYPE: cDNA (ix) FEATURE:
       (A) NAME/KEY: CDS
       (B) LOCATION: 142..2640

(xi) SEQUENCE DESCRIPTION: SEQ ID NO:1:

```
GAATTCGGAG GAATTATTCA AAACATAAAC ACAATAAACA ATTTGAGTAG TTGCCGCACA        60

CACACACACA CACAGCCCGT GGATTATTAC ACTAAAAGCG ACACTCAATC CAAAAAATCA       120

GCAACAAAAA CATCAATAAA C ATG CAT TGG ATT AAA TGT TTA TTA ACA GCA        171
                         Met His Trp Ile Lys Cys Leu Leu Thr Ala
                          1               5                  10

TTC ATT TGC TTC ACA GTC ATC GTG CAG GTT CAC AGT TCC GGC AGC TTT         219
Phe Ile Cys Phe Thr Val Ile Val Gln Val His Ser Ser Gly Ser Phe
             15                  20                  25

GAG TTG CGC CTG AAG TAC TTC AGC AAC GAT CAC GGG CGG GAC AAC GAG         267
Glu Leu Arg Leu Lys Tyr Phe Ser Asn Asp His Gly Arg Asp Asn Glu
         30                  35                  40

GGT CGC TGC TGC AGC GGG GAG TCG GAC GGA GCG ACG GGC AAG TGC CTG         315
Gly Arg Cys Cys Ser Gly Glu Ser Asp Gly Ala Thr Gly Lys Cys Leu
     45                  50                  55

GGC AGC TGC AAG ACG CGG TTT CGC GTC TGC CTA AAG CAC TAC CAG GCC         363
Gly Ser Cys Lys Thr Arg Phe Arg Val Cys Leu Lys His Tyr Gln Ala
 60                  65                  70

ACC ATC GAC ACC ACC TCC CAG TGC ACC TAC GGG GAC GTG ATC ACG CCC         411
Thr Ile Asp Thr Thr Ser Gln Cys Thr Tyr Gly Asp Val Ile Thr Pro
 75                  80                  85                  90

ATT CTC GGC GAG AAC TCG GTC AAT CTG ACC GAC GCC CAG CGC TTC CAG         459
Ile Leu Gly Glu Asn Ser Val Asn Leu Thr Asp Ala Gln Arg Phe Gln
                 95                 100                 105
```

```
AAC AAG GGC TTC ACG AAT CCC ATC CAG TTC CCC TTC TCG TTC TCA TGG         507
Asn Lys Gly Phe Thr Asn Pro Ile Gln Phe Pro Phe Ser Phe Ser Trp
            110                 115                 120

CCG GGT ACC TTC TCG CTG ATC GTC GAG GCC TGG CAT GAT ACG AAC AAT         555
Pro Gly Thr Phe Ser Leu Ile Val Glu Ala Trp His Asp Thr Asn Asn
            125                 130                 135

AGC GGC AAT GCG CGA ACC AAC AAG CTC CTC ATC CAG CGA CTC TTG GTG         603
Ser Gly Asn Ala Arg Thr Asn Lys Leu Leu Ile Gln Arg Leu Leu Val
        140                 145                 150

CAG CAG GTA CTG GAG GTG TCC TCC GAA TGG AAG ACG AAC AAG TCG AAA         651
Gln Gln Val Leu Glu Val Ser Ser Glu Trp Lys Thr Asn Lys Ser Glu
155                 160                 165                 170

TCG CAG TAC ACG TCG CTG GAG TAC GAT TTC CGT GTC ACC TGC GAT CTC         699
Ser Gln Tyr Thr Ser Leu Glu Tyr Asp Phe Arg Val Thr Cys Asp Leu
                175                 180                 185

AAC TAC TAC GGA TCC GGC TGT GCC AAG TTC TGC CGG CCC CGC GAC GAT         747
Asn Tyr Tyr Gly Ser Gly Cys Ala Lys Phe Cys Arg Pro Arg Asp Asp
            190                 195                 200

TCA TTT GGA CAC TCG ACT TGC TCG GAG ACG GGC GAA ATT ATC TGT TTG         795
Ser Phe Gly His Ser Thr Cys Ser Glu Thr Gly Glu Ile Ile Cys Leu
        205                 210                 215

ACC GGA TGG CAG GGC GAT TAC TGT CAC ATA CCC AAA TGC GCC AAA GGC         843
Thr Gly Trp Gln Gly Asp Tyr Cys His Ile Pro Lys Cys Ala Lys Gly
220                 225                 230

TGT GAA CAT GGA CAT TGC GAC AAA CCC AAT CAA TGC GTT TGC CAA CTG         891
Cys Glu His Gly His Cys Asp Lys Pro Asn Gln Cys Val Cys Gln Leu
235                 240                 245                 250

GGC TGG AAG GGA GCC TTG TGC AAC GAG TGC GTT CTG GAA CCG AAC TGC         939
Gly Trp Lys Gly Ala Leu Cys Asn Glu Cys Val Leu Glu Pro Asn Cys
                255                 260                 265

ATC CAT GGC ACC TGC AAC AAA CCC TGG ACT TGC ATC TGC AAC GAG GGT         987
Ile His Gly Thr Cys Asn Lys Pro Trp Thr Cys Ile Cys Asn Glu Gly
            270                 275                 280

TGG GGA GGC TTG TAC TGC AAC CAG GAT CTG AAC TAC TGC ACC AAC CAC        1035
Trp Gly Gly Leu Tyr Cys Asn Gln Asp Leu Asn Tyr Cys Thr Asn His
        285                 290                 295

AGA CCC TGC AAG AAT GGC GGA ACC TGC TTC AAC ACC GGC GAG GGA TTG        1083
Arg Pro Cys Lys Asn Gly Gly Thr Cys Phe Asn Thr Gly Glu Gly Leu
300                 305                 310

TAC ACA TGC AAA TGC GCT CCA GGA TAC AGT GGT GAT GAT TGC GAA AAT        1131
Tyr Thr Cys Lys Cys Ala Pro Gly Tyr Ser Gly Asp Asp Cys Glu Asn
315                 320                 325                 330

GAG ATC TAC TCC TGC GAT GCC GAT GTC AAT CCC TGC CAG AAT GGT GGT        1179
Glu Ile Tyr Ser Cys Asp Ala Asp Val Asn Pro Cys Gln Asn Gly Gly
                335                 340                 345

ACC TGC ATC GAT GAG CCG CAC ACA AAA ACC GGC TAC AAG TGT CAT TGC        1227
Thr Cys Ile Asp Glu Pro His Thr Lys Thr Gly Tyr Lys Cys His Cys
            350                 355                 360

GCC AAC GGC TGG AGC GGA AAG ATG TGC GAG GAG AAA GTG CTC ACG TGT        1275
Ala Asn Gly Trp Ser Gly Lys Met Cys Glu Glu Lys Val Leu Thr Cys
        365                 370                 375

TCG GAC AAA CCC TGT CAT CAG GGA ATC TGC CGC AAC GTT CGT CCT GGC        1323
Ser Asp Lys Pro Cys His Gln Gly Ile Cys Arg Asn Val Arg Pro Gly
380                 385                 390

TTG GGA AGC AAG GGT CAG GGC TAC CAG TGC GAA TGT CCC ATT GGC TAC        1371
Leu Gly Ser Lys Gly Gln Gly Tyr Gln Cys Glu Cys Pro Ile Gly Tyr
395                 400                 405                 410

AGC GGA CCC AAC TGC GAT CTC CAG CTG GAC AAC TGC AGT CCG AAT CCA        1419
Ser Gly Pro Asn Cys Asp Leu Gln Leu Asp Asn Cys Ser Pro Asn Pro
                415                 420                 425
```

```
TGC ATA AAC GGT GGA AGC TGT CAG CCG AGC GGA AAG TGT ATT TGC CCA        1467
Cys Ile Asn Gly Gly Ser Cys Gln Pro Ser Gly Lys Cys Ile Cys Pro
        430                 435                 440

GCG GGA TTT TCG GGA ACG AGA TGC GAG ACC AAC ATT GAC GAT TGT CTT        1515
Ala Gly Phe Ser Gly Thr Arg Cys Glu Thr Asn Ile Asp Asp Cys Leu
        445                 450                 455

GGC CAC CAG TGC GAG AAC GGA GGC ACC TGC ATA GAT ATG GTC AAC CAA        1563
Gly His Gln Cys Glu Asn Gly Gly Thr Cys Ile Asp Met Val Asn Gln
        460                 465                 470

TAT CGC TGC CAA TGC GTT CCC GGT TTC CAT GGC ACC CAC TGT AGT AGC        1611
Tyr Arg Cys Gln Cys Val Pro Gly Phe His Gly Thr His Cys Ser Ser
475                 480                 485                 490

AAA GTT GAC TTG TGC CTC ATC AGA CCG TGT GCC AAT GGA GGA ACC TGC        1659
Lys Val Asp Leu Cys Leu Ile Arg Pro Cys Ala Asn Gly Gly Thr Cys
                495                 500                 505

TTG AAT CTC AAC AAC GAT TAC CAG TGC ACC TGT CGT GCG GGA TTT ACT        1707
Leu Asn Leu Asn Asn Asp Tyr Gln Cys Thr Cys Arg Ala Gly Phe Thr
        510                 515                 520

GGC AAG GAT TGC TCT GTG GAC ATC GAT GAG TGC AGC AGT GGA CCC TGT        1755
Gly Lys Asp Cys Ser Val Asp Ile Asp Glu Cys Ser Ser Gly Pro Cys
        525                 530                 535

CAT AAC GGC GGC ACT TGC ATG AAC CGC GTC AAT TCG TTC GAA TGC GTG        1803
His Asn Gly Gly Thr Cys Met Asn Arg Val Asn Ser Phe Glu Cys Val
        540                 545                 550

TGT GCC AAT GGT TTC AGG GGC AAG CAG TGC GAT GAG GAG TCC TAC GAT        1851
Cys Ala Asn Gly Phe Arg Gly Lys Gln Cys Asp Glu Glu Ser Tyr Asp
555                 560                 565                 570

TCG GTG ACC TTC GAT GCC CAC CAA TAT GGA GCG ACC ACA CAA GCG AGA        1899
Ser Val Thr Phe Asp Ala His Gln Tyr Gly Ala Thr Thr Gln Ala Arg
                575                 580                 585

GCC GAT GGT TTG ACC AAT GCC CAG GTA GTC CTA ATT GCT GTT TTC TCC        1947
Ala Asp Gly Leu Thr Asn Ala Gln Val Val Leu Ile Ala Val Phe Ser
        590                 595                 600

GTT GCG ATG CCT TTG GTG GCG GTT ATT GCG GCG TGC GTG GTC TTC TGC        1995
Val Ala Met Pro Leu Val Ala Val Ile Ala Ala Cys Val Val Phe Cys
        605                 610                 615

ATG AAG CGC AAG CGT AAG CGT GCT CAG GAA AAG GAC GAC GCG GAG GCC        2043
Met Lys Arg Lys Arg Lys Arg Ala Gln Glu Lys Asp Asp Ala Glu Ala
        620                 625                 630

AGG AAG CAG AAC GAA CAG AAT GCG GTG GCC ACA ATG CAT CAC AAT GGC        2091
Arg Lys Gln Asn Glu Gln Asn Ala Val Ala Thr Met His His Asn Gly
635                 640                 645                 650

AGT GGG GTG GGT GTA GCT TTG GCT TCA GCC TCT CTG GGC GGC AAA ACT        2139
Ser Gly Val Gly Val Ala Leu Ala Ser Ala Ser Leu Gly Gly Lys Thr
                655                 660                 665

GGC AGC AAC AGC GGT CTC ACC TTC GAT GGC GGC AAC CCG AAT ATC ATC        2187
Gly Ser Asn Ser Gly Leu Thr Phe Asp Gly Gly Asn Pro Asn Ile Ile
        670                 675                 680

AAA AAC ACC TGG GAC AAG TCG GTC AAC AAC ATT TGT GCC TCA GCA GCA        2235
Lys Asn Thr Trp Asp Lys Ser Val Asn Asn Ile Cys Ala Ser Ala Ala
        685                 690                 695

GCA GCG GCG GCG GCA GCA GCG GAC GAG TGT CTC ATG TAC GGC              2283
Ala Ala Ala Ala Ala Ala Ala Ala Asp Glu Cys Leu Met Tyr Gly
        700                 705                 710

GGA TAT GTG GCC TCG GTG GCG GAT AAC AAC AAT GCC AAC TCA GAC TTT        2331
Gly Tyr Val Ala Ser Val Ala Asp Asn Asn Asn Ala Asn Ser Asp Phe
715                 720                 725                 730

TGT GTG GCT CCG CTA CAA AGA GCC AAG TCG CAA AAG CAA CTC AAC ACC        2379
Cys Val Ala Pro Leu Gln Arg Ala Lys Ser Gln Lys Gln Leu Asn Thr
```

-continued

```
                   735                 740                 745
GAT CCC ACG CTC ATG CAC CGC GGT TCG CCG GCA GGC AGC TCA GCC AAG    2427
Asp Pro Thr Leu Met His Arg Gly Ser Pro Ala Gly Ser Ser Ala Lys
            750                 755                 760

GGA GCG TCT GGC GGA GGA CCG GGA GCG GCG GAG GGC AAG AGG ATC TCT    2475
Gly Ala Ser Gly Gly Gly Pro Gly Ala Ala Glu Gly Lys Arg Ile Ser
            765                 770                 775

GTT TTA GGC GAG GGT TCC TAC TGT AGC CAG CGT TGG CCC TCG TTG GCG    2523
Val Leu Gly Glu Gly Ser Tyr Cys Ser Gln Arg Trp Pro Ser Leu Ala
            780                 785                 790

GCG GCG GGA GTG GCC GGA GCC TGT TCA TCC CAG CTA ATG GCT GCA GCT    2571
Ala Ala Gly Val Ala Gly Ala Cys Ser Ser Gln Leu Met Ala Ala Ala
795                 800                 805                 810

TCG GCA GCG GGC AGC GGA GCG GGG ACG GCG CAA CAG CAG CGA TCC GTG    2619
Ser Ala Ala Gly Ser Gly Ala Gly Thr Ala Gln Gln Gln Arg Ser Val
                815                 820                 825

GTC TGC GGC ACT CCG CAT ATG TAACTCCAAA AATCCGGAAG GGCTCCTGGT       2670
Val Cys Gly Thr Pro His Met
                830

AAATCCGGAG AAATCCGCAT GGAGGAGCTG ACAGCACATA CACAAAGAAA AGACTGGGTT    2730

GGGTTCAAAA TGTGAGAGAG ACGCCAAAAT GTTGTTGTTG ATTGAAGCAG TTTAGTCGTC    2790

ACGAAAAATG AAAAATCTGT AACAGGCATA ACTCGTAAAC TCCCTAAAAA ATTTGTATAG    2850

TAATTAGCAA AGCTGTGACC CAGCCGTTTC GATCCCGAAT TC                      2892

(2) INFORMATION FOR SEQ ID NO:2:

(i) SEQUENCE CHARACTERISTICS:
        (A) LENGTH: 833 amino acids
        (B) TYPE: amino acid
        (D) TOPOLOGY: unknown (ii) MOLECULE TYPE: protein (xi) SEQUENCE DESCRIPTION: SEQ ID NO:2:

Met His Trp Ile Lys Cys Leu Leu Thr Ala Phe Ile Cys Phe Thr Val
  1               5                  10                  15

Ile Val Gln Val His Ser Ser Gly Ser Phe Glu Leu Arg Leu Lys Tyr
             20                  25                  30

Phe Ser Asn Asp His Gly Arg Asp Asn Glu Gly Arg Cys Cys Ser Gly
         35                  40                  45

Glu Ser Asp Gly Ala Thr Gly Lys Cys Leu Gly Ser Cys Lys Thr Arg
     50                  55                  60

Phe Arg Val Cys Leu Lys His Tyr Gln Ala Thr Ile Asp Thr Thr Ser
 65                  70                  75                  80

Gln Cys Thr Tyr Gly Asp Val Ile Thr Pro Ile Leu Gly Glu Asn Ser
                 85                  90                  95

Val Asn Leu Thr Asp Ala Gln Arg Phe Gln Asn Lys Gly Phe Thr Asn
            100                 105                 110

Pro Ile Gln Phe Pro Phe Ser Phe Ser Trp Pro Gly Thr Phe Ser Leu
        115                 120                 125

Ile Val Glu Ala Trp His Asp Thr Asn Asn Ser Gly Asn Ala Arg Thr
    130                 135                 140

Asn Lys Leu Leu Ile Gln Arg Leu Leu Val Gln Val Leu Glu Val
145                 150                 155                 160

Ser Ser Glu Trp Lys Thr Asn Lys Ser Glu Ser Gln Tyr Thr Ser Leu
                165                 170                 175
```

-continued

Glu Tyr Asp Phe Arg Val Thr Cys Asp Leu Asn Tyr Tyr Gly Ser Gly
              180                 185                 190
Cys Ala Lys Phe Cys Arg Pro Arg Asp Asp Ser Phe Gly His Ser Thr
              195                 200                 205
Cys Ser Glu Thr Gly Glu Ile Ile Cys Leu Thr Gly Trp Gln Gly Asp
              210                 215                 220
Tyr Cys His Ile Pro Lys Cys Ala Lys Gly Cys Glu His Gly His Cys
225                 230                 235                 240
Asp Lys Pro Asn Gln Cys Val Cys Gln Leu Gly Trp Lys Gly Ala Leu
              245                 250                 255
Cys Asn Glu Cys Val Leu Glu Pro Asn Cys Ile His Gly Thr Cys Asn
              260                 265                 270
Lys Pro Trp Thr Cys Ile Cys Asn Glu Gly Trp Gly Gly Leu Tyr Cys
              275                 280                 285
Asn Gln Asp Leu Asn Tyr Cys Thr Asn His Arg Pro Cys Lys Asn Gly
              290                 295                 300
Gly Thr Cys Phe Asn Thr Gly Glu Gly Leu Tyr Thr Cys Lys Cys Ala
305                 310                 315                 320
Pro Gly Tyr Ser Gly Asp Asp Cys Glu Asn Glu Ile Tyr Ser Cys Asp
              325                 330                 335
Ala Asp Val Asn Pro Cys Gln Asn Gly Gly Thr Cys Ile Asp Glu Pro
              340                 345                 350
His Thr Lys Thr Gly Tyr Lys Cys His Cys Ala Asn Gly Trp Ser Gly
              355                 360                 365
Lys Met Cys Glu Glu Lys Val Leu Thr Cys Ser Asp Lys Pro Cys His
              370                 375                 380
Gln Gly Ile Cys Arg Asn Val Arg Pro Gly Leu Gly Ser Lys Gly Gln
385                 390                 395                 400
Gly Tyr Gln Cys Glu Cys Pro Ile Gly Tyr Ser Gly Pro Asn Cys Asp
              405                 410                 415
Leu Gln Leu Asp Asn Cys Ser Pro Asn Pro Cys Ile Asn Gly Gly Ser
              420                 425                 430
Cys Gln Pro Ser Gly Lys Cys Ile Cys Pro Ala Gly Phe Ser Gly Thr
              435                 440                 445
Arg Cys Glu Thr Asn Ile Asp Asp Cys Leu Gly His Gln Cys Glu Asn
              450                 455                 460
Gly Gly Thr Cys Ile Asp Met Val Asn Gln Tyr Arg Cys Gln Cys Val
465                 470                 475                 480
Pro Gly Phe His Gly Thr His Cys Ser Ser Lys Val Asp Leu Cys Leu
              485                 490                 495
Ile Arg Pro Cys Ala Asn Gly Gly Thr Cys Leu Asn Leu Asn Asn Asp
              500                 505                 510
Tyr Gln Cys Thr Cys Arg Ala Gly Phe Thr Gly Lys Asp Cys Ser Val
              515                 520                 525
Asp Ile Asp Glu Cys Ser Ser Gly Pro Cys His Asn Gly Gly Thr Cys
530                 535                 540
Met Asn Arg Val Asn Ser Phe Glu Cys Val Cys Ala Asn Gly Phe Arg
545                 550                 555                 560
Gly Lys Gln Cys Asp Glu Glu Ser Tyr Asp Ser Val Thr Phe Asp Ala
              565                 570                 575
His Gln Tyr Gly Ala Thr Thr Gln Ala Arg Ala Asp Gly Leu Thr Asn
              580                 585                 590
Ala Gln Val Val Leu Ile Ala Val Phe Ser Val Ala Met Pro Leu Val

```
                 595                 600                 605
Ala Val Ile Ala Ala Cys Val Val Phe Cys Met Lys Arg Lys Arg Lys
                610                 615                 620
Arg Ala Gln Glu Lys Asp Asp Ala Glu Ala Arg Lys Gln Asn Glu Gln
625                 630                 635                 640
Asn Ala Val Ala Thr Met His His Asn Gly Ser Gly Val Gly Val Ala
                645                 650                 655
Leu Ala Ser Ala Ser Leu Gly Gly Lys Thr Gly Ser Asn Ser Gly Leu
                660                 665                 670
Thr Phe Asp Gly Gly Asn Pro Asn Ile Ile Lys Asn Thr Trp Asp Lys
                675                 680                 685
Ser Val Asn Asn Ile Cys Ala Ser Ala Ala Ala Ala Ala Ala Ala Ala
                690                 695                 700
Ala Ala Ala Asp Glu Cys Leu Met Tyr Gly Gly Tyr Val Ala Ser Val
705                 710                 715                 720
Ala Asp Asn Asn Asn Ala Asn Ser Asp Phe Cys Val Ala Pro Leu Gln
                725                 730                 735
Arg Ala Lys Ser Gln Lys Gln Leu Asn Thr Asp Pro Thr Leu Met His
                740                 745                 750
Arg Gly Ser Pro Ala Gly Ser Ser Ala Lys Gly Ala Ser Gly Gly Gly
                755                 760                 765
Pro Gly Ala Ala Glu Gly Lys Arg Ile Ser Val Leu Gly Glu Gly Ser
770                 775                 780
Tyr Cys Ser Gln Arg Trp Pro Ser Leu Ala Ala Gly Val Ala Gly
785                 790                 795                 800
Ala Cys Ser Ser Gln Leu Met Ala Ala Ser Ala Ala Gly Ser Gly
                805                 810                 815
Ala Gly Thr Ala Gln Gln Gln Arg Ser Val Val Cys Gly Thr Pro His
                820                 825                 830
Met
```

(2) INFORMATION FOR SEQ ID NO:3:

(i) SEQUENCE CHARACTERISTICS:
        (A) LENGTH: 1320 base pairs
        (B) TYPE: nucleic acid
        (C) STRANDEDNESS: double
        (D) TOPOLOGY: unknown (ii) MOLECULE TYPE: cDNA (ix) FEATURE:
        (A) NAME/KEY: CDS
        (B) LOCATION: 442..1320

(xi) SEQUENCE DESCRIPTION: SEQ ID NO:3:

```
CCGAGTCGAG CGCCGTGCTT CGAGCGGTGA TGAGCCCCTT TTCTGTCAAC GCTAAAGATC      60

TACAAAACAT CAGCGCCTAT CAAGTGGAAG TGTCAAGTGT GAACAAAACA AAAACGAGAG     120

AAGCACATAC TAAGGTCCAT ATAAATAATA AATAATAATT GTGTGTGATA ACAACATTAT     180

CCAAACAAAA CCAAACAAAA CGAAGGCAAA GTGGAGAAAA TGATACAGCA TCCAGAGTAC     240

GGCCGTTATT CAGCTATCCA GAGCAAGTGT AGTGTGGCAA AATAGAAACA AACAAAGGCA     300

CCAAAATCTG CATACATGGG CTAATTAAGG CTGCCCAGCG AATTTACATT TGTGTGGTGC     360

CAATCCAGAG TGAATCCGAA ACAAACTCCA TCTAGATCGC CAACCAGCAT CACGCTCGCA     420

AACGCCCCCA GAATGTACAA A ATG TTT AGG AAA CAT TTT CGG CGA AAA CCA     471
                       Met Phe Arg Lys His Phe Arg Arg Lys Pro
```

```
                    1               5                    10
GCT ACG TCG TCG TCG TTG GAG TCA ACA ATA GAA TCA GCA GAC AGC CTG          519
Ala Thr Ser Ser Ser Leu Glu Ser Thr Ile Glu Ser Ala Asp Ser Leu
                    15                  20                  25

GGA ATG TCC AAG AAG ACG GCG ACA AAA AGG CAG CGT CCG AGG CAT CGG          567
Gly Met Ser Lys Lys Thr Ala Thr Lys Arg Gln Arg Pro Arg His Arg
                30                  35                  40

GTA CCC AAA ATC GCG ACC CTG CCA TCG ACG ATC CGC GAT TGT CGA TCA          615
Val Pro Lys Ile Ala Thr Leu Pro Ser Thr Ile Arg Asp Cys Arg Ser
            45                  50                  55

TTA AAG TCT GCC TGC AAC TTA ATT GCT TTA ATT TTA ATA CTG TTA GTC          663
Leu Lys Ser Ala Cys Asn Leu Ile Ala Leu Ile Leu Ile Leu Leu Val
        60                  65                  70

CAT AAG ATA TCC GCA GCT GGT AAC TTC GAG CTG GAA ATA TTA GAA ATC          711
His Lys Ile Ser Ala Ala Gly Asn Phe Glu Leu Glu Ile Leu Glu Ile
    75                  80                  85                  90

TCA AAT ACC AAC AGC CAT CTA CTC AAC GGC TAT TGC TGC GGC ATG CCA          759
Ser Asn Thr Asn Ser His Leu Leu Asn Gly Tyr Cys Cys Gly Met Pro
                    95                  100                 105

GCG GAA CTT AGG GCC ACC AAG ACG ATA GGC TGC TCG CCA TGC ACG ACG          807
Ala Glu Leu Arg Ala Thr Lys Thr Ile Gly Cys Ser Pro Cys Thr Thr
                110                 115                 120

GCA TTC CGG CTG TGC CTG AAG GAG TAC CAG ACC ACG GAG CAG GGT GCC          855
Ala Phe Arg Leu Cys Leu Lys Glu Tyr Gln Thr Thr Glu Gln Gly Ala
            125                 130                 135

AGC ATA TCC ACG GGC TGT TCG TTT GGC AAC GCC ACC ACC AAG ATA CTG          903
Ser Ile Ser Thr Gly Cys Ser Phe Gly Asn Ala Thr Thr Lys Ile Leu
        140                 145                 150

GGT GGC TCC AGC TTT GTG CTC AGC GAT CCG GGT GTG GGA GCC ATT GTG          951
Gly Gly Ser Ser Phe Val Leu Ser Asp Pro Gly Val Gly Ala Ile Val
155                 160                 165                 170

CTG CCC TTT ACG TTT CGT TGG ACG AAG TCG TTT ACG CTG ATA CTG CAG          999
Leu Pro Phe Thr Phe Arg Trp Thr Lys Ser Phe Thr Leu Ile Leu Gln
                175                 180                 185

GCG TTG GAT ATG TAC AAC ACA TCC TAT CCA GAT GCG GAG AGG TTA ATT         1047
Ala Leu Asp Met Tyr Asn Thr Ser Tyr Pro Asp Ala Glu Arg Leu Ile
                190                 195                 200

GAG GAA ACA TCA TAC TCG GGC GTG ATA CTG CCG TCG CCG GAG TGG AAG         1095
Glu Glu Thr Ser Tyr Ser Gly Val Ile Leu Pro Ser Pro Glu Trp Lys
            205                 210                 215

ACG CTG GAC CAC ATC GGG CGG AAC GCG CGG ATC ACC TAC CGT GTC CGG         1143
Thr Leu Asp His Ile Gly Arg Asn Ala Arg Ile Thr Tyr Arg Val Arg
        220                 225                 230

GTG CAA TGC GCC GTT ACC TAC TAC AAC ACG ACC TGC ACG ACC TTC TGC         1191
Val Gln Cys Ala Val Thr Tyr Tyr Asn Thr Thr Cys Thr Thr Phe Cys
235                 240                 245                 250

CGT CCG CGG GAC GAT CAG TTC GGT CAC TAC GCC TGC GGC TCC GAG GGT         1239
Arg Pro Arg Asp Asp Gln Phe Gly His Tyr Ala Cys Gly Ser Glu Gly
                255                 260                 265

CAG AAG CTC TGC CTG AAT GGC TGG CAG GGC GTC AAC TGC GAG GAG GCC         1287
Gln Lys Leu Cys Leu Asn Gly Trp Gln Gly Val Asn Cys Glu Glu Ala
                270                 275                 280

ATA TGC AAG GCG GGC TGC GAC CCC GTC CAC GGC                             1320
Ile Cys Lys Ala Gly Cys Asp Pro Val His Gly
                285                 290
```

(2) INFORMATION FOR SEQ ID NO:4:

(i) SEQUENCE CHARACTERISTICS:
        (A) LENGTH: 293 amino acids (B) TYPE: amino acid
            (D) TOPOLOGY: unknown (ii) MOLECULE TYPE: protein (xi) SEQUENCE DESCRIPTION: SEQ ID NO:4:

Met Phe Arg Lys His Phe Arg Arg Lys Pro Ala Thr Ser Ser Ser Leu
 1               5                  10                  15

Glu Ser Thr Ile Glu Ser Ala Asp Ser Leu Gly Met Ser Lys Lys Thr
                20                  25                  30

Ala Thr Lys Arg Gln Arg Pro Arg His Arg Val Pro Lys Ile Ala Thr
            35                  40                  45

Leu Pro Ser Thr Ile Arg Asp Cys Arg Ser Leu Lys Ser Ala Cys Asn
     50                  55                  60

Leu Ile Ala Leu Ile Leu Ile Leu Leu Val His Lys Ile Ser Ala Ala
 65                  70                  75                  80

Gly Asn Phe Glu Leu Glu Ile Leu Glu Ile Ser Asn Thr Asn Ser His
                85                  90                  95

Leu Leu Asn Gly Tyr Cys Cys Gly Met Pro Ala Glu Leu Arg Ala Thr
                100                 105                 110

Lys Thr Ile Gly Cys Ser Pro Cys Thr Thr Ala Phe Arg Leu Cys Leu
            115                 120                 125

Lys Glu Tyr Gln Thr Thr Glu Gln Gly Ala Ser Ile Ser Thr Gly Cys
    130                 135                 140

Ser Phe Gly Asn Ala Thr Thr Lys Ile Leu Gly Gly Ser Ser Phe Val
145                 150                 155                 160

Leu Ser Asp Pro Gly Val Gly Ala Ile Val Leu Pro Phe Thr Phe Arg
                165                 170                 175

Trp Thr Lys Ser Phe Thr Leu Ile Leu Gln Ala Leu Asp Met Tyr Asn
                180                 185                 190

Thr Ser Tyr Pro Asp Ala Glu Arg Leu Ile Glu Glu Thr Ser Tyr Ser
            195                 200                 205

Gly Val Ile Leu Pro Ser Pro Glu Trp Lys Thr Leu Asp His Ile Gly
    210                 215                 220

Arg Asn Ala Arg Ile Thr Tyr Arg Val Arg Val Gln Cys Ala Val Thr
225                 230                 235                 240

Tyr Tyr Asn Thr Thr Cys Thr Thr Phe Cys Arg Pro Arg Asp Asp Gln
                245                 250                 255

Phe Gly His Tyr Ala Cys Gly Ser Glu Gly Gln Lys Leu Cys Leu Asn
                260                 265                 270

Gly Trp Gln Gly Val Asn Cys Glu Glu Ala Ile Cys Lys Ala Gly Cys
            275                 280                 285

Asp Pro Val His Gly
            290

(2) INFORMATION FOR SEQ ID NO:5:

(i) SEQUENCE CHARACTERISTICS:
         (A) LENGTH: 267 base pairs
         (B) TYPE: nucleic acid
         (C) STRANDEDNESS: double
         (D) TOPOLOGY: unknown (ii) MOLECULE TYPE: cDNA (xi) SEQUENCE DESCRIPTION: SEQ ID NO:5:

CGGTGGACTT CCTTCGTGTA TTGGTGGGAG CCCTCGGGAA CGGGGGGTAA CACTGAAAGG      60

```
TCGAGTACCC ATTTCCGTCA TAACGGGTTG GTCGCCCCCT AGGGGTCGGA GTCAGGTGGA      120

CGGGAGGTCG ACAACGCCCG GGGGACGGGT GGTACATGGT GTAAGGTCTT TACCGGACCG      180

GGCAAACGGG TCACACCGAA AGGGGTGAAC GGTAACTACG GGGTCGTCCT GCCCGTCCAT      240

CGAGTCTGGT AAGAGGGTCG CCTTAAG                                          267
```

(2) INFORMATION FOR SEQ ID NO:6:

(i) SEQUENCE CHARACTERISTICS:
        (A) LENGTH: 574 base pairs
        (B) TYPE: nucleic acid
        (C) STRANDEDNESS: double
        (D) TOPOLOGY: unknown (ii) MOLECULE TYPE: cDNA (xi) SEQUENCE DESCRIPTION: SEQ ID NO:6:

```
GAATTCCTTC CATTATACGT GACTTTTCTG AAACTGTAGC CACCCTAGTG TCTCTAACTC       60

CCTCTGGAGT TTGTCAGCTT TGGTCTTTTC AAAGAGCAGG CTCTCTTCAA GCTCCTTAAT      120

GCGGGCATGC TCCAGTTTGG TCTGCGTCTC AAGATCACCT TTGGTAATTG ATTCTTCTTC      180

AACCCGGAAC TGAAGGCTGG CTCTCACCCT CTAGGCAGAG CAGGAATTCC GAGGTGGATG      240

TGTTAGATGT GAATGTCCGT GGCCCAGATG GCTGCACCCC ATTGATGTTG GCTTCTCTCC      300

GAGGAGGCAG CTCAGATTTG AGTGATGAAG ATGAAGATGC AGAGGACTGT TCTGCTAACA      360

TCATCACAGA CTTGGTCTAC CAGGGTGCCA GCCTCCAGNC CAGACAGACC GGACTGGTGA      420

GATGGCCCTG CACCTTGCAG CCCGCTACTC ACGGGCTGAT GCTGCCAAGC GTCTCCTGGA      480

TGCAGGTGCA GATGCCAATG CCCAGGACAA CATGGGCCGC TGTCCACTCC ATGCTGCAGT      540

GGCACGTGAT GCCAAGGTGT ATTCAGATCT GTTA                                  574
```

(2) INFORMATION FOR SEQ ID NO:7:

(i) SEQUENCE CHARACTERISTICS:
        (A) LENGTH: 295 base pairs
        (B) TYPE: nucleic acid
        (C) STRANDEDNESS: double
        (D) TOPOLOGY: unknown (ii) MOLECULE TYPE: cDNA (xi) SEQUENCE DESCRIPTION: SEQ ID NO:7:

```
TCCAGATTCT GATTCGCAAC CGAGTAACTG ATCTAGATGC CAGGATGAAT GATGGTACTA       60

CACCCCTGAT CCTGGCTGCC CGCCTGGCTG TGGAGGGAAT GGTGGCAGAA CTGATCAACT      120

GCCAAGCGGA TGTGAATGCA GTGGATGACC ATGGAAAATC TGCTCTTCAC TGGGCAGCTG      180

CTGTCAATAA TGTGGAGGCA ACTCTTTTGT TGTTGAAAAA TGGGGCCAAC CGAGACATGC      240

AGGACAACAA GGAAGAGACA CCTCTGTTTC TTGCTGCCCG GGAGGAGCTA TAAGC           295
```

(2) INFORMATION FOR SEQ ID NO:8:

(i) SEQUENCE CHARACTERISTICS:
        (A) LENGTH: 248 base pairs
        (B) TYPE: nucleic acid
        (C) STRANDEDNESS: double
        (D) TOPOLOGY: unknown (ii) MOLECULE TYPE: cDNA (xi) SEQUENCE DESCRIPTION: SEQ ID NO:8:

```
GAATTCCATT CAGGAGGAAA GGGTGGGGAG AGAAGCAGGC ACCCACTTTC CCGTGGCTGG       60
```

```
ACTCGTTCCC AGGTGGCTCC ACCGGCAGCT GTGACCGCCG CAGGTGGGGG CGGAGTGCCA       120

TTCAGAAAAT TCCAGAAAAG CCCTACCCCA ACTCGGACGG CAACGTCACA CCCGTGGGTA       180

GCAACTGGCA CACAAACAGC CAGCGTGTCT GGGGCACGGG GGGATGGCAC CCCCTGCAGG       240

CAGAGCTG                                                                248

(2) INFORMATION FOR SEQ ID NO:9:

(i) SEQUENCE CHARACTERISTICS:
        (A) LENGTH: 323 base pairs
        (B) TYPE: nucleic acid
        (C) STRANDEDNESS: double
        (D) TOPOLOGY: unknown (ii) MOLECULE TYPE: cDNA (xi) SEQUENCE DESCRIPTION: SEQ ID NO:9:

TACGTATCTC GAGCACAGAC AGCTGACGTA CACTTTTNNA GTGCGAGGGA CATTCGTCCG        60

ACCAGTACGA ACATTTAGGC TCAGTACGGT AGGTCCATGG CCAAGACTAG GAGACGTAGG       120

GAGCTACAGG TCCCGCTCGC TAAACTCGGA CCACTGAAAC CTCCGGTCGA CAGTCGGTAA       180

GCGAACAAGA GGGCCAGATC TTAGAGAAGG TGTCGCGGCG AGACTCGGGC TCGGGTCAGG       240

CGGCCTTAAG GACGTCGGGC CCNNNAGGTG ATCAAGATCT CGNCNCGGCG GGCGCCACCT       300

CGAGGNCGAA AACAAGGGAA ATC                                               323

(2) INFORMATION FOR SEQ ID NO:10:

(i) SEQUENCE CHARACTERISTICS:
        (A) LENGTH: 3234 base pairs
        (B) TYPE: nucleic acid
        (C) STRANDEDNESS: double
        (D) TOPOLOGY: unknown (ii) MOLECULE TYPE: cDNA (ix) FEATURE:
        (A) NAME/KEY: CDS
        (B) LOCATION: 1..3234

(xi) SEQUENCE DESCRIPTION: SEQ ID NO:10:
```

| | | | | | | | | | | | | | | | | |
|---|---|---|---|---|---|---|---|---|---|---|---|---|---|---|---|---|
| TGC | CAG | GAG | GAC | GCG | GGC | AAC | AAG | GTC | TGC | AGC | CTG | CAG | TGC | AAC | AAC | 48 |
| Cys | Gln | Glu | Asp | Ala | Gly | Asn | Lys | Val | Cys | Ser | Leu | Gln | Cys | Asn | Asn | |
| 1 | | | | 5 | | | | | 10 | | | | | 15 | | |
| CAC | GCG | TGC | GGC | TGG | GAC | GGC | GGT | GAC | TGC | TCC | CTC | AAC | TTC | AAT | GAC | 96 |
| His | Ala | Cys | Gly | Trp | Asp | Gly | Gly | Asp | Cys | Ser | Leu | Asn | Phe | Asn | Asp | |
| | | | 20 | | | | | 25 | | | | | 30 | | | |
| CCC | TGG | AAG | AAC | TGC | ACG | CAG | TCT | CTG | CAG | TGC | TGG | AAG | TAC | TTC | AGT | 144 |
| Pro | Trp | Lys | Asn | Cys | Thr | Gln | Ser | Leu | Gln | Cys | Trp | Lys | Tyr | Phe | Ser | |
| | 35 | | | | | 40 | | | | | 45 | | | | | |
| GAC | GGC | CAC | TGT | GAC | AGC | CAG | TGC | AAC | TCA | GCC | GGC | TGC | CTC | TTC | GAC | 192 |
| Asp | Gly | His | Cys | Asp | Ser | Gln | Cys | Asn | Ser | Ala | Gly | Cys | Leu | Phe | Asp | |
| | 50 | | | | | 55 | | | | | 60 | | | | | |
| GGC | TTT | GAC | TGC | CAG | CGT | GCG | GAA | GGC | CAG | TGC | AAC | CCC | CTG | TAC | GAC | 240 |
| Gly | Phe | Asp | Cys | Gln | Arg | Ala | Glu | Gly | Gln | Cys | Asn | Pro | Leu | Tyr | Asp | |
| 65 | | | | | 70 | | | | | 75 | | | | | 80 | |
| CAG | TAC | TGC | AAG | GAC | CAC | TTC | AGC | GAC | GGG | CAC | TGC | GAC | CAG | GGC | TGC | 288 |
| Gln | Tyr | Cys | Lys | Asp | His | Phe | Ser | Asp | Gly | His | Cys | Asp | Gln | Gly | Cys | |
| | | | | 85 | | | | | 90 | | | | | 95 | | |
| AAC | AGC | GCG | GAG | TGC | GAG | TGG | GAC | GGG | CTG | GAC | TGT | GCG | GAG | CAT | GTA | 336 |
| Asn | Ser | Ala | Glu | Cys | Glu | Trp | Asp | Gly | Leu | Asp | Cys | Ala | Glu | His | Val | |
| | | | 100 | | | | | 105 | | | | | 110 | | | |
| CCC | GAG | AGG | CTG | GCG | GCC | GGC | ACG | CTG | GTG | GTG | GTG | GTG | CTG | ATG | CCG | 384 |

```
                Pro Glu Arg Leu Ala Ala Gly Thr Leu Val Val Val Leu Met Pro
                        115                 120                 125

CCG GAG CAG CTG CGC AAC AGC TCC TTC CAC TTC CTG CGG GAG CTC AGC              432
Pro Glu Gln Leu Arg Asn Ser Ser Phe His Phe Leu Arg Glu Leu Ser
        130                 135                 140

CGC GTG CTG CAC ACC AAC GTG GTC TTC AAG CGT GAC GCA CAC GGC CAG              480
Arg Val Leu His Thr Asn Val Val Phe Lys Arg Asp Ala His Gly Gln
145                 150                 155                 160

CAG ATG ATC TTC CCC TAC TAC GGC CGC GAG GAG GAG CTG CGC AAG CAC              528
Gln Met Ile Phe Pro Tyr Tyr Gly Arg Glu Glu Glu Leu Arg Lys His
                165                 170                 175

CCC ATC AAG CGT GCC GCC GAG GGC TGG GCC GCA CCT GAC GCC CTG CTG              576
Pro Ile Lys Arg Ala Ala Glu Gly Trp Ala Ala Pro Asp Ala Leu Leu
        180                 185                 190

GGC CAG GTG AAG GCC TCG CTG CTC CCT GGT GGC AGC GAG GGT GGG CGG              624
Gly Gln Val Lys Ala Ser Leu Leu Pro Gly Gly Ser Glu Gly Gly Arg
            195                 200                 205

CGG CGG AGG GAG CTG GAC CCC ATG GAC GTC CGC GGC TCC ATC GTC TAC              672
Arg Arg Arg Glu Leu Asp Pro Met Asp Val Arg Gly Ser Ile Val Tyr
        210                 215                 220

CTG GAG ATT GAC AAC CGG CAG TGT GTG CAG GCC TCC TCG CAG TGC TTC              720
Leu Glu Ile Asp Asn Arg Gln Cys Val Gln Ala Ser Ser Gln Cys Phe
225                 230                 235                 240

CAG AGT GCC ACC GAC GTG GCC GCA TTC CTG GGA GCG CTC GCC TCG CTG              768
Gln Ser Ala Thr Asp Val Ala Ala Phe Leu Gly Ala Leu Ala Ser Leu
                245                 250                 255

GGC AGC CTC AAC ATC CCC TAC AAG ATC GAG GCC GTG CAG AGT GAG ACC              816
Gly Ser Leu Asn Ile Pro Tyr Lys Ile Glu Ala Val Gln Ser Glu Thr
        260                 265                 270

GTG GAG CCG CCC CCG GCG CAG CTG CAC TTC ATG TAC GTG GCG GCG              864
Val Glu Pro Pro Pro Ala Gln Leu His Phe Met Tyr Val Ala Ala
        275                 280                 285

GCC GCC TTT GTG CTT CTG TTC TTC GTG GGC TGC GGG GTG CTG CTG TCC              912
Ala Ala Phe Val Leu Leu Phe Phe Val Gly Cys Gly Val Leu Leu Ser
290                 295                 300

CGC AAG CGC CGG CGG CAG CAT GGC CAG CTC TGG TTC CCT GAG GGC TTC              960
Arg Lys Arg Arg Arg Gln His Gly Gln Leu Trp Phe Pro Glu Gly Phe
305                 310                 315                 320

AAA GTG TCT GAG GCC AGC AAG AAG AAG CGG CGG GAG CCC CTC GGC GAG             1008
Lys Val Ser Glu Ala Ser Lys Lys Lys Arg Arg Glu Pro Leu Gly Glu
                325                 330                 335

GAC TCC GTG GGC CTC AAG CCC CTG AAG AAC GCT TCA GAC GGT GCC CTC             1056
Asp Ser Val Gly Leu Lys Pro Leu Lys Asn Ala Ser Asp Gly Ala Leu
        340                 345                 350

ATG GAC GAC AAC CAG AAT GAG TGG GGG GAC GAG GAC CTG GAG ACC AAG             1104
Met Asp Asp Asn Gln Asn Glu Trp Gly Asp Glu Asp Leu Glu Thr Lys
            355                 360                 365

AAG TTC CGG TTC GAG GAG CCC GTG GTT CTG CCT GAC CTG GAC GAC CAG             1152
Lys Phe Arg Phe Glu Glu Pro Val Val Leu Pro Asp Leu Asp Asp Gln
        370                 375                 380

ACA GAC CAC CGG CAG TGG ACT CAG CAG CAC CTG GAT GCC GCT GAC CTG             1200
Thr Asp His Arg Gln Trp Thr Gln Gln His Leu Asp Ala Ala Asp Leu
385                 390                 395                 400

CGC ATG TCT GCC ATG GCC CCC ACA CCG CCC CAG GGT GAG GTT GAC GCC             1248
Arg Met Ser Ala Met Ala Pro Thr Pro Pro Gln Gly Glu Val Asp Ala
                405                 410                 415

GAC TGC ATG GAC GTC AAT GTC CGC GGG CCT GAT GGC TTC ACC CCG CTC             1296
Asp Cys Met Asp Val Asn Val Arg Gly Pro Asp Gly Phe Thr Pro Leu
        420                 425                 430
```

```
ATG ATC GCC TCC TGC AGC GGG GGC GGC CTG GAG ACG GGC AAC AGC GAG        1344
Met Ile Ala Ser Cys Ser Gly Gly Gly Leu Glu Thr Gly Asn Ser Glu
        435                 440                 445

GAA GAG GAG GAC GCG CCG GCC GTC ATC TCC GAC TTC ATC TAC CAG GGC        1392
Glu Glu Glu Asp Ala Pro Ala Val Ile Ser Asp Phe Ile Tyr Gln Gly
450                 455                 460

GCC AGC CTG CAC AAC CAG ACA GAC CGC ACG GGC GAG ACC GCC TTG CAC        1440
Ala Ser Leu His Asn Gln Thr Asp Arg Thr Gly Glu Thr Ala Leu His
465                 470                 475                 480

CTG GCC GCC CGC TAC TCA CGC TCT GAT GCC GCC AAG CGC CTG CTG GAG        1488
Leu Ala Ala Arg Tyr Ser Arg Ser Asp Ala Ala Lys Arg Leu Leu Glu
                485                 490                 495

GCC AGC GCA GAT GCC AAC ATC CAG GAC AAC ATG GGC CGC ACC CCG CTG        1536
Ala Ser Ala Asp Ala Asn Ile Gln Asp Asn Met Gly Arg Thr Pro Leu
        500                 505                 510

CAT GCG GCT GTG TCT GCC GAC GCA CAA GGT GTC TTC CAG ATC CTG ATC        1584
His Ala Ala Val Ser Ala Asp Ala Gln Gly Val Phe Gln Ile Leu Ile
        515                 520                 525

CGG AAC CGA GCC ACA GAC CTG GAT GCC CGC ATG CAT GAT GGC ACG ACG        1632
Arg Asn Arg Ala Thr Asp Leu Asp Ala Arg Met His Asp Gly Thr Thr
530                 535                 540

CCA CTG ATC CTG GCT GCC CGC CTG GCC GTG GAG GGC ATG CTG GAG GAC        1680
Pro Leu Ile Leu Ala Ala Arg Leu Ala Val Glu Gly Met Leu Glu Asp
545                 550                 555                 560

CTC ATC AAC TCA CAC GCC GAC GTC AAC GCC GTA GAT GAC CTG GGC AAG        1728
Leu Ile Asn Ser His Ala Asp Val Asn Ala Val Asp Asp Leu Gly Lys
                565                 570                 575

TCC GCC CTG CAC TGG GCC GCC GCC GTG AAC AAT GTG GAT GCC GCA GTT        1776
Ser Ala Leu His Trp Ala Ala Ala Val Asn Asn Val Asp Ala Ala Val
                580                 585                 590

GTG CTC CTG AAG AAC GGG GCT AAC AAA GAT ATG CAG AAC AAC AGG GAG        1824
Val Leu Leu Lys Asn Gly Ala Asn Lys Asp Met Gln Asn Asn Arg Glu
                595                 600                 605

GAG ACA CCC CTG TTT CTG GCC GCC CGG GAG GGC AGC TAC GAG ACC GCC        1872
Glu Thr Pro Leu Phe Leu Ala Ala Arg Glu Gly Ser Tyr Glu Thr Ala
        610                 615                 620

AAG GTG CTG CTG GAC CAC TTT GCC AAC CGG GAC ATC ACG GAT CAT ATG        1920
Lys Val Leu Leu Asp His Phe Ala Asn Arg Asp Ile Thr Asp His Met
625                 630                 635                 640

GAC CGC CTG CCG CGC GAC ATC GCA CAG GAG CGC ATG CAT CAC GAC ATC        1968
Asp Arg Leu Pro Arg Asp Ile Ala Gln Glu Arg Met His His Asp Ile
                645                 650                 655

GTG AGG CTG CTG GAC GAG TAC AAC CTG GTG CGC AGC CCG CAG CTG CAC        2016
Val Arg Leu Leu Asp Glu Tyr Asn Leu Val Arg Ser Pro Gln Leu His
                660                 665                 670

GGA GCC CCG CTG GGG GGC ACG CCC ACC CTG TCG CCC CCG CTC TGC TCG        2064
Gly Ala Pro Leu Gly Gly Thr Pro Thr Leu Ser Pro Pro Leu Cys Ser
                675                 680                 685

CCC AAC GGC TAC CTG GGC AGC CTC AAG CCC GGC GTG CAG GGC AAG AAG        2112
Pro Asn Gly Tyr Leu Gly Ser Leu Lys Pro Gly Val Gln Gly Lys Lys
        690                 695                 700

GTC CGC AAG CCC AGC AGC AAA GGC CTG GCC TGT GGA AGC AAG GAG GCC        2160
Val Arg Lys Pro Ser Ser Lys Gly Leu Ala Cys Gly Ser Lys Glu Ala
705                 710                 715                 720

AAG GAC CTC AAG GCA CGG AGG AAG AAG TCC CAG GAT GGC AAG GGC TGC        2208
Lys Asp Leu Lys Ala Arg Arg Lys Lys Ser Gln Asp Gly Lys Gly Cys
                725                 730                 735

CTG CTG GAC AGC TCC GGC ATG CTC TCG CCC GTG GAC TCC CTG GAG TCA        2256
Leu Leu Asp Ser Ser Gly Met Leu Ser Pro Val Asp Ser Leu Glu Ser
                740                 745                 750
```

```
CCC CAT GGC TAC CTG TCA GAC GTG GCC TCG CCG CCA CTG CTG CCC TCC          2304
Pro His Gly Tyr Leu Ser Asp Val Ala Ser Pro Pro Leu Leu Pro Ser
        755                 760                 765

CCG TTC CAG CAG TCT CCG TCC GTG CCC CTC AAC CAC CTG CCT GGG ATG          2352
Pro Phe Gln Gln Ser Pro Ser Val Pro Leu Asn His Leu Pro Gly Met
770                 775                 780

CCC GAC ACC CAC CTG GGC ATC GGG CAC CTG AAC GTG GCG GCC AAG CCC          2400
Pro Asp Thr His Leu Gly Ile Gly His Leu Asn Val Ala Ala Lys Pro
785                 790                 795                 800

GAG ATG GCG GCG CTG GGT GGG GGC GGC CGG CTG GCC TTT GAG ACT GGC          2448
Glu Met Ala Ala Leu Gly Gly Gly Gly Arg Leu Ala Phe Glu Thr Gly
                    805                 810                 815

CCA CCT CGT CTC TCC CAC CTG CCT GTG GCC TCT GGC ACC AGC ACC GTC          2496
Pro Pro Arg Leu Ser His Leu Pro Val Ala Ser Gly Thr Ser Thr Val
            820                 825                 830

CTG GGC TCC AGC AGC GGA GGG GCC CTG AAT TTC ACT GTG GGC GGG TCC          2544
Leu Gly Ser Ser Ser Gly Gly Ala Leu Asn Phe Thr Val Gly Gly Ser
        835                 840                 845

ACC AGT TTG AAT GGT CAA TGC GAG TGG CTG TCC CGG CTG CAG AGC GGC          2592
Thr Ser Leu Asn Gly Gln Cys Glu Trp Leu Ser Arg Leu Gln Ser Gly
    850                 855                 860

ATG GTG CCG AAC CAA TAC AAC CCT CTG CGG GGG AGT GTG GCA CCA GGC          2640
Met Val Pro Asn Gln Tyr Asn Pro Leu Arg Gly Ser Val Ala Pro Gly
865                 870                 875                 880

CCC CTG AGC ACA CAG GCC CCC TCC CTG CAG CAT GGC ATG GTA GGC CCG          2688
Pro Leu Ser Thr Gln Ala Pro Ser Leu Gln His Gly Met Val Gly Pro
                885                 890                 895

CTG CAC AGT AGC CTT GCT GCC AGC GCC CTG TCC CAG ATG ATG AGC TAC          2736
Leu His Ser Ser Leu Ala Ala Ser Ala Leu Ser Gln Met Met Ser Tyr
            900                 905                 910

CAG GGC CTG CCC AGC ACC CGG CTG GCC ACC CAG CCT CAC CTG GTG CAG          2784
Gln Gly Leu Pro Ser Thr Arg Leu Ala Thr Gln Pro His Leu Val Gln
        915                 920                 925

ACC CAG CAG GTG CAG CCA CAA AAC TTA CAG ATG CAG CAG CAG AAC CTG          2832
Thr Gln Gln Val Gln Pro Gln Asn Leu Gln Met Gln Gln Gln Asn Leu
    930                 935                 940

CAG CCA GCA AAC ATC CAG CAG CAG CAA AGC CTG CAG CCG CCA CCA CCA          2880
Gln Pro Ala Asn Ile Gln Gln Gln Gln Ser Leu Gln Pro Pro Pro Pro
945                 950                 955                 960

CCA CCA CAG CCG CAC CTT GGC GTG AGC TCA GCA GCC AGC GGC CAC CTG          2928
Pro Pro Gln Pro His Leu Gly Val Ser Ser Ala Ala Ser Gly His Leu
                965                 970                 975

GGC CGG AGC TTC CTG AGT GGA GAG CCG AGC CAG GCA GAC GTG CAG CCA          2976
Gly Arg Ser Phe Leu Ser Gly Glu Pro Ser Gln Ala Asp Val Gln Pro
            980                 985                 990

CTG GGC CCC AGC AGC CTG GCG GTG CAC ACT ATT CTG CCC CAG GAG AGC          3024
Leu Gly Pro Ser Ser Leu Ala Val His Thr Ile Leu Pro Gln Glu Ser
        995                 1000                1005

CCC GCC CTG CCC ACG TCG CTG CCA TCC TCG CTG GTC CCA CCC GTG ACC          3072
Pro Ala Leu Pro Thr Ser Leu Pro Ser Ser Leu Val Pro Pro Val Thr
    1010                1015                1020

GCA GCC CAG TTC CTG ACG CCC CCC TCG CAG CAC AGC TAC TCC TCG CCT          3120
Ala Ala Gln Phe Leu Thr Pro Pro Ser Gln His Ser Tyr Ser Ser Pro
1025                1030                1035                1040

GTG GAC AAC ACC CCC AGC CAC CAG CTA CAG GTG CCT GTT CCT GTA ATG          3168
Val Asp Asn Thr Pro Ser His Gln Leu Gln Val Pro Val Pro Val Met
                1045                1050                1055

GTA ATG ATC CGA TCT TCG GAT CCT TCT AAA GGC TCA TCA ATT TTG ATC          3216
Val Met Ile Arg Ser Ser Asp Pro Ser Lys Gly Ser Ser Ile Leu Ile
```

```
                         1060              1065              1070
GAA GCT CCC GAC TCA TGG                                                    3234
Glu Ala Pro Asp Ser Trp
        1075
```

(2) INFORMATION FOR SEQ ID NO:11:

(i) SEQUENCE CHARACTERISTICS:
        (A) LENGTH: 1078 amino acids
        (B) TYPE: amino acid
        (D) TOPOLOGY: unknown (ii) MOLECULE TYPE: protein (xi) SEQUENCE DESCRIPTION: SEQ ID NO:11:

```
Cys Gln Glu Asp Ala Gly Asn Lys Val Cys Ser Leu Gln Cys Asn Asn
 1               5                  10                  15

His Ala Cys Gly Trp Asp Gly Gly Asp Cys Ser Leu Asn Phe Asn Asp
            20                  25                  30

Pro Trp Lys Asn Cys Thr Gln Ser Leu Gln Cys Trp Lys Tyr Phe Ser
        35                  40                  45

Asp Gly His Cys Asp Ser Gln Cys Asn Ser Ala Gly Cys Leu Phe Asp
    50                  55                  60

Gly Phe Asp Cys Gln Arg Ala Glu Gly Gln Cys Asn Pro Leu Tyr Asp
65                  70                  75                  80

Gln Tyr Cys Lys Asp His Phe Ser Asp Gly His Cys Asp Gln Gly Cys
            85                  90                  95

Asn Ser Ala Glu Cys Glu Trp Asp Gly Leu Asp Cys Ala Glu His Val
            100                 105                 110

Pro Glu Arg Leu Ala Ala Gly Thr Leu Val Val Val Leu Met Pro
            115                 120                 125

Pro Glu Gln Leu Arg Asn Ser Ser Phe His Phe Leu Arg Glu Leu Ser
        130                 135                 140

Arg Val Leu His Thr Asn Val Val Phe Lys Arg Asp Ala His Gly Gln
145                 150                 155                 160

Gln Met Ile Phe Pro Tyr Tyr Gly Arg Glu Glu Leu Arg Lys His
            165                 170                 175

Pro Ile Lys Arg Ala Ala Glu Gly Trp Ala Ala Pro Asp Ala Leu Leu
            180                 185                 190

Gly Gln Val Lys Ala Ser Leu Leu Pro Gly Gly Ser Glu Gly Gly Arg
        195                 200                 205

Arg Arg Arg Glu Leu Asp Pro Met Asp Val Arg Gly Ser Ile Val Tyr
    210                 215                 220

Leu Glu Ile Asp Asn Arg Gln Cys Val Gln Ala Ser Ser Gln Cys Phe
225                 230                 235                 240

Gln Ser Ala Thr Asp Val Ala Ala Phe Leu Gly Ala Leu Ala Ser Leu
            245                 250                 255

Gly Ser Leu Asn Ile Pro Tyr Lys Ile Glu Ala Val Gln Ser Glu Thr
            260                 265                 270

Val Glu Pro Pro Pro Ala Gln Leu His Phe Met Tyr Val Ala Ala
        275                 280                 285

Ala Ala Phe Val Leu Leu Phe Phe Val Gly Cys Gly Val Leu Leu Ser
    290                 295                 300

Arg Lys Arg Arg Arg Gln His Gly Gln Leu Trp Phe Pro Glu Gly Phe
305                 310                 315                 320

Lys Val Ser Glu Ala Ser Lys Lys Lys Arg Arg Glu Pro Leu Gly Glu
```

-continued

```
                325                 330                 335
Asp Ser Val Gly Leu Lys Pro Leu Lys Asn Ala Ser Asp Gly Ala Leu
                340                 345                 350
Met Asp Asp Asn Gln Asn Glu Trp Gly Asp Glu Asp Leu Glu Thr Lys
                355                 360                 365
Lys Phe Arg Phe Glu Glu Pro Val Val Leu Pro Asp Leu Asp Asp Gln
                370                 375                 380
Thr Asp His Arg Gln Trp Thr Gln Gln His Leu Asp Ala Ala Asp Leu
385                 390                 395                 400
Arg Met Ser Ala Met Ala Pro Thr Pro Gln Gly Glu Val Asp Ala
                405                 410                 415
Asp Cys Met Asp Val Asn Val Arg Gly Pro Asp Gly Phe Thr Pro Leu
                420                 425                 430
Met Ile Ala Ser Cys Ser Gly Gly Gly Leu Glu Thr Gly Asn Ser Glu
                435                 440                 445
Glu Glu Glu Asp Ala Pro Ala Val Ile Ser Asp Phe Ile Tyr Gln Gly
                450                 455                 460
Ala Ser Leu His Asn Gln Thr Asp Arg Thr Gly Glu Thr Ala Leu His
465                 470                 475                 480
Leu Ala Ala Arg Tyr Ser Arg Ser Asp Ala Ala Lys Arg Leu Leu Glu
                485                 490                 495
Ala Ser Ala Asp Ala Asn Ile Gln Asp Asn Met Gly Arg Thr Pro Leu
                500                 505                 510
His Ala Ala Val Ser Ala Asp Ala Gln Gly Val Phe Gln Ile Leu Ile
                515                 520                 525
Arg Asn Arg Ala Thr Asp Leu Asp Ala Arg Met His Asp Gly Thr Thr
                530                 535                 540
Pro Leu Ile Leu Ala Ala Arg Leu Ala Val Glu Gly Met Leu Glu Asp
545                 550                 555                 560
Leu Ile Asn Ser His Ala Asp Val Asn Ala Val Asp Asp Leu Gly Lys
                565                 570                 575
Ser Ala Leu His Trp Ala Ala Ala Val Asn Asn Val Asp Ala Ala Val
                580                 585                 590
Val Leu Leu Lys Asn Gly Ala Asn Lys Asp Met Gln Asn Asn Arg Glu
                595                 600                 605
Glu Thr Pro Leu Phe Leu Ala Ala Arg Glu Gly Ser Tyr Glu Thr Ala
                610                 615                 620
Lys Val Leu Leu Asp His Phe Ala Asn Arg Asp Ile Thr Asp His Met
625                 630                 635                 640
Asp Arg Leu Pro Arg Asp Ile Ala Gln Glu Arg Met His His Asp Ile
                645                 650                 655
Val Arg Leu Leu Asp Glu Tyr Asn Leu Val Arg Ser Pro Gln Leu His
                660                 665                 670
Gly Ala Pro Leu Gly Gly Thr Pro Thr Leu Ser Pro Pro Leu Cys Ser
                675                 680                 685
Pro Asn Gly Tyr Leu Gly Ser Leu Lys Pro Gly Val Gln Gly Lys Lys
                690                 695                 700
Val Arg Lys Pro Ser Ser Lys Gly Leu Ala Cys Gly Ser Lys Glu Ala
705                 710                 715                 720
Lys Asp Leu Lys Ala Arg Arg Lys Lys Ser Gln Asp Gly Lys Gly Cys
                725                 730                 735
Leu Leu Asp Ser Ser Gly Met Leu Ser Pro Val Asp Ser Leu Glu Ser
                740                 745                 750
```

```
Pro His Gly Tyr Leu Ser Asp Val Ala Ser Pro Leu Leu Pro Ser
        755                 760                 765

Pro Phe Gln Gln Ser Pro Ser Val Pro Leu Asn His Leu Pro Gly Met
        770                 775                 780

Pro Asp Thr His Leu Gly Ile Gly His Leu Asn Val Ala Ala Lys Pro
785                 790                 795                 800

Glu Met Ala Ala Leu Gly Gly Gly Arg Leu Ala Phe Glu Thr Gly
                805                 810                 815

Pro Pro Arg Leu Ser His Leu Pro Val Ala Ser Gly Thr Ser Thr Val
                820                 825                 830

Leu Gly Ser Ser Ser Gly Gly Ala Leu Asn Phe Thr Val Gly Gly Ser
            835                 840                 845

Thr Ser Leu Asn Gly Gln Cys Glu Trp Leu Ser Arg Leu Gln Ser Gly
850                 855                 860

Met Val Pro Asn Gln Tyr Asn Pro Leu Arg Gly Ser Val Ala Pro Gly
865                 870                 875                 880

Pro Leu Ser Thr Gln Ala Pro Ser Leu Gln His Gly Met Val Gly Pro
                885                 890                 895

Leu His Ser Ser Leu Ala Ala Ser Ala Leu Ser Gln Met Met Ser Tyr
                900                 905                 910

Gln Gly Leu Pro Ser Thr Arg Leu Ala Thr Gln Pro His Leu Val Gln
            915                 920                 925

Thr Gln Gln Val Gln Pro Gln Asn Leu Gln Met Gln Gln Gln Asn Leu
        930                 935                 940

Gln Pro Ala Asn Ile Gln Gln Gln Ser Leu Gln Pro Pro Pro
945                 950                 955                 960

Pro Pro Gln Pro His Leu Gly Val Ser Ser Ala Ala Ser Gly His Leu
                965                 970                 975

Gly Arg Ser Phe Leu Ser Gly Glu Pro Ser Gln Ala Asp Val Gln Pro
            980                 985                 990

Leu Gly Pro Ser Ser Leu Ala Val His Thr Ile Leu Pro Gln Glu Ser
        995                 1000                1005

Pro Ala Leu Pro Thr Ser Leu Pro Ser Ser Leu Val Pro Val Thr
    1010                1015                1020

Ala Ala Gln Phe Leu Thr Pro Pro Ser Gln His Ser Tyr Ser Ser Pro
1025                1030                1035                1040

Val Asp Asn Thr Pro Ser His Gln Leu Gln Val Pro Val Pro Val Met
                1045                1050                1055

Val Met Ile Arg Ser Ser Asp Pro Ser Lys Gly Ser Ser Ile Leu Ile
                1060                1065                1070

Glu Ala Pro Asp Ser Trp
        1075

(2) INFORMATION FOR SEQ ID NO:12:

(i) SEQUENCE CHARACTERISTICS:
        (A) LENGTH: 4268 base pairs
        (B) TYPE: nucleic acid
        (C) STRANDEDNESS: double
        (D) TOPOLOGY: unknown (ii) MOLECULE TYPE: cDNA (ix) FEATURE:
        (A) NAME/KEY: CDS
        (B) LOCATION: 2..1972
```

(xi) SEQUENCE DESCRIPTION: SEQ ID NO:12:

```
G GAG GTG GAT GTG TTA GAT GTG AAT GTC CGT GGC CCA GAT GGC TGC           46
  Glu Val Asp Val Leu Asp Val Asn Val Arg Gly Pro Asp Gly Cys
  1               5                   10                  15

ACC CCA TTG ATG TTG GCT TCT CTC CGA GGA GGC AGC TCA GAT TTG AGT         94
Thr Pro Leu Met Leu Ala Ser Leu Arg Gly Gly Ser Ser Asp Leu Ser
                20                  25                  30

GAT GAA GAT GAA GAT GCA GAG GAC TCT TCT GCT AAC ATC ATC ACA GAC         142
Asp Glu Asp Glu Asp Ala Glu Asp Ser Ser Ala Asn Ile Ile Thr Asp
                35                  40                  45

TTG GTC TAC CAG GGT GCC AGC CTC CAG GCC CAG ACA GAC CGG ACT GGT         190
Leu Val Tyr Gln Gly Ala Ser Leu Gln Ala Gln Thr Asp Arg Thr Gly
            50                  55                  60

GAG ATG GCC CTG CAC CTT GCA GCC CGC TAC TCA CGG GCT GAT GCT GCC         238
Glu Met Ala Leu His Leu Ala Ala Arg Tyr Ser Arg Ala Asp Ala Ala
        65                  70                  75

AAG CGT CTC CTG GAT GCA GGT GCA GAT GCC AAT GCC CAG GAC AAC ATG         286
Lys Arg Leu Leu Asp Ala Gly Ala Asp Ala Asn Ala Gln Asp Asn Met
80                  85                  90                  95

GGC CGC TGT CCA CTC CAT GCT GCA GTG GCA GCT GAT GCC CAA GGT GTC         334
Gly Arg Cys Pro Leu His Ala Ala Val Ala Ala Asp Ala Gln Gly Val
                100                 105                 110

TTC CAG ATT CTG ATT CGC AAC CGA GTA ACT GAT CTA GAT GCC AGG ATG         382
Phe Gln Ile Leu Ile Arg Asn Arg Val Thr Asp Leu Asp Ala Arg Met
                115                 120                 125

AAT GAT GGT ACT ACA CCC CTG ATC CTG GCT GCC CGC CTG GCT GTG GAG         430
Asn Asp Gly Thr Thr Pro Leu Ile Leu Ala Ala Arg Leu Ala Val Glu
            130                 135                 140

GGA ATG GTG GCA GAA CTG ATC AAC TGC CAA GCG GAT GTG AAT GCA GTG         478
Gly Met Val Ala Glu Leu Ile Asn Cys Gln Ala Asp Val Asn Ala Val
145                 150                 155

GAT GAC CAT GGA AAA TCT GCT CTT CAC TGG GCA GCT GCT GTC AAT AAT         526
Asp Asp His Gly Lys Ser Ala Leu His Trp Ala Ala Ala Val Asn Asn
160                 165                 170                 175

GTG GAG GCA ACT CTT TTG TTG TTG AAA AAT GGG GCC AAC CGA GAC ATG         574
Val Glu Ala Thr Leu Leu Leu Leu Lys Asn Gly Ala Asn Arg Asp Met
                180                 185                 190

CAG GAC AAC AAG GAA GAG ACA CCT CTG TTT CTT GCT GCC CGG GAG GGG         622
Gln Asp Asn Lys Glu Glu Thr Pro Leu Phe Leu Ala Ala Arg Glu Gly
                195                 200                 205

AGC TAT GAA GCA GCC AAG ATC CTG TTA GAC CAT TTT GCC AAT CGA GAC         670
Ser Tyr Glu Ala Ala Lys Ile Leu Leu Asp His Phe Ala Asn Arg Asp
            210                 215                 220

ATC ACA GAC CAT ATG GAT CGT CTT CCC CGG GAT GTG GCT CGG GAT CGC         718
Ile Thr Asp His Met Asp Arg Leu Pro Arg Asp Val Ala Arg Asp Arg
        225                 230                 235

ATG CAC CAT GAC ATT GTG CGC CTT CTG GAT GAA TAC AAT GTG ACC CCA         766
Met His His Asp Ile Val Arg Leu Leu Asp Glu Tyr Asn Val Thr Pro
240                 245                 250                 255

AGC CCT CCA GGC ACC GTG TTG ACT TCT GCT CTC TCA CCT GTC ATC TGT         814
Ser Pro Pro Gly Thr Val Leu Thr Ser Ala Leu Ser Pro Val Ile Cys
                260                 265                 270

GGG CCC AAC AGA TCT TTC CTC AGC CTG AAG CAC ACC CCA ATG GGC AAG         862
Gly Pro Asn Arg Ser Phe Leu Ser Leu Lys His Thr Pro Met Gly Lys
                275                 280                 285

AAG TCT AGA CGG CCC AGT GCC AAG AGT ACC ATG CCT ACT AGC CTC CCT         910
Lys Ser Arg Arg Pro Ser Ala Lys Ser Thr Met Pro Thr Ser Leu Pro
            290                 295                 300

AAC CTT GCC AAG GAG GCA AAG GAT GCC AAG GGT AGT AGG AGG AAG AAG         958
```

```
                -continued

Asn Leu Ala Lys Glu Ala Lys Asp Ala Lys Gly Ser Arg Arg Lys Lys
    305                 310                 315

TCT CTG AGT GAG AAG GTC CAA CTG TCT GAG AGT TCA GTA ACT TTA TCC    1006
Ser Leu Ser Glu Lys Val Gln Leu Ser Glu Ser Ser Val Thr Leu Ser
320                 325                 330                 335

CCT GTT GAT TCC CTA GAA TCT CCT CAC ACG TAT GTT TCC GAC ACC ACA    1054
Pro Val Asp Ser Leu Glu Ser Pro His Thr Tyr Val Ser Asp Thr Thr
                340                 345                 350

TCC TCT CCA ATG ATT ACA TCC CCT GGG ATC TTA CAG GCC TCA CCC AAC    1102
Ser Ser Pro Met Ile Thr Ser Pro Gly Ile Leu Gln Ala Ser Pro Asn
            355                 360                 365

CCT ATG TTG GCC ACT GCC GCC CCT CCT GCC CCA GTC CAT GCC CAG CAT    1150
Pro Met Leu Ala Thr Ala Ala Pro Pro Ala Pro Val His Ala Gln His
        370                 375                 380

GCA CTA TCT TTT TCT AAC CTT CAT GAA ATG CAG CCT TTG GCA CAT GGG    1198
Ala Leu Ser Phe Ser Asn Leu His Glu Met Gln Pro Leu Ala His Gly
    385                 390                 395

GCC AGC ACT GTG CTT CCC TCA GTG AGC CAG TTG CTA TCC CAC CAC CAC    1246
Ala Ser Thr Val Leu Pro Ser Val Ser Gln Leu Leu Ser His His His
400                 405                 410                 415

ATT GTG TCT CCA GGC AGT GGC AGT GCT GGA AGC TTG AGT AGG CTC CAT    1294
Ile Val Ser Pro Gly Ser Gly Ser Ala Gly Ser Leu Ser Arg Leu His
                420                 425                 430

CCA GTC CCA GTC CCA GCA GAT TGG ATG AAC CGC ATG GAG GTG AAT GAG    1342
Pro Val Pro Val Pro Ala Asp Trp Met Asn Arg Met Glu Val Asn Glu
            435                 440                 445

ACC CAG TAC AAT GAG ATG TTT GGT ATG GTC CTG GCT CCA GCT GAG GGC    1390
Thr Gln Tyr Asn Glu Met Phe Gly Met Val Leu Ala Pro Ala Glu Gly
        450                 455                 460

ACC CAT CCT GGC ATA GCT CCC CAG AGC AGG CCA CCT GAA GGG AAG CAC    1438
Thr His Pro Gly Ile Ala Pro Gln Ser Arg Pro Pro Glu Gly Lys His
    465                 470                 475

ATA ACC ACC CCT CGG GAG CCC TTG CCC CCC ATT GTG ACT TTC CAG CTC    1486
Ile Thr Thr Pro Arg Glu Pro Leu Pro Pro Ile Val Thr Phe Gln Leu
480                 485                 490                 495

ATC CCT AAA GGC AGT ATT GCC CAA CCA GCG GGG GCT CCC CAG CCT CAG    1534
Ile Pro Lys Gly Ser Ile Ala Gln Pro Ala Gly Ala Pro Gln Pro Gln
                500                 505                 510

TCC ACC TGC CCT CCA GCT GTT GCG GGC CCC CTG CCC ACC ATG TAC CAG    1582
Ser Thr Cys Pro Pro Ala Val Ala Gly Pro Leu Pro Thr Met Tyr Gln
            515                 520                 525

ATT CCA GAA ATG GCC CGT TTG CCC AGT GTG GCT TTC CCC ACT GCC ATG    1630
Ile Pro Glu Met Ala Arg Leu Pro Ser Val Ala Phe Pro Thr Ala Met
        530                 535                 540

ATG CCC CAG CAG GAC GGG CAG GTA GCT CAG ACC ATT CTC CCA GCC TAT    1678
Met Pro Gln Gln Asp Gly Gln Val Ala Gln Thr Ile Leu Pro Ala Tyr
    545                 550                 555

CAT CCT TTC CCA GCC TCT GTG GGC AAG TAC CCC ACA CCC CCT TCA CAG    1726
His Pro Phe Pro Ala Ser Val Gly Lys Tyr Pro Thr Pro Pro Ser Gln
560                 565                 570                 575

CAC AGT TAT GCT TCC TCA AAT GCT GCT GAG CGA ACA CCC AGT CAC AGT    1774
His Ser Tyr Ala Ser Ser Asn Ala Ala Glu Arg Thr Pro Ser His Ser
                580                 585                 590

GGT CAC CTC CAG GGT GAG CAT CCC TAC CTG ACA CCA TCC CCA GAG TCT    1822
Gly His Leu Gln Gly Glu His Pro Tyr Leu Thr Pro Ser Pro Glu Ser
            595                 600                 605

CCT GAC CAG TGG TCA AGT TCA TCA CCC CAC TCT GCT TCT GAC TGG TCA    1870
Pro Asp Gln Trp Ser Ser Ser Ser Pro His Ser Ala Ser Asp Trp Ser
        610                 615                 620
```

-continued

| | |
|---|---|
| GAT GTG ACC ACC AGC CCT ACC CCT GGG GGT GCT GGA GGA GGT CAG CGG<br>Asp Val Thr Thr Ser Pro Thr Pro Gly Gly Ala Gly Gly Gly Gln Arg<br>625                            630                      635 | 1918 |
| GGA CCT GGG ACA CAC ATG TCT GAG CCA CCA CAC AAC AAC ATG CAG GTT<br>Gly Pro Gly Thr His Met Ser Glu Pro Pro His Asn Asn Met Gln Val<br>640                            645                      650                      655 | 1966 |
| TAT GCG TGAGAGAGTC CACCTCCAGT GTAGAGACAT AACTGACTTT TGTAAATGCT<br>Tyr Ala | 2022 |
| GCTGAGGAAC AAATGAAGGT CATCCGGGAG AGAAATGAAG AAATCTCTGG AGCCAGCTTC | 2082 |
| TAGAGGTAGG AAAGAGAAGA TGTTCTTATT CAGATAATGC AAGAGAAGCA ATTCGTCAGT | 2142 |
| TTCACTGGGT ATCTGCAAGG CTTATTGATT ATTCTAATCT AATAAGACAA GTTTGTGGAA | 2202 |
| ATGCAAGATG AATACAAGCC TTGGGTCCAT GTTTACTCTC TTCTATTTGG AGAATAAGAT | 2262 |
| GGATGCTTAT TGAAGCCCAG ACATTCTTGC AGCTTGGACT GCATTTTAAG CCCTGCAGGC | 2322 |
| TTCTGCCATA TCCATGAGAA GATTCTACAC TAGCGTCCTG TTGGGAATTA TGCCCTGGAA | 2382 |
| TTCTGCCTGA ATTGACCTAC GCATCTCCTC CTCCTTGGAC ATTCTTTTGT CTTCATTTGG | 2442 |
| TGCTTTTGGT TTTGCACCTC TCCGTGATTG TAGCCCTACC AGCATGTTAT AGGGCAAGAC | 2502 |
| CTTTGTGCTT TTGATCATTC TGGCCCATGA AAGCAACTTT GGTCTCCTTT CCCCTCCTGT | 2562 |
| CTTCCCGGTA TCCCTTGGAG TCTCACAAGG TTTACTTTGG TATGGTTCTC AGCACAAACC | 2622 |
| TTTCAAGTAT GTTGTTTCTT TGGAAAATGG ACATACTGTA TTGTGTTCTC CTGCATATAT | 2682 |
| CATTCCTGGA GAGAGAAGGG GAGAAGAATA CTTTTCTTCA ACAAATTTTG GGGGCAGGAG | 2742 |
| ATCCCTTCAA GAGGCTGCAC CTTAATTTTT CTTGTCTGTG TGCAGGTCTT CATATAAACT | 2802 |
| TTACCAGGAA GAAGGGTGTG AGTTTGTTGT TTTTCTGTGT ATGGGCCTGG TCAGTGTAAA | 2862 |
| GTTTTATCCT TGATAGTCTA GTTACTATGA CCCTCCCCAC TTTTTTAAAA CCAGAAAAAG | 2922 |
| GTTTGGAATG TTGGAATGAC CAAGAGACAA GTTAACTCGT GCAAGAGCCA GTTACCCACC | 2982 |
| CACAGGTCCC CCTACTTCCT GCCAAGCATT CCATTGACTG CCTGTATGGA ACACATTTGT | 3042 |
| CCCAGATCTG AGCATTCTAG GCCTGTTTCA CTCACTCACC CAGCATATGA AACTAGTCTT | 3102 |
| AACTGTTGAG CCTTTCCTTT CATATCCACA GAAGACACTG TCTCAAATGT TGTACCCTTG | 3162 |
| CCATTTAGGA CTGAACTTTC CTTAGCCCAA GGGACCCAGT GACAGTTGTC TTCCGTTTGT | 3222 |
| CAGATGATCA GTCTCTACTG ATTATCTTGC TGCTTAAAGG CCTGCTCACC AATCTTTCTT | 3282 |
| TCACACCGTG TGGTCCGTGT TACTGGTATA CCCAGTATGT TCTCACTGAA GACATGGACT | 3342 |
| TTATATGTTC AAGTGCAGGA ATTGGAAAGT TGGACTTGTT TTCTATGATC CAAAACAGCC | 3402 |
| CTATAAGAAG GTTGGAAAAG GAGGAACTAT ATAGCAGCCT TTGCTATTTT CTGCTACCAT | 3462 |
| TTCTTTTCCT CTGAAGCGGC CATGACATTC CCTTTGGCAA CTAACGTAGA AACTCAACAG | 3522 |
| AACATTTTCC TTTCCTAGAG TCACCTTTTA GATGATAATG GACAACTATA GACTTGCTCA | 3582 |
| TTGTTCAGAC TGATTGCCCC TCACCTGAAT CCACTCTCTG TATTCATGCT CTTGGCAATT | 3642 |
| TCTTTGACTT TCTTTTAAGG GCAGAAGCAT TTTAGTTAAT TGTAGATAAA GAATAGTTTT | 3702 |
| CTTCCTCTTC TCCTTGGGCC AGTTAATAAT TGGTCCATGG CTACACTGCA ACTTCCGTCC | 3762 |
| AGTGCTGTGA TGCCCATGAC ACCTGCAAAA TAAGTTCTGC CTGGGCATTT TGTAGATATT | 3822 |
| AACAGGTGAA TTCCCGACTC TTTTGGTTTG AATGACAGTT CTCATTCCTT CTATGGCTGC | 3882 |
| AAGTATGCAT CAGTGCTTCC CACTTACCTG ATTTGTCTGT CGGTGGCCCC ATATGGAAAC | 3942 |
| CCTGCGTGTC TGTTGGCATA ATAGTTTACA AATGGTTTTT TCAGTCCTAT CCAAATTTAT | 4002 |
| TGAACCAACA AAAATAATTA CTTCTGCCCT GAGATAAGCA GATTAAGTTT GTTCATTCTC | 4062 |

```
TGCTTTATTC TCTCCATGTG GCAACATTCT GTCAGCCTCT TTCATAGTGT GCAAACATTT    4122

TATCATTCTA AATGGTGACT CTCTGCCCTT GGACCCATTT ATTATTCACA GATGGGAGA    4182

ACCTATCTGC ATGGACCCTC ACCATCCTCT GTGCAGCACA CACAGTGCAG GGAGCCAGTG   4242

GCGATGGCGA TGACTTTCTT CCCCTG                                        4268
```

(2) INFORMATION FOR SEQ ID NO:13:

(i) SEQUENCE CHARACTERISTICS:
        (A) LENGTH: 657 amino acids
        (B) TYPE: amino acid
        (D) TOPOLOGY: unknown (ii) MOLECULE TYPE: protein (xi) SEQUENCE DESCRIPTION: SEQ ID NO:13:

```
Glu Val Asp Val Leu Asp Val Asn Val Arg Gly Pro Asp Gly Cys Thr
 1               5                  10                  15

Pro Leu Met Leu Ala Ser Leu Arg Gly Gly Ser Ser Asp Leu Ser Asp
             20                  25                  30

Glu Asp Glu Asp Ala Glu Asp Ser Ser Ala Asn Ile Ile Thr Asp Leu
         35                  40                  45

Val Tyr Gln Gly Ala Ser Leu Gln Ala Gln Thr Asp Arg Thr Gly Glu
     50                  55                  60

Met Ala Leu His Leu Ala Ala Arg Tyr Ser Arg Ala Asp Ala Ala Lys
 65                  70                  75                  80

Arg Leu Leu Asp Ala Gly Ala Asp Ala Asn Ala Gln Asp Asn Met Gly
                 85                  90                  95

Arg Cys Pro Leu His Ala Ala Val Ala Ala Asp Ala Gln Gly Val Phe
            100                 105                 110

Gln Ile Leu Ile Arg Asn Arg Val Thr Asp Leu Asp Ala Arg Met Asn
        115                 120                 125

Asp Gly Thr Thr Pro Leu Ile Leu Ala Ala Arg Leu Ala Val Glu Gly
    130                 135                 140

Met Val Ala Glu Leu Ile Asn Cys Gln Ala Asp Val Asn Ala Val Asp
145                 150                 155                 160

Asp His Gly Lys Ser Ala Leu His Trp Ala Ala Ala Val Asn Asn Val
                165                 170                 175

Glu Ala Thr Leu Leu Leu Leu Lys Asn Gly Ala Asn Arg Asp Met Gln
            180                 185                 190

Asp Asn Lys Glu Glu Thr Pro Leu Phe Leu Ala Ala Arg Glu Gly Ser
        195                 200                 205

Tyr Glu Ala Ala Lys Ile Leu Leu Asp His Phe Ala Asn Arg Asp Ile
    210                 215                 220

Thr Asp His Met Asp Arg Leu Pro Arg Asp Val Ala Arg Asp Arg Met
225                 230                 235                 240

His His Asp Ile Val Arg Leu Leu Asp Glu Tyr Asn Val Thr Pro Ser
                245                 250                 255

Pro Pro Gly Thr Val Leu Thr Ser Ala Leu Ser Pro Val Ile Cys Gly
            260                 265                 270

Pro Asn Arg Ser Phe Leu Ser Leu Lys His Thr Pro Met Gly Lys Lys
        275                 280                 285

Ser Arg Arg Pro Ser Ala Lys Ser Thr Met Pro Thr Ser Leu Pro Asn
    290                 295                 300

Leu Ala Lys Glu Ala Lys Asp Ala Lys Gly Ser Arg Arg Lys Lys Ser
305                 310                 315                 320
```

Leu Ser Glu Lys Val Gln Leu Ser Glu Ser Ser Val Thr Leu Ser Pro
            325                 330                 335

Val Asp Ser Leu Glu Ser Pro His Thr Tyr Val Ser Asp Thr Thr Ser
            340                 345                 350

Ser Pro Met Ile Thr Ser Pro Gly Ile Leu Gln Ala Ser Pro Asn Pro
            355                 360                 365

Met Leu Ala Thr Ala Ala Pro Pro Ala Pro Val His Ala Gln His Ala
            370                 375                 380

Leu Ser Phe Ser Asn Leu His Glu Met Gln Pro Leu Ala His Gly Ala
385                 390                 395                 400

Ser Thr Val Leu Pro Ser Val Ser Gln Leu Leu Ser His His His Ile
            405                 410                 415

Val Ser Pro Gly Ser Gly Ser Ala Gly Ser Leu Ser Arg Leu His Pro
            420                 425                 430

Val Pro Val Pro Ala Asp Trp Met Asn Arg Met Glu Val Asn Glu Thr
            435                 440                 445

Gln Tyr Asn Glu Met Phe Gly Met Val Leu Ala Pro Ala Glu Gly Thr
            450                 455                 460

His Pro Gly Ile Ala Pro Gln Ser Arg Pro Pro Glu Gly Lys His Ile
465                 470                 475                 480

Thr Thr Pro Arg Glu Pro Leu Pro Pro Ile Val Thr Phe Gln Leu Ile
            485                 490                 495

Pro Lys Gly Ser Ile Ala Gln Pro Ala Gly Ala Pro Gln Pro Gln Ser
            500                 505                 510

Thr Cys Pro Pro Ala Val Ala Gly Pro Leu Pro Thr Met Tyr Gln Ile
            515                 520                 525

Pro Glu Met Ala Arg Leu Pro Ser Val Ala Phe Pro Thr Ala Met Met
            530                 535                 540

Pro Gln Gln Asp Gly Gln Val Ala Gln Thr Ile Leu Pro Ala Tyr His
545                 550                 555                 560

Pro Phe Pro Ala Ser Val Gly Lys Tyr Pro Thr Pro Pro Ser Gln His
            565                 570                 575

Ser Tyr Ala Ser Ser Asn Ala Ala Glu Arg Thr Pro Ser His Ser Gly
            580                 585                 590

His Leu Gln Gly Glu His Pro Tyr Leu Thr Pro Ser Pro Glu Ser Pro
            595                 600                 605

Asp Gln Trp Ser Ser Ser Pro His Ser Ala Ser Asp Trp Ser Asp
            610                 615                 620

Val Thr Thr Ser Pro Thr Pro Gly Gly Ala Gly Gly Gly Gln Arg Gly
625                 630                 635                 640

Pro Gly Thr His Met Ser Glu Pro Pro His Asn Asn Met Gln Val Tyr
            645                 650                 655

Ala (2) INFORMATION FOR SEQ ID NO:14:

(i) SEQUENCE CHARACTERISTICS:
       (A) LENGTH: 77 amino acids
       (B) TYPE: amino acid
       (C) STRANDEDNESS: single
       (D) TOPOLOGY: unknown (ii) MOLECULE TYPE: peptide (xi) SEQUENCE DESCRIPTION: SEQ ID NO:14:

```
Glu Asp Ile Asp Glu Cys Asp Gln Gly Ser Pro Cys Glu His Asn Gly
1               5                  10                 15

Ile Cys Val Asn Thr Pro Gly Ser Tyr Arg Cys Asn Cys Ser Gln Gly
            20                  25                  30

Phe Thr Gly Pro Arg Cys Glu Thr Asn Ile Asn Glu Cys Glu Ser His
        35                  40                  45

Pro Cys Gln Asn Glu Gly Ser Cys Leu Asp Asp Pro Gly Thr Phe Arg
    50                  55                  60

Cys Val Cys Met Pro Gly Phe Thr Gly Thr Gln Cys Glu
65                  70                  75
```

(2) INFORMATION FOR SEQ ID NO:15:

(i) SEQUENCE CHARACTERISTICS:
        (A) LENGTH: 78 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:15:

```
Asn Asp Val Asp Glu Cys Ser Leu Gly Ala Asn Pro Cys Glu His Gly
1               5                  10                 15

Gly Arg Cys Thr Asn Thr Leu Gly Ser Phe Gln Cys Asn Cys Pro Gln
            20                  25                  30

Gly Tyr Ala Gly Pro Arg Cys Glu Ile Asp Val Asn Glu Cys Leu Ser
        35                  40                  45

Asn Pro Cys Gln Asn Asp Ser Thr Cys Leu Asp Gln Ile Gly Glu Phe
    50                  55                  60

Gln Cys Ile Cys Met Pro Gly Tyr Glu Gly Leu Tyr Cys Glu
65                  70                  75
```

(2) INFORMATION FOR SEQ ID NO:16:

(i) SEQUENCE CHARACTERISTICS:
        (A) LENGTH: 654 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:16:

```
Thr Pro Pro Gln Gly Glu Ile Glu Ala Asp Cys Met Asp Val Asn Val
1               5                  10                 15

Arg Gly Pro Asp Gly Phe Thr Pro Leu Met Ile Ala Ser Cys Ser Gly
            20                  25                  30

Gly Gly Leu Glu Thr Gly Asn Ser Glu Glu Glu Glu Asp Ala Ser Ala
        35                  40                  45

Asn Met Ile Ser Asp Phe Ile Gly Gln Gly Ala Gln Leu His Asn Gln
    50                  55                  60

Thr Asp Arg Thr Gly Glu Thr Ala Leu His Leu Ala Ala Arg Tyr Ala
65                  70                  75                  80

Arg Ala Asp Ala Ala Lys Arg Leu Leu Glu Ser Ser Ala Asp Ala Asn
            85                  90                  95

Val Gln Asp Asn Met Gly Arg Thr Pro Leu His Ala Ala Val Ala Ala
            100                 105                 110

Asp Ala Gln Gly Val Phe Gln Ile Leu Ile Arg Asn Arg Ala Thr Asp
        115                 120                 125
```

```
Leu Asp Ala Arg Met Phe Asp Gly Thr Thr Pro Leu Ile Leu Ala Ala
    130                 135                 140

Arg Leu Ala Val Glu Gly Met Val Glu Glu Leu Ile Asn Ala His Ala
145                 150                 155                 160

Asp Val Asn Ala Val Asp Glu Phe Gly Lys Ser Ala Leu His Trp Ala
                165                 170                 175

Ala Ala Val Asn Asn Val Asp Ala Ala Ala Val Leu Leu Lys Asn Ser
            180                 185                 190

Ala Asn Lys Asp Met Gln Asn Asn Lys Glu Glu Thr Ser Leu Phe Leu
        195                 200                 205

Ala Ala Arg Glu Gly Ser Tyr Glu Thr Ala Lys Val Leu Leu Asp His
    210                 215                 220

Tyr Ala Asn Arg Asp Ile Thr Asp His Met Asp Arg Leu Pro Arg Asp
225                 230                 235                 240

Ile Ala Gln Glu Arg Met His His Asp Ile Val His Leu Leu Asp Glu
                245                 250                 255

Tyr Asn Leu Val Lys Ser Pro Thr Leu His Asn Gly Pro Leu Gly Ala
            260                 265                 270

Thr Thr Leu Ser Pro Pro Ile Cys Ser Pro Asn Gly Tyr Met Gly Asn
        275                 280                 285

Met Lys Pro Ser Val Gln Ser Lys Lys Ala Arg Lys Pro Ser Ile Lys
    290                 295                 300

Gly Asn Gly Cys Lys Glu Ala Lys Glu Leu Lys Ala Arg Arg Lys Lys
305                 310                 315                 320

Ser Gln Asp Gly Lys Thr Thr Leu Leu Asp Ser Gly Ser Ser Gly Val
                325                 330                 335

Leu Ser Pro Val Asp Ser Leu Glu Ser Thr His Gly Tyr Leu Ser Asp
            340                 345                 350

Val Ser Ser Pro Pro Leu Met Thr Ser Pro Phe Gln Gln Ser Pro Ser
        355                 360                 365

Met Pro Leu Asn His Leu Thr Ser Met Pro Glu Ser Gln Leu Gly Met
    370                 375                 380

Asn His Ile Asn Met Ala Thr Lys Gln Glu Met Ala Ala Gly Ser Asn
385                 390                 395                 400

Arg Met Ala Phe Asp Ala Met Val Pro Arg Leu Thr His Leu Asn Ala
                405                 410                 415

Ser Ser Pro Asn Thr Ile Met Ser Asn Gly Ser Met His Phe Thr Val
            420                 425                 430

Gly Gly Ala Pro Thr Met Asn Ser Gln Cys Asp Trp Leu Ala Arg Leu
        435                 440                 445

Gln Asn Gly Met Val Gln Asn Gln Tyr Asp Pro Ile Arg Asn Gly Ile
    450                 455                 460

Gln Gln Gly Asn Ala Gln Gln Ala Gln Ala Leu Gln His Gly Leu Met
465                 470                 475                 480

Thr Ser Leu His Asn Gly Leu Pro Ala Thr Thr Leu Ser Gln Met Met
                485                 490                 495

Thr Tyr Gln Ala Met Pro Asn Thr Arg Leu Ala Asn Gln Pro His Leu
            500                 505                 510

Met Gln Ala Gln Gln Met Gln Gln Gln Asn Leu Gln Leu His Gln
        515                 520                 525

Ser Met Gln Gln Gln His His Asn Ser Ser Thr Thr Ser Thr His Ile
    530                 535                 540
```

```
Asn Ser Pro Phe Cys Ser Ser Asp Ile Ser Gln Thr Asp Leu Gln Gln
545                 550                 555                 560

Met Ser Ser Asn Asn Ile His Ser Val Met Pro Gln Asp Thr Gln Ile
                565                 570                 575

Phe Ala Ala Ser Leu Pro Ser Asn Leu Thr Gln Ser Met Thr Thr Ala
            580                 585                 590

Gln Phe Leu Thr Pro Pro Ser Gln His Ser Tyr Ser Ser Pro Met Asp
        595                 600                 605

Asn Thr Pro Ser His Gln Leu Gln Val Pro Asp His Pro Phe Leu Thr
    610                 615                 620

Pro Ser Pro Glu Ser Pro Asp Gln Trp Ser Ser Ser Pro His Ser
625                 630                 635                 640

Asn Met Ser Asp Trp Ser Glu Gly Ile Ser Ser Pro Pro Thr
                645                 650
```

(2) INFORMATION FOR SEQ ID NO:17:

(i) SEQUENCE CHARACTERISTICS:
        (A) LENGTH: 666 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:17:

```
Thr Pro Pro Gln Gly Glu Val Asp Ala Asp Cys Met Asp Val Asn Val
1               5                   10                  15

Arg Gly Pro Asp Gly Phe Thr Pro Leu Met Ile Ala Ser Cys Ser Gly
                20                  25                  30

Gly Gly Leu Glu Thr Gly Asn Ser Glu Glu Glu Glu Asp Ala Pro Ala
            35                  40                  45

Val Ile Ser Asp Phe Ile Tyr Gln Gly Ala Ser Leu His Asn Gln Thr
    50                  55                  60

Asp Arg Thr Gly Glu Thr Ala Leu His Leu Ala Ala Arg Tyr Ser Arg
65                  70                  75                  80

Ser Asp Ala Ala Lys Arg Leu Leu Glu Ala Ser Ala Asp Ala Asn Ile
                85                  90                  95

Gln Asp Asn Met Gly Arg Thr Pro Leu His Ala Ala Val Ser Ala Asp
                100                 105                 110

Ala Gln Gly Val Phe Gln Ile Leu Leu Arg Asn Arg Ala Thr Asp Leu
            115                 120                 125

Asp Ala Arg Met His Asp Gly Thr Thr Pro Leu Ile Leu Ala Ala Arg
130                 135                 140

Leu Ala Val Glu Gly Met Leu Glu Asp Leu Ile Asn Ser His Ala Asp
145                 150                 155                 160

Val Asn Ala Val Asp Asp Leu Gly Lys Ser Ala Leu His Trp Ala Ala
                165                 170                 175

Ala Val Asn Asn Val Asp Ala Ala Val Val Leu Leu Lys Asn Gly Ala
                180                 185                 190

Asn Lys Asp Met Gln Asn Asn Lys Glu Glu Thr Pro Leu Phe Leu Ala
            195                 200                 205

Ala Arg Glu Gly Ser Tyr Glu Thr Ala Lys Val Leu Leu Asp His Phe
        210                 215                 220

Ala Asn Arg Asp Ile Thr Asp His Met Asp Arg Leu Pro Arg Asp Ile
225                 230                 235                 240
```

-continued

```
Ala Gln Glu Arg Met His His Asp Ile Val Arg Leu Leu Asp Glu Tyr
                245                 250                 255

Asn Leu Val Arg Ser Pro Gln Leu His Gly Thr Ala Leu Gly Gly Thr
            260                 265                 270

Pro Thr Leu Ser Pro Thr Leu Cys Ser Pro Asn Gly Tyr Leu Gly Asn
        275                 280                 285

Leu Lys Ser Ala Thr Gln Gly Lys Lys Ala Arg Lys Pro Ser Thr Lys
    290                 295                 300

Gly Leu Ala Cys Ser Ser Lys Glu Ala Lys Asp Leu Lys Ala Arg Arg
305                 310                 315                 320

Lys Lys Ser Gln Asp Gly Lys Gly Cys Leu Leu Asp Ser Ser Met
                325                 330                 335

Leu Ser Pro Val Asp Ser Leu Glu Ser Pro His Gly Tyr Leu Ser Asp
            340                 345                 350

Val Ala Ser Pro Pro Leu Pro Ser Pro Phe Gln Gln Ser Pro Ser Met
        355                 360                 365

Pro Leu Ser His Leu Pro Gly Met Pro Asp Thr His Leu Gly Ile Ser
    370                 375                 380

His Leu Asn Val Ala Ala Lys Pro Glu Met Ala Ala Leu Ala Gly Gly
385                 390                 395                 400

Ser Arg Leu Ala Phe Glu Pro Pro Pro Arg Leu Ser His Leu Pro
                405                 410                 415

Val Ala Ser Ser Ala Ser Thr Val Leu Ser Thr Asn Gly Thr Gly Ala
            420                 425                 430

Met Asn Phe Thr Val Gly Ala Pro Ala Ser Leu Asn Gly Gln Cys Glu
        435                 440                 445

Trp Leu Pro Arg Leu Gln Asn Gly Met Val Pro Ser Gln Tyr Asn Pro
    450                 455                 460

Leu Arg Pro Gly Val Thr Pro Gly Thr Leu Ser Thr Gln Ala Ala Gly
465                 470                 475                 480

Leu Gln His Gly Met Met Ser Pro Ile His Ser Ser Leu Ser Thr Asn
                485                 490                 495

Thr Leu Ser Pro Ile Ile Tyr Gln Gly Leu Pro Asn Thr Arg Leu Ala
            500                 505                 510

Thr Gln Pro His Leu Val Gln Thr Gln Gln Val Gln Pro Gln Asn Leu
        515                 520                 525

Gln Ile Gln Pro Gln Asn Leu Gln Pro Pro Ser Gln Pro His Leu Ser
    530                 535                 540

Val Ser Ser Ala Ala Asn Gly His Leu Gly Arg Ser Phe Leu Ser Gly
545                 550                 555                 560

Glu Pro Ser Gln Ala Asp Val Gln Pro Leu Gly Pro Ser Ser Leu Pro
                565                 570                 575

Val His Thr Ile Leu Pro Gln Gly Ser Gln Ala Leu Pro Thr Ser Leu
            580                 585                 590

Pro Ser Ser Met Val Pro Pro Met Thr Thr Thr Gln Phe Leu Thr Pro
        595                 600                 605

Pro Ser Gln His Ser Tyr Ser Ser Pro Val Asp Asn Thr Pro Ser
    610                 615                 620

His Gln Leu Gln Val Pro Glu His Pro Phe Leu Thr Pro Ser Pro Glu
625                 630                 635                 640

Ser Pro Asp Gln Trp Ser Ser Ser Arg His Ser Asn Ile Ser Asp
                645                 650                 655

Trp Ser Glu Gly Ile Ser Ser Pro Pro Thr
```

660                 665

(2) INFORMATION FOR SEQ ID NO:18:

(i) SEQUENCE CHARACTERISTICS:
        (A) LENGTH: 681 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:18:

Thr Pro Pro Gln Gly Glu Val Asp Ala Asp Cys Met Asp Val Asn Val
 1               5                  10                  15

Arg Gly Pro Asp Gly Phe Thr Pro Leu Met Ile Ala Ser Cys Ser Gly
            20                  25                  30

Gly Gly Leu Glu Thr Gly Asn Ser Glu Glu Glu Asp Ala Pro Ala
        35                  40                  45

Val Ile Ser Asp Phe Ile Tyr Gln Gly Ala Ser Leu His Asn Gln Thr
50                  55                  60

Asp Arg Thr Gly Glu Thr Ala Leu His Leu Ala Ala Arg Tyr Ser Arg
65                  70                  75                  80

Ser Asp Ala Ala Lys Arg Leu Leu Glu Ala Ser Ala Asp Ala Asn Ile
                85                  90                  95

Gln Asp Asn Met Gly Arg Thr Pro Leu His Ala Ala Val Ser Ala Asp
            100                 105                 110

Ala Gln Gly Val Phe Gln Ile Leu Ile Arg Asn Arg Ala Thr Asp Leu
        115                 120                 125

Asp Ala Arg Met His Asp Gly Thr Thr Pro Leu Ile Leu Ala Ala Arg
130                 135                 140

Leu Ala Val Glu Gly Met Leu Glu Asp Leu Ile Asn Ser His Ala Asp
145                 150                 155                 160

Val Asn Ala Val Asp Asp Leu Gly Lys Ser Ala Leu His Trp Ala Ala
                165                 170                 175

Ala Val Asn Asn Val Asp Ala Ala Val Val Leu Leu Lys Asn Gly Ala
            180                 185                 190

Asn Lys Asp Met Gln Asn Asn Arg Glu Glu Thr Pro Leu Phe Leu Ala
        195                 200                 205

Ala Arg Glu Gly Ser Tyr Glu Thr Ala Lys Val Leu Leu Asp His Phe
210                 215                 220

Ala Asn Arg Asp Ile Thr Asp His Met Asp Arg Leu Pro Arg Asp Ile
225                 230                 235                 240

Ala Gln Glu Arg Met His His Asp Ile Val Arg Leu Leu Asp Glu Tyr
                245                 250                 255

Asn Leu Val Arg Ser Pro Gln Leu His Gly Ala Pro Leu Gly Gly Thr
            260                 265                 270

Pro Thr Leu Ser Pro Pro Leu Cys Ser Pro Asn Gly Tyr Leu Gly Ser
        275                 280                 285

Leu Lys Pro Gly Val Gln Gly Lys Lys Val Arg Lys Pro Ser Ser Lys
290                 295                 300

Gly Leu Ala Cys Gly Ser Lys Glu Ala Lys Asp Leu Lys Ala Arg Arg
305                 310                 315                 320

Lys Lys Ser Gln Asp Gly Lys Gly Cys Leu Leu Asp Ser Ser Gly Met
                325                 330                 335

Leu Ser Pro Val Asp Ser Leu Glu Ser Pro His Gly Tyr Leu Ser Asp

```
                    340                 345                 350
Val Ala Ser Pro Pro Leu Leu Pro Ser Pro Phe Gln Gln Ser Pro Ser
                355                 360                 365
Val Pro Leu Asn His Leu Pro Gly Met Pro Asp Thr His Leu Gly Ile
370                 375                 380
Gly His Leu Asn Val Ala Ala Lys Pro Glu Met Ala Ala Leu Gly Gly
385                 390                 395                 400
Gly Gly Arg Leu Ala Phe Glu Thr Gly Pro Pro Arg Leu Ser His Leu
                405                 410                 415
Pro Val Ala Ser Gly Thr Ser Thr Val Leu Gly Ser Ser Gly Gly
                420                 425                 430
Ala Leu Asn Phe Thr Val Gly Gly Ser Thr Ser Leu Asn Gly Gln Cys
                435                 440                 445
Glu Trp Leu Ser Arg Leu Gln Ser Gly Met Val Pro Asn Gln Tyr Asn
                450                 455                 460
Pro Leu Arg Gly Ser Val Ala Pro Gly Pro Leu Ser Thr Gln Ala Pro
465                 470                 475                 480
Ser Leu Gln His Gly Met Val Gly Pro Leu His Ser Ser Leu Ala Ala
                485                 490                 495
Ser Ala Leu Ser Gln Met Met Ser Tyr Gln Gly Leu Pro Ser Thr Arg
                500                 505                 510
Leu Ala Thr Gln Pro His Leu Val Gln Thr Gln Gln Val Gln Pro Gln
                515                 520                 525
Asn Leu Gln Met Gln Gln Asn Leu Gln Pro Ala Asn Ile Gln Gln
                530                 535                 540
Gln Gln Ser Leu Gln Pro Pro Pro Pro Gln Pro His Leu Gly
545                 550                 555                 560
Val Ser Ser Ala Ala Ser Gly His Leu Gly Arg Ser Phe Leu Ser Gly
                565                 570                 575
Glu Pro Ser Gln Ala Asp Val Gln Pro Leu Gly Pro Ser Ser Leu Ala
                580                 585                 590
Val His Thr Ile Leu Pro Gln Glu Ser Pro Ala Leu Pro Thr Ser Leu
                595                 600                 605
Pro Ser Ser Leu Val Pro Pro Val Thr Ala Ala Gln Phe Leu Thr Pro
610                 615                 620
Pro Ser Gln His Ser Tyr Ser Ser Pro Val Glu Asn Thr Pro Ser His
625                 630                 635                 640
Gln Leu Gln Val Pro Glu His Pro Phe Leu Thr Pro Ser Pro Glu Ser
                645                 650                 655
Pro Asp Gln Trp Ser Ser Ser Ser Pro His Ser Asn Val Ser Asp Trp
                660                 665                 670
Ser Glu Gly Val Ser Ser Pro Pro Thr
                675                 680

(2) INFORMATION FOR SEQ ID NO:19:

(i) SEQUENCE CHARACTERISTICS:
        (A) LENGTH: 2471 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:19:

Met Pro Ala Leu Arg Pro Ala Leu Leu Trp Ala Leu Leu Ala Leu Trp
```

-continued

```
1               5               10              15
Leu Cys Cys Ala Ala Pro Ala His Ala Leu Gln Cys Arg Asp Gly Tyr
                20              25              30
Glu Pro Cys Val Asn Glu Gly Met Cys Val Thr Tyr His Asn Gly Thr
        35              40              45
Gly Tyr Cys Lys Cys Pro Glu Gly Phe Leu Gly Glu Tyr Cys Gln His
        50              55              60
Arg Asp Pro Cys Glu Lys Asn Arg Cys Gln Asn Gly Gly Thr Cys Val
65              70              75              80
Ala Gln Ala Met Leu Gly Lys Ala Thr Cys Arg Cys Ala Ser Gly Phe
                85              90              95
Thr Gly Glu Asp Cys Gln Tyr Ser Thr Ser His Pro Cys Phe Val Ser
            100             105             110
Arg Pro Cys Leu Asn Gly Gly Thr Cys His Met Leu Ser Arg Asp Thr
            115             120             125
Tyr Glu Cys Thr Cys Gln Val Gly Phe Thr Gly Lys Glu Cys Gln Trp
        130             135             140
Thr Asp Ala Cys Leu Ser His Pro Cys Ala Asn Gly Ser Thr Cys Thr
145             150             155             160
Thr Val Ala Asn Gln Phe Ser Cys Lys Cys Leu Thr Gly Phe Thr Gly
                165             170             175
Gln Lys Cys Glu Thr Asp Val Asn Glu Cys Asp Ile Pro Gly His Cys
            180             185             190
Gln His Gly Gly Thr Cys Leu Asn Leu Pro Gly Ser Tyr Gln Cys Gln
        195             200             205
Cys Pro Gln Gly Phe Thr Gly Gln Tyr Cys Asp Ser Leu Tyr Val Pro
    210             215             220
Cys Ala Pro Ser Pro Cys Val Asn Gly Gly Thr Cys Arg Gln Thr Gly
225             230             235             240
Asp Phe Thr Phe Glu Cys Asn Cys Leu Pro Gly Phe Glu Gly Ser Thr
                245             250             255
Cys Glu Arg Asn Ile Asp Asp Cys Pro Asn His Arg Cys Gln Asn Gly
            260             265             270
Gly Val Cys Val Asp Gly Val Asn Thr Tyr Asn Cys Arg Cys Pro Pro
        275             280             285
Gln Trp Thr Gly Gln Phe Cys Thr Glu Asp Val Asp Glu Cys Leu Leu
    290             295             300
Gln Pro Asn Ala Cys Gln Asn Gly Gly Thr Cys Ala Asn Arg Asn Gly
305             310             315             320
Gly Tyr Gly Cys Val Cys Val Asn Gly Trp Ser Gly Asp Asp Cys Ser
                325             330             335
Glu Asn Ile Asp Asp Cys Ala Phe Ala Ser Cys Thr Pro Gly Ser Thr
            340             345             350
Cys Ile Asp Arg Val Ala Ser Phe Ser Cys Met Cys Pro Glu Gly Lys
        355             360             365
Ala Gly Leu Leu Cys His Leu Asp Asp Ala Cys Ile Ser Asn Pro Cys
    370             375             380
His Lys Gly Ala Leu Cys Asp Thr Asn Pro Leu Asn Gly Gln Tyr Ile
385             390             395             400
Cys Thr Cys Pro Gln Gly Tyr Lys Gly Ala Asp Cys Thr Glu Asp Val
                405             410             415
Asp Glu Cys Ala Met Ala Asn Ser Asn Pro Cys Glu His Ala Gly Lys
            420             425             430
```

-continued

```
Cys Val Asn Thr Asp Gly Ala Phe His Cys Glu Cys Leu Lys Gly Tyr
         435                 440                 445

Ala Gly Pro Arg Cys Glu Met Asp Ile Asn Glu Cys His Ser Asp Pro
    450                 455                 460

Cys Gln Asn Asp Ala Thr Cys Leu Asp Lys Ile Gly Gly Phe Thr Cys
465                 470                 475                 480

Leu Cys Met Pro Gly Phe Lys Gly Val His Cys Glu Leu Glu Ile Asn
                485                 490                 495

Glu Cys Gln Ser Asn Pro Cys Val Asn Asn Gly Gln Cys Val Asp Lys
            500                 505                 510

Val Asn Arg Phe Gln Cys Leu Cys Pro Pro Gly Phe Thr Gly Pro Val
        515                 520                 525

Cys Gln Ile Asp Ile Asp Asp Cys Ser Ser Thr Pro Cys Leu Asn Gly
530                 535                 540

Ala Lys Cys Ile Asp His Pro Asn Gly Tyr Glu Cys Gln Cys Ala Thr
545                 550                 555                 560

Gly Phe Thr Gly Val Leu Cys Glu Glu Asn Ile Asp Asn Cys Asp Pro
                565                 570                 575

Asp Pro Cys His His Gly Gln Cys Gln Asp Gly Ile Asp Ser Tyr Thr
            580                 585                 590

Cys Ile Cys Asn Pro Gly Tyr Met Gly Ala Ile Cys Ser Asp Gln Ile
        595                 600                 605

Asp Glu Cys Tyr Ser Ser Pro Cys Leu Asn Asp Gly Arg Cys Ile Asp
    610                 615                 620

Leu Val Asn Gly Tyr Gln Cys Asn Cys Gln Pro Gly Thr Ser Gly Val
625                 630                 635                 640

Asn Cys Glu Ile Asn Phe Asp Asp Cys Ala Ser Asn Pro Cys Ile His
                645                 650                 655

Gly Ile Cys Met Asp Gly Ile Asn Arg Tyr Ser Cys Val Cys Ser Pro
            660                 665                 670

Gly Phe Thr Gly Gln Arg Cys Asn Ile Asp Ile Asp Glu Cys Ala Ser
        675                 680                 685

Asn Pro Cys Arg Lys Gly Ala Thr Cys Ile Asn Gly Val Asn Gly Phe
    690                 695                 700

Arg Cys Ile Cys Pro Glu Gly Pro His His Pro Ser Cys Tyr Ser Gln
705                 710                 715                 720

Val Asn Glu Cys Leu Ser Asn Pro Cys Ile His Gly Asn Cys Thr Gly
                725                 730                 735

Gly Leu Ser Gly Tyr Lys Cys Leu Cys Asp Ala Gly Trp Val Gly Ile
            740                 745                 750

Asn Cys Glu Val Asp Lys Asn Glu Cys Leu Ser Asn Pro Cys Gln Asn
        755                 760                 765

Gly Gly Thr Cys Asp Asn Leu Val Asn Gly Tyr Arg Cys Thr Cys Lys
    770                 775                 780

Lys Gly Phe Lys Gly Tyr Asn Cys Gln Val Asn Ile Asp Glu Cys Ala
785                 790                 795                 800

Ser Asn Pro Cys Leu Asn Gln Gly Thr Cys Phe Asp Asp Ile Ser Gly
                805                 810                 815

Tyr Thr Cys His Cys Val Leu Pro Tyr Thr Gly Lys Asn Cys Gln Thr
            820                 825                 830

Val Leu Ala Pro Cys Ser Pro Asn Pro Cys Glu Asn Ala Ala Val Cys
        835                 840                 845
```

-continued

```
Lys Glu Ser Pro Asn Phe Glu Ser Tyr Thr Cys Leu Cys Ala Pro Gly
    850                 855                 860

Trp Gln Gly Gln Arg Cys Thr Ile Asp Ile Asp Glu Cys Ile Ser Lys
865                 870                 875                 880

Pro Cys Met Asn His Gly Leu Cys His Asn Thr Gln Gly Ser Tyr Met
                885                 890                 895

Cys Glu Cys Pro Pro Gly Phe Ser Gly Met Asp Cys Glu Glu Asp Ile
            900                 905                 910

Asp Asp Cys Leu Ala Asn Pro Cys Gln Asn Gly Gly Ser Cys Met Asp
        915                 920                 925

Gly Val Asn Thr Phe Ser Cys Leu Cys Leu Pro Gly Phe Thr Gly Asp
    930                 935                 940

Lys Cys Gln Thr Asp Met Asn Glu Cys Leu Ser Glu Pro Cys Lys Asn
945                 950                 955                 960

Gly Gly Thr Cys Ser Asp Tyr Val Asn Ser Tyr Thr Cys Lys Cys Gln
                965                 970                 975

Ala Gly Phe Asp Gly Val His Cys Glu Asn Asn Ile Asn Glu Cys Thr
            980                 985                 990

Glu Ser Ser Cys Phe Asn Gly Gly Thr Cys Val Asp Gly Ile Asn Ser
        995                 1000                1005

Phe Ser Cys Leu Cys Pro Val Gly Phe Thr Gly Ser Phe Cys Leu His
    1010                1015                1020

Glu Ile Asn Glu Cys Ser Ser His Pro Cys Leu Asn Glu Gly Thr Cys
1025                1030                1035                1040

Val Asp Gly Leu Gly Thr Tyr Arg Cys Ser Cys Pro Leu Gly Tyr Thr
                1045                1050                1055

Gly Lys Asn Cys Gln Thr Leu Val Asn Leu Cys Ser Arg Ser Pro Cys
            1060                1065                1070

Lys Asn Lys Gly Thr Cys Val Gln Lys Lys Ala Glu Ser Gln Cys Leu
        1075                1080                1085

Cys Pro Ser Gly Trp Ala Gly Ala Tyr Cys Asp Val Pro Asn Val Ser
    1090                1095                1100

Cys Asp Ile Ala Ala Ser Arg Arg Gly Val Leu Val Glu His Leu Cys
1105                1110                1115                1120

Gln His Ser Gly Val Cys Ile Asn Ala Gly Asn Thr His Tyr Cys Gln
                1125                1130                1135

Cys Pro Leu Gly Tyr Thr Gly Ser Tyr Cys Glu Glu Gln Leu Asp Glu
            1140                1145                1150

Cys Ala Ser Asn Pro Cys Gln His Gly Ala Thr Cys Ser Asp Phe Ile
        1155                1160                1165

Gly Gly Tyr Arg Cys Glu Cys Val Pro Gly Tyr Gln Gly Val Asn Cys
    1170                1175                1180

Glu Tyr Glu Val Asp Glu Cys Gln Asn Gln Pro Cys Gln Asn Gly Gly
1185                1190                1195                1200

Thr Cys Ile Asp Leu Val Asn His Phe Lys Cys Ser Cys Pro Pro Gly
                1205                1210                1215

Thr Arg Gly Leu Leu Cys Glu Glu Asn Ile Asp Asp Cys Ala Arg Gly
            1220                1225                1230

Pro His Cys Leu Asn Gly Gly Gln Cys Met Asp Arg Ile Gly Gly Tyr
        1235                1240                1245

Ser Cys Arg Cys Leu Pro Gly Phe Ala Gly Glu Arg Cys Glu Gly Asp
    1250                1255                1260

Ile Asn Glu Cys Leu Ser Asn Pro Cys Ser Ser Glu Gly Ser Leu Asp
```

```
                  1265                1270                1275                1280

Cys Ile Gln Leu Thr Asn Asp Tyr Leu Cys Val Cys Arg Ser Ala Phe
                        1285                1290                1295

Thr Gly Arg His Cys Glu Thr Phe Val Asp Val Cys Pro Gln Met Pro
                    1300                1305                1310

Cys Leu Asn Gly Gly Thr Cys Ala Val Ala Ser Asn Met Pro Asp Gly
                    1315                1320                1325

Phe Ile Cys Arg Cys Pro Pro Gly Phe Ser Gly Ala Arg Cys Gln Ser
                    1330                1335                1340

Ser Cys Gly Gln Val Lys Cys Arg Lys Gly Glu Gln Cys Val His Thr
        1345                1350                1355                1360

Ala Ser Gly Pro Arg Cys Phe Cys Pro Ser Pro Arg Asp Cys Glu Ser
                        1365                1370                1375

Gly Cys Ala Ser Ser Pro Cys Gln His Gly Gly Ser Cys His Pro Gln
                    1380                1385                1390

Arg Gln Pro Pro Tyr Tyr Ser Cys Gln Cys Ala Pro Pro Phe Ser Gly
                    1395                1400                1405

Ser Arg Cys Glu Leu Tyr Thr Ala Pro Pro Ser Thr Pro Pro Ala Thr
                1410                1415                1420

Cys Leu Ser Gln Tyr Cys Ala Asp Lys Ala Arg Asp Gly Val Cys Asp
        1425                1430                1435                1440

Glu Ala Cys Asn Ser His Ala Cys Gln Trp Asp Gly Gly Asp Cys Ser
                        1445                1450                1455

Leu Thr Met Glu Asn Pro Trp Ala Asn Cys Ser Ser Pro Leu Pro Cys
                    1460                1465                1470

Trp Asp Tyr Ile Asn Asn Gln Cys Asp Glu Leu Cys Asn Thr Val Glu
                1475                1480                1485

Cys Leu Phe Asp Asn Phe Glu Cys Gln Gly Asn Ser Lys Thr Cys Lys
                1490                1495                1500

Tyr Asp Lys Tyr Cys Ala Asp His Phe Lys Asp Asn His Cys Asn Gln
        1505                1510                1515                1520

Gly Cys Asn Ser Glu Glu Cys Gly Trp Asp Gly Leu Asp Cys Ala Ala
                        1525                1530                1535

Asp Gln Pro Glu Asn Leu Ala Glu Gly Thr Leu Val Ile Val Val Leu
                    1540                1545                1550

Met Pro Pro Glu Gln Leu Leu Gln Asp Ala Arg Ser Phe Leu Arg Ala
                    1555                1560                1565

Leu Gly Thr Leu Leu His Thr Asn Leu Arg Ile Lys Arg Asp Ser Gln
                1570                1575                1580

Gly Glu Leu Met Val Tyr Pro Tyr Tyr Gly Glu Lys Ser Ala Ala Met
        1585                1590                1595                1600

Lys Lys Gln Arg Met Thr Arg Arg Ser Leu Pro Gly Glu Gln Glu Gln
                        1605                1610                1615

Glu Val Ala Gly Ser Lys Val Phe Leu Glu Ile Asp Asn Arg Gln Cys
                    1620                1625                1630

Val Gln Asp Ser Asp His Cys Phe Lys Asn Thr Asp Ala Ala Ala Ala
                    1635                1640                1645

Leu Leu Ala Ser His Ala Ile Gln Gly Thr Leu Ser Tyr Pro Leu Val
                1650                1655                1660

Ser Val Val Ser Glu Ser Leu Thr Pro Glu Arg Thr Gln Leu Leu Tyr
        1665                1670                1675                1680

Leu Leu Ala Val Ala Val Val Ile Ile Leu Phe Ile Ile Leu Leu Gly
                        1685                1690                1695
```

-continued

Val Ile Met Ala Lys Arg Lys Arg Lys His Gly Ser Leu Trp Leu Pro
            1700            1705            1710

Glu Gly Phe Thr Leu Arg Arg Asp Ala Ser Asn His Lys Arg Arg Glu
        1715            1720            1725

Pro Val Gly Gln Asp Ala Val Gly Leu Lys Asn Leu Ser Val Gln Val
        1730            1735            1740

Ser Glu Ala Asn Leu Ile Gly Thr Gly Thr Ser His Trp Val Asp
1745            1750            1755            1760

Asp Glu Gly Pro Gln Pro Lys Lys Val Lys Ala Glu Asp Glu Ala Leu
            1765            1770            1775

Leu Ser Glu Glu Asp Asp Pro Ile Asp Arg Arg Pro Trp Thr Gln Gln
            1780            1785            1790

His Leu Glu Ala Ala Asp Ile Arg Arg Thr Pro Ser Leu Ala Leu Thr
            1795            1800            1805

Pro Pro Gln Ala Glu Gln Glu Val Asp Val Leu Asp Val Asn Val Arg
        1810            1815            1820

Gly Pro Asp Gly Cys Thr Pro Leu Met Leu Ala Ser Leu Arg Gly Gly
1825            1830            1835            1840

Ser Ser Asp Leu Ser Asp Glu Asp Glu Asp Ala Glu Asp Ser Ser Ala
            1845            1850            1855

Asn Ile Ile Thr Asp Leu Val Tyr Gln Gly Ala Ser Leu Gln Ala Gln
            1860            1865            1870

Thr Asp Arg Thr Gly Glu Met Ala Leu His Leu Ala Ala Arg Tyr Ser
            1875            1880            1885

Arg Ala Asp Ala Ala Lys Arg Leu Leu Asp Ala Gly Ala Asp Ala Asn
        1890            1895            1900

Ala Gln Asp Asn Met Gly Arg Cys Pro Leu His Ala Ala Val Ala Ala
1905            1910            1915            1920

Asp Ala Gln Gly Val Phe Gln Ile Leu Ile Arg Asn Arg Val Thr Asp
            1925            1930            1935

Leu Asp Ala Arg Met Asn Asp Gly Thr Thr Pro Leu Ile Leu Ala Ala
            1940            1945            1950

Arg Leu Ala Val Glu Gly Met Val Ala Glu Leu Ile Asn Cys Gln Ala
            1955            1960            1965

Asp Val Asn Ala Val Asp Asp His Gly Lys Ser Ala Leu His Trp Ala
        1970            1975            1980

Ala Ala Val Asn Asn Val Glu Ala Thr Leu Leu Leu Leu Lys Asn Gly
1985            1990            1995            2000

Ala Asn Arg Asp Met Gln Asp Asn Lys Glu Glu Thr Pro Leu Phe Leu
        2005            2010            2015

Ala Ala Arg Glu Gly Ser Tyr Glu Ala Ala Lys Ile Leu Leu Asp His
            2020            2025            2030

Phe Ala Asn Arg Asp Ile Thr Asp His Met Asp Arg Leu Pro Arg Asp
            2035            2040            2045

Val Ala Arg Asp Arg Met His His Asp Ile Val Arg Leu Leu Asp Glu
            2050            2055            2060

Tyr Asn Val Thr Pro Ser Pro Pro Gly Thr Val Leu Thr Ser Ala Leu
2065            2070            2075            2080

Ser Pro Val Ile Cys Gly Pro Asn Arg Ser Phe Leu Ser Leu Lys His
            2085            2090            2095

Thr Pro Met Gly Lys Lys Ser Arg Arg Pro Ser Ala Lys Ser Thr Met
            2100            2105            2110

```
Pro Thr Ser Leu Pro Asn Leu Ala Lys Glu Ala Lys Asp Ala Lys Gly
        2115                2120                2125

Ser Arg Arg Lys Lys Ser Leu Ser Glu Lys Val Gln Leu Ser Glu Ser
    2130                2135                2140

Ser Val Thr Leu Ser Pro Val Asp Ser Leu Glu Ser Pro His Thr Tyr
2145                2150                2155                2160

Val Ser Asp Thr Thr Ser Ser Pro Met Ile Thr Ser Pro Gly Ile Leu
            2165                2170                2175

Gln Ala Ser Pro Asn Pro Met Leu Ala Thr Ala Ala Pro Pro Ala Pro
                2180                2185                2190

Val His Ala Gln His Ala Leu Ser Phe Ser Asn Leu His Glu Met Gln
        2195                2200                2205

Pro Leu Ala His Gly Ala Ser Thr Val Leu Pro Ser Val Ser Gln Leu
    2210                2215                2220

Leu Ser His His His Ile Val Ser Pro Gly Ser Gly Ser Ala Gly Ser
2225                2230                2235                2240

Leu Ser Arg Leu His Pro Val Pro Val Pro Ala Asp Trp Met Asn Arg
            2245                2250                2255

Met Glu Val Asn Glu Thr Gln Tyr Asn Glu Met Phe Gly Met Val Leu
                2260                2265                2270

Ala Pro Ala Glu Gly Thr His Pro Gly Ile Ala Pro Gln Ser Arg Pro
        2275                2280                2285

Pro Glu Gly Lys His Ile Thr Thr Pro Arg Glu Pro Leu Pro Pro Ile
    2290                2295                2300

Val Thr Phe Gln Leu Ile Pro Lys Gly Ser Ile Ala Gln Pro Ala Gly
2305                2310                2315                2320

Ala Pro Gln Pro Gln Ser Thr Cys Pro Pro Ala Val Ala Gly Pro Leu
            2325                2330                2335

Pro Thr Met Tyr Gln Ile Pro Glu Met Ala Arg Leu Pro Ser Val Ala
                2340                2345                2350

Phe Pro Thr Ala Met Met Pro Gln Gln Asp Gly Gln Val Ala Gln Thr
        2355                2360                2365

Ile Leu Pro Ala Tyr His Pro Phe Pro Ala Ser Val Gly Lys Tyr Pro
    2370                2375                2380

Thr Pro Pro Ser Gln His Ser Tyr Ala Ser Ser Asn Ala Ala Glu Arg
2385                2390                2395                2400

Thr Pro Ser His Ser Gly His Leu Gln Gly Glu His Pro Tyr Leu Thr
            2405                2410                2415

Pro Ser Pro Glu Ser Pro Asp Gln Trp Ser Ser Ser Pro His Ser
                2420                2425                2430

Ala Ser Asp Trp Ser Asp Val Thr Thr Ser Pro Thr Pro Gly Gly Ala
        2435                2440                2445

Gly Gly Gly Gln Arg Gly Pro Gly Thr His Met Ser Glu Pro Pro His
    2450                2455                2460

Asn Asn Met Gln Val Tyr Ala
2465                2470

(2) INFORMATION FOR SEQ ID NO:20:

(i) SEQUENCE CHARACTERISTICS:
        (A) LENGTH: 2556 amino acids
        (B) TYPE: amino acid
        (C) STRANDEDNESS: single
        (D) TOPOLOGY: unknown (ii) MOLECULE TYPE: peptide
```

(xi) SEQUENCE DESCRIPTION: SEQ ID NO:20:

```
Met Pro Pro Leu Leu Ala Pro Leu Leu Cys Leu Ala Leu Leu Pro Ala
1               5                   10                  15

Leu Ala Ala Arg Gly Pro Arg Cys Ser Gln Pro Gly Glu Thr Cys Leu
                20                  25                  30

Asn Gly Gly Lys Cys Glu Ala Ala Asn Gly Thr Glu Ala Cys Val Cys
            35                  40                  45

Gly Gly Ala Phe Val Gly Pro Arg Cys Gln Asp Pro Asn Pro Cys Leu
        50                  55                  60

Ser Thr Pro Cys Lys Asn Ala Gly Thr Cys His Val Val Asp Arg Arg
65                  70                  75                  80

Gly Val Ala Asp Tyr Ala Cys Ser Cys Ala Leu Gly Phe Ser Gly Pro
                85                  90                  95

Leu Cys Leu Thr Pro Leu Asp Asn Ala Cys Leu Thr Asn Pro Cys Arg
            100                 105                 110

Asn Gly Gly Thr Cys Asp Leu Leu Thr Leu Thr Glu Tyr Lys Cys Arg
            115                 120                 125

Cys Pro Pro Gly Trp Ser Gly Lys Ser Cys Gln Gln Ala Asp Pro Cys
        130                 135                 140

Ala Ser Asn Pro Cys Ala Asn Gly Gly Gln Cys Leu Pro Phe Glu Ala
145                 150                 155                 160

Ser Tyr Ile Cys His Cys Pro Pro Ser Phe His Gly Pro Thr Cys Arg
                165                 170                 175

Gln Asp Val Asn Glu Cys Gly Gln Lys Pro Arg Leu Cys Arg His Gly
            180                 185                 190

Gly Thr Cys His Asn Glu Val Gly Ser Tyr Arg Cys Val Cys Arg Ala
        195                 200                 205

Thr His Thr Gly Pro Asn Cys Glu Arg Pro Tyr Val Pro Cys Ser Pro
    210                 215                 220

Ser Pro Cys Gln Asn Gly Gly Thr Cys Arg Pro Thr Gly Asp Val Thr
225                 230                 235                 240

His Glu Cys Ala Cys Leu Pro Gly Phe Thr Gly Gln Asn Cys Glu Glu
                245                 250                 255

Asn Ile Asp Asp Cys Pro Gly Asn Asn Cys Lys Asn Gly Gly Ala Cys
            260                 265                 270

Val Asp Gly Val Asn Thr Tyr Asn Cys Pro Cys Pro Pro Glu Trp Thr
        275                 280                 285

Gly Gln Tyr Cys Thr Glu Asp Val Asp Glu Cys Gln Leu Met Pro Asn
    290                 295                 300

Ala Cys Gln Asn Gly Gly Thr Cys His Asn Thr His Gly Gly Tyr Asn
305                 310                 315                 320

Cys Val Cys Val Asn Gly Trp Thr Gly Glu Asp Cys Ser Glu Asn Ile
                325                 330                 335

Asp Asp Cys Ala Ser Ala Ala Cys Phe His Gly Ala Thr Cys His Asp
            340                 345                 350

Arg Val Ala Ser Phe Tyr Cys Glu Cys Pro His Gly Arg Thr Gly Leu
        355                 360                 365

Leu Cys His Leu Asn Asp Ala Cys Ile Ser Asn Pro Cys Asn Glu Gly
    370                 375                 380

Ser Asn Cys Asp Thr Asn Pro Val Asn Gly Lys Ala Ile Cys Thr Cys
385                 390                 395                 400

Pro Ser Gly Tyr Thr Gly Pro Ala Cys Ser Gln Asp Val Asp Glu Cys
```

-continued

```
                405                 410                 415
Ser Leu Gly Ala Asn Pro Cys Glu His Ala Gly Lys Cys Ile Asn Thr
            420                 425                 430
Leu Gly Ser Phe Glu Cys Gln Cys Leu Gln Gly Tyr Thr Gly Pro Arg
            435                 440                 445
Cys Glu Ile Asp Val Asn Glu Cys Val Ser Asn Pro Cys Gln Asn Asp
            450                 455                 460
Ala Thr Cys Leu Asp Gln Ile Gly Glu Phe Gln Cys Met Cys Met Pro
465                 470                 475                 480
Gly Tyr Glu Gly Val His Cys Glu Val Asn Thr Asp Glu Cys Ala Ser
                485                 490                 495
Ser Pro Cys Leu His Asn Gly Arg Cys Leu Asp Lys Ile Asn Glu Phe
            500                 505                 510
Gln Cys Glu Cys Pro Thr Gly Phe Thr Gly His Leu Cys Gln Tyr Asp
            515                 520                 525
Val Asp Glu Cys Ala Ser Thr Pro Cys Lys Asn Gly Ala Lys Cys Leu
530                 535                 540
Asp Gly Pro Asn Thr Tyr Thr Cys Val Cys Thr Glu Gly Tyr Thr Gly
545                 550                 555                 560
Thr His Cys Glu Val Asp Ile Asp Glu Cys Asp Pro Asp Pro Cys His
                565                 570                 575
Tyr Gly Ser Cys Lys Asp Gly Val Ala Thr Phe Thr Cys Leu Cys Arg
            580                 585                 590
Pro Gly Tyr Thr Gly His His Cys Glu Thr Asn Ile Asn Glu Cys Ser
            595                 600                 605
Ser Gln Pro Cys Arg Leu Arg Gly Thr Cys Gln Asp Pro Asp Asn Ala
    610                 615                 620
Tyr Leu Cys Phe Cys Leu Lys Gly Thr Thr Gly Pro Asn Cys Glu Ile
625                 630                 635                 640
Asn Leu Asp Asp Cys Ala Ser Ser Pro Cys Asp Ser Gly Thr Cys Leu
                645                 650                 655
Asp Lys Ile Asp Gly Tyr Glu Cys Ala Cys Glu Pro Gly Tyr Thr Gly
            660                 665                 670
Ser Met Cys Asn Ser Asn Ile Asp Glu Cys Ala Gly Asn Pro Cys His
            675                 680                 685
Asn Gly Gly Thr Cys Glu Asp Gly Ile Asn Gly Phe Thr Cys Arg Cys
    690                 695                 700
Pro Glu Gly Tyr His Asp Pro Thr Cys Leu Ser Glu Val Asn Glu Cys
705                 710                 715                 720
Asn Ser Asn Pro Cys Val His Gly Ala Cys Arg Asp Ser Leu Asn Gly
                725                 730                 735
Tyr Lys Cys Asp Cys Asp Pro Gly Trp Ser Gly Thr Asn Cys Asp Ile
            740                 745                 750
Asn Asn Asn Glu Cys Glu Ser Asn Pro Cys Val Asn Gly Gly Thr Cys
            755                 760                 765
Lys Asp Met Thr Ser Gly Ile Val Cys Thr Cys Arg Glu Gly Phe Ser
770                 775                 780
Gly Pro Asn Cys Gln Thr Asn Ile Asn Glu Cys Ala Ser Asn Pro Cys
785                 790                 795                 800
Leu Asn Lys Gly Thr Cys Ile Asp Asp Val Ala Gly Tyr Lys Cys Asn
                805                 810                 815
Cys Leu Leu Pro Tyr Thr Gly Ala Thr Cys Glu Val Val Leu Ala Pro
            820                 825                 830
```

-continued

```
Cys Ala Pro Ser Pro Cys Arg Asn Gly Gly Glu Cys Arg Gln Ser Glu
            835                 840                 845
Asp Tyr Glu Ser Phe Ser Cys Val Cys Pro Thr Ala Gly Ala Lys Gly
        850                 855                 860
Gln Thr Cys Glu Val Asp Ile Asn Glu Cys Val Leu Ser Pro Cys Arg
865                 870                 875                 880
His Gly Ala Ser Cys Gln Asn Thr His Gly Tyr Arg Cys His Cys
                885                 890                 895
Gln Ala Gly Tyr Ser Gly Arg Asn Cys Glu Thr Asp Ile Asp Asp Cys
            900                 905                 910
Arg Pro Asn Pro Cys His Asn Gly Ser Cys Thr Asp Gly Ile Asn
            915                 920                 925
Thr Ala Phe Cys Asp Cys Leu Pro Gly Phe Arg Gly Thr Phe Cys Glu
        930                 935                 940
Glu Asp Ile Asn Glu Cys Ala Ser Asp Pro Cys Arg Asn Gly Ala Asn
945                 950                 955                 960
Cys Thr Asp Cys Val Asp Ser Tyr Thr Cys Thr Cys Pro Ala Gly Phe
                965                 970                 975
Ser Gly Ile His Cys Glu Asn Asn Thr Pro Asp Cys Thr Glu Ser Ser
            980                 985                 990
Cys Phe Asn Gly Gly Thr Cys Val Asp Gly Ile Asn Ser Phe Thr Cys
            995                 1000                1005
Leu Cys Pro Pro Gly Phe Thr Gly Ser Tyr Cys Gln His Val Val Asn
            1010                1015                1020
Glu Cys Asp Ser Arg Pro Cys Leu Leu Gly Gly Thr Cys Gln Asp Gly
1025                1030                1035                1040
Arg Gly Leu His Arg Cys Thr Cys Pro Gln Gly Tyr Thr Gly Pro Asn
                1045                1050                1055
Cys Gln Asn Leu Val His Trp Cys Asp Ser Ser Pro Cys Lys Asn Gly
            1060                1065                1070
Gly Lys Cys Trp Gln Thr His Thr Gln Tyr Arg Cys Glu Cys Pro Ser
            1075                1080                1085
Gly Trp Thr Gly Leu Tyr Cys Asp Val Pro Ser Val Ser Cys Glu Val
        1090                1095                1100
Ala Ala Gln Arg Gln Gly Val Asp Val Ala Arg Leu Cys Gln His Gly
1105                1110                1115                1120
Gly Leu Cys Val Asp Ala Gly Asn Thr His His Cys Arg Cys Gln Ala
                1125                1130                1135
Gly Tyr Thr Gly Ser Tyr Cys Glu Asp Leu Val Asp Glu Cys Ser Pro
            1140                1145                1150
Ser Pro Cys Gln Asn Gly Ala Thr Cys Thr Asp Tyr Leu Gly Gly Tyr
            1155                1160                1165
Ser Cys Lys Cys Val Ala Gly Tyr His Gly Val Asn Cys Ser Glu Glu
            1170                1175                1180
Ile Asp Glu Cys Leu Ser His Pro Cys Gln Asn Gly Gly Thr Cys Leu
1185                1190                1195                1200
Asp Leu Pro Asn Thr Tyr Lys Cys Ser Cys Pro Arg Gly Thr Gln Gly
                1205                1210                1215
Val His Cys Glu Ile Asn Val Asp Asp Cys Asn Pro Pro Val Asp Pro
            1220                1225                1230
Val Ser Arg Ser Pro Lys Cys Phe Asn Asn Gly Thr Cys Val Asp Gln
            1235                1240                1245
```

-continued

Val Gly Gly Tyr Ser Cys Thr Cys Pro Pro Gly Phe Val Gly Glu Arg
        1250                1255                1260

Cys Glu Gly Asp Val Asn Glu Cys Leu Ser Asn Pro Cys Asp Ala Arg
1265                1270                1275                1280

Gly Thr Gln Asn Cys Val Gln Arg Val Asn Asp Phe His Cys Glu Cys
            1285                1290                1295

Arg Ala Gly His Thr Gly Arg Arg Cys Glu Ser Val Ile Asn Gly Cys
        1300                1305                1310

Lys Gly Lys Pro Cys Lys Asn Gly Gly Thr Cys Ala Val Ala Ser Asn
    1315                1320                1325

Thr Ala Arg Gly Phe Ile Cys Lys Cys Pro Ala Gly Phe Glu Gly Ala
        1330                1335                1340

Thr Cys Glu Asn Asp Ala Arg Thr Cys Gly Ser Leu Arg Cys Leu Asn
1345                1350                1355                1360

Gly Gly Thr Cys Ile Ser Gly Pro Arg Ser Pro Thr Cys Leu Cys Leu
            1365                1370                1375

Gly Pro Phe Thr Gly Pro Glu Cys Gln Phe Pro Ala Ser Ser Pro Cys
        1380                1385                1390

Leu Gly Gly Asn Pro Cys Tyr Asn Gln Gly Thr Cys Glu Pro Thr Ser
        1395                1400                1405

Glu Ser Pro Phe Tyr Arg Cys Leu Cys Pro Ala Lys Phe Asn Gly Leu
    1410                1415                1420

Leu Cys His Ile Leu Asp Tyr Ser Phe Gly Gly Gly Ala Gly Arg Asp
1425                1430                1435                1440

Ile Pro Pro Pro Leu Ile Glu Glu Ala Cys Glu Leu Pro Glu Cys Gln
            1445                1450                1455

Glu Asp Ala Gly Asn Lys Val Cys Ser Leu Gln Cys Asn Asn His Ala
        1460                1465                1470

Cys Gly Trp Asp Gly Gly Asp Cys Ser Leu Asn Phe Asn Asp Pro Trp
    1475                1480                1485

Lys Asn Cys Thr Gln Ser Leu Gln Cys Trp Lys Tyr Phe Ser Asp Gly
    1490                1495                1500

His Cys Asp Ser Gln Cys Asn Ser Ala Gly Cys Leu Phe Asp Gly Phe
1505                1510                1515                1520

Asp Cys Gln Arg Ala Glu Gly Gln Cys Asn Pro Leu Tyr Asp Gln Tyr
            1525                1530                1535

Cys Lys Asp His Phe Ser Asp Gly His Cys Asp Gln Gly Cys Asn Ser
        1540                1545                1550

Ala Glu Cys Glu Trp Asp Gly Leu Asp Cys Ala Glu His Val Pro Glu
        1555                1560                1565

Arg Leu Ala Ala Gly Thr Leu Val Val Val Val Leu Met Pro Pro Glu
    1570                1575                1580

Gln Leu Arg Asn Ser Ser Phe His Phe Leu Arg Glu Leu Ser Arg Val
1585                1590                1595                1600

Leu His Thr Asn Val Val Phe Lys Arg Asp Ala His Gly Gln Gln Met
            1605                1610                1615

Ile Phe Pro Tyr Tyr Gly Arg Glu Glu Glu Leu Arg Lys His Pro Ile
        1620                1625                1630

Lys Arg Ala Ala Glu Gly Trp Ala Ala Pro Asp Ala Leu Leu Gly Gln
        1635                1640                1645

Val Lys Ala Ser Leu Leu Pro Gly Gly Ser Glu Gly Gly Arg Arg Arg
    1650                1655                1660

Arg Glu Leu Asp Pro Met Asp Val Arg Gly Ser Ile Val Tyr Leu Glu

-continued

```
          1665                1670                1675                1680
Ile Asp Asn Arg Gln Cys Val Gln Ala Ser Ser Gln Cys Phe Gln Ser
                1685                1690                1695

Ala Thr Asp Val Ala Ala Phe Leu Gly Ala Leu Ala Ser Leu Gly Ser
            1700                1705                1710

Leu Asn Ile Pro Tyr Lys Ile Glu Ala Val Gln Ser Glu Thr Val Glu
        1715                1720                1725

Pro Pro Pro Ala Gln Leu His Phe Met Tyr Val Ala Ala Ala Ala
    1730                1735                1740

Phe Val Leu Leu Phe Phe Val Gly Cys Gly Val Leu Leu Ser Arg Lys
1745                1750                1755                1760

Arg Arg Arg Gln His Gly Gln Leu Trp Phe Pro Glu Gly Phe Lys Val
                1765                1770                1775

Ser Glu Ala Ser Lys Lys Lys Arg Arg Glu Glu Leu Gly Glu Asp Ser
            1780                1785                1790

Val Gly Leu Lys Pro Leu Lys Asn Ala Ser Asp Gly Ala Leu Met Asp
        1795                1800                1805

Asp Asn Gln Asn Glu Trp Gly Asp Glu Asp Leu Glu Thr Lys Lys Phe
    1810                1815                1820

Arg Phe Glu Glu Pro Val Val Leu Pro Asp Leu Asp Asp Gln Thr Asp
1825                1830                1835                1840

His Arg Gln Trp Thr Gln Gln His Leu Asp Ala Ala Asp Leu Arg Met
                1845                1850                1855

Ser Ala Met Ala Pro Thr Pro Pro Gln Gly Glu Val Asp Ala Asp Cys
            1860                1865                1870

Met Asp Val Asn Val Arg Gly Pro Asp Gly Phe Thr Pro Leu Met Ile
        1875                1880                1885

Ala Ser Cys Ser Gly Gly Gly Leu Glu Thr Gly Asn Ser Glu Glu Glu
    1890                1895                1900

Glu Asp Ala Pro Ala Val Ile Ser Asp Phe Ile Tyr Gln Gly Ala Ser
1905                1910                1915                1920

Leu His Asn Gln Thr Asp Arg Thr Gly Glu Thr Ala Leu His Leu Ala
                1925                1930                1935

Ala Arg Tyr Ser Arg Ser Asp Ala Ala Lys Arg Leu Leu Glu Ala Ser
            1940                1945                1950

Ala Asp Ala Asn Ile Gln Asp Asn Met Gly Arg Thr Pro Leu His Ala
        1955                1960                1965

Ala Val Ser Ala Asp Ala Gln Gly Val Phe Gln Ile Leu Ile Arg Asn
    1970                1975                1980

Arg Ala Thr Asp Leu Asp Ala Arg Met His Asp Gly Thr Thr Pro Leu
1985                1990                1995                2000

Ile Leu Ala Ala Arg Leu Ala Val Glu Gly Met Leu Glu Asp Leu Ile
                2005                2010                2015

Asn Ser His Ala Asp Val Asn Ala Val Asp Asp Leu Gly Lys Ser Ala
            2020                2025                2030

Leu His Trp Ala Ala Ala Val Asn Asn Val Asp Ala Ala Val Val Leu
        2035                2040                2045

Leu Lys Asn Gly Ala Asn Lys Asp Met Gln Asn Asn Arg Glu Glu Thr
    2050                2055                2060

Pro Leu Phe Leu Ala Ala Arg Glu Gly Ser Tyr Glu Thr Ala Lys Val
2065                2070                2075                2080

Leu Leu Asp His Phe Ala Asn Arg Asp Ile Thr Asp His Met Asp Arg
                2085                2090                2095
```

-continued

```
Leu Pro Arg Asp Ile Ala Gln Glu Arg Met His His Asp Ile Val Arg
            2100                2105                2110

Leu Leu Asp Glu Tyr Asn Leu Val Arg Ser Pro Gln Leu His Gly Ala
        2115                2120                2125

Pro Leu Gly Gly Thr Pro Thr Leu Ser Pro Pro Leu Cys Ser Pro Asn
        2130                2135                2140

Gly Tyr Leu Gly Ser Leu Lys Pro Gly Val Gln Gly Lys Lys Val Arg
2145                2150                2155                2160

Lys Pro Ser Ser Lys Gly Leu Ala Cys Gly Ser Lys Glu Ala Lys Asp
            2165                2170                2175

Leu Lys Ala Arg Arg Lys Lys Ser Gln Asp Gly Lys Gly Cys Leu Leu
            2180                2185                2190

Asp Ser Ser Gly Met Leu Ser Pro Val Asp Ser Leu Glu Ser Pro His
        2195                2200                2205

Gly Tyr Leu Ser Asp Val Ala Ser Pro Pro Leu Leu Pro Ser Pro Phe
        2210                2215                2220

Gln Gln Ser Pro Ser Val Pro Leu Asn His Leu Pro Gly Met Pro Asp
2225                2230                2235                2240

Thr His Leu Gly Ile Gly His Leu Asn Val Ala Ala Lys Pro Glu Met
            2245                2250                2255

Ala Ala Leu Gly Gly Gly Arg Leu Ala Phe Glu Thr Gly Pro Pro
            2260                2265                2270

Arg Leu Ser His Leu Pro Val Ala Ser Gly Thr Ser Thr Val Leu Gly
            2275                2280                2285

Ser Ser Ser Gly Gly Ala Leu Asn Phe Thr Val Gly Gly Ser Thr Ser
    2290                2295                2300

Leu Asn Gly Gln Cys Glu Trp Leu Ser Arg Leu Gln Ser Gly Met Val
2305                2310                2315                2320

Pro Asn Gln Tyr Asn Pro Leu Arg Gly Ser Val Ala Pro Gly Pro Leu
            2325                2330                2335

Ser Thr Gln Ala Pro Ser Leu Gln His Gly Met Val Gly Pro Leu His
            2340                2345                2350

Ser Ser Leu Ala Ala Ser Ala Leu Ser Gln Met Met Ser Tyr Gln Gly
    2355                2360                2365

Leu Pro Ser Thr Arg Leu Ala Thr Gln Pro His Leu Val Gln Thr Gln
    2370                2375                2380

Gln Val Gln Pro Gln Asn Leu Gln Met Gln Gln Asn Leu Gln Pro
2385                2390                2395                2400

Ala Asn Ile Gln Gln Gln Gln Ser Leu Gln Pro Pro Pro Pro Pro
            2405                2410                2415

Gln Pro His Leu Gly Val Ser Ser Ala Ala Ser Gly His Leu Gly Arg
            2420                2425                2430

Ser Phe Leu Ser Gly Glu Pro Ser Gln Ala Asp Val Gln Pro Leu Gly
    2435                2440                2445

Pro Ser Ser Leu Ala Val His Thr Ile Leu Pro Gln Glu Ser Pro Ala
    2450                2455                2460

Leu Pro Thr Ser Leu Pro Ser Ser Leu Val Pro Pro Val Thr Ala Ala
2465                2470                2475                2480

Gln Phe Leu Thr Pro Pro Ser Gln His Ser Tyr Ser Ser Pro Val Glu
            2485                2490                2495

Asn Thr Pro Ser His Gln Leu Gln Val Pro Glu His Pro Phe Leu Thr
            2500                2505                2510
```

```
Pro Ser Pro Glu Ser Pro Asp Gln Trp Ser Ser Ser Pro His Ser
        2515                2520                2525

Asn Val Ser Asp Trp Ser Glu Gly Val Ser Ser Pro Pro Thr Ser Met
            2530                2535                2540

Gln Ser Gln Ile Ala Arg Ile Pro Glu Ala Phe Lys
2545                2550                2555

(2) INFORMATION FOR SEQ ID NO:21:

(i) SEQUENCE CHARACTERISTICS:
        (A) LENGTH: 9723 base pairs
        (B) TYPE: nucleic acid
        (C) STRANDEDNESS: double
        (D) TOPOLOGY: unknown (ii) MOLECULE TYPE: cDNA (ix) FEATURE:
        (A) NAME/KEY: CDS
        (B) LOCATION: 10..7419

(xi) SEQUENCE DESCRIPTION: SEQ ID NO:21:
```

| | | | | | | | | | | | | |
|---|---|---|---|---|---|---|---|---|---|---|---|---|
| GGAATTCCG | CCC | GCC | CTG | CGC | CCC | GCT | CTG | CTG | TGG | GCG | CTG CTG GCG | 48 |
| | Pro | Ala | Leu | Arg | Pro | Ala | Leu | Leu | Trp | Ala | Leu Leu Ala | |
| | 1 | | | 5 | | | | | 10 | | | |

```
CTC TGG CTG TGC TGC GCG GCC CCC GCG CAT GCA TTG CAG TGT CGA GAT    96
Leu Trp Leu Cys Cys Ala Ala Pro Ala His Ala Leu Gln Cys Arg Asp
    15                  20                  25

GGC TAT GAA CCC TGT GTA AAT GAA GGA ATG TGT GTT ACC TAC CAC AAT   144
Gly Tyr Glu Pro Cys Val Asn Glu Gly Met Cys Val Thr Tyr His Asn
30                  35                  40                  45

GGC ACA GGA TAC TGC AAA TGT CCA GAA GGC TTC TTG GGG GAA TAT TGT   192
Gly Thr Gly Tyr Cys Lys Cys Pro Glu Gly Phe Leu Gly Glu Tyr Cys
                50                  55                  60

CAA CAT CGA GAC CCC TGT GAG AAG AAC CGC TGC CAG AAT GGT GGG ACT   240
Gln His Arg Asp Pro Cys Glu Lys Asn Arg Cys Gln Asn Gly Gly Thr
            65                  70                  75

TGT GTG GCC CAG GCC ATG CTG GGG AAA GCC ACG TGC CGA TGT GCC TCA   288
Cys Val Ala Gln Ala Met Leu Gly Lys Ala Thr Cys Arg Cys Ala Ser
        80                  85                  90

GGG TTT ACA GGA GAG GAC TGC CAG TAC TCA ACA TCT CAT CCA TGC TTT   336
Gly Phe Thr Gly Glu Asp Cys Gln Tyr Ser Thr Ser His Pro Cys Phe
    95                  100                 105

GTG TCT CGA CCC TGC CTG AAT GGC GGA ACA TGC CAT ATG CTC AGC CGG   384
Val Ser Arg Pro Cys Leu Asn Gly Gly Thr Cys His Met Leu Ser Arg
110                 115                 120                 125

GAT ACC TAT GAG TGC ACC TGT CAA GTC GGG TTT ACA GGT AAG GAG TGC   432
Asp Thr Tyr Glu Cys Thr Cys Gln Val Gly Phe Thr Gly Lys Glu Cys
                130                 135                 140

CAA TGG ACG GAT GCC TGC CTG TCT CAT CCC TGT GCA AAT GGA AGT ACC   480
Gln Trp Thr Asp Ala Cys Leu Ser His Pro Cys Ala Asn Gly Ser Thr
            145                 150                 155

TGT ACC ACT GTG GCC AAC CAG TTC TCC TGC AAA TGC CTC ACA GGC TTC   528
Cys Thr Thr Val Ala Asn Gln Phe Ser Cys Lys Cys Leu Thr Gly Phe
        160                 165                 170

ACA GGG CAG AAA TGT GAG ACT GAT GTC AAT GAG TGT GAC ATT CCA GGA   576
Thr Gly Gln Lys Cys Glu Thr Asp Val Asn Glu Cys Asp Ile Pro Gly
    175                 180                 185

CAC TGC CAG CAT GGT GGC ACC TGC CTC AAC CTG CCT GGT TCC TAC CAG   624
His Cys Gln His Gly Gly Thr Cys Leu Asn Leu Pro Gly Ser Tyr Gln
190                 195                 200                 205

TGC CAG TGC CCT CAG GGC TTC ACA GGC CAG TAC TGT GAC AGC CTG TAT   672
```

```
Cys Gln Cys Pro Gln Gly Phe Thr Gly Gln Tyr Cys Asp Ser Leu Tyr
            210                 215                 220

GTG CCC TGT GCA CCC TCA CCT TGT GTC AAT GGA GGC ACC TGT CGG CAG        720
Val Pro Cys Ala Pro Ser Pro Cys Val Asn Gly Gly Thr Cys Arg Gln
            225                 230                 235

ACT GGT GAC TTC ACT TTT GAG TGC AAC TGC CTT CCA GGT TTT GAA GGG        768
Thr Gly Asp Phe Thr Phe Glu Cys Asn Cys Leu Pro Gly Phe Glu Gly
            240                 245                 250

AGC ACC TGT GAG AGG AAT ATT GAT GAC TGC CCT AAC CAC AGG TGT CAG        816
Ser Thr Cys Glu Arg Asn Ile Asp Asp Cys Pro Asn His Arg Cys Gln
        255                 260                 265

AAT GGA GGG GTT TGT GTG GAT GGG GTC AAC ACT TAC AAC TGC CGC TGT        864
Asn Gly Gly Val Cys Val Asp Gly Val Asn Thr Tyr Asn Cys Arg Cys
270                 275                 280                 285

CCC CCA CAA TGG ACA GGA CAG TTC TGC ACA GAG GAT GTG GAT GAA TGC        912
Pro Pro Gln Trp Thr Gly Gln Phe Cys Thr Glu Asp Val Asp Glu Cys
                290                 295                 300

CTG CTG CAG CCC AAT GCC TGT CAA AAT GGG GGC ACC TGT GCC AAC CGC        960
Leu Leu Gln Pro Asn Ala Cys Gln Asn Gly Gly Thr Cys Ala Asn Arg
            305                 310                 315

AAT GGA GGC TAT GGC TGT GTA TGT GTC AAC GGC TGG AGT GGA GAT GAC       1008
Asn Gly Gly Tyr Gly Cys Val Cys Val Asn Gly Trp Ser Gly Asp Asp
            320                 325                 330

TGC AGT GAG AAC ATT GAT GAT TGT GCC TTC GCC TCC TGT ACT CCA GGC       1056
Cys Ser Glu Asn Ile Asp Asp Cys Ala Phe Ala Ser Cys Thr Pro Gly
        335                 340                 345

TCC ACC TGC ATC GAC CGT GTG GCC TCC TTC TCT TGC ATG TGC CCA GAG       1104
Ser Thr Cys Ile Asp Arg Val Ala Ser Phe Ser Cys Met Cys Pro Glu
350                 355                 360                 365

GGG AAG GCA GGT CTC CTG TGT CAT CTG GAT GAT GCA TGC ATC AGC AAT       1152
Gly Lys Ala Gly Leu Leu Cys His Leu Asp Asp Ala Cys Ile Ser Asn
                370                 375                 380

CCT TGC CAC AAG GGG GCA CTG TGT GAC ACC AAC CCC TTA AAT GGG CAA       1200
Pro Cys His Lys Gly Ala Leu Cys Asp Thr Asn Pro Leu Asn Gly Gln
            385                 390                 395

TAT ATT TGC ACC TGC CCA CAA GGC TAC AAA GGG GCT GAC TGC ACA GAA       1248
Tyr Ile Cys Thr Cys Pro Gln Gly Tyr Lys Gly Ala Asp Cys Thr Glu
            400                 405                 410

GAT GTG GAT GAA TGT GCC ATG GCC AAT AGC AAT CCT TGT GAG CAT GCA       1296
Asp Val Asp Glu Cys Ala Met Ala Asn Ser Asn Pro Cys Glu His Ala
        415                 420                 425

GGA AAA TGT GTG AAC ACG GAT GGC GCC TTC CAC TGT GAG TGT CTG AAG       1344
Gly Lys Cys Val Asn Thr Asp Gly Ala Phe His Cys Glu Cys Leu Lys
430                 435                 440                 445

GGT TAT GCA GGA CCT CGT TGT GAG ATG GAC ATC AAT GAG TGC CAT TCA       1392
Gly Tyr Ala Gly Pro Arg Cys Glu Met Asp Ile Asn Glu Cys His Ser
                450                 455                 460

GAC CCC TGC CAG AAT GAT GCT ACC TGT CTG GAT AAG ATT GGA GGC TTC       1440
Asp Pro Cys Gln Asn Asp Ala Thr Cys Leu Asp Lys Ile Gly Gly Phe
            465                 470                 475

ACA TGT CTG TGC ATG CCA GGT TTC AAA GGT GTG CAT TGT GAA TTA GAA       1488
Thr Cys Leu Cys Met Pro Gly Phe Lys Gly Val His Cys Glu Leu Glu
            480                 485                 490

ATA AAT GAA TGT CAG AGC AAC CCT TGT GTG AAC AAT GGG CAG TGT GTG       1536
Ile Asn Glu Cys Gln Ser Asn Pro Cys Val Asn Asn Gly Gln Cys Val
        495                 500                 505

GAT AAA GTC AAT CGT TTC CAG TGC CTG TGT CCT CCT GGT TTC ACT GGG       1584
Asp Lys Val Asn Arg Phe Gln Cys Leu Cys Pro Pro Gly Phe Thr Gly
510                 515                 520                 525
```

```
CCA GTT TGC CAG ATT GAT ATT GAT GAC TGT TCC AGT ACT CCG TGT CTG         1632
Pro Val Cys Gln Ile Asp Ile Asp Asp Cys Ser Ser Thr Pro Cys Leu
                530                 535                 540

AAT GGG GCA AAG TGT ATC GAT CAC CCG AAT GGC TAT GAA TGC CAG TGT         1680
Asn Gly Ala Lys Cys Ile Asp His Pro Asn Gly Tyr Glu Cys Gln Cys
                545                 550                 555

GCC ACA GGT TTC ACT GGT GTG TTG TGT GAG GAG AAC ATT GAC AAC TGT         1728
Ala Thr Gly Phe Thr Gly Val Leu Cys Glu Glu Asn Ile Asp Asn Cys
                560                 565                 570

GAC CCC GAT CCT TGC CAC CAT GGT CAG TGT CAG GAT GGT ATT GAT TCC         1776
Asp Pro Asp Pro Cys His His Gly Gln Cys Gln Asp Gly Ile Asp Ser
575                 580                 585

TAC ACC TGC ATC TGC AAT CCC GGG TAC ATG GGC GCC ATC TGC AGT GAC         1824
Tyr Thr Cys Ile Cys Asn Pro Gly Tyr Met Gly Ala Ile Cys Ser Asp
590                 595                 600                 605

CAG ATT GAT GAA TGT TAC AGC AGC CCT TGC CTG AAC GAT GGT CGC TGC         1872
Gln Ile Asp Glu Cys Tyr Ser Ser Pro Cys Leu Asn Asp Gly Arg Cys
                610                 615                 620

ATT GAC CTG GTC AAT GGC TAC CAG TGC AAC TGC CAG CCA GGC ACG TCA         1920
Ile Asp Leu Val Asn Gly Tyr Gln Cys Asn Cys Gln Pro Gly Thr Ser
                625                 630                 635

GGG GTT AAT TGT GAA ATT AAT TTT GAT GAC TGT GCA AGT AAC CCT TGT         1968
Gly Val Asn Cys Glu Ile Asn Phe Asp Asp Cys Ala Ser Asn Pro Cys
                640                 645                 650

ATC CAT GGA ATC TGT ATG GAT GGC ATT AAT CGC TAC AGT TGT GTC TGC         2016
Ile His Gly Ile Cys Met Asp Gly Ile Asn Arg Tyr Ser Cys Val Cys
655                 660                 665

TCA CCA GGA TTC ACA GGG CAG AGA TGT AAC ATT GAC ATT GAT GAG TGT         2064
Ser Pro Gly Phe Thr Gly Gln Arg Cys Asn Ile Asp Ile Asp Glu Cys
670                 675                 680                 685

GCC TCC AAT CCC TGT CGC AAG GGT GCA ACA TGT ATC AAC GGT GTG AAT         2112
Ala Ser Asn Pro Cys Arg Lys Gly Ala Thr Cys Ile Asn Gly Val Asn
                690                 695                 700

GGT TTC CGC TGT ATA TGC CCC GAG GGA CCC CAT CAC CCC AGC TGC TAC         2160
Gly Phe Arg Cys Ile Cys Pro Glu Gly Pro His His Pro Ser Cys Tyr
                705                 710                 715

TCA CAG GTG AAC GAA TGC CTG AGC AAT CCC TGC ATC CAT GGA AAC TGT         2208
Ser Gln Val Asn Glu Cys Leu Ser Asn Pro Cys Ile His Gly Asn Cys
                720                 725                 730

ACT GGA GGT CTC AGT GGA TAT AAG TGT CTC TGT GAT GCA GGC TGG GTT         2256
Thr Gly Gly Leu Ser Gly Tyr Lys Cys Leu Cys Asp Ala Gly Trp Val
735                 740                 745

GGC ATC AAC TGT GAA GTG GAC AAA AAT GAA TGC CTT TCG AAT CCA TGC         2304
Gly Ile Asn Cys Glu Val Asp Lys Asn Glu Cys Leu Ser Asn Pro Cys
750                 755                 760                 765

CAG AAT GGA GGA ACT TGT GAC AAT CTG GTG AAT GGA TAC AGG TGT ACT         2352
Gln Asn Gly Gly Thr Cys Asp Asn Leu Val Asn Gly Tyr Arg Cys Thr
                770                 775                 780

TGC AAG AAG GGC TTT AAA GGC TAT AAC TGC CAG GTG AAT ATT GAT GAA         2400
Cys Lys Lys Gly Phe Lys Gly Tyr Asn Cys Gln Val Asn Ile Asp Glu
                785                 790                 795

TGT GCC TCA AAT CCA TGC CTG AAC CAA GGA ACC TGC TTT GAT GAC ATA         2448
Cys Ala Ser Asn Pro Cys Leu Asn Gln Gly Thr Cys Phe Asp Asp Ile
                800                 805                 810

AGT GGC TAC ACT TGC CAC TGT GTG CTG CCA TAC ACA GGC AAG AAT TGT         2496
Ser Gly Tyr Thr Cys His Cys Val Leu Pro Tyr Thr Gly Lys Asn Cys
815                 820                 825

CAG ACA GTA TTG GCT CCC TGT TCC CCA AAC CCT TGT GAG AAT GCT GCT         2544
Gln Thr Val Leu Ala Pro Cys Ser Pro Asn Pro Cys Glu Asn Ala Ala
830                 835                 840                 845
```

```
GTT TGC AAA GAG TCA CCA AAT TTT GAG AGT TAT ACT TGC TTG TGT GCT      2592
Val Cys Lys Glu Ser Pro Asn Phe Glu Ser Tyr Thr Cys Leu Cys Ala
            850                 855                 860

CCT GGC TGG CAA GGT CAG CGG TGT ACC ATT GAC ATT GAC GAG TGT ATC      2640
Pro Gly Trp Gln Gly Gln Arg Cys Thr Ile Asp Ile Asp Glu Cys Ile
            865                 870                 875

TCC AAG CCC TGC ATG AAC CAT GGT CTC TGC CAT AAC ACC CAG GGC AGC      2688
Ser Lys Pro Cys Met Asn His Gly Leu Cys His Asn Thr Gln Gly Ser
            880                 885                 890

TAC ATG TGT GAA TGT CCA CCA GGC TTC AGT GGT ATG GAC TGT GAG GAG      2736
Tyr Met Cys Glu Cys Pro Pro Gly Phe Ser Gly Met Asp Cys Glu Glu
        895                 900                 905

GAC ATT GAT GAC TGC CTT GCC AAT CCT TGC CAG AAT GGA GGT TCC TGT      2784
Asp Ile Asp Asp Cys Leu Ala Asn Pro Cys Gln Asn Gly Gly Ser Cys
910                 915                 920                 925

ATG GAT GGA GTG AAT ACT TTC TCC TGC CTC TGC CTT CCG GGT TTC ACT      2832
Met Asp Gly Val Asn Thr Phe Ser Cys Leu Cys Leu Pro Gly Phe Thr
                930                 935                 940

GGG GAT AAG TGC CAG ACA GAC ATG AAT GAG TGT CTG AGT GAA CCC TGT      2880
Gly Asp Lys Cys Gln Thr Asp Met Asn Glu Cys Leu Ser Glu Pro Cys
            945                 950                 955

AAG AAT GGA GGG ACC TGC TCT GAC TAC GTC AAC AGT TAC ACT TGC AAG      2928
Lys Asn Gly Gly Thr Cys Ser Asp Tyr Val Asn Ser Tyr Thr Cys Lys
            960                 965                 970

TGC CAG GCA GGA TTT GAT GGA GTC CAT TGT GAG AAC AAC ATC AAT GAG      2976
Cys Gln Ala Gly Phe Asp Gly Val His Cys Glu Asn Asn Ile Asn Glu
        975                 980                 985

TGC ACT GAG AGC TCC TGT TTC AAT GGT GGC ACA TGT GTT GAT GGG ATT      3024
Cys Thr Glu Ser Ser Cys Phe Asn Gly Gly Thr Cys Val Asp Gly Ile
990                 995                 1000                1005

AAC TCC TTC TCT TGC TTG TGC CCT GTG GGT TTC ACT GGA TCC TTC TGC      3072
Asn Ser Phe Ser Cys Leu Cys Pro Val Gly Phe Thr Gly Ser Phe Cys
                1010                1015                1020

CTC CAT GAG ATC AAT GAA TGC AGC TCT CAT CCA TGC CTG AAT GAG GGA      3120
Leu His Glu Ile Asn Glu Cys Ser Ser His Pro Cys Leu Asn Glu Gly
            1025                1030                1035

ACG TGT GTT GAT GGC CTG GGT ACC TAC CGC TGC AGC TGC CCC CTG GGC      3168
Thr Cys Val Asp Gly Leu Gly Thr Tyr Arg Cys Ser Cys Pro Leu Gly
            1040                1045                1050

TAC ACT GGG AAA AAC TGT CAG ACC CTG GTG AAT CTC TGC AGT CGG TCT      3216
Tyr Thr Gly Lys Asn Cys Gln Thr Leu Val Asn Leu Cys Ser Arg Ser
            1055                1060                1065

CCA TGT AAA AAC AAA GGT ACT TGT GTT CAG AAA AAA GCA GAG TCC CAG      3264
Pro Cys Lys Asn Lys Gly Thr Cys Val Gln Lys Lys Ala Glu Ser Gln
1070                1075                1080                1085

TGC CTA TGT CCA TCT GGA TGG GCT GGT GCC TAT TGT GAC GTG CCC AAT      3312
Cys Leu Cys Pro Ser Gly Trp Ala Gly Ala Tyr Cys Asp Val Pro Asn
                1090                1095                1100

GTC TCT TGT GAC ATA GCA GCC TCC AGG AGA GGT GTG CTT GTT GAA CAC      3360
Val Ser Cys Asp Ile Ala Ala Ser Arg Arg Gly Val Leu Val Glu His
            1105                1110                1115

TTG TGC CAG CAC TCA GGT GTC TGC ATC AAT GCT GGC AAC ACG CAT TAC      3408
Leu Cys Gln His Ser Gly Val Cys Ile Asn Ala Gly Asn Thr His Tyr
            1120                1125                1130

TGT CAG TGC CCC CTG GGC TAT ACT GGG AGC TAC TGT GAG GAG CAA CTC      3456
Cys Gln Cys Pro Leu Gly Tyr Thr Gly Ser Tyr Cys Glu Glu Gln Leu
            1135                1140                1145

GAT GAG TGT GCG TCC AAC CCC TGC CAG CAC GGG GCA ACA TGC AGT GAC      3504
Asp Glu Cys Ala Ser Asn Pro Cys Gln His Gly Ala Thr Cys Ser Asp
```

-continued

```
           1150                1155                1160                1165

TTC ATT GGT GGA TAC AGA TGC GAG TGT GTC CCA GGC TAT CAG GGT GTC              3552
Phe Ile Gly Gly Tyr Arg Cys Glu Cys Val Pro Gly Tyr Gln Gly Val
                1170                1175                1180

AAC TGT GAG TAT GAA GTG GAT GAG TGC CAG AAT CAG CCC TGC CAG AAT              3600
Asn Cys Glu Tyr Glu Val Asp Glu Cys Gln Asn Gln Pro Cys Gln Asn
                1185                1190                1195

GGA GGC ACC TGT ATT GAC CTT GTG AAC CAT TTC AAG TGC TCT TGC CCA              3648
Gly Gly Thr Cys Ile Asp Leu Val Asn His Phe Lys Cys Ser Cys Pro
                1200                1205                1210

CCA GGC ACT CGG GGC CTA CTC TGT GAA GAG AAC ATT GAT GAC TGT GCC              3696
Pro Gly Thr Arg Gly Leu Leu Cys Glu Glu Asn Ile Asp Asp Cys Ala
                1215                1220                1225

CGG GGT CCC CAT TGC CTT AAT GGT GGT CAG TGC ATG GAT AGG ATT GGA              3744
Arg Gly Pro His Cys Leu Asn Gly Gly Gln Cys Met Asp Arg Ile Gly
1230                1235                1240                1245

GGC TAC AGT TGT CGC TGC TTG CCT GGC TTT GCT GGG GAG CGT TGT GAG              3792
Gly Tyr Ser Cys Arg Cys Leu Pro Gly Phe Ala Gly Glu Arg Cys Glu
                1250                1255                1260

GGA GAC ATC AAC GAG TGC CTC TCC AAC CCC TGC AGC TCT GAG GGC AGC              3840
Gly Asp Ile Asn Glu Cys Leu Ser Asn Pro Cys Ser Ser Glu Gly Ser
                1265                1270                1275

CTG GAC TGT ATA CAG CTC ACC AAT GAC TAC CTG TGT GTT TGC CGT AGT              3888
Leu Asp Cys Ile Gln Leu Thr Asn Asp Tyr Leu Cys Val Cys Arg Ser
                1280                1285                1290

GCC TTT ACT GGC CGG CAC TGT GAA ACC TTC GTC GAT GTG TGT CCC CAG              3936
Ala Phe Thr Gly Arg His Cys Glu Thr Phe Val Asp Val Cys Pro Gln
                1295                1300                1305

ATG CCC TGC CTG AAT GGA GGG ACT TGT GCT GTG GCC AGT AAC ATG CCT              3984
Met Pro Cys Leu Asn Gly Gly Thr Cys Ala Val Ala Ser Asn Met Pro
1310                1315                1320                1325

GAT GGT TTC ATT TGC CGT TGT CCC CCG GGA TTT TCC GGG GCA AGG TGC              4032
Asp Gly Phe Ile Cys Arg Cys Pro Pro Gly Phe Ser Gly Ala Arg Cys
                1330                1335                1340

CAG AGC AGC TGT GGA CAA GTG AAA TGT AGG AAG GGG GAG CAG TGT GTG              4080
Gln Ser Ser Cys Gly Gln Val Lys Cys Arg Lys Gly Glu Gln Cys Val
                1345                1350                1355

CAC ACC GCC TCT GGA CCC CGC TGC TTC TGC CCC AGT CCC CGG GAC TGC              4128
His Thr Ala Ser Gly Pro Arg Cys Phe Cys Pro Ser Pro Arg Asp Cys
                1360                1365                1370

GAG TCA GGC TGT GCC AGT AGC CCC TGC CAG CAC GGG GGC AGC TGC CAC              4176
Glu Ser Gly Cys Ala Ser Ser Pro Cys Gln His Gly Gly Ser Cys His
                1375                1380                1385

CCT CAG CGC CAG CCT CCT TAT TAC TCC TGC CAG TGT GCC CCA CCA TTC              4224
Pro Gln Arg Gln Pro Pro Tyr Tyr Ser Cys Gln Cys Ala Pro Pro Phe
1390                1395                1400                1405

TCG GGT AGC CGC TGT GAA CTC TAC ACG GCA CCC CCC AGC ACC CCT CCT              4272
Ser Gly Ser Arg Cys Glu Leu Tyr Thr Ala Pro Pro Ser Thr Pro Pro
                1410                1415                1420

GCC ACC TGT CTG AGC CAG TAT TGT GCC GAC AAA GCT CGG GAT GGC GTC              4320
Ala Thr Cys Leu Ser Gln Tyr Cys Ala Asp Lys Ala Arg Asp Gly Val
                1425                1430                1435

TGT GAT GAG GCC TGC AAC AGC CAT GCC TGC CAG TGG GAT GGG GGT GAC              4368
Cys Asp Glu Ala Cys Asn Ser His Ala Cys Gln Trp Asp Gly Gly Asp
                1440                1445                1450

TGT TCT CTC ACC ATG GAG AAC CCC TGG GCC AAC TGC TCC TCC CCA CTT              4416
Cys Ser Leu Thr Met Glu Asn Pro Trp Ala Asn Cys Ser Ser Pro Leu
                1455                1460                1465

CCC TGC TGG GAT TAT ATC AAC AAC CAG TGT GAT GAG CTG TGC AAC ACG              4464
```

-continued

```
Pro Cys Trp Asp Tyr Ile Asn Asn Gln Cys Asp Glu Leu Cys Asn Thr
1470                1475                1480                1485

GTC GAG TGC CTG TTT GAC AAC TTT GAA TGC CAG GGG AAC AGC AAG ACA    4512
Val Glu Cys Leu Phe Asp Asn Phe Glu Cys Gln Gly Asn Ser Lys Thr
            1490                1495                1500

TGC AAG TAT GAC AAA TAC TGT GCA GAC CAC TTC AAA GAC AAC CAC TGT    4560
Cys Lys Tyr Asp Lys Tyr Cys Ala Asp His Phe Lys Asp Asn His Cys
        1505                1510                1515

AAC CAG GGG TGC AAC AGT GAG GAG TGT GGT TGG GAT GGG CTG GAC TGT    4608
Asn Gln Gly Cys Asn Ser Glu Glu Cys Gly Trp Asp Gly Leu Asp Cys
    1520                1525                1530

GCT GCT GAC CAA CCT GAG AAC CTG GCA GAA GGT ACC CTG GTT ATT GTG    4656
Ala Ala Asp Gln Pro Glu Asn Leu Ala Glu Gly Thr Leu Val Ile Val
1535                1540                1545

GTA TTG ATG CCA CCT GAA CAA CTG CTC CAG GAT GCT CGC AGC TTC TTG    4704
Val Leu Met Pro Pro Glu Gln Leu Leu Gln Asp Ala Arg Ser Phe Leu
1550                1555                1560                1565

CGG GCA CTG GGT ACC CTG CTC CAC ACC AAC CTG CGC ATT AAG CGG GAC    4752
Arg Ala Leu Gly Thr Leu Leu His Thr Asn Leu Arg Ile Lys Arg Asp
            1570                1575                1580

TCC CAG GGG GAA CTC ATG GTG TAC CCC TAT TAT GGT GAG AAG TCA GCT    4800
Ser Gln Gly Glu Leu Met Val Tyr Pro Tyr Tyr Gly Glu Lys Ser Ala
        1585                1590                1595

GCT ATG AAG AAA CAG AGG ATG ACA CGC AGA TCC CTT CCT GGT GAA CAA    4848
Ala Met Lys Lys Gln Arg Met Thr Arg Arg Ser Leu Pro Gly Glu Gln
    1600                1605                1610

GAA CAG GAG GTG GCT GGC TCT AAA GTC TTT CTG GAA ATT GAC AAC CGC    4896
Glu Gln Glu Val Ala Gly Ser Lys Val Phe Leu Glu Ile Asp Asn Arg
1615                1620                1625

CAG TGT GTT CAA GAC TCA GAC CAC TGC TTC AAG AAC ACG GAT GCA GCA    4944
Gln Cys Val Gln Asp Ser Asp His Cys Phe Lys Asn Thr Asp Ala Ala
1630                1635                1640                1645

GCA GCT CTC CTG GCC TCT CAC GCC ATA CAG GGG ACC CTG TCA TAC CCT    4992
Ala Ala Leu Leu Ala Ser His Ala Ile Gln Gly Thr Leu Ser Tyr Pro
            1650                1655                1660

CTT GTG TCT GTC GTC AGT GAA TCC CTG ACT CCA GAA CGC ACT CAG CTC    5040
Leu Val Ser Val Val Ser Glu Ser Leu Thr Pro Glu Arg Thr Gln Leu
        1665                1670                1675

CTC TAT CTC CTT GCT GTT GCT GTT GTC ATC ATT CTG TTT ATT ATT CTG    5088
Leu Tyr Leu Leu Ala Val Ala Val Val Ile Ile Leu Phe Ile Ile Leu
    1680                1685                1690

CTG GGG GTA ATC ATG GCA AAA CGA AAG CGT AAG CAT GGC TCT CTC TGG    5136
Leu Gly Val Ile Met Ala Lys Arg Lys Arg Lys His Gly Ser Leu Trp
1695                1700                1705

CTG CCT GAA GGT TTC ACT CTT CGC CGA GAT GCA AGC AAT CAC AAG CGT    5184
Leu Pro Glu Gly Phe Thr Leu Arg Arg Asp Ala Ser Asn His Lys Arg
1710                1715                1720                1725

CGT GAG CCA GTG GGA CAG GAT GCT GTG GGG CTG AAA AAT CTC TCA GTG    5232
Arg Glu Pro Val Gly Gln Asp Ala Val Gly Leu Lys Asn Leu Ser Val
            1730                1735                1740

CAA GTC TCA GAA GCT AAC CTA ATT GGT ACT GGA ACA AGT GAA CAC TGG    5280
Gln Val Ser Glu Ala Asn Leu Ile Gly Thr Gly Thr Ser Glu His Trp
        1745                1750                1755

GTC GAT GAT GAA GGG CCC CAG CCA AAG AAA GTA AAG GCT GAA GAT GAG    5328
Val Asp Asp Glu Gly Pro Gln Pro Lys Lys Val Lys Ala Glu Asp Glu
    1760                1765                1770

GCC TTA CTC TCA GAA GAA GAT GAC CCC ATT GAT CGA CGG CCA TGG ACA    5376
Ala Leu Leu Ser Glu Glu Asp Asp Pro Ile Asp Arg Arg Pro Trp Thr
1775                1780                1785
```

```
CAG CAG CAC CTT GAA GCT GCA GAC ATC CGT AGG ACA CCA TCG CTG GCT         5424
Gln Gln His Leu Glu Ala Ala Asp Ile Arg Arg Thr Pro Ser Leu Ala
1790            1795                1800                1805

CTC ACC CCT CCT CAG GCA GAG CAG GAG GTG GAT GTG TTA GAT GTG AAT         5472
Leu Thr Pro Pro Gln Ala Glu Gln Glu Val Asp Val Leu Asp Val Asn
        1810                1815                1820

GTC CGT GGC CCA GAT GGC TGC ACC CCA TTG ATG TTG GCT TCT CTC CGA         5520
Val Arg Gly Pro Asp Gly Cys Thr Pro Leu Met Leu Ala Ser Leu Arg
                1825                1830                1835

GGA GGC AGC TCA GAT TTG AGT GAT GAA GAT GAA GAT GCA GAG GAC TCT         5568
Gly Gly Ser Ser Asp Leu Ser Asp Glu Asp Glu Asp Ala Glu Asp Ser
            1840                1845                1850

TCT GCT AAC ATC ATC ACA GAC TTG GTC TAC CAG GGT GCC AGC CTC CAG         5616
Ser Ala Asn Ile Ile Thr Asp Leu Val Tyr Gln Gly Ala Ser Leu Gln
        1855                1860                1865

GCC CAG ACA GAC CGG ACT GGT GAG ATG GCC CTG CAC CTT GCA GCC CGC         5664
Ala Gln Thr Asp Arg Thr Gly Glu Met Ala Leu His Leu Ala Ala Arg
1870            1875                1880                1885

TAC TCA CGG GCT GAT GCT GCC AAG CGT CTC CTG GAT GCA GGT GCA GAT         5712
Tyr Ser Arg Ala Asp Ala Ala Lys Arg Leu Leu Asp Ala Gly Ala Asp
                1890                1895                1900

GCC AAT GCC CAG GAC AAC ATG GGC CGC TGT CCA CTC CAT GCT GCA GTG         5760
Ala Asn Ala Gln Asp Asn Met Gly Arg Cys Pro Leu His Ala Ala Val
            1905                1910                1915

GCA GCT GAT GCC CAA GGT GTC TTC CAG ATT CTG ATT CGC AAC CGA GTA         5808
Ala Ala Asp Ala Gln Gly Val Phe Gln Ile Leu Ile Arg Asn Arg Val
        1920                1925                1930

ACT GAT CTA GAT GCC AGG ATG AAT GAT GGT ACT ACA CCC CTG ATC CTG         5856
Thr Asp Leu Asp Ala Arg Met Asn Asp Gly Thr Thr Pro Leu Ile Leu
1935            1940                1945

GCT GCC CGC CTG GCT GTG GAG GGA ATG GTG GCA GAA CTG ATC AAC TGC         5904
Ala Ala Arg Leu Ala Val Glu Gly Met Val Ala Glu Leu Ile Asn Cys
1950            1955                1960                1965

CAA GCG GAT GTG AAT GCA GTG GAT GAC CAT GGA AAA TCT GCT CTT CAC         5952
Gln Ala Asp Val Asn Ala Val Asp Asp His Gly Lys Ser Ala Leu His
                1970                1975                1980

TGG GCA GCT GCT GTC AAT AAT GTG GAG GCA ACT CTT TTG TTG TTG AAA         6000
Trp Ala Ala Ala Val Asn Asn Val Glu Ala Thr Leu Leu Leu Leu Lys
            1985                1990                1995

AAT GGG GCC AAC CGA GAC ATG CAG GAC AAC AAG GAA GAG ACA CCT CTG         6048
Asn Gly Ala Asn Arg Asp Met Gln Asp Asn Lys Glu Glu Thr Pro Leu
        2000                2005                2010

TTT CTT GCT GCC CGG GAG GGG AGC TAT GAA GCA GCC AAG ATC CTG TTA         6096
Phe Leu Ala Ala Arg Glu Gly Ser Tyr Glu Ala Ala Lys Ile Leu Leu
2015            2020                2025

GAC CAT TTT GCC AAT CGA GAC ATC ACA GAC CAT ATG GAT CGT CTT CCC         6144
Asp His Phe Ala Asn Arg Asp Ile Thr Asp His Met Asp Arg Leu Pro
2030            2035                2040                2045

CGG GAT GTG GCT CGG GAT CGC ATG CAC CAT GAC ATT GTG CGC CTT CTG         6192
Arg Asp Val Ala Arg Asp Arg Met His His Asp Ile Val Arg Leu Leu
                2050                2055                2060

GAT GAA TAC AAT GTG ACC CCA AGC CCT CCA GGC ACC GTG TTG ACT TCT         6240
Asp Glu Tyr Asn Val Thr Pro Ser Pro Pro Gly Thr Val Leu Thr Ser
            2065                2070                2075

GCT CTC TCA CCT GTC ATC TGT GGG CCC AAC AGA TCT TTC CTC AGC CTG         6288
Ala Leu Ser Pro Val Ile Cys Gly Pro Asn Arg Ser Phe Leu Ser Leu
        2080                2085                2090

AAG CAC ACC CCA ATG GGC AAG AAG TCT AGA CGG CCC AGT GCC AAG AGT         6336
Lys His Thr Pro Met Gly Lys Lys Ser Arg Arg Pro Ser Ala Lys Ser
2095            2100                2105
```

```
ACC ATG CCT ACT AGC CTC CCT AAC CTT GCC AAG GAG GCA AAG GAT GCC      6384
Thr Met Pro Thr Ser Leu Pro Asn Leu Ala Lys Glu Ala Lys Asp Ala
2110            2115                2120                2125

AAG GGT AGT AGG AGG AAG AAG TCT CTG AGT GAG AAG GTC CAA CTG TCT      6432
Lys Gly Ser Arg Arg Lys Lys Ser Leu Ser Glu Lys Val Gln Leu Ser
                2130                2135                2140

GAG AGT TCA GTA ACT TTA TCC CCT GTT GAT TCC CTA GAA TCT CCT CAC      6480
Glu Ser Ser Val Thr Leu Ser Pro Val Asp Ser Leu Glu Ser Pro His
            2145                2150                2155

ACG TAT GTT TCC GAC ACC ACA TCC TCT CCA ATG ATT ACA TCC CCT GGG      6528
Thr Tyr Val Ser Asp Thr Thr Ser Ser Pro Met Ile Thr Ser Pro Gly
            2160                2165                2170

ATC TTA CAG GCC TCA CCC AAC CCT ATG TTG GCC ACT GCC GCC CCT CCT      6576
Ile Leu Gln Ala Ser Pro Asn Pro Met Leu Ala Thr Ala Ala Pro Pro
        2175                2180                2185

GCC CCA GTC CAT GCC CAG CAT GCA CTA TCT TTT TCT AAC CTT CAT GAA      6624
Ala Pro Val His Ala Gln His Ala Leu Ser Phe Ser Asn Leu His Glu
2190                2195                2200                2205

ATG CAG CCT TTG GCA CAT GGG GCC AGC ACT GTG CTT CCC TCA GTG AGC      6672
Met Gln Pro Leu Ala His Gly Ala Ser Thr Val Leu Pro Ser Val Ser
                2210                2215                2220

CAG TTG CTA TCC CAC CAC CAC ATT GTG TCT CCA GGC AGT GGC AGT GCT      6720
Gln Leu Leu Ser His His His Ile Val Ser Pro Gly Ser Gly Ser Ala
            2225                2230                2235

GGA AGC TTG AGT AGG CTC CAT CCA GTC CCA GTC CCA GCA GAT TGG ATG      6768
Gly Ser Leu Ser Arg Leu His Pro Val Pro Val Pro Ala Asp Trp Met
            2240                2245                2250

AAC CGC ATG GAG GTG AAT GAG ACC CAG TAC AAT GAG ATG TTT GGT ATG      6816
Asn Arg Met Glu Val Asn Glu Thr Gln Tyr Asn Glu Met Phe Gly Met
        2255                2260                2265

GTC CTG GCT CCA GCT GAG GGC ACC CAT CCT GGC ATA GCT CCC CAG AGC      6864
Val Leu Ala Pro Ala Glu Gly Thr His Pro Gly Ile Ala Pro Gln Ser
2270                2275                2280                2285

AGG CCA CCT GAA GGG AAG CAC ATA ACC ACC CCT CGG GAG CCC TTG CCC      6912
Arg Pro Pro Glu Gly Lys His Ile Thr Thr Pro Arg Glu Pro Leu Pro
                2290                2295                2300

CCC ATT GTG ACT TTC CAG CTC ATC CCT AAA GGC AGT ATT GCC CAA CCA      6960
Pro Ile Val Thr Phe Gln Leu Ile Pro Lys Gly Ser Ile Ala Gln Pro
            2305                2310                2315

GCG GGG GCT CCC CAG CCT CAG TCC ACC TGC CCT CCA GCT GTT GCG GGC      7008
Ala Gly Ala Pro Gln Pro Gln Ser Thr Cys Pro Pro Ala Val Ala Gly
            2320                2325                2330

CCC CTG CCC ACC ATG TAC CAG ATT CCA GAA ATG GCC CGT TTG CCC AGT      7056
Pro Leu Pro Thr Met Tyr Gln Ile Pro Glu Met Ala Arg Leu Pro Ser
        2335                2340                2345

GTG GCT TTC CCC ACT GCC ATG ATG CCC CAG CAG GAC GGG CAG GTA GCT      7104
Val Ala Phe Pro Thr Ala Met Met Pro Gln Gln Asp Gly Gln Val Ala
2350                2355                2360                2365

CAG ACC ATT CTC CCA GCC TAT CAT CCT TTC CCA GCC TCT GTG GGC AAG      7152
Gln Thr Ile Leu Pro Ala Tyr His Pro Phe Pro Ala Ser Val Gly Lys
                2370                2375                2380

TAC CCC ACA CCC CCT TCA CAG CAC AGT TAT GCT TCC TCA AAT GCT GCT      7200
Tyr Pro Thr Pro Pro Ser Gln His Ser Tyr Ala Ser Ser Asn Ala Ala
            2385                2390                2395

GAG CGA ACA CCC AGT CAC AGT GGT CAC CTC CAG GGT GAG CAT CCC TAC      7248
Glu Arg Thr Pro Ser His Ser Gly His Leu Gln Gly Glu His Pro Tyr
            2400                2405                2410

CTG ACA CCA TCC CCA GAG TCT CCT GAC CAG TGG TCA AGT TCA TCA CCC      7296
Leu Thr Pro Ser Pro Glu Ser Pro Asp Gln Trp Ser Ser Ser Ser Pro
```

-continued

```
             2415              2420              2425
CAC TCT GCT TCT GAC TGG TCA GAT GTG ACC ACC AGC CCT ACC CCT GGG    7344
His Ser Ala Ser Asp Trp Ser Asp Val Thr Thr Ser Pro Thr Pro Gly
2430              2435              2440              2445

GGT GCT GGA GGA GGT CAG CGG GGA CCT GGG ACA CAC ATG TCT GAG CCA    7392
Gly Ala Gly Gly Gly Gln Arg Gly Pro Gly Thr His Met Ser Glu Pro
              2450              2455              2460

CCA CAC AAC AAC ATG CAG GTT TAT GCG TGAGAGAGTC CACCTCCAGT          7439
Pro His Asn Asn Met Gln Val Tyr Ala
            2465              2470

GTAGAGACAT AACTGACTTT TGTAAATGCT GCTGAGGAAC AAATGAAGGT CATCCGGGAG   7499

AGAAATGAAG AAATCTCTGG AGCCAGCTTC TAGAGGTAGG AAAGAAGA TGTTCTTATT    7559

CAGATAATGC AAGAGAAGCA ATTCGTCAGT TTCACTGGGT ATCTGCAAGG CTTATTGATT   7619

ATTCTAATCT AATAAGACAA GTTTGTGGAA ATGCAAGATG AATACAAGCC TTGGGTCCAT   7679

GTTTACTCTC TTCTATTTGG AGAATAAGAT GGATGCTTAT TGAAGCCCAG ACATTCTTGC   7739

AGCTTGGACT GCATTTTAAG CCCTGCAGGC TTCTGCCATA TCCATGAGAA GATTCTACAC   7799

TAGCGTCCTG TTGGGAATTA TGCCCTGGAA TTCTGCCTGA ATTGACCTAC GCATCTCCTC   7859

CTCCTTGGAC ATTCTTTTGT CTTCATTTGG TGCTTTTGGT TTTGCACCTC TCCGTGATTG   7919

TAGCCCTACC AGCATGTTAT AGGGCAAGAC CTTTGTGCTT TTGATCATTC TGGCCCATGA   7979

AAGCAACTTT GGTCTCCTTT CCCTCCTGT CTTCCCGGTA TCCCTTGGAG CTCACAAGG    8039

TTTACTTTGG TATGGTTCTC AGCACAAACC TTTCAAGTAT GTTGTTTCTT TGGAAAATGG   8099

ACATACTGTA TTGTGTTCTC CTGCATATAT CATTCCTGGA GAGAGAAGGG GAGAAGAATA   8159

CTTTTCTTCA ACAAATTTTG GGGGCAGGAG ATCCCTTCAA GAGGCTGCAC CTTAATTTTT   8219

CTTGTCTGTG TGCAGGTCTT CATATAAACT TTACCAGGAA GAAGGGTGTG AGTTTGTTGT   8279

TTTTCTGTGT ATGGGCCTGG TCAGTGTAAA GTTTTATCCT TGATAGTCTA GTTACTATGA   8339

CCCTCCCCAC TTTTTTAAAA CCAGAAAAAG GTTTGGAATG TTGGAATGAC AAGAGACAA    8399

GTTAACTCGT GCAAGAGCCA GTTACCCACC CACAGGTCCC CCTACTTCCT GCCAAGCATT   8459

CCATTGACTG CCTGTATGGA ACACATTTGT CCCAGATCTG AGCATTCTAG GCCTGTTTCA   8519

CTCACTCACC CAGCATATGA AACTAGTCTT AACTGTTGAG CCTTTCCTTT CATATCCACA   8579

GAAGACACTG TCTCAAATGT TGTACCCTTG CCATTTAGGA CTGAACTTTC CTTAGCCCAA   8639

GGGACCCAGT GACAGTTGTC TTCCGTTTGT CAGATGATCA GTCTCTACTG ATTATCTTGC   8699

TGCTTAAAGG CCTGCTCACC AATCTTTCTT TCACACCGTG TGGTCCGTGT TACTGGTATA   8759

CCCAGTATGT TCTCACTGAA GACATGGACT TTATATGTTC AAGTGCAGGA ATTGGAAAGT   8819

TGGACTTGTT TTCTATGATC CAAAACAGCC CTATAAGAAG GTTGGAAAAG GAGGAACTAT   8879

ATAGCAGCCT TTGCTATTTT CTGCTACCAT TTCTTTTCCT CTGAAGCGGC CATGACATTC   8939

CCTTTGGCAA CTAACGTAGA AACTCAACAG AACATTTTCC TTTCCTAGAG TCACCTTTTA   8999

GATGATAATG GACAACTATA GACTTGCTCA TTGTTCAGAC TGATTGCCCC TCACCTGAAT   9059

CCACTCTCTG TATTCATGCT CTTGGCAATT TCTTTGACTT TCTTTTAAGG GCAGAAGCAT   9119

TTTAGTTAAT TGTAGATAAA GAATAGTTTT CTTCCTCTTC TCCTTGGGCC AGTTAATAAT   9179

TGGTCCATGG CTACACTGCA ACTTCCGTCC AGTGCTGTGA TGCCCATGAC ACCTGCAAAA   9239

TAAGTTCTGC CTGGGCATTT TGTAGATATT AACAGGTGAA TTCCCGACTC TTTTGGTTTG   9299

AATGACAGTT CTCATTCCTT CTATGGCTGC AAGTATGCAT CAGTGCTTCC CACTTACCTG   9359

ATTTGTCTGT CGGTGGCCCC ATATGGAAAC CCTGCGTGTC TGTTGGCATA ATAGTTTACA   9419
```

-continued

| | | | | | |
|---|---|---|---|---|---|
| AATGGTTTTT | TCAGTCCTAT | CCAAATTTAT | TGAACCAACA | AAAATAATTA | CTTCTGCCCT | 9479
| GAGATAAGCA | GATTAAGTTT | GTTCATTCTC | TGCTTTATTC | TCTCCATGTG | GCAACATTCT | 9539
| GTCAGCCTCT | TTCATAGTGT | GCAAACATTT | TATCATTCTA | AATGGTGACT | CTCTGCCCTT | 9599
| GGACCCATTT | ATTATTCACA | GATGGGGAGA | ACCTATCTGC | ATGGACCCTC | ACCATCCTCT | 9659
| GTGCAGCACA | CACAGTGCAG | GGAGCCAGTG | GCGATGGCGA | TGACTTTCTT | CCCCTGGGAA | 9719
| TTCC | | | | | | 9723

What is claimed is:

1. A method for changing differentiation phenotype of a cell from what would otherwise occur comprising contacting a cell with an amount of a molecule which promotes Notch signal transduction, effective to change the differentiation phenotype of the contacted cell.

2. The method according to claim 1 wherein the molecule is a protein consisting of at least a fragment of a toporythmic protein, the fragment being characterized by the ability to bind to a Notch protein.

3. The method according to claim 1 wherein the molecule is a protein consisting of at least a fragment of a Notch protein, the fragment being characterized by the ability to bind to a toporythmic protein.

4. The method according to claim 1 wherein the molecule is a Delta protein.

5. The method according to claim 1 wherein the molecule is a Notch protein.

6. The method according to claim 1 wherein the molecule is a Serrate protein.

7. The method according to claim 1 wherein the molecule is encoded by a gene which is a member of the Notch signaling pathway.

8. A method for changing differentiation phenotype of a cell from what would otherwise occur comprising contacting a cell with an amount of a toporythmic protein effective to change the differentiation phenotype of the contacted cell.

9. The method according to claim 8 wherein the toporythmic protein is a Delta protein.

10. The method according to claim 8 wherein the toporythmic protein is a Serrate protein.

11. The method according to claim 8 wherein the toporythmicc protein is a Notch protein.

* * * * *